United States Patent
Ryu et al.

(10) Patent No.: US 8,008,329 B2
(45) Date of Patent: *Aug. 30, 2011

(54) METHOD OF TREATING OR PREVENTING OSTEOPOROSIS COMPRISING ADMINISTERING TO A PATIENT IN NEED THEREOF AN EFFECTIVE AMOUNT OF PHARMACUETICAL COMPOSITION COMPRISING BENZAMIDINE DERIVATIVE OR IT'S SALT, AND BISPHOSPHONATE

(75) Inventors: Jei Man Ryu, Gyeonggi-do (KR); Jin Soo Lee, Gyeonggi-do (KR); Yun-Ha Hwang, Gyeonggi-do (KR); Young G. Jin, Gyeonggi-do (KR); Ki Y. Kim, Gyeonggi-do (KR)

(73) Assignee: Dong Wha Pharmaceutical Co., Ltd., Seoul (KR)

( * ) Notice: Subject to any disclaimer, the term of this patent is extended or adjusted under 35 U.S.C. 154(b) by 60 days.

This patent is subject to a terminal disclaimer.

(21) Appl. No.: 12/533,842

(22) Filed: Jul. 31, 2009

(65) Prior Publication Data
US 2010/0029596 A1    Feb. 4, 2010

Related U.S. Application Data

(60) Provisional application No. 61/085,603, filed on Aug. 1, 2008, provisional application No. 61/207,889, filed on Jan. 30, 2009.

(51) Int. Cl.
*A61K 31/66* (2006.01)
*A61K 31/685* (2006.01)
*A61K 31/675* (2006.01)
*A01N 43/48* (2006.01)

(52) U.S. Cl. ............... 514/365; 514/108; 514/89

(58) Field of Classification Search ............... None
See application file for complete search history.

(56) References Cited

FOREIGN PATENT DOCUMENTS
WO    WO 2006014087 A1 *    2/2006

OTHER PUBLICATIONS

U.S. Appl. No. 12/533,537, filed Jul. 2009, Ryu et al.*

* cited by examiner

*Primary Examiner* — Sreeni Padmanabhan
*Assistant Examiner* — Svetlana M Ivanova
(74) *Attorney, Agent, or Firm* — Arent Fox LLP

(57) ABSTRACT

The present invention provides a method of treating or preventing osteoporosis comprising administering to a patient in need thereof an effective amount of pharmaceutical composition comprising benzamidine derivative or its salt, and bisphosphonate for the purpose of using simultaneously, separately, or sequentially as active ingredients. As a prophylactic or therapeutic composition for osteoporosis, the combination treatment of the benzamidine derivative and the bisphosphonate compound exhibits excellent inhibitory effect on osteoclast differentiation than the total effect of each individual treatment, thereby being used for the prevention or treatment of osteoporosis.

28 Claims, No Drawings

METHOD OF TREATING OR PREVENTING OSTEOPOROSIS COMPRISING ADMINISTERING TO A PATIENT IN NEED THEREOF AN EFFECTIVE AMOUNT OF PHARMACUETICAL COMPOSITION COMPRISING BENZAMIDINE DERIVATIVE OR IT'S SALT, AND BISPHOSPHONATE

CROSS-REFERENCE TO RELATED APPLICATION

This application claims the benefit of priority to U.S. Provisional Application No. 61/085,603, filed Aug. 1, 2008, and U.S. Provisional Application No. 61/207,889, filed Jan. 30, 2009. The contents of these applications are incorporated herein by reference in their entirety.

TECHNICAL FIELD

The present invention relates to a method of treating or preventing osteoporosis comprising administering to a patient in need thereof an effective amount of pharmaceutical composition comprising benzamidine derivative or its salt, and bisphosphonate. More particularly, the present invention relates to a method of treating or preventing osteoporosis comprising administering to a patient in need thereof an effective amount of pharmaceutical composition comprising benzamidine derivative or its salt, and bisphosphonate having an improved effect over the pharmaceutical compositions comprising the benzamidine of Formula 1 or salt thereof, or bisphosphonate, individually.

BACKGROUND ART

Bone is a supporting material for the body's framework and serves to conserve the necessary bone mass and structure. Bone also functions as a reservoir of calcium ($Ca^{2+}$) or the like, and plays an important role in maintaining the calcium level in the blood. To this end, bone undergoes continuous degradation and remodeling. Thus, bone is in a dynamic steady state, which maintains a delicate balance by continuously performing both bone resorption and bone formation. When the balance between bone resorption and bone formation is disrupted, the degree of bone resorption is relatively higher than that of bone formation, which may lead to osteoporosis, a condition which causes reduction in bone density or bone mass, resulting in decrease in bone strength. This is a disease which frequently occurs in middle-aged or elderly women.

Osteoporosis is a disease, which results from a disturbance in the balance between bone resorption and bone formation, and is caused by having a higher degree of bone resorption relative to that of bone formation. Osteoporosis reduces calcification of bone tissues, and decreases the level of the compact substances in the bone, which broadens the marrow cavity. As osteoporosis progresses, bone becomes brittle, and bone fracture may easily occur even with a small impact. Bone is a steady state structure, in which the bone formation by osteoblast and the bone resorption by osteoclast occur continuously.

Previous studies on osteoporosis have focused mainly on the metabolism of bone minerals, such as calcium and phosphorus. However, such studies did not provide sufficient findings on the mechanisms of osteoporosis.

Bone fracture is associated with an increased mortality rate of patients with osteoporosis, and also causes serious problems such as negative impact on patient's quality of life. Thus, various strategies have been established to produce drugs capable of preventing loss of bone density and bone fracture.

To date, bisphosphonate (alendronate, etidronate), hormones (raloxifen), vitamin D, calcitonin, calcium agents, or the like have been used as an anti-osteoporotic agent, and Forteo™, a form of parathyroid hormone responsible for bone formation, is currently used to treat advanced osteoporosis. However, they are known to have adverse effects. Specifically, hormone agents must be administered throughout patient's life and in the case of long-term administration, side effects such as breast cancer, uterus cancer, gallstones and thrombosis may be induced. Vitamin D agents are expensive and show little efficacy, and calcitonin agents are also very expensive and difficult to administer. Calcium agents have few side effects, but their effects are restricted to the prevention of osteoporosis, not the treatment itself. Forteo™, a commercially available parathyroid hormone, has an advantage in that it stimulates bone formation, whereas the known drugs are restricted to the prevention of bone resorption. However, Forteo™ should be given as a daily injection for a long period of time and may increase the risk of osteosarcoma. Its application is also restricted due to the high price.

A bisphosphonate drug, alendronate or risedronate, represented by the following Formula, has been widely used for the treatment of osteoporosis and shown to increase bone density and prevent fractures as an inhibitor of bone resorption. Owing to advantages of oral administration and lower cost, it has been widely used in clinical fields for the treatment of calcium metabolic disorders including osteoporosis.

However, bisphosphonate agents show low absorptivity and may induce esophagitis, and thus should be taken with a sufficient amount of water before meals. In addition, patients should wait at least 30 minutes before ingesting other beverage or food and avoid lying down for a predetermined time following administration. They are also reported to increase the risk of hypocalcemia. Recent studies have suggested problems such as reduction in bone turnover rate due to excessive inhibition of bone resorption, inhibition of bone formation, gastrointestinal disorders and osteonecrosis of the jaw. Furthermore, it is recently reported that its long term administration increases the risk of bone fractures (Andrew S Neviaser et al, *Journal of Othopaedic Trauma*, 2008, 22(5), 346~350).

As described above, the current therapeutic agents for osteoporosis are not those which act on both bone resorption and formation. Accordingly, in order to treat osteoporosis, there is a need for the development of drugs and therapies which lead to balanced increase in the bone mass and improvement of bone quality and thus reduce the risk of bone fractures.

To overcome the above drawbacks and improve the clinical efficacy, many studies have been made, and recent studies suggested combination therapy of a bone resorption inhibitor and a commercially available parathyroid hormone that stimulates bone formation. The detailed description thereof is as follows.

The combination therapy of alendronate and other bone resorption inhibitor are exemplified by alendronate and estrogen (literature—Lindsay et al, *J. Clin. Endocrinol. Metab.* 84, 3073-3081 (1999)), alendronate and raloxifene (literature—Johnell et al, *J. Clin. Endocrinol. Metab.* 87, 985-992 (2002)), alendronate and HRT (hormone replacement therapy) (literature—Greenspan et al, *JAMA*, 289, 2525-2533 (2003)), and alendronate and calcitriol (WO 01/28564). These studies demonstrated that the combination therapy showed an increase in bone density, compared to their individual administration, but no reduction in the risk of bone fracture. More-over, problems including reduction in bone turnover rate due to inhibitory effect on bone resorption and inhibition of bone formation still remain, even though there are differences between their mechanisms. Thus, there are needs for considerations and further studies regarding the therapies.

In this regard, there was a trial of combination therapy with a bone formation stimulator, which was intended to reduce inhibitory effect on bone formation and adverse effects of alendronate. Combination therapy of alendronate with a parathyroid hormone is exemplified by two literatures: The effects of parathyroid hormone and alendronate in combination in postmenopausal osteoporosis (literature—Black et al, N. Eng. J. Med. 349, 1207-1215, (2003)) and in elderly men with osteoporosis (literature—Finkelstein et al, N. Eng. J. Med. 349, 1216-1226, (2003)). However, the literatures did not demonstrate the increase in bone density, compared to their individual administration. In this regard, some researchers suggested the possibility that a strong bone resorption inhibitor, alendronate counteracts the stimulating effect of parathyroid hormone. Subsequently, a sequential administration of two drugs has been tried, but further studies are still needed for a meaningful clinical outcome.

The inventors have already disclosed the therapeuric use of the benzamidine derivatives in osteoporosis in Korea Patent No. 705875, Korea Patent No. 875596, and Korea Patent Application No. 2008-0073710.

The present inventors have also studied the method to increase the prophylactic or therapeutic effect of the benzamidine compounds of Formula I or salt thereof, by the combined administration with other compounds, and developed the present compositions with an improved effect over the the individual administration that can be used in the prevention and treatment of osteopossis.

[DISCLOSURE]

[Technical Problem]

An object of the present inventions is to provide a method of treating or preventing osteoporosis comprising administering to a patient in need thereof an effective amount of pharmaceutical composition comprising benzamidine derivative or its salt, and bisphosphonate.

Another object of the present invention is to provide a method of treating or preventing osteoporosis comprising administering to a patient in need thereof an effective amount of pharmaceutical composition comprising benzamidine derivative or its salt, and bisphosphonate, with an improved effect when administered together than administered individually.

The foregoing and other objects of the present invention can be accomplished by the following descriptions of the present invention.

[Technical Solution]

In accordance with an aspect, the present invention provides a method of treating or preventing osteoporosis comprising administering to a patient in need thereof an effective amount of pharmaceutical composition comprising the following compounds (a) and (b) for the purpose of using simultaneously, separately, or sequentially as active ingredients:

(a) a benzamidine derivative represented by the following Formula 1 or salt thereof, and (b) bisphosphonate represented by the following Formula 2,

[Formula 1]

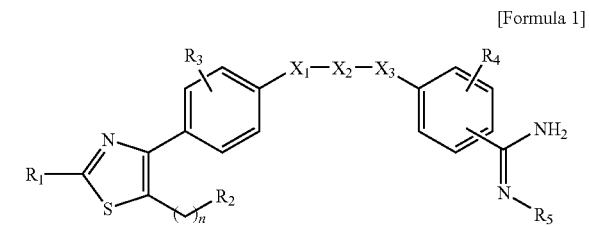

wherein $R_1$ is $C_1$~$C_6$ alkyl which is unsubstituted or substituted with pyridinyl; and straight or branched $C_1$~$C_6$ alkyl which is substituted with

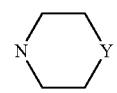

unsubstituted or substituted with hydroxy; $C_3$~$C_6$ cycloalkyl; phenyl; benzyl; pyridinyl which is unsubstituted or substituted with $C_1$~$C_6$ alkyl; guanidino; $NR_6R_7$; $CH_2NR_6R_7$; pyridinyl or

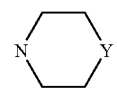

group which is substituted with straight or branched $C_1$~$C_6$ alkyl;

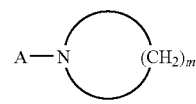

(wherein A is $C_1$~$C_6$ alkyl, and m is an integer of 2 to 6); or

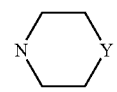

group which is unsubstituted or substituted with $C_1$~$C_6$ alkyl, $R_2$ is hydrogen; straight or branched $C_1$~$C_6$ alkyl which is unsubstituted or substituted with $NR_8R_9$; $C_3$~$C_6$ cycloalkyl; phenyl; benzyl; $C_2$~$C_6$ alkenyl; carbonyl which is substituted with $NR_8R_9$; amino; dimethylamino; morpholinyl; thiomorpholinyl; 4-methylpiperazinyl; or straight or branched $C_1$~$C_6$ alkyl which is substituted with hydroxy, $C_1$~$C_6$ alkoxy, halogen, $C_3$~$C_6$ cycloalkyl,

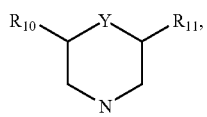

imidazolyl, or pyrrolidinyl;

$R_3$ and $R_4$ are each independently hydrogen; halogen; hydroxy; $C_1\sim C_6$ alkyl which is unsubstituted or substituted with halogen; $C_3\sim C_6$ cycloalkylamino; $C_1\sim C_6$ alkoxy; $C_1\sim C_6$ alkanoyloxy; $C_2\sim C_6$ alkenyloxy; phenyl-$C_1\sim C_6$ alkoxy; phenoxy; $C_2\sim C_6$ alkenoyloxy or phenyl-$C_1\sim C_6$ alkanoyloxy; $C_3\sim C_6$ cycloalkyloxy which is substituted with one group selected from carboxy, esterified carboxy and amidated carboxy; or an aminooxy group;

$R_5$ is hydrogen or hydroxy group;

$R_6$ and $R_7$ are each independently hydrogen; $C_1\sim C_6$ alkyl which is unsubstituted or substituted with one group selected from hydroxy, $C_1\sim C_6$ alkoxy, pyridine and

phenyl; benzyl; pyridinyl; carbonyl which is substituted with one group selected from $C_1\sim C6$ alkyl, hydroxy, $C_1\sim C_6$ alkoxy, phenyl, benzyl, pyridine and

or $C_1\sim C_6$ alkanesulfonyl;

$R_8$ and $R_9$ are each independently hydrogen; $C_1\sim C_6$ alkyl which is unsubstituted or substituted with one group selected from hydroxy, $C_1\sim C_6$ alkoxy, morpholine, imidazole and $NR_6R_7$; $C_1\sim C_6$ alkoxy; $C_3\sim C_6$ cycloalkyl; phenyl; benzyl; pyridinyl; morpholine; carbonyl which is substituted with one group selected from $C_1\sim C_6$ alkyl, $C_1\sim C_6$ alkoxy, phenyl, benzyl, pyridine and

carbonyl which is substituted with $C_1\sim C_6$ alkyl substituted with one group selected from halogen, $C_1\sim C_6$ alkoxy and imidazole; or $C_1\sim C_6$ alkanesulfonyl;

$R_{10}$ and $R_{11}$ are each independently hydrogen, $C_1\sim C_2$ alkyl, $C_1\sim C_3$ alkoxy or halide;

$X_1$ and $X_3$ are each independently O; S; NH; or N—$C_1\sim C_6$ alkyl, N—$C_3\sim C_6$ cycloalkyl, N-benzyl or N-phenyl group;

$X_2$ is $C_3\sim C_7$ alkylene; $C_1\sim C_3$ alkylene-$C_2\sim C_7$ alkenylene-$C_1\sim C_3$ alkylene; $C_1\sim C_3$ alkylene-O—$C_1\sim C_3$ alkylene; $C_1\sim C_3$ alkylene-S—$C_1\sim C_3$ alkylene; $C_1\sim C_3$ alkylene-NH—$C_1\sim C_3$ alkylene; $C_1\sim C_3$ alkylene-phenylene-$C_1\sim C_3$ alkylene; $C_1$-$C_3$ alkylene-pyridylene-$C_1$-$C_3$ alkylene or $C_1$-$C_3$ alkylene-naphthylene-$C_1\sim C_3$ alkylene; $C_3\sim C_7$ alkylene which is substituted with $C_1\sim C_3$ alkyl and hydroxyl; $C_3\sim C_7$ alkylene carbonyl; or $C_3\sim C_7$ alkylene which is interrupted by piperazine;

Y is O, S, $NR_6$ or $CH_2$ group; and

N is an integer of 0, 1 and 2.

[Formula 2]

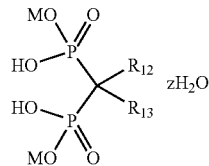

wherein $R_{12}$ is methyl, chloro, 2-aminoethyl, 3-aminopropyl, 4-aminobutyl, 5-aminopentyl, 4-chlorophenylthio, 3-pyridylmethyl, (imidazo[1,2-a]pyridine-3-yl)methyl, 2-(N-methyl-N-n-pentyl)aminoethyl, cycloheptylamino, (1-imidazolyl)methyl or 1-pyrrolidinylethyl group, $R_{13}$ is hydrogen, chloro or hydroxy group, M is hydrogen or sodium, and Z is any number, preferably an integer of 0 to 7.

In Formula 1, $R_1$ is particularly methyl, ethyl, isopropyl, cyclohexyl, phenyl, aminomethyl, aminoethyl, amino, pyridinyl, $NR_6R_7$, $CH_2NR_6R_7$,

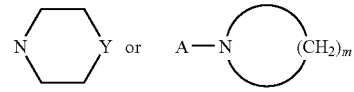

(wherein A is $C_1\sim C_2$ alkyl, and m is an integer of 4 to 5);

$R_2$ is hydrogen; methyl; ethyl; isopropyl; isobutyl; methoxymethyl; hydroxymethyl; chloromethyl; chloroethyl; cyclopentyl; cyclopentylmethyl; vinyl; methyl or ethyl which is substituted with $NR_8R_9$; carbonyl which is substituted with $NR_8R_9$; methyl or ethyl which is substituted with

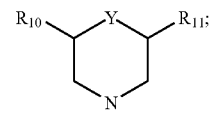

methyl or ethyl which is substituted with pyrrolidine, piperidine or imidazole;

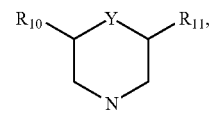

piperidine or triazole;

$R_3$ and $R_4$ are each independently hydrogen, halogen, hydroxy or methoxy group;

$R_5$ is hydrogen or hydroxy group;

$R_6$ and $R_7$ are each independently hydrogen, methyl, ethyl, propyl, hydroxyethyl, methoxyethyl, 2-morpholinoethyl, benzyl, pyridine-3-yl, pyridine-4-yl, 2-morpholinoethyl, 4-pyridinylcarbonyl, 3-pyridinylcarbonyl, isobutylcarbonyl, ethanesulfonyl, hydroxyethyl, or methoxyethyl group;

$R_8$ and $R_9$ are each independently hydrogen; methyl; ethyl; propyl; isopropyl; butyl; isobutyl; t-butyl; cyclopropyl; cyclohexyl; ethyl which is substituted with one group selected from hydroxy, methoxy, 2-morpholino and $NR_6R_7$; propyl which is substituted with one group selected from 3-isopropoxy and 3-imidazole; carbonyl which is substituted with one group selected from 3-pyridinyl, 4-pyridinyl and isopropyl;

$R_{10}$ and $R_{11}$ are each independently hydrogen or methyl; $X_1$ and $X_3$ are each independently oxygen, sulfur, amine or methylamine group;

$X_2$ is propylene, butylene, pentylene, hexylene, ethylene-O-ethylene, ethylene-NH-ethylene, butylene carbonyl, 2-butenyl, methylene-1,2-phenylene-methylene, methylene-1,3-phenylene-methylene, methylene-1,4-phenylene-methylene or methylene-pyridinyl-methylene; and n is an integer of 0, 1 and 2.

In the compound of Formula 1 of the present invention, $R_3$ and $R_4$ are in the ortho or meta position relative to —$X_1$— or —$X_3$—, and —$C(NH_2)=N$—$R_5$ is in the meta or para position.

In one embodiment, the $R_1$ is $C_1$~$C_5$ alkyl; $C_1$~$C_5$ alkyl substituted with piperidinyl ; $C_3$~$C_6$ cycloalkyl; phenyl; pyridinyl; guanidino; $NR_6R_7$; piperidinyl or piperazinyl substituted with straight $C_1$~$C_3$ alkyl; morpholinyl; or piperidinyl;

the $R_2$ is hydrogen; straight or branched $C_1$~$C_4$ alkyl which is unsubstituted or substituted with $NR_8R_9$; $C_3$~$C_6$ cycloalkyl; benzyl; $C_2$~$C_6$ alkenyl; carbonyl which is substituted with $NR_8R_9$; amino; dimethylamino; morpholinyl; thiomorpholinyl; 4-methylpiperazinyl; or straight or branched $C_1$~$C_3$ alkyl which is substituted with $C_1$~$C_3$ alkoxy, halogen, $C_3$~$C_6$ cycloalkyl, morpholinyl, dimethylmorpholinyl, thiomorpholinyl, 4-methylpiperazinyl, piperidinyl, imidazolyl, or pyrrolidinyl, the $R_3$ is hydrogen, the $R_4$ is hydrogen, hydroxy or fluoro, the $R_5$ is hydrogen or hydroxy;

the $R_6$ and $R_7$ are each independently hydrogen; $C_1$~$C_3$ alkyl which is unsubstituted or substituted with one group selected from hydroxy, $C_1$~$C_3$ alkoxy, pyridinyl, morpholinyl and piperidinyl; benzyl; carbonyl which is substituted with one group selected from $C_1$~$C_3$ alkyl, $C_1$~$C_3$ alkyl substituted with hydroxy and pyridinyl; or $C_1$~$C_3$ alkanesulfonyl;

the $R_8$ and $R_9$ are each independently hydrogen; $C_1$~$C_4$ alkyl which is unsubstituted or substituted with one group selected from hydroxy, $C_1$~$C_3$ alkoxy, morpholinyl and imidazolyl; $C_3$~$C_6$ cycloalkyl; benzyl; or pyridinoyl; and the $X_1$—$X_2$—$X_3$ is

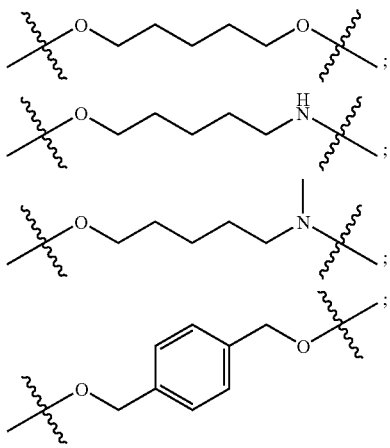

-continued

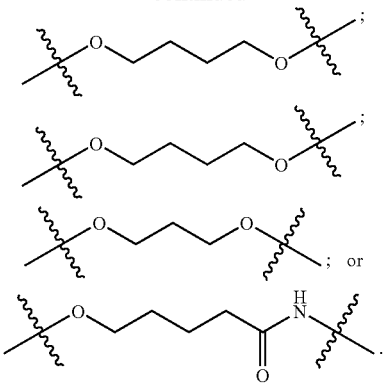

In one embodiment, the $R_1$ is methyl; ethyl; isopropyl; tert-butyl; pentyl; piperidin-1-ylmethyl; cyclohexyl; phenyl; pyridin-3-yl; guanidino; $NR_6R_7$; 1-propyl-piperidin-4-yl; 4-methyl-piperazin-1-yl; morpholin-4-yl; or piperidin-4-yl;

the $R_2$ is hydrogen; methyl, ethyl, propyl, isopropyl or butyl which is unsubstituted or substituted with $NR_8R_9$; cyclopentyl; benzyl; ehthenyl; carbonyl which is substituted with $NR_8R_9$; amino; dimethylamino; morpholin-4-yl; thiomorpholin-4-yl; 4-methylpiperazin-1-yl; or straight or branched $C_1$~$C_3$ alkyl which is substituted with methoxy, chloro, cyclopentyl, morpholin-4-yl, 2,6-dimethylmorpholin-4-yl, thiomorpholin-4-yl, 4-methylpiperazin-1-yl, piperidin-1-yl, imidazol-1-yl, or pyrrolidin-1-yl;

the $R_6$ and $R_7$ are each independently hydrogen; methyl; ethyl; propyl; $C_1$~$C_3$ alkyl which is substituted with one group selected from hydroxy, methoxy, pyridin-3-yl, pyridin-4-yl, morpholin-4-yl and piperidin-1-yl; benzyl; carbonyl which is substituted with one group selected from isopropyl, hydroxymethyl, pyridin-3-yl and pyridin-4-yl; or ethanesulfonyl; and the $R_8$ and $R_9$ are each independently hydrogen; methyl; ethyl; propyl; isopropyl; butyl; isobutyl; tert-butyl; $C_1$~$C_3$ alkyl which is substituted with one group selected from hydroxy, methoxy, isopropoxy, morpholin-4-yl and imidazol-1-yl; cyclopropyl; cyclohexyl; benzyl; 3-pyridinoyl or 4-pyridinoyl.

In one embodiment, the only one between the $R_6$ and the $R_7$ is hydrogen.

In one embodiment, the $R_6$ and $R_7$ are both hydrogen; or $C_1$~$C_6$ alkyl which is unsubstituted or substituted with one group selected from hydroxy, $C_1$~$C_6$ alkoxy and pyridinyl.

Preferably, the $R_6$ and $R_7$ are both hydrogen; methyl; methyl substituted with pyridinyl; ethyl; ethyl substituted with hydroxy or methoxy; or propyl.

In one embodiment, the $R_6$ is methyl; and
the $R_7$ is $C_1$~$C_6$ alkyl which is unsubstituted or substituted with one group selected from hydroxy, $C_1$~$C_6$ alkoxy, pyridinyl and morpholinyl; benzyl; or carbonyl which is substituted with $C_1$~$C_6$ alkyl.

Preferably, the $R_7$ is methyl which is substituted with pyridin-3-yl or pyridin-4-yl; ethyl which is unsubstituted or substituted with one group selected from hydroxy, methoxy and morpholin-4-yl; benzyl; carbonyl which is substituted with isopropyl.

In one embodiment, the $R_6$ is ethyl; and
the $R_7$ is $C_1$~$C_6$ alkyl which is unsubstituted or substituted with hydroxy or morpholinyl; or benzyl.

Preferably, the $R_7$ is ethyl which is substituted with hydroxy or morpholinyl; or benzyl.

In one embodiment, the only one between the $R_8$ and the $R_9$ is hydrogen.

In one embodiment, the $R_8$ and $R_9$ are both $C_1~C_6$ alkyl which is unsubstituted or substituted with hydroxy.

Preferably, the $R_8$ and $R_9$ are both ethyl, hydroxyethyl or propyl.

In one embodiment, the $R_8$ is $C_3~C_6$ cycloalkyl; and
the $R_9$ is carbonyl substituted with pyridinyl.

Preferably, the $R_8$ is cyclohexyl;
the $R_9$ is 3-pyridinoyl or 4-pyridinoyl.

In one embodiment, the $R_1$ is $C_1~C_6$ alkyl which is unsubstituted or substituted with pyridinyl; and
the $R_2$ is hydrogen; straight or branched $C_1~C_6$ alkyl which is unsubstituted or substituted with $NR_8R_9$; $C_3~C_6$ cycloalkyl; $C_2~C_6$ alkenyl; carbonyl which is substituted with $NR_8R_9$; amino; dimethylamino; morpholinyl; or straight or branched $C_1~C_6$ alkyl which is substituted with hydroxy, $C_1~C_6$ alkoxy, halogen, $C_3~C_6$ cycloalkyl,

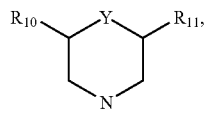

imidazolyl, or pyrrolidinyl.

In one embodiment, the $R_1$ is straight or branched $C_1~C_6$ alkyl which is substituted with

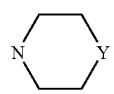

unsubstituted or substituted with hydroxyl; and
the $R_2$ is straight or branched $C_1~C_6$ alkyl which is substituted with hydroxy, $C_1~C_6$ alkoxy, halogen, $C_3~C_6$ cycloalkyl,

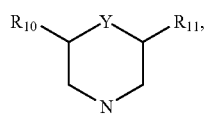

imidazolyl, or pyrrolidinyl.

In one embodiment, the $R_1$ is $C_3~C_6$ cycloalkyl; and
the $R_2$ is hydrogen; straight or branched $C_1~C_6$ alkyl which is unsubstituted or substituted with $NR_8R_9$; or straight or branched $C_1~C_6$ alkyl which is substituted with hydroxy, $C_1~C_6$ alkoxy, halogen, $C_3~C_6$ cycloalkyl,

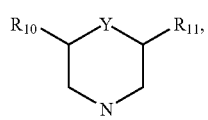

imidazolyl, or pyrrolidinyl.

In one embodiment, the $R_1$ is phenyl or benzyl; and
the $R_2$ is phenyl; benzyl; amino; or straight or branched $C_1~C_6$ alkyl which is substituted with hydroxy, $C_1~C_6$ alkoxy, halogen, $C_3~C_6$ cycloalkyl,

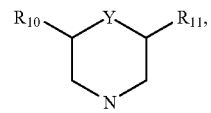

imidazolyl, or pyrrolidinyl.

In one embodiment, the $R_1$ is pyridinyl which is unsubstituted or substituted with $C_1~C_6$ alkyl; and
the $R_2$ is hydrogen; straight or branched $C_1~C_6$ alkyl which is unsubstituted or substituted with $NR_8R_9$; phenyl; benzyl; $C_2~C_6$ alkenyl; or straight or branched $C_1~C_6$ alkyl which is substituted with hydroxy, $C_1~C_6$ alkoxy, halogen, $C_3~C_6$ cycloalkyl,

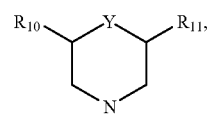

imidazolyl, or pyrrolidinyl.

In one embodiment, the $R_1$ is guanidino; and
the $R_2$ is straight or branched $C_1~C_6$ alkyl which is unsubstituted or substituted with $NR_8R_9$.

In one embodiment, the $R_1$ is $NR_6R_7$ or $CH_2NR_6R_7$; and
the $R_2$ is hydrogen; straight or branched $C_1~C_6$ alkyl which is unsubstituted or substituted with $NR_8R_9$; $C_3~C_6$ cycloalkyl; $C_2~C_6$ alkenyl; carbonyl which is substituted with $NR_8R_9$; or straight or branched $C_1~C_6$ alkyl which is substituted with hydroxy, $C_1~C_6$ alkoxy, halogen, $C_3~C_6$ cycloalkyl,

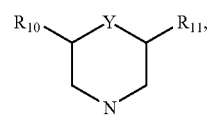

imidazolyl, or pyrrolidinyl.

In one embodiment, the $R_1$ is

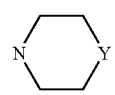

group which is substituted with straight or branched $C_1~C_6$ alkyl; and
the $R_2$ is straight or branched $C_1~C_6$ alkyl which is unsubstituted or substituted with $NR_8R_9$; $C_3~C_6$ cycloalkyl; morpholinyl; thiomorpholinyl; 4-methylpiperazinyl; or straight or branched $C_1~C_6$ alkyl which is substituted with hydroxy, $C_1~C_6$ alkoxy, halogen, $C_3~C_6$ cycloalkyl,

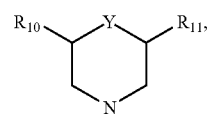

imidazolyl, or pyrrolidinyl.

Among the benzamidine derivatives of Formula 1 of the present invention, the preferred compounds are as follows:

1) N-hydroxy-4-{5-[4-(2-isopropyl-5-methyl-1,3-thiazol-4-yl)phenoxy]pentyloxy}-benzamidine,
2) 4-{5-[4-(2-isopropyl-5-methyl-1,3-thiazol-4-yl)phenoxy]pentyloxy}-benzamidine,
3) N-hydroxy-4-{5-[4-(2-methyl-1,3-thiazol-4-yl)phenoxy]pentyloxy}-benzamidine,
4) N-hydroxy-4-{5-[4-(2-ethyl-1,3-thiazol-4-yl)phenoxy]pentyloxy}-benzamidine,
5) N-hydroxy-4-{5-[4-(2-isopropyl-1,3-thiazol-4-yl)phenoxy]pentyloxy}-benzamidine,
6) N-hydroxy-4-{5-[4-(2-phenyl-1,3-thiazol-4-yl)phenoxy]pentyloxy}-benzamidine,
7) N-hydroxy-4-{5-[4-(2-pyridine-3-yl-1,3-thiazol-4-yl)phenoxy]pentyloxy}-benzamidine,
8) N-hydroxy-4-{5-[4-(2-cyclohexyl-1,3-thiazol-4-yl)phenoxy]pentyloxy}-benzamidine,
9) N-hydroxy-4-{5-[4-(2-pentyl-1,3-thiazol-4-yl)phenoxy]pentyloxy}-benzamidine,
10) N-hydroxy-4-{5-[4-(2,5-dimethyl-1,3-thiazol-4-yl)phenoxy]pentyloxy}-benzamidine,
11) N-hydroxy-4-{5-[4-(2-ethyl-5-methyl-1,3-thiazol-4-yl)phenoxy]pentyloxy}-benzamidine,
12) N-hydroxy-4-{5-[4-(5-methyl-2-phenyl-1,3-thiazol-4-yl)phenoxy]pentyloxy}-benzamidine,
13) N-hydroxy-4-{5-[4-(5-methyl-2-pyridin-3-yl -1,3-thiazol-4-yl)phenoxy]pentyloxy}-benzamidine,
14) N-hydroxy-4-{5-[4-(2-cyclohexyl-5-methyl-1,3-thiazol-4-yl)phenoxy]pentyloxy}-benzamidine,
15) N-hydroxy-4-{5-[4-(5-methyl-2-pentyl-1,3-thiazol-4-yl)phenoxy]pentyloxy}-benzamidine,
16) N-hydroxy-4-{5-[4-(2-t-butyl-5-methyl-1,3-thiazol-4-yl)phenoxy]pentyloxy}-benzamidine,
17) N-hydroxy-4-{5-[4-(5-ethyl-2-methyl-1,3-thiazol-4-yl)phenoxy]pentyloxy}-benzamidine,
18) N-hydroxy-4-{5-[4-(2,5-diethyl-1,3-thiazol-4-yl)phenoxy]pentyloxy}-benzamidine,
19) N-hydroxy-4-{5-[4-(5-ethyl-2-isopropyl-1,3-thiazol-4-yl)phenoxy]pentyloxy}-benzamidine,
20) N-hydroxy-4-{5-[4-(5-ethyl-2-phenyl-1,3-thiazol-4-yl)phenoxy]pentyloxy}-benzamidine,
21) N-hydroxy-4-{5-[4-(5-ethyl-2-pyridin-3-yl -1,3-thiazol-4-yl)phenoxy]pentyloxy}-benzamidine,
22) N-hydroxy-4-{5-[4-(2-cyclohexyl-5-ethyl-1,3-thiazol-4-yl)phenoxy]pentyloxy}-benzamidine,
23) N-hydroxy-4-{5-[4-(5-ethyl-2-pentyl-1,3-thiazol-4-yl)phenoxy]pentyloxy}-benzamidine,
24) N-hydroxy-4-{5-[4-(2-ethyl-5-isopropyl-1,3-thiazol-4-yl)phenoxy]pentyloxy}-benzamidine,
25) N-hydroxy-4-{5-[4-(2,5-diisopropyl-1,3-thiazol-4-yl)phenoxy]pentyloxy}-benzamidine,
26) N-hydroxy-4-{5-[4-(5-isopropyl-2-phenyl-1,3-thiazol-4-yl)phenoxy]pentyloxy}-benzamidine,
27) N-hydroxy-4-{5-[4-(5-isopropyl-2-pyridin-3-yl-1,3-thiazol-4-yl)phenoxy]pentyloxy}-benzamidine,
28) N-hydroxy-4-{5-[4-(5-isopropyl-2-pentyl-1,3-thiazol-4-yl)phenoxy]pentyloxy}-benzamidine,
29) N-hydroxy-4-{5-[4-(2-methyl-5-propyl-1,3-thiazol-4-yl)phenoxy]pentyloxy}-benzamidine,
30) N-hydroxy-4-{5-[4-(5-butyl-2-methyl-1,3-thiazol-4-yl)phenoxy]pentyloxy}-benzamidine,
31) N-hydroxy-4-{5-[4-(5-butyl-2-ethyl-1,3-thiazol-4-yl)phenoxy]pentyloxy}-benzamidine,
32) N-hydroxy-4-{5-[4-(5-butyl-2-isopropyl-1,3-thiazol-4-yl)phenoxy]pentyloxy}-benzamidine,
33) N-hydroxy-4-{5-[4-(5-butyl-2-phenyl-1,3-thiazol-4-yl)phenoxy]pentyloxy}-benzamidine,
34) N-hydroxy-4-{5-[4-(5-butyl-2-pyridin-3-yl-1,3-thiazol-4-yl)phenoxy]pentyloxy}-benzamidine,
35) N-hydroxy-4-{5-[4-(5-butyl-2-cyclohexyl-1,3-thiazol-4-yl)phenoxy]pentyloxy}-benzamidine,
36) N-hydroxy-4-{5-[4-(5-butyl-2-pentyl-1,3-thiazol-4-yl)phenoxy]pentyloxy}-benzamidine,
37) N-hydroxy-4-{5-[4-(5-butyl-2-t-butyl-1,3-thiazol-4-yl)phenoxy]pentyloxy}-benzamidine,
38) N-hydroxy-4-{5-[4-(5-benzyl-2-methyl-1,3-thiazol-4-yl)phenoxy]pentyloxy}-benzamidine,
39) N-hydroxy-4-{5-[4-(5-benzyl-2-isopropyl-1,3-thiazol-4-yl)phenoxy]pentyloxy}-benzamidine,
40) N-hydroxy-4-{5-[4-(5-benzyl-2-phenyl-1,3-thiazol-4-yl)phenoxy]pentyloxy}-benzamidine,
41) N-hydroxy-4-{5-[4-(5-benzyl-2-pyridin-3-yl-1,3-thiazol-4-yl)phenoxy]pentyloxy}-benzamidine,
42) N-hydroxy-4-{5-[4-(5-(2-chloro-ethyl)-2-methyl-1,3-thiazol-4-yl)phenoxy]pentyloxy}-benzamidine,
43) N-hydroxy-4-{5-[4-(5-cyclopentyl-2-methyl-1,3-thiazol-4-yl)phenoxy]pentyloxy}-benzamidine,
44) N-hydroxy-4-{5-[4-(5-isobutyl-2-methyl-1,3-thiazol-4-yl)phenoxy]pentyloxy}-benzamidine,
45) N-hydroxy-4-{5-[4-(5-cyclopentylmethyl-2-methyl -1,3-thiazol-4-yl)phenoxy]pentyloxy}-benzamidine,
46) N-hydroxy-4-{5-[4-(5-cyclopentylmethyl-2-ethyl-1,3-thiazol-4-yl)phenoxy]pentyloxy}-benzamidine,
47) N-hydroxy-4-{5-[4-(5-cyclopentylmethyl-2-isopropyl-1,3-thiazol-4-yl)phenoxy]pentyloxy}-benzamidine,
48) N-hydroxy-4-{5-[4-(5-cyclopentylmethyl-2-phenyl -1,3-thiazol-4-yl)phenoxy]pentyloxy}-benzamidine,
49) N-hydroxy-4-{5-[4-(5-cyclopentylmethyl-2-pyridin -3-yl-1,3-thiazol-4-yl)phenoxy]pentyloxy}-benzamidine,
50) N-hydroxy-4-{5-[4-(5-cyclopentylmethyl-2-cyclohexyl-1,3-thiazol-4-yl)phenoxy]pentyloxy}-benzamidine,
51) N-hydroxy-4-{5-[4-(5-cyclopentylmethyl-2-pentyl -1,3-thiazol-4-yl)phenoxy]pentyloxy}-benzamidine,
52) 4-{5-[4-(2-methyl-1,3-thiazol-4-yl)phenoxy]pentyloxy}-benzamidine,
53) 4-{5-[4-(2-isopropyl-1,3-thiazol-4-yl)phenoxy]pentyloxy}-benzamidine,
54) 4-{5-[4-(2,5-dimethyl-1,3-thiazol-4-yl)phenoxy]pentyloxy}-benzamidine,
55) 4-{5-[4-(5-ethyl-2-isopropyl-1,3-thiazol-4-yl)phenoxy]pentyloxy}-benzamidine,
56) 4-{5-[4-(5-ethyl-2-phenyl-1,3-thiazol-4-yl)phenoxy]pentyloxy}-benzamidine,
57) N-hydroxy-4-{5-[4-(2-amino-1,3-thiazol-4-yl)phenoxy]pentyloxy}-benzamidine,
58) N-hydroxy-4-{5-[4-(2-amino-5-methyl-1,3-thiazol-4-yl)phenoxy]pentyloxy}-benzamidine,
59) N-hydroxy-4-{5-[4-(2-guanidino-5-methyl-1,3-thiazol-4-yl)phenoxy]pentyloxy}-benzamidine,
60) N-hydroxy-4-{5-[4-(2-amino-5-ethyl-1,3-thiazol-4-yl)phenoxy]pentyloxy}-benzamidine,
61) N-hydroxy-4-{5-[4-(2-amino-5-isopropyl-1,3-thiazol-4-yl)phenoxy]pentyloxy}-benzamidine,
62) N-hydroxy-4-{5-[4-(2-guanidino-5-isopropyl-1,3-thiazol-4-yl)phenoxy]pentyloxy}-benzamidine,
63) N-hydroxy-4-{5-[4-(2-amino-5-butyl-1,3-thiazol-4-yl)phenoxy]pentyloxy}-benzamidine,
64) N-hydroxy-4-{5-[4-(5-butyl-2-guanidino-1,3-thiazol-4-yl)phenoxy]pentyloxy}-benzamidine,
65) N-hydroxy-4-{5-[4-(2-amino-5-benzyl-1,3-thiazol-4-yl)phenoxy]pentyloxy}-benzamidine,
66) N-hydroxy-4-{5-[4-(5-benzyl-2-guanidino-1,3-thiazol-4-yl)phenoxy]pentyloxy}-benzamidine, 67) N-hydroxy-4-{5-[4-(2-amino-5-cyclopentylmethyl-1,3-thiazol-4-yl)phenoxy]pentyloxy}-benzamidine,
68) N-hydroxy-4-{5-[4-(5-cyclopentylmethyl-2-(1-propyl-piperidin-4-yl)-1,3-thiazol-4-yl)phenoxy]pentyloxy}-benzamidine,
69) N-hydroxy-4-{5-[4-(2-(isobutyryl)amino-5-methyl-1,3-thiazol-4-yl)phenoxy]pentyloxy}-benzamidine,
70) N-hydroxy-4-{5-[4-(5-isopropyl-2-morpholinomethyl-1,3-thiazol-4-yl)phenoxy]pentyloxy}-benzamidine,
71) N-hydroxy-4-{5-[4-(2-aminomethyl-5-benzyl-1,3-thiazol-4-yl)phenoxy]pentyloxy}-benzamidine,
72) N-hydroxy-4-{5-[4-(5-methyl-2-(1-propyl-piperidin-4-yl)-1,3-thiazol-4-yl)phenoxy]pentyloxy}-benzamidine,
73) N-hydroxy-4-{5-[4-(5-isopropyl-2-aminomethyl-1,3-thiazol-4-yl)phenoxy]pentyloxy}-benzamidine,
74) N-hydroxy-4-{5-[4-(5-vinyl-2-methyl-1,3-thiazole-4-yl)phenoxy]pentyloxy}-benzamidine,
75) N-hydroxy-4-{5-[4-(5-hydroxymethyl-2-methyl-1,3-thiazol-4-yl)phenoxy]pentyloxy}-benzamidine,
76) N-hydroxy-4-{5-[4-(5-methoxymethyl-2-methyl-1,3-thiazol-4-yl)phenoxy]pentyloxy}-benzamidine,
77) N-hydroxy-4-{5-[4-(5-(2-chloroethyl)-2-amino-1,3-thiazol-4-yl)phenoxy]pentyloxy}-benzamidine,
78) N-hydroxy-4-{5-[4-(5-vinyl-2-amino-1,3-thiazol-4-yl)phenoxy]pentyloxy}-benzamidine,
79) N-hydroxy-4-{5-[4-(5-vinyl-2-(pyridin-3-yl)-1,3-thiazol-4-yl)phenoxy]pentyloxy}-benzamidine,
80) N-hydroxy-4-{5-[4-(5-(2-chloroethyl)-2-(pyridin-3-yl)-1,3-thiazol-4-yl)phenoxy]pentyloxy}-benzamidine,
81) N-hydroxy-4-{5-[4-(2-amino-5-cyclopentyl-1,3-thiazol-4-yl)phenoxy]pentyloxy}-benzamidine,
82) N-hydroxy-4-{5-[4-(5-ethyl-2-aminomethyl-1,3-thiazol-4-yl)phenoxy]pentyloxy}-benzamidine,
83) N-hydroxy-4-{5-[4-(5-isopropyl-2-(piperidin-3-yl)-1,3-thiazol-4-yl)phenoxy]pentyloxy}-benzamidine,
84) N-hydroxy-4-{5-[4-(2-ethylamino-1,3-thiazol-4-yl)phenoxy]pentyloxy}-benzamidine,
85) N-hydroxy-4-{5-[4-(2-ethanesulphonylamino-1,3-thiazol-4-yl)phenoxy]pentyloxy}-benzamidine,
86) N-hydroxy-4-{5-[4-(5-methyl-2-methylamino-1,3-thiazol-4-yl)phenoxy]pentyloxy}-benzamidine,
87) N-hydroxy-4-{5-[4-(2-ethylamino-5-methyl-1,3-thiazol-4-yl)phenoxy]pentyloxy}-benzamidine,
88) N-hydroxy-4-{5-[4-(5-methyl-2-propylamino-1,3-thiazol-4-yl)phenoxy]pentyloxy}-benzamidine,
89) N-hydroxy-4-{5-[4-(5-cyclopentylmethyl-2-(3-pyridylcarbonyl)amino-1,3-thiazol-4-yl)phenoxy]pentyloxy}-benzamidine,
90) N-hydroxy-4-{5-[4-(2-hydroxyacetylamino-5-methyl-1,3-thiazol-4-yl)phenoxy]pentyloxy}-benzamidine,
91) N-hydroxy-4-{5-[4-(5-methyl-2-(4-pyridylcarbonyl)amino-1,3-thiazol-4-yl)phenoxy]pentyloxy}-benzamidine,
92) N-hydroxy-4-{5-[4-(5-methyl-2-(3-pyridylcarbonyl)amino-1,3-thiazol-4-yl)phenoxy]pentyloxy}-benzamidine,
93) N-hydroxy-4-{5-[4-(2-ethanesulphonylamino-5-methyl-1,3-thiazol-4-yl)phenoxy]pentyloxy}-benzamidine,
94) N-hydroxy-4-{5-[4-(2-(2-methoxyethyl)amino-5-methyl-1,3-thiazol-4-yl)phenoxy]pentyloxy}-benzamidine,
95) N-hydroxy-4-{5-[4-(2-ethanesulphonylamino-5-ethyl-1,3-thiazol-4-yl)phenoxy]pentyloxy}-benzamidine,
96) N-hydroxy-4-{5-[4-(5-ethyl-2-methylamino-1,3-thiazol-4-yl)phenoxy]pentyloxy}-benzamidine,
97) N-hydroxy-4-{5-[4-(5-ethyl-2-ethylamino-1,3-thiazol-4-yl)phenoxy]pentyloxy}-benzamidine,
98) N-hydroxy-4-{5-[4-(5-ethyl-2-propylamino-1,3-thiazol-4-yl)phenoxy]pentyloxy}-benzamidine,
99) N-hydroxy-4-{5-[4-(5-ethyl-2-methoxyacetylamino-1,3-thiazol-4-yl)phenoxy]pentyloxy}-benzamidine,
100) N-hydroxy-4-{5-[4-(5-ethyl-2-(4-pyridylcarbonyl)amino-1,3-thiazol-4-yl)phenoxy]pentyloxy}-benzamidine,
101) N-hydroxy-4-{5-[4-(5-ethyl-2-(3-pyridylcarbonyl)amino-1,3-thiazol-4-yl)phenoxy]pentyloxy}-benzamidine,
102) N-hydroxy-4-{5-[4-(5-ethyl-2-(2-methoxyethyl)amino-1,3-thiazol-4-yl)phenoxy]pentyloxy}-benzamidine,
103) N-hydroxy-4-{5-[4-(5-isopropyl-2-methylamino-1,3-thiazol-4-yl)phenoxy]pentyloxy}-benzamidine,
104) N-hydroxy-4-{5-[4-(2-ethylamino-5-isopropyl-1,3-thiazol-4-yl)phenoxy]pentyloxy}-benzamidine,
105) N-hydroxy-4-{5-[4-(5-butyl-2-methylamino-1,3-thiazol-4-yl)phenoxy]pentyloxy}-benzamidine,
106) N-hydroxy-4-{5-[4-(5-butyl-2-ethylamino-1,3-thiazol-4-yl)phenoxy]pentyloxy}-benzamidine,
107) N-hydroxy-4-{5-[4-(5-benzyl-2-methylamino-1,3-thiazol-4-yl)phenoxy]pentyloxy}-benzamidine,
108) N-hydroxy-4-{5-[4-(5-benzyl-2-ethylamino-1,3-thiazol-4-yl)phenoxy]pentyloxy}-benzamidine,
109) N-hydroxy-4-{5-[4-(5-cyclopentylmethyl-2-methylamino-1,3-thiazol-4-yl)phenoxy]pentyloxy}-benzamidine,
110) N-hydroxy-4-{5-[4-(5-cyclopentylmethyl-2-ethylamino-1,3-thiazol-4-yl)phenoxy]pentyloxy}-benzamidine,
111) N-hydroxy-4-{5-[4-(5-cyclopentylmethyl-2-propylamino-1,3-thiazol-4-yl)phenoxy]pentyloxy}-benzamidine,
112) N-hydroxy-4-{5-[4-(5-cyclopentylmethyl-2-(4-pyridylcarbonyl)amino-1,3-thiazol-4-yl)phenoxy]pentyloxy}-benzamidine,
113) N-hydroxy-4-{5-[4-(5-cyclopentyl-2-propylamino-1,3-thiazol-4-yl)phenoxy]pentyloxy}-benzamidine,
114) N-hydroxy-4-{5-[4-(5-isopropyl-2-[(pyridin-3-ylmethyl)amino]-1,3-thiazol-4-yl)phenoxy]pentyloxy}-benzamidine,
115) N-hydroxy-4-{5-[4-(5-(2-chloroethyl)-2-methylamino-1,3-thiazol-4-yl)phenoxy]pentyloxy}-benzamidine,
116) N-hydroxy-4-{5-[4-(2-methylamino-1,3-thiazol-4-yl)phenoxy]pentyloxy}-benzamidine,
117) N-hydroxy-4-{5-[4-(5-ethyl-2-(pyridin-3-ylmethyl)amino-1,3-thiazol-4-yl)phenoxy]pentyloxy}-benzamidine,
118) N-hydroxy-4-{5-[4-(2-(ethanesulphonyl-methylamino)-1,3-thiazol-4-yl)phenoxy]pentyloxy}-benzamidine,
119) N-hydroxy-4-[5-(4-{2-[methyl-(2-morpholinoethyl)amino]-1,3-thiazol-4-yl}phenoxy)pentyloxy]-benzamidine,
120) N-hydroxy-4-[5-(4-{2-[(2-hydroxyethyl)-methyl-amino]-5-methyl-1,3-thiazol-4-yl}phenoxy)pentyloxy]-benzamidine,
121) N-hydroxy-4-[5-(4-{2-[ethyl-(2-hydroxyethyl)-amino]-5-methyl-1,3-thiazol-4-yl}phenoxy)pentyloxy]-benzamidine,
122) N-hydroxy-4-[5-(4-{2-[bis-(2-methoxyethyl)-amino]-5-methyl-1,3-thiazol-4-yl}phenoxy)pentyloxy]-benzamidine,
123) N-hydroxy-4-[5-(4-{5-methyl-2-[methyl-(2-morpholinoethyl)-amino]-1,3-thiazol-4-yl}phenoxy)pentyloxy]-benzamidine,
124) N-hydroxy-4-[5-(4-{2-[ethyl-1-(2-morpholinoethyl)-amino]-5-methyl-1,3-thiazol-4-yl}phenoxy)pentyloxy]-benzamidine,
125) N-hydroxy-4-{5-(4-[2-(benzyl-methyl-amino)-5-methyl-1,3-thiazol-4-yl]phenoxy)pentyloxy}-benzamidine,
126) N-hydroxy-4-[5-{4-[5-methyl-2-(methyl-pyridin-3-yl-methyl-amino)-1,3-thiazol-4-yl]phenoxy}pentyloxy]-benzamidine,
127) N-hydroxy-4-[5-{4-[2-(benzyl-ethyl-amino)-5-methyl-1,3-thiazol-4-yl]phenoxy}pentyloxy]-benzamidine, 128) N-hydroxy-4-[5-(4-{2-[bis-(2-hydroxyethyl)-amino]-5-methyl-1,3-thiazol-4-yl}phenoxy)pentyloxy]-benzamidine,
129) N-hydroxy-4-[5-(4-{5-ethyl-2-[(2-hydroxyethyl)-methyl-amino]-1,3-thiazol-4-yl}phenoxy)pentyloxy]-benzamidine,
130) N-hydroxy-4-[5-(4-{5-ethyl-2-[ethyl-(2-hydroxyethyl)-amino]-1,3-thiazol-4-yl}phenoxy)pentyloxy]-benzamidine,
131) N-hydroxy-4-[5-(4-{5-ethyl-2-[methyl-(2-morpholinoethyl)-amino]-1,3-thiazol-4-yl}phenoxy)pentyloxy]-benzamidine,
132) N-hydroxy-4-[5-(4-{5-ethyl-2-[ethyl-(2-morpholinoethyl)-amino]-1,3-thiazol-4-yl}phenoxy)pentyloxy]-benzamidine,
133) N-hydroxy-4-[5-{4-[2-(benzyl-methyl-amino)-5-ethyl-1,3-thiazol-4-yl]phenoxy}pentyloxy]-benzamidine,
134) N-hydroxy-4-[5-(4-{5-ethyl-2-[methyl-(pyridin-3-ylmethyl)amino]-1,3-thiazol-4-yl}phenoxy)pentyloxy]-benzamidine,
135) N-hydroxy-4-(5-{4-[2-(benzyl-ethyl-amino)-5-ethyl-1,3-thiazol-4-yl]phenoxy}pentyloxy)-benzamidine,
136) N-hydroxy-4-{5-(4-[5-ethyl-2-(ethyl-[pyridin-3-ylmethyl]amino)-1,3-thiazol-4-yl]phenoxy)pentyloxy}-benzamidine,
137) N-hydroxy-4-[5-(4-{2-[bis-(pyridin-3-ylmethyl)amino]-5-ethyl-1,3-thiazol-4-yl}phenoxy)pentyloxy]-benzamidine,
138) N-hydroxy-4-{5-[4-(2-dipropylamino-5-ethyl-1,3-thiazol-4-yl)phenoxy]pentyloxy}-benzamidine,
139) N-hydroxy-4-[5-(4-{2-[bis-(2-hydroxyethyl)amino]-5-ethyl-1,3-thiazol-4-yl}phenoxy)pentyloxy]-benzamidine,
140) N-hydroxy-4-[5-(4-{2-[(2-hydroxyethyl)-methyl-amino]-5-isopropyl-1,3-thiazol-4-yl}phenoxy)pentyloxy]-benzamidine,
141) N-hydroxy-4-[5-(4-{5-isopropyl-2-[methyl-(pyridin-3-ylmethyl)amino]-1,3-thiazol-4-yl}phenoxy)pentyloxy]-benzamidine,
142) N-hydroxy-4-(5-{4-[2-(ethanesulphonyl-methyl-amino)-5-isopropyl-1,3-thiazol-4-yl]phenoxy}pentyloxy)-benzamidine,
143) N-hydroxy-4-[5-(4-{5-butyl-2-[(2-hydroxyethyl)-methyl-amino]-1,3-thiazol-4-yl}phenoxy)pentyloxy]-benzamidine,
144) N-hydroxy-4-[5-(4-{5-butyl-2-[methyl-(2-morpholinoethyl)amino]-1,3-thiazol-4-yl}phenoxy)pentyloxy]-benzamidine,
145) N-hydroxy-4-[5-(4-{5-butyl-2-[methyl-(pyridin-3-ylmethyl)amino]-1,3-thiazol-4-yl}phenoxy)pentyloxy]-benzamidine,
146) N-hydroxy-4-{5-[4-(5-butyl-2-dipropylamino-1,3-thiazol-4-yl)phenoxy]pentyloxy}-benzamidine,
147) N-hydroxy-4-[5-(4-{5-cyclopentylmethyl-2-[methyl-(pyridin-3-ylmethyl)amino]-1,3-thiazol-4-yl}phenoxy)pentyloxy]-benzamidine,
148) N-hydroxy-4-[5-(4-{5-cyclopentylmethyl-2-[methyl-(2-morpholinoethyl)amino]-1,3-thiazol-4-yl}phenoxy)pentyloxy]-benzamidine,
149) N-hydroxy-4-{5-[4-(5-cyclopentylmethyl-2-dipropylamino-1,3-thiazol-4-yl)phenoxy]pentyloxy}-benzamidine,
150) N-hydroxy-4-{5-[4-(5-butyl-2-diethylamino-1,3-thiazol-4-yl)phenoxy]pentyloxy}-benzamidine,
151) N-hydroxy-4-{5-[4-(5-butyl-2-ethylmethylamino-1,3-thiazol-4-yl)phenoxy]pentyloxy}-benzamidine,
152) N-hydroxy-4-{5-[4-(5-butyl-2-dimethylamino-1,3-thiazol-4-yl)phenoxy]pentyloxy}-benzamidine,
153) N-hydroxy-4-[5-(4-{5-cyclopentyl-2-[methyl-(2-morpholinoethyl)amino]-1,3-thiazol-4-yl}phenoxy)pentyloxy]-benzamidine,
154) N-hydroxy-4-[5-(4-{5-isobutyl-2-[methyl-(2-morpholinoethyl)amino]-1,3-thiazol-4-yl}phenoxy)pentyloxy]-benzamidine,
155) N-hydroxy-4-(5-{4-[5-(2-chloroehtyl)-2-dimethylamino-1,3-thiazol-4-yl]phenoxy}pentyloxy)-benzamidine,
156) N-hydroxy-4-{5-[4-(5-cyclopentyl-2-diethylamino-1,3-thiazol-4-yl)phenoxy]pentyloxy}-benzamidine,
157) N-hydroxy-4-{5-[4-(5-isopropyl-2-dipropylamino-1,3-thiazol-4-yl)phenoxy]pentyloxy}-benzamidine,
158) N-hydroxy-4-{5-[4-(5-ethyl-2-diethylamino-1,3-thiazol-4-yl)phenoxy]pentyloxy}-benzamidine,
159) N-hydroxy-4-[5-(4-{5-isopropyl-2-[methyl-(2-morpholinoethyl)amino]-1,3-thiazol-4-yl}phenoxy)pentyloxy]-benzamidine,
160) N-hydroxy-4-{5-[4-(5-cyclopentylmethyl-2-diethylamino-1,3-thiazol-4-yl)phenoxy]pentyloxy}-benzamidine,
161) N-hydroxy-4-{5-[4-(5-isopropyl-2-dimethylamino-1,3-thiazol-4-yl)phenoxy]pentyloxy}-benzamidine,
162) N-hydroxy-4-{5-[4-(5-isopropyl-2-diethylamino-1,3-thiazol-4-yl)phenoxy]pentyloxy}-benzamidine,
163) N-hydroxy-4-{5-[4-(5-cyclopentylmethyl-2-dimethylamino-1,3-thiazol-4-yl)phenoxy]pentyloxy}-benzamidine,
164) N-hydroxy-4-{5-[4-(5-methyl-2-piperidino-1,3-thiazol-4-yl)phenoxy]pentyloxy}-benzamidine,
165) N-hydroxy-4-{5-[4-(5-methyl-2-morpholino-1,3-thiazol-4-yl)phenoxy]pentyloxy}-benzamidine,
166) N-hydroxy-4-{5-[4-(5-ethyl-2-piperidino-1,3-thiazol-4-yl)phenoxy]pentyloxy}-benzamidine,
167) N-hydroxy-4-{5-[4-(5-cyclopentylmethyl-2-piperidino-1,3-thiazol-4-yl)phenoxy]pentyloxy}-benzamidine,
168) N-hydroxy-4-{5-[4-(5-cyclopentylmethyl-2-morpholino-1,3-thiazol-4-yl)phenoxy]pentyloxy}-benzamidine,
169) N-hydroxy-4-{5-[4-(5-isopropyl-2-morpholino-1,3-thiazol-4-yl)phenoxy]pentyloxy}-benzamidine,
170) N-hydroxy-4-{5-(4-[5-cyclopentylmethyl-2-(4-methylpiperazino)-1,3-thiazol-4-yl]phenoxy)pentyloxy}-benzamidine,
171) N-hydroxy-4-{5-[4-(5-vinyl-2-morpholin-4-yl-1,3-thiazol-4-yl)phenoxy]pentyloxy}-benzamidine,
172) N-hydroxy-4-{5-[4-(5-cyclopentyl-2-morpholin-4-yl-1,3-thiazol-4-yl)phenoxy]pentyloxy}-benzamidine,
173) N-hydroxy-4-{5-[4-(5-isobutyl-2-morpholin-4-yl-1,3-thiazol-4-yl)phenoxy]pentyloxy}-benzamidine,
174) N-hydroxy-4-{5-(4-[5-ethyl-2-(4-methylpiperazino)-1,3-thiazol-4-yl]phenoxy)pentyloxy}-benzamidine,
175) N-hydroxy-4-{5-(4-(2-morpholin-4-yl-1,3-thiazol-4-yl)phenoxy]pentyloxy}-benzamidine,
176) N-hydroxy-4-{5-(4-[5-isopropyl-2-(4-methylpiperazino)-1,3-thiazol-4-yl]phenoxy)pentyloxy}-benzamidine,
177) N-hydroxy-4-{5-[4-(5-isopropyl-2-methyl-1,3-thiazol-4-yl)-phenoxy]-pentylamino}-benzamidine,
178) N-hydroxy-4-(2-{2-[4-(5-isopropyl-2-methyl-1,3-thiazol-4-yl)-phenoxy]-ethoxy}-ethoxy)-benzamidine,
179) N-hydroxy-4-{3-hydroxy-5-[4-(5-isopropyl-2-methyl-1,3-thiazol-4-yl)-phenoxy]-3-methyl-pentyloxy}-benzamidine,
180) N-hydroxy-4-(2-{2-[4-(5-isopropyl-2-methyl-1,3-thiazol-4-yl)-phenoxy]-1-methyl-ethylamino}-ethoxy)-benzamidine,
181) N-hydroxy-4-[3-(4-{3-[4-(5-isopropyl-2-methyl-1,3-thiazol-4-yl)-phenoxy]-propyl}-piperazine-1-yl)-propoxy]-benzamidine, 182) N-hydroxy-4-{5-[4-(5-isopropyl-2-methyl-1,3-thiazol-4-yl)-phenoxy]-pentanoyl-amino}-benzamidine,
183) N-hydroxy-4-({5-[4-(5-isopropyl-2-methyl-1,3-thiazol-4-yl)-phenoxy]-pentyl}-methyl-amino)-benzamidine,
184) N-hydroxy-4-{4-[4-(5-isopropyl-2-methyl-1,3-thiazol-4-yl)-phenoxy]-but-2-enyloxy}-benzamidine,
185) N-hydroxy-4-{4-[4-(5-isopropyl-2-methyl-1,3-thiazol-4-yl)-phenoxymethyl]-benzyloxy}-benzamidine,
186) N-hydroxy-4-(2-{2-[4-(5-isopropyl-2-methyl-1,3-thiazol-4-yl)phenoxy]-ethylamino}-ethoxy)-benzamidine,
187) N-hydroxy-2-fluoro-4-{5-[4-(5-isopropyl-2-methyl-1,3-thiazol-4-yl)-phenoxy]-pentyloxy}-benzamidine,
188) 2,N-dihydroxy-4-{5-[4-(5-isopropyl-2-methyl-1,3-thiazol-4-yl)-phenoxy]-pentyloxy}-benzamidine,
189) N-hydroxy-4-{5-[4-(5-isopropyl-2-methyl-1,3-thiazol-4-yl)-phenoxy]-pentyloxy}-3-methoxy-benzamidine,
190) N-hydroxy-2-cyclohexylamino-4-{5-[4-(5-isopropyl-2-methyl-1,3-thiazol-4-yl)-phenoxy]-pentyloxy}-benzamidine,
191) N-hydroxy-4-{5-[3-fluoro-4-(5-isopropyl-2-methyl-1,3-thiazol-4-yl)-phenoxy]-pentyloxy}-benzamidine,
192) N-hydroxy-2-fluoro-4-{5-[3-fluoro-4-(5-isopropyl-2-methyl-1,3-thiazol-4-yl)-phenoxy]-pentyloxy}-benzamidine,
193) N-hydroxy-4-{3-[4-(5-isopropyl-2-methyl-1,3-thiazol-4-yl)phenoxy]propoxy}-benzamidine,
194) N-hydroxy-4-{4-[4-(5-isopropyl-2-methyl-1,3-thiazol-4-yl)phenoxy]butoxy}-benzamidine,
195) N-hydroxy-3-{5-[4-(5-isopropyl-2-methyl-thiazol-4-yl)-phenoxy]-pentylamino}-benzamidine,
196) N-hydroxy-4-{4-[4-(2-cyclohexyl-5-ethyl-thiazol-4-yl)-phenoxy]-butoxy}-benzamidine,
197) N-hydroxy-4-[5-(4-{5-ethyl-2-[(2-hydroxyethyl)-methyl-amino]-thiazol-4-yl}phenoxy)propoxy]-benzamidine,
198) N-hydroxy-4-[5-(4-{5-ethyl-2-[(2-hydroxyethyl)-methyl-amino]-thiazol-4-yl}phenoxy)butoxy]-benzamidine,
199) N-hydroxy-4-[5-(4-{5-ethyl-2-[methyl-(pyridin-3-ylmethyl)amino]-thiazol-4-yl}phenoxy)propoxy]-benzamidine,
200) N-hydroxy-4-[5-(4-{5-ethyl-2-[methyl-(pyridin-3-ylmethyl)amino]-thiazol-4-yl}phenoxy)butoxy]-benzamidine,
201) N-hydroxy-4-{4-[4-(5-cyclopentylmethyl-2-isopropyl-thiazol-4-yl)-phenoxymethyl]-benzyloxy}-benzamidine,
202) N-hydroxy-4-{4-[4-(5-butyl-2-isopropyl-thiazol-4-yl)-phenoxymethyl]-benzyloxy}-benzamidine,
203) N-hydroxy-4-{4-[4-(5-cyclopentylmethyl-2-amino-thiazol-4-yl)-phenoxymethyl]-benzyloxy}-benzamidine,
204) N-hydroxy-4-{4-[4-(5-cyclopentylmethyl-2-amino-thiazol-4-yl)-phenoxymethyl]-benzyloxy}-2-fluoro-benzamidine,
205) N-hydroxy-4-{4-[4-(2-methylamino-thiazol-4-yl)-phenoxymethyl]-benzyloxy}-benzamidine,
206) N-hydroxy-4-{6-[4-(5-isopropyl-2-methyl-thiazol-4-yl)-phenoxymethyl]-pyridine-2-yl-methoxy}-benzamidine,
207) N-hydroxy-2-fluoro-4-{5-[4-(5-isopropyl-2-methyl-thiazol-4-yl)-phenoxy]-butoxy}-benzamidine,
208) N-hydroxy-4-{2-[4-(5-isopropyl-2-methyl-thiazol-4-yl)-phenoxymethyl]-benzyloxy}-benzamidine,
209) N-hydroxy-4-{3-[4-(5-isopropyl-2-methyl-thiazol-4-yl)-phenoxymethyl]-benzyloxy}-benzamidine,
210) N-hydroxy-4-{4-[4-(5-cyclopentylmethyl-2-cyclohexyl-thiazol-4-yl)-phenoxymethyl]-benzyloxy}-benzamidine,
211) N-hydroxy-4-{6-[4-(5-isopropyl-2-methyl-thiazol-4-yl)phenoxy]-hexyloxy}-benzamidine,
212) N-hydroxy-4-{5-[2-ethyl-5-hydroxy-4-(2-methyl-thiazol-4-yl)phenoxy]-pentyloxy}-benzamidine,
213) N-hydroxy-4-{5-[2-ethyl-4-(2-methyl-thiazol-4-yl)-5-propoxy-phenoxy]-pentyloxy}-benzamidine,
214) N-hydroxy-4-(5-{4-[5-(2-isobutylamino-ethyl)-2-methyl-thiazol-4-yl]-phenoxy}-pentyloxy)-benzamidine,
215) 4-(5-{4-[5-(2-isobutylaminoethyl)-2-methyl-thiazol-4-yl]-phenoxy}-pentyloxy)-benzamidine,
216) N-hydroxy-4-(5-{4-[2-methyl-5-(2-piperidin-1-yl-ethyl)-thiazol-4-yl]-phenoxy}-pentyloxy)-benzamidine,
217) N-hydroxy-4-[5-(4-{2-methyl-5-[2-(2-morpholin-4-yl-ethylamino)-ethyl]-thiazol-4-yl}-phenoxy)--pentyloxy]-benzamidine,
218) N-hydroxy-4-[5-(4-{5-[2-(3-imidazol-1-yl-propylamino)-ethyl]-2-methyl-thiazol-4-yl}-phenoxy)-pentyloxy]-benzamidine,
219) N-hydroxy-4-(5-{4-[5-(2-isopropylamino-ethyl)-2-methyl-thiazol-4-yl]-phenoxy}-pentyloxy)-benzamidine,
220) N-hydroxy-4-[5-(4-{5-[2-(3-isopropoxy-propylamino)-ethyl]-2-methyl-thiazol-4-yl}-phenoxy)-pentyloxy]-benzamidine,
221) N-hydroxy-4-(5-{4-[5-(2-butylamino-ethyl)-2-methyl-thiazol-4-yl]-phenoxy}-pentyloxy)-benzamidine,
222) N-hydroxy-4-(5-{4-[5-(2-imidazol-1-yl-ethyl)-2-methyl-thiazol-4-yl]-phenoxy}-pentyloxy)-benzamidine,
223) N-hydroxy-4-(5-{4-[5-(2-cyclohexylamino-ethyl)-2-methyl-thiazol-4-yl]-phenoxy}-pentyloxy)-benzamidine,
224) N-hydroxy-4-(5-{4-[5-(2-diethylamino-ethyl)-2-methyl-thiazol-4-yl]-phenoxy}-pentyloxy)-benzamidine,
225) N-hydroxy-4-{5-[4-(5-{2-[bis-(2-hydroxy-ethyl)-amino]-ethyl}-2-methyl-thiazol-4-yl)-phenoxy]-pentyloxy}-benzamidine,
226) N-hydroxy-4-(5-{4-[5-(2-diisopropylamino-ethyl)-2-methyl-thiazol-4-yl]-phenoxy}-pentyloxy)-benzamidine,
227) N-hydroxy-4-[5-(4-{5-[2-(2,6-dimethyl-morpholin-4-yl)-ethyl]-2-methyl-thiazol-4-yl}-phenoxy)-pentyloxy]-benzamidine,
228) N-hydroxy-4-(5-{4-[2-methyl-5-(2-thiomorpholin-4-yl-ethyl)-thiazol-4-yl]-phenoxy}-pentyloxy)-benzamidine,
229) N-hydroxy-4-(5-{4-[2-amino-5-(2-morpholin-4-yl-ethyl)-thiazol-4-yl]-phenoxy}-pentyloxy)-benzamidine,
230) N-hydroxy-4-[5-(4-{5-[2-(2-dimethylamino-ethylamino)-ethyl]-2-methyl-thiazol-4-yl}-phenoxy)-pentyloxy]-benzamidine,
231) N-hydroxy-4-(5-{4-[2-methyl-5-(2-morpholin-4-yl-ethyl)-thiazol-4-yl]-phenoxy}-pentyloxy)-benzamidine,
232) N-hydroxy-4-[5-(4-{2-methyl-5-[2-(4-methyl-piperazin-1-yl)-ethyl]-thiazol-4-yl}-phenoxy)-pentyloxy]-benzamidine,
233) N-hydroxy-4-{5-[4-(5-{2-[bis-(2-methoxy-ethyl)-amino]-ethyl}-2-methyl-thiazol-4-yl)-phenoxy]-pentyloxy}-benzamidine,
234) N-hydroxy-4-(5-{4-[5-(2-tert-butylamino-ethyl)-2-methyl-thiazol-4-yl]-phenoxy}-pentyloxy)-benzamidine,
235) N-hydroxy-4-(5-{4-[5-(2-isobutylamino-ethyl)-2-methyl-thiazol-4-yl]-phenoxy}-pentyloxy)-benzamidine,
236) N-hydroxy-4-(5-{4-[5-(2-morpholin-4-yl-ethyl)-2-pyridine-3-yl-thiazol-4-yl]-phenoxy}-pentyloxy)-benzamidine,
237) N-hydroxy-4-[5-(4-{5-[2-(4-methyl-piperazin-1-yl)-ethyl]-2-pyridin-3-yl-thiazol-4-yl}-phenoxy)-pentyloxy]-benzamidine, 238) N-hydroxy-4-(5-{4-[2-pyridin-3-yl-5-(2-thiomorpholin-4-yl-ethyl)-thiazol-4-yl]-phenoxy}-pentyloxy)-benzamidine,
239) N-hydroxy-4-(5-{4-[5-(2-imidazol-1-yl-ethyl)-2-pyridin-3-yl-thiazol-4-yl]-phenoxy}-pentyloxy)-benzamidine,
240) N-hydroxy-4-(5-{4-[2-isopropyl-5-(2-morpholin-4-yl-ethyl)-thiazol-4-yl]-phenoxy}-pentyloxy)-benzamidine,
241) N-hydroxy-4-[5-(4-{2-isopropyl-5-[2-(4-methyl-piperazin-1-yl)-ethyl]-thiazol-4-yl}-phenoxy)-pentyloxy]-benzamidine,
242) N-hydroxy-4-(5-{4-[5-(2-imidazol-1-yl-ethyl)-2-isopropyl-thiazol-4-yl]-phenoxy}-pentyloxy)-benzamidine,
243) N-hydroxy-4-[5-(4-{2-isopropyl-5-[2-(2-morpholin-4-yl-ethylamino)-ethyl]-thiazol-4-yl}-phenoxy)-pentyloxy]-benzamidine,
244) N-hydroxy-4-[5-(4-{5-[2-(3-imidazol-1-yl-propylamino)-ethyl]-2-isopropyl-thiazol-4-yl}-phenoxy)-pentyloxy]-benzamidine,
245) N-hydroxy-4-(5-{4-[2-isopropyl-5-(2-thiomorpholin-4-yl-ethyl)-thiazol-4-yl]-phenoxy}-pentyloxy)-benzamidine,
246) N-hydroxy-4-(5-{4-[2-cyclohexyl-5-(2-morpholin-4-yl-ethyl)-thiazol-4-yl]-phenoxy}-pentyloxy)-benzamidine,
247) N-hydroxy-4-[5-(4-{2-cyclohexyl-5-[2-(4-methyl-piperazin-1-yl)-ethyl]-thiazol-4-yl}-phenoxy)-pentyloxy]-benzamidine,
248) N-hydroxy-4-[5-(4-{2-cyclohexyl-5-[2-(2-morpholin-4-yl-ethylamino)-ethyl]-thiazol-4-yl}-phenoxy)-pentyloxy]-benzamidine,
249) N-hydroxy-4-(5-{4-[2-cyclohexyl-5-(2-thiomorpholin-4-yl-ethyl)-thiazol-4-yl]-phenoxy}-pentyloxy)-benzamidine,
250) N-hydroxy-4-(5-{4-[2-cyclohexyl-5-(2-dimethylamino-ethyl)-thiazol-4-yl]-phenoxy}-pentyloxy)-benzamidine,
251) N-hydroxy-4-(5-{4-[2-cyclohexyl-5-(2-dipropylamino-ethyl)-thiazol-4-yl]-phenoxy}-pentyloxy)-benzamidine,
252) N-hydroxy-4-(5-{4-[2-cyclohexyl-5-(2-cyclopropylamino-ethyl)-thiazol-4-yl]-phenoxy}-pentyloxy)-benzamidine,
253) N-hydroxy-4-[5-(4-{2-amino-5-[2-(2-morpholin-4-yl-ethylamino)-ethyl]-thiazol-4-yl}-phenoxy)-pentyloxy]-benzamidine,
254) N-hydroxy-4-(5-{4-[5-(2-morpholin-4-yl-ethyl)-2-phenyl-thiazol-4-yl]-phenoxy}-pentyloxy)-benzamidine,
255) N-hydroxy-4-(5-{4-[2-ethyl-5-(2-morpholin-4-yl-ethyl)-thiazol-4-yl]-phenoxy}-pentyloxy)-benzamidine,
256) N-hydroxy-4-(5-{4-[2-ethyl-5-(2-thiomorpholin-4-yl-ethyl)-thiazol-4-yl]-phenoxy}-pentyloxy)-benzamidine,
257) N-hydroxy-4-(4-{4-[2-methyl-5-(2-morpholin-4-yl-ethyl)-thiazol-4-yl]-phenoxy}-butoxy)-benzamidine,
258) 4-(5-{4-[2-cyclohexyl-5-(2-morpholin-4-yl-ethyl)-thiazol-4-yl]-phenoxy}-pentyloxy)-benzamidine,
259) 4-(5-{4-[2-methyl-5-(2-morpholin-4-yl-ethyl)-thiazol-4-yl]-phenoxy}-pentyloxy)-benzamidine,
260) N-hydroxy-4-(5-{4-[2-methylamino-5-(2-morpholin-4-yl-ethyl)-thiazol-4-yl]-phenoxy}-pentyloxy)-benzamidine,
261) N-hydroxy-4-[5-(4-{2-methylamino-5-[2-(4-methyl-piperazin-1-yl)-ethyl]-thiazol-4-yl}-phenoxy)-pentyloxy]-benzamidine,
262) N-hydroxy-4-(5-{4-[2-methylamino-5-(2-thiomorpholin-4-yl-ethyl)-thiazol-4-yl]-phenoxy}-pentyloxy)-benzamidine,
263) N-hydroxy-4-[5-(4-{2-methylamino-5-[2-(2-morpholin-4-yl-ethylamino)-ethyl]-thiazol-4-yl}-phenoxy)-pentyloxy]-benzamidine,
264) N-hydroxy-4-[5-(4-{5-[2-(3-imidazol-1-yl-propylamino)-ethyl]-2-methylamino-thiazol-4-yl}-phenoxy)-pentyloxy]-benzamidine,
265) 4-(5-{4-[2-methylamino-5-(2-morpholin-4-yl-ethyl)-thiazol-4-yl]-phenoxy}-pentyloxy)-benzamidine,
266) N-hydroxy-4-(5-{4-[2-dimethylamino-5-(2-morpholin-4-yl-ethyl)-thiazol-4-yl]-phenoxy}-pentyloxy)-benzamidine,
267) N-hydroxy-4-(5-{4-[2-dimethylamino-5-(2-thiomorpholin-4-yl-ethyl)-thiazol-4-yl]-phenoxy}-pentyloxy)-benzamidine,
268) N-hydroxy-4-(5-{4-[2-(isobutyryl-methyl-amino)-5-(2-morpholin-4-yl-ethyl)-thiazol-4-yl]-phenoxy}-pentyloxy)-benzamidine,
269) N-hydroxy-4-(5-{4-[2-[benzyl-(2-morpholin-4-yl-ethyl)-amino]-5-(2-morpholin-4-yl-ethyl)-thiazol-4-yl]-phenoxy}-pentyloxy)-benzamidine,
270) N-hydroxy-4-(5-{4-[2-diethylamino-5-(2-morpholin-4-yl-ethyl)-thiazol-4-yl]-phenoxy}-pentyloxy)-benzamidine,
271) N-hydroxy-4-(5-{4-[2-[bis-(2-methoxy-ethyl)-amino]-5-(2-morpholin-4-yl-ethyl)-thiazol-4-yl]-phenoxy}-pentyloxy)-benzamidine,
272) N-hydroxy-4-(5-{4-[2-morpholin-4-yl-5-(2-morpholine-4-yl-ethyl)-thiazol-4-yl]-phenoxy}-pentyloxy)-benzamidine,
273) N-hydroxy-4-(5-{4-[2-morpholin-4-yl-5-(2-thiomorpholin-4-yl-ethyl)-thiazol-4-yl]-phenoxy}-pentyloxy)-benzamidine,
274) N-hydroxy-4-[5-(4-{5-[2-(4-methyl-piperazin-1-yl)-ethyl]-2-morpholin-4-yl-thiazol-4-yl}-phenoxy)-pentyloxy]-benzamidine,
275) N-hydroxy-4-[5-(4-{2-morpholin-4-yl-5-[2-(2-morpholin-4-yl-ethylamino)-ethyl]-thiazole-4-yl}-phenoxy)-pentyloxy]-benzamidine,
276) N-hydroxy-4-(5-{4-[5-(2-morpholin-4-yl-ethyl)-2-piperidin-1-yl-methyl-thiazol-4-yl]-phenoxy}-pentyloxy)-benzamidine,
277) 4-(5-{4-[2-morpholin-4-yl-5-(2-morpholin-4-yl-ethyl)-thiazol-4-yl]-phenoxy}-pentyloxy)-benzamidine,
278) N-hydroxy-4-(5-{4-[5-(2-isobutyrylamino-ethyl) -2-methyl-thiazol-4-yl]-phenoxy}-pentyloxy)-benzamidine,
279) N-hydroxy-4-{5-[4-(5-{2-[isobutyl -(pyridin-3-carbonyl)-amino]-ethyl}-2-methyl-thiazol-4-yl)-phenoxy]-pentyloxy}-benzamidine,
280) N-hydroxy-4-{5-[4-(5-{2-[cyclopropyl-(pyridin-4-carbonyl)-amino]-ethyl}-2-isopropyl-thiazol-4-yl)-phenoxy]-pentyloxy}-benzamidine,
281) N-hydroxy-4-{5-[4-(2-cyclohexyl-5-{2-[cyclopropyl-(pyridin-3-carbonyl)-amino]-ethyl}-thiazol-4-yl)-phenoxy]-pentyloxy}-benzamidine,
282) N-hydroxy-4-{5-[4-(5-methylcarbamoyl-2-methyl-thiazol-4-yl)-phenoxy]-pentyloxy}-benzamidine,
283) N-hydroxy-4-{5-[4-(5-isopropylcarbamoyl-2-methyl-thiazol-4-yl)-phenoxy]-pentyloxy}-benzamidine,
284) N-hydroxy-4-{5-[4-(5-{3-imidazol-1-yl-propylcarbamoyl}-2-methyl-thiazol-4-yl)-phenoxy]-pentyloxy}-benzamidine,
285) N-hydroxy-4-{5-[4-(2-amino-5-methylcarbamoyl -thiazol-4-yl)-phenoxy]-pentyloxy}-benzamidine,
286) N-hydroxy-4-{5-[4-(2-methyl-5-morpholin-4-yl-thiazol-4-yl)-phenoxy]-pentyloxy}-benzamidine,
287) N-hydroxy-4-(5-{4-[2-methyl-5-(4-methyl -piperazin-1-yl)-thiazol-4-yl]-phenoxy}-pentyloxy)-benzamidine, 288) N-hydroxy-4-{5-[4-(2-amino-5-morpholin-4-yl-thiazol-4-yl)-phenoxy]-pentyloxy}-benzamidine, 289) N-hydroxy-4-(5-{4-[5-(4-methyl-piperazin-1-yl)-2-morpholine-4-yl-thiazol-4-yl]-phenoxy}-pentyloxy)-benzamidine, 290) N-hydroxy-4-{5-[4-(2,5-di-morpholin-4-yl-thiazol-4-yl)-phenoxy]-pentyloxy}-benzamidine, 291) N-hydroxy-4-{5-[4-(2-morpholin-4-yl-5-thiomorpholin-4-yl-thiazol-4-yl)-phenoxy]-pentyloxy}-benzamidine, 292) N-hydroxy-4-{5-[4-(2-morpholin-4-yl-5-pyrolidin-1-yl-thiazol-4-yl)-phenoxy]-pentyloxy}-benzamidine, 293) N-hydroxy-4-{5-[4-(2-methyl-5-morpholin-4-ylmethyl-thiazol-4-yl)-phenoxy]-pentyloxy}-benzamidine, 294) N-hydroxy-4-(5-{4-[2-methyl-5-(4-methyl-piperazin-1-ylmethyl)-thiazol-4-yl]-phenoxy}-pentyloxy)-benzamidine, 295) N-hydroxy-4-{5-[4-(2-methyl-5-thiomorpholin-4-ylmethyl-thiazol-4-yl)-phenoxy]-pentyloxy}-benzamidine, 296) N-hydroxy-4-{5-[4-(2-methyl-5-piperidin-1-ylmethyl-thiazol-4-yl)-phenoxy]-pentyloxy}-benzamidine, 297) N-hydroxy-4-{5-[4-(5-dimethylaminomethyl-2-methyl-thiazol-4-yl)-phenoxy]-pentyloxy}-benzamidine, 298) N-hydroxy-4-{5-[4-(5-butylaminomethyl-2-methyl-thiazol-4-yl)-phenoxy]-pentyloxy}-benzamidine, 299) N-hydroxy-4-(5-{4-[5-(isobutylamino-methyl)-2-methyl-thiazol-4-yl]-phenoxy}-pentyloxy)-benzamidine, 300) N-hydroxy-4-(5-{4-[5-(tert-butylamino-methyl)-2-methyl-thiazol-4-yl]-phenoxy}-pentyloxy)-benzamidine, 301) N-hydroxy-4-{5-[4-(2-methyl-5-propylaminomethyl-thiazol-4-yl)-phenoxy]-pentyloxy}-benzamidine, 302) N-hydroxy-4-[5-(4-{2-methyl-5-[(2-morpholin-4-yl-ethylamino)-methyl]-thiazol-4-yl}-phenoxy)-pentyloxy]-benzamidine, 303) N-hydroxy-4-[5-(4-{5-[(3-imidazol-1-yl-propylamino)-methyl]-2-methyl-thiazol-4-yl}-phenoxy)-pentyloxy]-benzamidine, 304) N-hydroxy-4-{5-[4-(2-methyl-5-pyrolidin-1-ylmethyl-thiazol-4-yl)-phenoxy]-pentyloxy}-benzamidine, 305) N-hydroxy-4-{5-[4-(5-imidazol-1-ylmethyl-2-methyl-thiazol-4-yl)-phenoxy]-pentyloxy}-benzamidine, 306) N-hydroxy-4-(5-{4-[5-(benzylamino-methyl)-2-methyl-thiazol-4-yl]-phenoxy}-pentyloxy)-benzamidine, 307) N-hydroxy-4-{5-[4-(5-cyclopropylaminomethyl-2-methyl-thiazol-4-yl)-phenoxy]-pentyloxy}-benzamidine, p
308) N-hydroxy-4-{5-[4-(2-methylamino-5-morpholin-4-yl-thiazol-4-yl)-phenoxy]-pentyloxy}-benzamidine, 309) N-hydroxy-4-(5-{4-[2-(methyl-pyridin-4-ylmethyl-amino)-5-morpholin-4-ylmethyl-thiazol-4-yl]-phenoxy}-pentyloxy)-benzamidine, 310) N-hydroxy-4-[5-(4-{2-[(2-hydroxy-ethyl)-methyl-amino]-5-morpholin-4-ylmethyl-thiazol-4-yl}-phenoxy)-pentyloxy]-benzamidine, 311) N-hydroxy-4-(5-{4-[2-(ethyl-methyl-amino)-5-morpholin-4-ylmethyl-thiazol-4-yl]-phenoxy}-pentyloxy)-benzamidine, 312) N-hydroxy-4-(5-{4-[2-(benzyl-methyl-amino)-5-morpholin-4-ylmethyl-thiazol-4-yl]-phenoxy}-pentyloxy)-benzamidine, 313) N-hydroxy-4-[5-(4-{2-[methyl-(2-morpholin-4-yl-ethyl)-amino]-5-morpholin-4-ylmethyl-thiazol-4-yl}-phenoxy)-pentyloxy]-benzamidine, 314) N-hydroxy-4-[5-(4-{2-[methyl-(2-morpholin-4-yl-ethyl)-amino]-5-thiomorpholin-4-ylmethyl-thiazol-4-yl}-phenoxy)-pentyloxy]-benzamidine, 315) N-hydroxy-4-[5-(4-{5-{[bis-(2-methoxy -ethyl)-amino]-methyl}-2-[methyl-(2-morpholin-4-yl-ethyl)-amino]-thiazol-4-yl}-phenoxy) -pentyloxy]-benzamidine, 316) N-hydroxy-4-(5-{4-[2-[methyl-(2-morpholin-4-yl-ethyl)-amino]-5-(4-methyl-piperazin-1-ylmethyl)-thiazol-4-yl]-phenoxy}-pentyloxy) -benzamidine, 317) N-hydroxy-4-[5-(4-{5-(isopropylamino-methyl)-2-[methyl-(2-morpholin-4-yl-ethyl)-amino]-thiazol-4-yl}-phenoxy)-pentyloxy]-benzamidine, 318) N-hydroxy-4-[5-(4-{5-[(2-methoxy-ethyl-amino) -methyl]-2-[methyl-(2-morpholin-4-yl-ethyl)-amino]-thiazol-4-yl}-phenoxy) -pentyloxy]-benzamidine, 319) N-hydroxy-4-[5-(4-{2-[(2-methoxy-ethyl) -methyl-amino]-5-morpholin-4-ylmethyl-thiazol-4-yl}-phenoxy)-pentyloxy]-benzamidine, 320) N-hydroxy-4-(5-{4-[2-(methyl-propyl-amino)-5-morpholin-4-ylmethyl-thiazol-4-yl]-phenoxy}-pentyloxy)-benzamidine, 321) N-hydroxy-4-(5-{4-[2-(methyl-pyridin-3-ylmethyl -amino)-5-morpholin-4-ylmethyl-thiazol-4-yl]-phenoxy}-pentyloxy)-benzamidine, 322) N-hydroxy-4-{5-[4-(2-methyl-5-methylamino -thiazol-4-yl)-phenoxy]-pentyloxy}-benzamidine, 323) N-hydroxy-4-[5-(4-{2-methyl-5-[(pyridin-4-carbonyl)-amino]-thiazol-4-yl}-phenoxy)-pentyloxy]-benzamidine, 324) N-hydroxy-4-[5-(4-{2-methyl-5-[(pyridin-3-carbonyl)-amino]-thiazol-4-yl}-phenoxy)-pentyloxy]-benzamidine, 325) N-hydroxy-4-[5-(4-{2-phenyl-5-[(pyridin-3-carbonyl)-amino]-thiazol-4-yl}-phenoxy)-pentyloxy]-benzamidine, 326) N-hydroxy-4-{5-[4-(5-dimethylamino-2-methyl-thiazol-4-yl)-phenoxy]-pentyloxy}-benzamidine, 327) N-hydroxy-4-{5-[4-(5-dimethylamino-2-phenyl-thiazol-4-yl)-phenoxy]-pentyloxy}-benzamidine, 328) N-hydroxy-4-{5-[4-(2-cyclohexyl-5-dimethylamino-thiazol-4-yl)-phenoxy]-pentyloxy}-benzamidine, 329) N-hydroxy-4-{5-[4-(2-methyl-5-[1,2,4]triazol-1-yl-thiazol-4-yl)-phenoxy]-pentyloxy}-benzamidine, 330) N-hydroxy-4-{5-[4-(5-amino-2-phenyl-thiazol-4-yl)-phenoxy]-pentyloxy}-benzamidine, 331) N-hydroxy-4-{5-[4-(5-amino-2-methyl-thiazol-4-yl)-phenoxy]-pentyloxy}-benzamidine, 332) N-hydroxy-4-{5-[4-(5-amino-2-pyridin-3-yl -thiazol-4-yl)-phenoxy]-pentyloxy}-benzamidine, 333) N-hydroxy-4-{5-[4-(5-amino-2-ethyl-thiazol-4-yl)-phenoxy]-pentyloxy}-benzamidine, 334) N-hydroxy-4-{5-[4-(5-amino-2-cyclohexyl-thiazol-4-yl)-phenoxy]-pentyloxy}-benzamidine, 335) N-hydroxy-4-{5-[4-(2-methylamino-5-morpholin-4-ylmethyl-thiazol-4-yl)-phenoxy]-pentyloxy}-benzamidine, 336) N-hydroxy-4-{5-[4-(2-morpholin-4-yl-5-morpholin-4-ylmethyl-thiazol-4-yl)-phenoxy]-pentyloxy}-benzamidine, and 337) N-hydroxy-4-{5-[4-(5-morpholin-4-yl-2-piperidin-1-yl-thiazol-4-yl)-phenoxy]-pentyloxy}-benzamidine.

Among the benzamidine derivatives of Formula 1 of the present invention, the more preferred compounds are as follows:

1) 4-{5-[4-(2,5-dimethyl-1,3-thiazol-4-yl)phenoxy]pentyloxy}-benzamidine,

2) N-hydroxy-4-{5-[4-(5-cyclopentylmethyl-2-(1-propyl-piperidin-4-yl)-1,3-thiazol-4-yl)phenoxy]pentyloxy}-benzamidine, 3) N-hydroxy-4-{5-[4-(5-vinyl-2-(pyridin-3-yl) -1,3-thiazol-4-yl)phenoxy]pentyloxy}-benzamidine, 4) N-hydroxy-4-{5-[4-(5-cyclopentylmethyl-2-(3-pyridylcarbonyl)amino-1,3-thiazol-4-yl)phenoxy]pentyloxy}-benzamidine, 5) N-hydroxy-4-{5-[4-(2-(2-methoxyethyl)amino-5-methyl-1,3-thiazol-4-yl)phenoxy]pentyloxy}-benzamidine, 6) N-hydroxy-4-{5-[4-(5-ethyl-2-(4-pyridylcarbonyl)amino-1,3-thiazol-4-yl)phenoxy]pentyloxy}-benzamidine, 7) N-hydroxy-4-{5-[4-(5-ethyl-2-(3-pyridylcarbonyl)amino-1,3-thiazol-4-yl)phenoxy]pentyloxy}-benzamidine, 8) N-hydroxy-4-[5-(4-{2-[methyl-(2-morpholinoethyl)amino]-1,3-thiazol-4-yl}phenoxy)pentyloxy]-benzamidine, 9) N-hydroxy-4-[5-{4-[5-methyl-2-(methyl-pyridin-3-ylmethyl-amino)-1,3-thiazol-4-yl]phenoxy}pentyloxy]-benzamidine, 10) N-hydroxy-4-{5-[4-(2-dipropylamino-5-ethyl-1,3-thiazol-4-yl)phenoxy]pentyloxy}-benzamidine, 11) N-hydroxy-4-[5-(4-{5-cyclopentylmethyl-2-[methyl-(pyridin-3-ylmethyl)amino]-1,3-thiazol-4-yl}phenoxy)pentyloxy]-benzamidine, 12) N-hydroxy-4-{5-[4-(5-methyl-2-morpholino-1,3-thiazol-4-yl)phenoxy]pentyloxy}-benzamidine, 13) N-hydroxy-4-{5-[4-(5-ethyl-2-piperidino-1,3-thiazol-4-yl)phenoxy]pentyloxy}-benzamidine, 14) N-hydroxy-4-{5-[4-(5-isopropyl-2-morpholino-1,3-thiazol-4-yl)phenoxy]pentyloxy}-benzamidine, 15) N-hydroxy-4-{5-[4-(5-isopropyl-2-methyl-1,3-thiazol-4-yl)-phenoxy]-pentylamino}-benzamidine, 16) N-hydroxy-2-fluoro-4-{5-[4-(5-isopropyl-2-methyl-1,3-thiazol-4-yl)-phenoxy]-pentyloxy}-benzamidine, 17) N-hydroxy-4-(5-{4-[5-(2-imidazol-1-yl -ethyl)-2-isopropyl-thiazol-4-yl]-phenoxy}-pentyloxy)-benzamidine, 18) N-hydroxy-4-[5-(4-{5-[2-(3-imidazol-1-yl-propylamino)-ethyl]-2-isopropyl-thiazol-4-yl}-phenoxy)-pentyloxy]-benzamidine, 19) N-hydroxy-4-(5-{4-[2-cyclohexyl-5-(2-dipropylamino-ethyl)-thiazol-4-yl]-phenoxy}-pentyloxy)-benzamidine, 20) N-hydroxy-4-(5-{4-[2-ethyl-5-(2-morpholin-4-yl-ethyl)-thiazol-4-yl]-phenoxy}-pentyloxy)-benzamidine, 21) N-hydroxy-4-(5-{4-[2-[benzyl-(2-morpholin-4-yl-ethyl)-amino]-5-(2-morpholin-4-yl-ethyl)-thiazol-4-yl]-phenoxy}-pentyloxy)-benzamidine, 22) N-hydroxy-4-(5-{4-[2-diethylamino-5-(2-morpholin-4-yl-ethyl)-thiazol-4-yl]-phenoxy}-pentyloxy)-benzamidine, 23) N-hydroxy-4-(5-{4-[2-morpholin-4-yl-5-(2-thiomorpholin-3-yl-ethyl)-thiazol-4-yl]-phenoxy}-pentyloxy)-benzamidine, 24) N-hydroxy-4-{5-[4-(2,5-di-morpholin-4-yl-thiazol-4-yl)-phenoxy]-pentyloxy}-benzamidine, 25) N-hydroxy-4-{5-[4-(2-morpholin-4-yl-5-thiomorpholin-4-yl-thiazol-4-yl)-phenoxy]-pentyloxy}-benzamidine, 26) N-hydroxy-4-{5-[4-(2-methyl-5-piperidin-1-ylmethyl-thiazol-4-yl)-phenoxy]-pentyloxy}-benzamidine, 27) N-hydroxy-4-(5-{4-[5-(isobutylamino-methyl)-2-methyl-thiazol-4-yl]-phenoxy}-pentyloxy)-benzamidine, 28) N-hydroxy-4-{5-[4-(2-methyl-5-propylaminomethyl-thiazol-4-yl)-phenoxy]-pentyloxy}-benzamidine, 29) N-hydroxy-4-(5-{4-[5-(benzylamino-methyl)-2-methyl-thiazol-4-yl]-phenoxy}-pentyloxy)-benzamidine, 30) N-hydroxy-4-(5-{4-[2-(methyl-pyridin-4-ylmethyl-amino)-5-morpholin-4-ylmethyl-thiazol-4-yl]-phenoxy}-pentyloxy)-benzamidine, 31) N-hydroxy-4-[5-(4-{2-[methyl-(2-morpholin-4-yl-ethyl)-amino]-5-thiomorpholin-4-ylmethyl-thiazol-4-yl}-phenoxy)-pentyloxy]-benzamidine, and 32) N-hydroxy-4-{5-[4-(5-amino-2-methyl-thiazol-4-yl)-phenoxy]-pentyloxy}-benzamidine.

Among the bisphosphonate compounds of Formula 2 of the present invention, the preferred compounds are as follows:

1) etidronic acid,
2) clodronic acid,
3) pamidronic acid,
4) tiludronic acid,
5) risedronic acid,
6) minodronic acid,
7) ibandronic acid,
8) zoledronic acid, and
9) alendronic acid.

The benzamidine derivatives of Formula 1 of the present invention may be used in the form of pharmaceutically acceptable salts. Preferable are acid addition salts prepared with pharmaceutically acceptable free acids. Free acids suitable for use in the present invention may be inorganic acids or organic acids. Examples of the inorganic acids may include hydrochloric acid, bromic acid, sulfuric acid, and phosphoric acid, and the organic acids may be exemplified by citric acid, acetic acid, lactic acid, tartaric acid, fumaric acid, formic acid, propionic acid, oxalic acid, trifluoroacetic acid, methane sulfonic acid, benzene sulfonic acid, maleic acid, benzoic acid, gluconic acid, glycolic acid, succinic acid, 4-morpholine ethane sulfonic acid, camphorsulfonic acid, 4-nitrobenzene sulfonic acid, hydroxy-O-sulfonic acid, 4-toluene sulfonic acid, galacturonic acid, embonic acid, glutamic acid, and aspartic acid. Preferably, hydrochloric acid or phosphoric acid as the inorganic acid and methane sulfonic acid as the organic acid may be used.

In the present invention, general definitions of the substituents of the compounds of Formulae 1 and 2 have the following meanings:

The term "halogen" means halogen group atoms including chlorine, fluorine, bromine, and iodine radicals.

The term "alkyl" means straight or branched, saturated hydrocarbon radicals having 1 to 6 carbon atoms, and examples thereof include methyl, ethyl, n-propyl, iso-propyl, n-butyl, sec-butyl and tert-butyl.

The term "alkoxy" means radicals having straight or branched alkyl having 1 to 6 carbon atoms that is linked to oxygen, and examples thereof include methoxy, ethoxy, propoxy, iso-propoxy, butoxy, sec-butoxy, and tert-butoxy.

The term "cycloalkyl" means a non-aromatic hydrocarbon ring having 3 to 6 carbon atoms, and examples thereof include cyclopropyl, cyclobutyl, cyclopentyl and cyclohexyl.

The term "alkenyl" means straight or branched, unsaturated hydrocarbons having 2 to 6 carbon atoms with one or more double bonds.

The term "alkanoyloxy" means an oxygen-containing radical in which a terminal carbon atom of an alkyl group is substituted with a carbonyl radical.

The term "alkenoyloxy" means an oxygen-containing radical in which a terminal carbon atom of an alkenyl group is substituted with a carbonyl radical.

The term "alkenyloxy" means an oxygen-containing alkenyl group.

The term "alkylene" means a straight or branched, saturated hydrocarbon radical having 1 to 7 carbon atoms, and 2 or more junction centers for a covalent bond, and examples thereof include methylene, ethylene, methylethylene and isopropylidene.

The term "alkenylene" means a straight or branched, unsaturated hydrocarbon radical having 2 to 7 carbon atoms, 2 or more conjunction centers for a covalent bond and one or more double bonds, and examples thereof include 1,1-vinylidene ($CH_2=C$), 1,2-vinylidene (—CH=CH—), and 1,4-butadienyl (—CH=CH—CH=CH—).

The term "carbonyl" means a carbon radical in which 2 of 4 covalent bonds are linked to oxygen atoms.

The benzamidine of Formula 1 or salts thereof used in the present invention can be used as a therapeutic or prophylactic agent for osteoporosis, having excellent inhibitory effect on bone resorption and stimulating effect on bone formation.

The benzamidine derivative of Formula 1 may be prepared by known processes, which are disclosed in Korea Patent No. 705875, and Korea Patent No. 875596, and Korea Patent Application No. 2008-0073710.

The term "osteoporosis" as used herein means the state that minerals and substrates forming the bone are reduced abnormally in large amounts, even without any defect in the structure of the remaining bone, so that many pores are generated in the bone, making it like sponge and more likely to fracture. This may be referred to as "osteopenia".

The dosage of benzamidine derivative of Formula 1 or salt thereof may vary depending on patient's body weight, age, gender, health state, diet, administration time period, administration route, excretion rate, disease severity, type of combination therapy, or treatment frequency. In the case of using as a therapeutic or prophylactic agent, the benzamidine derivative of Formula 1 or salt thereof may be generally administered in an effective amount for the treatment of osteoporosis via each administration route, and its formulation, dosage or the like may be easily determined by those skilled in the art, considering administration purpose, route, health state and body weight of a subject. In particular, the benzamidine derivative or salt thereof may be administered in a daily dose of about 1 to 1,000 mg, and preferably 5 to 400 mg.

In addition, the dosage of bisphosphonate of Formula 2 may vary depending on patient's body weight, age, gender, health state, diet, administration time period, administration route, excretion rate, disease severity, type of combination therapy, or treatment frequency. In the case of using as a therapeutic or prophylactic agent, the bisphosphonate of Formula 2 may be generally administered in an effective amount for the treatment of osteoporosis via each administration route and its formulation, dosage or the like may be easily determined by those skilled in the art, considering administration purpose, route, and health state and body weight of a subject. In particular, the bisphosphonate may be administered in a daily dose of about 1 to 1,000 mg, and preferably 1 to 400 mg.

In the present invention, the benzamidine of Formula 1 or salt thereof and bisphosphonate of Formula 2 may be used in any combination thereof.

In the present invention, the benzamidine of Formula 1 or salt thereof and bisphosphonate of Formula 2 may be simultaneously administered by mixing together, or each of them may be administered separately either simultaneously or sequentially, or may be administered separately at different times. In the case of administering separately, two active ingredients may be administered alternately or one active ingredient may be administered after completion of the administration of the other active ingredient.

In the present invention, the benzamidine of Formula 1 or salt thereof and bisphosphonate of Formula 2 may be formulated into any pharmaceutical dosage form, for example, a combined formulation comprising two active ingredients or each single formulation. As used herein, the combined formulation means that two active ingredients of the benzamidine of Formula 1 or salt thereof and bisphosphonate of Formula 2 are blended in one formulation, and the single formulation means that one active ingredient is contained in one formulation. In the present invention, if two active ingredients are prepared into single formulations, the therapeutic and prophylactic agent of the present invention refers to a drug using the single formulations in combination thereof. Thus, each drug containing the active ingredient may be prepared into each different formulation. If two active ingredients are prepared into single formulation, two formulations may be provided in one kit.

In addition, the prophylactic or therapeutic agent for osteoporosis of the present invention may be administered, either daily or intermittently, and may be administered once or 2~3 times a day. If each of the active ingredients is a single formulation, their administration frequency may be the same as or different from each other.

The benzamidine of Formula 1 or salt thereof and bisphosphonate of Formula 2 of the present invention may be formulated alone or along with the following suitable excipients by a known method. Specific examples of the formulation may include oral dosage forms such as soft capsule, hard capsule, tablet, and syrup, and injectable and topical preparations.

As the excipient, the pharmaceutically acceptable carrier includes any of standard pharmaceutical carriers used for the preparation of the known formulations, such as sterile liquids, tablets, coated tablets and capsules. Typically, such carriers include excipients such as polyvinylpyrrolidone, dextrin, starch, milk, sugar, certain types of clay, gelatin, stearic acid, talc, vegetable oils (e.g., edible oil, cotton seed oil, coconut oil, almond oil, peanut oil), liquid ester such as triglyceride, mineral oil, Vaseline, animal fat, cellulose derivatives (e.g., crystalline cellulose, hydroxypropylcellulose, hydroxypropylmethylcellulose, methylcellulose) and other known excipients. Such carriers may also include antioxidants, wetting agents, viscosity stabilizers, flavoring agents, coloring additives and other additives. The composition containing these carriers may be formulated by a known method.

The prophylactic or therapeutic composition for osteoporosis of the present invention means that two types of active ingredients having a different mechanism from each other, including the benzamidine of Formula 1 or salt thereof and bisphosphonate of Formula 2, are used in combination, and provides excellent effects of improving bone density and strength, compared to other single drugs.

For the prevention and treatment of osteoporosis, the prophylactic or therapeutic composition of the present invention may be used alone or in combination with surgical operations, hormone therapies, chemical therapies, and other methods using biological reaction regulators.

[Best Mode]

Hereinafter, the present invention will be described in more detail with reference to examples. However, these examples are for illustrative purposes only, and the invention is not intended to be limited by these examples.

PREPARATION EXAMPLE 1

Preparation of Benzamidine Derivative of Formula 1

Benzamidine derivatives of Formula 1 were prepared according to the preparation methods disclosed in Korea Patent No. 705875, Korea Patent No. 875596, and Korea Patent Application No. 2008-0073710, the disclosure of which is incorporated herein by reference in its entirety.

Prepared compounds were identified as following Table 1.

TABLE 1

| No. | Chemical name | NMR data | Sol. |
|---|---|---|---|
| 1 | N-hydroxy-4-{5-[4-(2-isopropyl-5-methyl-1,3-thiazol-4-yl)phenoxy]pentyloxy}-benzamidine | 1.31 (d, 6H), 1.58 (m, 2H), 1.79 (m, 4H), 2.47 (s, 3H), 3.21 (m, 1H), 4.00 (m, 4H), 5.71 (s, 2H), 6.91 (d, 2H), 6.99 (d, 2H), 7.56 (m, 4H), 9.44 (s, 1H) | DMSO-$d_6$ |
| 2 | 4-{5-[4-(2-isopropyl-5-methyl-1,3-thiazol-4-yl)phenoxy]pentyloxy}-benzamidine | 1.33 (d, 6H), 1.61 (m, 2H), 1.82 (brm, 4H), 2.49 (s, 3H), 3.22 (m, 1H), 4.04 (t, 2H), 4.14 (t, 2H), 7.01 (d, 2H), 7.17 (d, 2H), 7.57 (d, 2H), 7.85 (d, 2H). | DMSO-$d_6$ |
| 3 | N-hydroxy-4-{5-[4-(2-methyl-1,3-thiazol-4-yl)phenoxy]pentyloxy}-benzamidine | 1.56 (m, 2H), 1.78 (brm, 4H), 2.68 (s, 3H), 4.00 (m, 4H), 5.70 (s, 2H), 6.90 (d, 2H), 6.96 (d, 2H), 7.57 (d, 2H), 7.72 (s, 1H), 7.83 (d, 2H), 9.43 (s, 1H) | DMSO-$d_6$ |
| 4 | N-hydroxy-4-{5-[4-(2-ethyl-1,3-thiazol-4-yl)phenoxy]pentyloxy}-benzamidine | 1.32 (t, 3H), 1.57 (brm, 2H), 1.77 (brm, 4H), 3.01 (q, 2H), 4.00 (m, 4H), 5.71 (s, 2H), 6.91 (d, 2H), 6.96 (d, 2H), 7.57 (d, 2H), 7.75 (s, 1H), 7.84 (d, 2H), 9.43 (s, 1H) | DMSO-$d_6$ |
| 5 | N-hydroxy-4-{5-[4-(2-isopropyl-1,3-thiazol-4-yl)phenoxy]pentyloxy}-benzamidine | 1.35 (d, 6H), 1.58 (m, 2H), 1.78 (brm, 4H), 3.28 (m, 1H), 4.00 (m, 4H), 5.79 (brs, 2H), 6.91 (d, 2H), 6.97 (d, 2H), 7.58 (d, 2H), 7.76 (s, 1H), 7.84 (d, 2H), 9.47 (s, 1H) | DMSO-$d_6$ |
| 6 | N-hydroxy-4-{5-[4-(2-phenyl-1,3-thiazol-4-yl)phenoxy]pentyloxy}-benzamidine | 1.58 (m, 2H), 1.80 (brm, 4H), 4.02 (m, 4H), 5.81 (brs, 2H), 6.92 (d, 2H), 7.01 (d, 2H), 7.51 (m, 3H), 7.58 (d, 2H), 7.96 (d, 2H), 8.01 (m, 3H), 9.49 (s, 1H) | DMSO-$d_6$ |
| 7 | N-hydroxy-4-{5-[4-(2-pyridine-3-yl-1,3-thiazol-4-yl)phenoxy]pentyloxy}-benzamidine | 1.58 (brm 2H), 1.80 (brm, 4H), 4.02 (t, 4H), 5.73 (s, 2H), 6.91 (d, 2H), 7.02 (d, 2H), 7.55 (m, 3H), 7.82 (d, 2H), 7.97 (d, 2H), 8.10 (s, 1H), 8.36 (d, 1H), 8.67 (d, 1H), 9.19 (s, 1H), 9.45 (s, 1H) | DMSO-$d_6$ |
| 8 | N-hydroxy-4-{5-[4-(2-cyclohexyl-1,3-thiazol-4-yl)phenoxy]pentyloxy}-benzamidine | 1.23 (m, 1H), 1.47 (m, 6H), 1.65 (m, 1H), 1.77 (brm, 6H), 2.06 (m, 2H), 2.99 (m, 1H), 4.00 (m, 4H), 5.70 (s, 2H), 6.90 (d, 2H), 6.96 (d, 2H), 7.57 (d, 2H), 7.74 (d, 2H), 7.83 (d, 2H), 9.44 (s, 1H) | DMSO-$d_6$ |
| 9 | N-hydroxy-4-{5-[4-(2-pentyl-1,3-thiazol-4-yl)phenoxy]pentyloxy}-benzamidine | 0.86 (t, 3H), 1.33 (brm, 4H), 1.56 (brm, 2H), 1.73 (brm, 6H), 2.97 (m, 2H), 4.00 (m, 4H), 5.70 (s, 2H), 6.90 (d, 2H), 6.96 (m, 2H), 7.57 (d, 2H), 7.74 (s, 1H), 7.83 (d, 2H), 9.44 (s, 1H) | DMSO-$d_6$ |
| 10 | N-hydroxy-4-{5-[4-(2,5-dimethyl-1,3-thiazol-4-yl)phenoxy]pentyloxy}-benzamidine | 1.57 (m, 2H), 1.78 (m, 4H), 2.44 (s, 3H), 2.58 (s, 3H), 4.01 (m, 4H), 5.72 (s, 2H), 6.97 (d, 2H), 7.54 (d, 2H), 7.57 (d, 2H), 9.44 (s, 1H) | DMSO-$d_6$ |
| 11 | N-hydroxy-4-{5-[4-(2-ethyl-5-methyl-1,3-thiazol-4-yl)phenoxy]pentyloxy}-benzamidine | 1.27 (t, 3H), 1.57 (m, 2H), 1.78 (brm, 4H), 2.45 (s, 3H), 2.91 (q, 2H), 4.01 (m, 4H), 5.75 (brs, 2H), 6.91 (d, 2H), 6.98 (d, 2H), 7.54 (d, 2H), 7.57 (d, 2H), 9.46 (s, 1H). | DMSO-$d_6$ |
| 12 | N-hydroxy-4-{5-[4-(5-methyl-2-phenyl-1,3-thiazol-4-yl)phenoxy]pentyloxy}-benzamidine | 1.58 (m, 2H), 1.79 (m, 4H), 2.56 (s, 3H), 4.02 (m, 4H), 5.78 (brs, 2H), 6.91 (d, 2H), 7.03 (d, 2H). 7.49 (m, 3H), 7.58 (d, 2H), 7.65 (d, 2H), 7.91 (d, 2H), 9.45 (s, 1H) | DMSO-$d_6$ |
| 13 | N-hydroxy-4-{5-[4-(5-methyl-2-pyridin-3-yl-1,3-thiazol-4-yl)phenoxy]pentyloxy}-benzamidine | 1.59 (m, 2H), 1.79 (m, 2H), 2.58 (s, 3H), 4.02 (m, 4H), 5.72 (s, 2H), 6.91 (d, 2H), 7.03 (d, 2H), 7.52 (m, 1H), 7.58 (d, 2H), 7.66 (d, 2H), 8.26 (d, 1H), 8.64 (d, 1H), 9.09 (d, 1H), 9.45 (s, 1H) | DMSO-$d_6$ |
| 14 | N-hydroxy-4-{5-[4-(2-cyclohexyl-5-methyl-1,3-thiazol-4-yl)phenoxy]pentyloxy}-benzamidine | 1.26 (m, 1H), 1.43 (brm, 4H), 1.61 (m, 2H), 1.67 (m, 1H), 1.80 (brm, 6H), 2.04 (m, 1H), 2.49 (s, 3H), 2.92 (m, 1H), 4.03 (m, 4H), 5.73 (s, 2H), 6.94 (d, 2H), 7.01 (d, 2H), 7.57 (d, 2H), 7.60 (d, 2H), 9.47 (s, 1H) | DMSO-$d_6$ |
| 15 | N-hydroxy-4-{5-[4-(5-methyl-2-pentyl-1,3-thiazol-4-yl)phenoxy]pentyloxy}-benzamidine | 0.86 (t, 3H), 1.31 (brm, 4H), 1.58 (m, 2H), 1.68 (m, 2H), 1.78 (brm, 4H), 2.46 (s, 3H), 2.88 (t, 2H), 4.01 (m, 4H), 5.72 (brs, 2H), 6.92 (d, 2H), 6.98 (d, 2H), 7.53 (d, 2H), 7.57 (d, 2H), 9.45 (s, 1H) | DMSO-$d_6$ |
| 16 | N-hydroxy-4-{5-[4-(2-t-butyl-5-methyl-1,3-thiazol-4- | 1.36 (s, 9H), 1.57 (m, 2H), 1.78 (brm, 4H), 2.45 (s, 3H), 4.00 (m, 4H), 5.72 (s, 2H), 6.91 (d, 2H), 6.98 (d, 2H), 7.55 (d, | DMSO-$d_6$ |

TABLE 1-continued

| No. | Chemical name | NMR data | Sol. |
|---|---|---|---|
| | yl)phenoxy]pentyloxy}-benzamidine | 2H), 7.58 (d, 2H), 9.44 (s, 1H) | |
| 17 | N-hydroxy-4-{5-[4-(5-ethyl-2-methyl-1,3-thiazol-4-yl)phenoxy]pentyloxy}-benzamidine | 1.26 (t, 3H), 1.66 (m, 2H), 1.85 (brm, 4H), 2.83 (s, 3H), 2.86 (q, 2H), 4.00 (m, 4H), 4.88 (brs, 1H), 6.87 (d, 2H), 6.91 (d, 2H), 7.46 (d, 2H), 7.52 (d, 2H) | CDCl$_3$ |
| 18 | N-hydroxy-4-{5-[4-(2,5-diethyl-1,3-thiazol-4-yl)phenoxy]pentyloxy}-benzamidine | 1..22 (t, 3H), 1.28 (t, 3H), 1.57 (m, 2H), 1.78 (brm, 4H), 2.85 (q, 2H), 4.01 (m, 2H), 5.73 (s, 2H), 6.91 (d, 2H), 6.98 (d, 2H), 7.48 (d, 2H), 7.57 (d, 2H), 9.44 (s, 1H) | DMSO-d$_6$ |
| 19 | N-hydroxy-4-{5-[4-(5-ethyl-2-isopropyl-1,3-thiazol-4-yl)phenoxy]pentyloxy}-benzamidine | 1.22 (t, 3H), 1.31 (d, 6H), 1.57 (m, 2H), 1.78 (brm, 4H), 2.86 (q, 2H), 3.24 (m, 1H), 4.01 (m, 4H), 5.70 (s, 2H), 6.90 (d, 2H), 6.98 (d, 2H), 7.49 (d, 2H), 7.58 (d, 2H), 9.43 (s, 1H) | DMSO-d$_6$ |
| 20 | N-hydroxy-4-{5-[4-(5-ethyl-2-phenyl-1,3-thiazol-4-yl)phenoxy]pentyloxy}-benzamidine | 1.29 (t, 2H), 1.58 (m, 2H), 1.79 (m, 4H), 2.96 (q, 2H), 4.03 (m, 4H), 5.70 (s, 2H), 6.91 (d, 2H), 7.03 (d, 2H), 7.43 (m, 3H), 7.58 (m, 4H), 7.90 (m, 2H), 9.43 (s, 1H) | DMSO-d$_6$ |
| 21 | N-hydroxy-4-{5-[4-(5-ethyl-2-pyridin-3-yl-1,3-thiazol-4-yl)phenoxy]pentyloxy}-benzamidine | 1.30 (t, 3H), 1.58 (m, 2H), 1.79 (m, 4H), 2.98 (q, 2H), 4.02 (m, 4H), 5.69 (s, 2H), 6.91 (d, 2H), 7.04 (d, 2H), 7.52 (m, 1H), 7.59 (m, 4H), 8.26 (m, 1H), 8.63 (m, 1H), 9.10 (s, 1H), 9.42 (s, 1H) | DMSO-d$_6$ |
| 22 | N-hydroxy-4-{5-[4-(2-cyclohexyl-5-ethyl-1,3-thiazol-4-yl)phenoxy]pentyloxy}-benzamidine | 1.22 (m, 4H), 1.38 (m, 4H), 1.58 (m, 2H), 1.64 (m, 1H), 1.89 (brm, 6H), 2.01 (m, 2H), 2.87 (m, 3H), 4.01 (m, 4H), 5.71 (s, 2H), 6.91 (s, 2H), 6.98 (d, 2H), 7.48 (d, 2H), 7.57 (d, 2H), 9.44 (s, 1H) | DMSO-d$_6$ |
| 23 | N-hydroxy-4-{5-[4-(5-ethyl-2-pentyl-1,3-thiazol-4-yl)phenoxy]pentyloxy}-benzamidine | 0.86 (t, 3H), 1.21 (t, 3H), 1.32 (brm, 4H), 1.58 (m, 2H), 1.69 (m, 2H), 1.78 (brm, 4H), 2.87 (m, 4H), 4.01 (m, 4H), 5.72 (s, 2H), 6.91 (d, 2H), 6.98 (d, 2H), 7.48 (d, 2H), 7.58 (d, 2H), 9.44 (s, 1H) | DMSO-d$_6$ |
| 24 | N-hydroxy-4-{5-[4-(2-ethyl-5-isopropyl-1,3-thiazol-4-yl)phenoxy]pentyloxy}-benzamidine | 1.26 (m, 9H), 1.57 (m, 2H), 1.79 (brm, 4H), 2.92 (q, 2H), 3.31 (m, 1H), 4.01 (m, 4H), 5.71 (brs, 2H), 6.91 (d, 2H), 6.98 (d, 2H), 7.43 (d, 2H), 7.57 (d, 2H) | DMSO-d$_6$ |
| 25 | N-hydroxy-4-{5-[4-(2,5-diisopropyl-1,3-thiazol-4-yl)phenoxy]pentyloxy}-benzamidine | 1.24 (d, 6H), 1.32 (d, 6H), 1.56 (brm, 2H), 1.76 (brm, 4H), 3.22-3.27 (m, 1H), 3.34-3.38 (m, 1H), 3.90 (t, 2H), 4.02 (t, 2H), 5.70 (s, 2H), 6.80 (d, 2H), 7.00 (d, 2H), 7.26 (d, 2H), 7.45 (d, 2H), 8.29 (s, 1H) | DMSO-d$_6$ |
| 26 | N-hydroxy-4-{5-[4-(5-isopropyl-2-phenyl-1,3-thiazol-4-yl)phenoxy]pentyloxy}-benzamidine | 1.31 (d, 6H), 1.58 (brm, 2H), 1.78 (brm, 4H), 3.44 (m, 1H), 4.02 (m, 4H), 5.70 (s, 2H), 6.91 (d, 2H), 7.03 (d, 2H), 7.47 (m, 3H), 7.56 (m, 4H), 7.90 (d, 2H), 9.44 (s, 1H) | DMSO-d$_6$ |
| 27 | N-hydroxy-4-{5-[4-(5-isopropyl-2-pyridin-3-yl-1,3-thiazol-4-yl)phenoxy]pentyloxy}-benzamidine | 1.32 (d, 6H), 1.57 (brm, 2H), 1.78 (brm, 4H), 4.00 (m, 4H), 5.71 (s, 2H), 6.91 (d, 2H), 7.04 (d, 2H), 7.51 (m, 1H), 7.58 (m, 4H), 8.27 (d, 1H), 8.64 (d, 1H), 9.10 (d, 1H), 9.44 (s, 1H) | DMSO-d$_6$ |
| 28 | N-hydroxy-4-{5-[4-(5-isopropyl-2-pentyl-1,3-thiazol-4-yl)phenoxy]pentyloxy}-benzamidine | 0.84 (t, 3H), 1.23 (d, 6H), 1.32 (brm, 4H), 1.56 (m, 2H), 1.69 (m, 2H), 1.78 (brm, 4H), 2.88 (m, 2H), 3.36 (m, 1H), 4.01 (m, 4H), 5.73 (s, 2H), 6.91 (d, 2H), 6.98 (d, 2H), 7.43 (d, 2H), 7.58 (d, 2H), 9.45 (s, 1H) | DMSO-d$_6$ |
| 29 | N-hydroxy-4-{5-[4-(2-methyl-5-propyl-1,3-thiazol-4-yl)phenoxy]pentyloxy}-benzamidine | 0.91 (t, 3H), 1.57~1.61 (m, 4H), 1.78 (m, 4H), 2.60 (s, 3H), 2.80 (m, 2H), 4.01 (m, 4H), 5.85 (brs, 2H), 6.93 (d, 2H), 6.98 (d, 2H), 7.47 (d, 2H), 7.58 (d, 2H), 9.51 (s, 1H) | DMSO-d$_6$ |
| 30 | N-hydroxy-4-{5-[4-(5-butyl-2-methyl-1,3-thiazol-4-yl)phenoxy]pentyloxy}-benzamidine | 0.83 (t, 3H), 1.30 (m, 2H), 1.53 (m, 4H), 1.78 (brm, 4H), 2.59 (s, 3H), 2.82 (m, 2H), 4.00 (m, 4H), 5.74 (brs, 2H), 6.91 (d, 2H), 7.46 (d, 2H), 7.57 (d, 2H), 9.45 (s, 1H) | DMSO-d$_6$ |
| 31 | N-hydroxy-4-{5-[4-(5-butyl-2-ethyl-1,3-thiazol-4- | 0.84 (t, 3H), 1.27 (t, 3H), 1.31 (m, 2H), 1.56 (m, 4H), 1.78 (brm, 4H), 2.83 (t, 2H), 2.92 (m, 2H), 4.01 (m, 4H), | DMSO-d$_6$ |

TABLE 1-continued

| No. | Chemical name | NMR data | Sol. |
|---|---|---|---|
|  | yl)phenoxy]pentyloxy}-benzamidine | 5.72 (brs, 2H), 6.91 (d, 2H), 6.98 (d, 2H), 7.47 (d, 2H), 7.58 (d, 2H), 9.45 (s, 2H) | |
| 32 | N-hydroxy-4-{5-[4-(5-butyl-2-isopropyl-1,3-thiazol-4-yl)phenoxy]pentyloxy}-benzamidine | 0.84 (t, 3H), 1.31 (m, 8H), 1.57 (m, 4H), 1.78 (brm, 4H), 2.83 (m, 2H), 3.24 (m, 1H), 4.01 (m, 4H), 5.74 (brs, 2H), 6.91 (d, 2H), 6.98 (d, 2H), 7.47 (d, 2H), 7.57 (d, 2H), 9.45 (s, 1H) | DMSO-$d_6$ |
| 33 | N-hydroxy-4-{5-[4-(5-butyl-2-phenyl-1,3-thiazol-4-yl)phenoxy]pentyloxy}-benzamidine | 0.86 (t, 3H), 1.33 (m, 2H), 1.61 (m, 4H), 1.80 (m, 4H), 2.92 (t, 2H), 4.01 (m, 4H), 5.72 (brs, 2H), 6.91 (d, 2H), 7.02 (d, 2H), 7.46 (m, 3H), 7.59 (m, 4H), 7.91 (d, 2H), 9.45 (s, 1H) | DMSO-$d_6$ |
| 34 | N-hydroxy-4-{5-[4-(5-butyl-2-pyridin-3-yl-1,3-thiazol-4-yl)phenoxy]pentyloxy}-benzamidine | 0.86 (t, 3H), 1.35 (m, 2H), 1.59 (m, 2H), 1.66 (m, 2H), 1.78 (m, 4H), 2.95 (t, 2H), 4.03 (m, 4H), 5.75 (brs, 2H), 6.91 (d, 2H), 7.04 (d, 2H), 7.51 (m, 1H), 7.58 (m, 4H), 8.26 (d, 1H), 8.63 (d, 1H), 9.09 (d, 1H), 9.45 (s, 1H) | DMSO-$d_6$ |
| 35 | N-hydroxy-4-{5-[4-(5-butyl-2-cyclohexyl-1,3-thiazol-4-yl)phenoxy]pentyloxy}-benzamidine | 0.84 (t, 3H), 1.28 (brm, 6H), 1.56 (brm, 6H), 1.77 (brm, 6H), 2.00 (m, 2H), 2.83 (t, 2H), 2.90 (m, 1H), 4.01 (m, 4H), 5.72 (s, 2H), 6.91 (d, 2H), 6.98 (d, 2H), 7.47 (d, 2H), 7.57 (d, 2H), 9.44 (s, 1H) | DMSO-$d_6$ |
| 36 | N-hydroxy-4-{5-[4-(5-butyl-2-pentyl-1,3-thiazol-4-yl)phenoxy]pentyloxy}-benzamidine | 0.85 (m, 6H), 1.31 (m, 6H), 1.58 (m, 4H), 1.69 (m, 2H), 1.78 (brm, 4H), 2.83 (t, 2H), 2.88 (t, 2H), 4.01 (m, 4H), 5.72 (brs, 2H), 6.91 (d, 2H), 6.98 (d, 2H), 7.47 (d, 2H), 7.57 (d, 2H), 9.44 (s, 1H) | DMSO-$d_6$ |
| 37 | N-hydroxy-4-{5-[4-(5-butyl-2-t-butyl-1,3-thiazol-4-yl)phenoxy]pentyloxy}-benzamidine | 0.84 (t, 3H), 1.31 (m, 2H), 1.36 (s, 9H), 1.57 (brm, 4H), 1.79 (brm, 4H), 2.83 (m, 2H), 4.01 (m, 4H), 5.74 (brs, 2H), 6.91 (d, 2H), 6.97 (d, 2H), 7.48 (d, 2H), 7.58 (d, 2H), 9.45 (s, 1H) | DMSO-$d_6$ |
| 38 | N-hydroxy-4-{5-[4-(5-benzyl-2-methyl-1,3-thiazol-4-yl)phenoxy]pentyloxy}-benzamidine | 1.56 (m, 2H), 1.78 (brm, 4H), 2.58 (s, 3H), 4.00 (m, 4H), 4.20 (s, 2H), 5.77 (brs, 2H), 6.91 (d, 2H), 6.98 (d, 2H), 7.17 (d, 2H), 7.22 (m, 1H), 7.30 (m, 2H), 7.52 (d, 2H), 7.57 (d, 2H), 9.47 (s, 1H) | DMSO-$d_6$ |
| 39 | N-hydroxy-4-{5-[4-(5-benzyl-2-isopropyl-1,3-thiazol-4-yl)phenoxy]pentyloxy}-benzamidine | 1.28 (d, 6H), 1.57 (m, 2H), 1.77 (brm, 4H), 3.19 (m, 1H), 4.00 (m, 2H), 4.21 (s, 2H), 5.70 (s, 2H), 6.90 (d, 2H), 6.98 (d, 2H), 7.19 (m, 3H), 7.30 (m, 2H), 7.53 (d, 2H), 7.56 (d, 2H), 9.44 (s, 1H) | DMSO-$d_6$ |
| 40 | N-hydroxy-4-{5-[4-(5-benzyl-2-phenyl-1,3-thiazol-4-yl)phenoxy]pentyloxy}-benzamidine | 1.58 (m, 2H), 1.79 (brm, 4H), 4.02 (m, 4H), 4.31 (s, 2H), 5.72 (brs, 2H), 6.91 (d, 2H), 7.03 (d, 2H), 7.24 (m, 3H), 7.32 (m, 2H), 7.46 (m, 3H), 7.58 (d, 2H), 7.64 (d, 2H), 7.89 (m, 2H), 9.44 (s, 2H) | DMSO-$d_6$ |
| 41 | N-hydroxy-4-{5-[4-(5-benzyl-2-pyridin-3-yl-1,3-thiazol-4-yl)phenoxy]pentyloxy}-benzamidine | 1.58 (m, 2H), 1.79 (brm, 4H), 4.02 (m, 4H), 4.34 (s, 2H), 5.73 (brs, 2H), 6.91 (d, 2H), 7.04 (d, 2H), 7.25 (m, 3H), 7.33 (,. 2H), 7.49 (m, 1H), 7.58 (d, 2H), 7.66 (d, 2H), 8.25 (d, 1H), 8.63 (d, 1H), 9.08 (s, 1H), 9.45 (s, 1H) | DMSO-$d_6$ |
| 42 | N-hydroxy-4-{5-[4-(5-(2-chloro-ethyl)-2-methyl-1,3-thiazol-4-yl)phenoxy]pentyloxy}-benzamidine | 1.65 (m, 2H), 1.86 (m, 4H), 2.72 (s, 3H), 3.30 (t, 2H), 3.67 (t, 2H), 4.02 (m, 4H), 5.70 (s, 2H), 6.92 (m, 4H), 7.45 (d, 2H), 9.43 (s, 1H) | DMSO-$d_6$ |
| 43 | N-hydroxy-4-{5-[4-(5-cyclopentyl-2-methyl-1,3-thiazol-4-yl)phenoxy]pentyloxy}-benzamidine | 1.58 (brs, 6H), 1.77 (brs, 6H), 2.07 (brs, 2H), 2.62 (s, 3H), 3.30 (m, 1H), 3.98 (m, 4H), 6.75~6.92 (m, 4H), 7.39~7.60 (m, 4H) | CDCl$_3$ |
| 44 | N-hydroxy-4-{5-[4-(5-isobutyl-2-methyl-1,3-thiazole-4-yl)phenoxy]pentyloxy}-benzamidine | 0.86 (d, 6H), 1.60 (m 2H), 1.78 (m, 5H), 2.61 (s, 3H), 2.72 (d, 2H), 4.01 (m, 4H), 5.77 (s, 2H), 6.91 (d, 2H), 6.98 (d, 2H), 7.45 (d, 2H), 7.59 (d, 2H), 9.47 (s, 1H) | DMSO-$d_6$ |
| 45 | N-hydroxy-4-{5-[4-(5-cyclopentylmethyl-2-methyl-1,3-thiazol-4-yl)phenoxy]pentyloxy}-benzamidine | 1.14 (m, 2H), 1.48 (brm 6H), 1.69 (m, 2H), 1.78 (brm, 4H), 2.02 (m, 1H), 2.59 (s, 3H), 2.82 (d, 2H), 4.00 (m, 4H), 5.70 (s, 2H), 6.90 (d, 2H), 6.97 (d, 2H), 7.46 (d, 2H), 7.57 (d, 2H), 9.44 (s, 1H) | DMSO-$d_6$ |

TABLE 1-continued

| No. | Chemical name | NMR data | Sol. |
|---|---|---|---|
| 46 | N-hydroxy-4-{5-[4-(5-cyclopentylmethyl-2-ethyl-1,3-thiazol-4-yl)phenoxy]pentyloxy}-benzamidine | 1.11 (m, 2H), 1.27 (t, 3H), 1.52 (brm, 6H), 1.70 (m, 2H), 1.78 (brm, 4H), 2.03 (m, 1H), 2.83 (d, 2H), 2.92 (q, 2H), 4.00 (m, 4H), 5.70 (s, 2H), 6.91 (d, 2H), 6.98 (d, 2H), 7.46 (d, 2H), 7.79 (d, 2H), 9.44 (s, 1H) | DMSO-$d_6$ |
| 47 | N-hydroxy-4-{5-[4-(5-cyclopentylmethyl-2-isopropyl-1,3-thiazol-4-yl)phenoxy]pentyloxy}-benzamidine | 1.11 (m, 2H), 1.31 (d, 6H), 1.49 (brm, 6H), 1.78 (brm, 6H), 2.04 (m, 1H), 2.83 (d, 2H), 3.21 (m, 1H), 4.01 (m, 4H), 5.72 (brs, 2H), 6.91 (d, 2H), 6.98 (d, 2H), 7.47 (d, 2H), 7.57 (d, 2H), 9.44 (s, 1H) | DMSO-$d_6$ |
| 48 | N-hydroxy-4-{5-[4-(5-cyclopentylmethyl-2-phenyl-1,3-thiazol-4-yl)phenoxy]pentyloxy}-benzamidine | 1.15 (m, 2H), 1.50 (brm, 6H), 1.78 (brm, 6H), 2.11 (m, 1H), 2.92 (d, 2H), 4.01 (m, 4H), 5.71 (s, 2H), 6.91 (d, 2H), 7.02 (d, 2H), 7.46 (m, 3H), 7.58 (m, 4H), 7.91 (dd, 2H), 9.44 (s, 1H) | DMSO-$d_6$ |
| 49 | N-hydroxy-4-{5-[4-(5-cyclopentylmethyl-2-pyridin-3-yl-1,3-thiazol-4-yl)phenoxy]pentyloxy}-benzamidine | 1.16 (m, 2H), 1.55 (brm, 6H), 1.78 (brm, 6H), 2.12 (m, 1H), 2.96 (d, 2H), 4.02 (m, 4H), 5.71 (brs, 2H), 6.91 (d, 2H), 7.04 (d, 2H), 7.52 (m, 1H), 7.58 (m, 4H), 8.26 (m, 1H), 8.64 (dd, 1H), 9.10 (d, 1H), 9.44 (s, 1H) | DMSO-$d_6$ |
| 50 | N-hydroxy-4-{5-[4-(5-cyclopentylmethyl-2-cyclohexyl-1,3-thiazol-4-yl)phenoxy]pentyloxy}-benzamidine | 1.10 (m, 2H), 1.23 (m, 1H), 1.46 (brm, 11H), 1.77 (brm, 8H), 2.02 (m, 3H), 2.83 (d, 2H), 2.90 (m, 1H), 4.00 (m, 4H), 5.71 (s, 2H), 6.91 (d, 2H), 6.97 (d, 2H), 7.46 (d, 2H), 7.57 (d, 2H), 9.44 (s, 1H) | DMSO-$d_6$ |
| 51 | N-hydroxy-4-{5-[4-(5-cyclopentylmethyl-2-pentyl-1,3-thiazol-4-yl)phenoxy]pentyloxy}-benzamidine | 0.85 (t, 3H), 1.10 (m, 2H), 1.31 (brm, 4H), 1.52 (brm, 6H), 1.58 (brm, 4H), 1.70 (brm, 4H), 2.03 (m, 1H), 2.83 (d, 2H), 2.89 (m, 2H), 4.01 (m, 4H), 5.71 (s, 2H), 6.91 (d, 2H), 6.98 (d, 2H), 7.46 (d, 2H), 7.57 (d, 2H), 9.44 (s, 1H) | DMSO-$d_6$ |
| 52 | 4-{5-[4-(2-methyl-1,3-thiazol-4-yl)phenoxy]pentyloxy}-benzamidine | 1.57 (brm, 2H), 1.79 (brm, 4H), 2.68 (s, 3H), 4.01 (t, 2H), 4.11 (t, 2H), 6.96 (d, 2H), 7.13 (d, 2H), 7.81 (m, 4H) | DMSO-$d_6$ |
| 53 | 4-{5-[4-(2-isopropyl-1,3-thiazol-4-yl)phenoxy]pentyloxy}-benzamidine | 1.35 (d, 6H), 1.56 (brm, 2H), 1.78 (brm, 4H), 3.30 (m, 1H), 4.02 (m, 4H), 6.95 (m, 4H) 7.77 (s, 1H), 7.83 (m, 4H) | DMSO-$d_6$ |
| 54 | 4-{5-[4-(2,5-dimethyl-1,3-thiazol-4-yl)phenoxy]pentyloxy}-benzamidine | 1.57 (brm, 2H), 1.79 (brm, 4H), 2.68 (s, 3H), 4.01 (t, 2H), 4.11 (t, 2H), 6.96 (d, 2H), 7.12 (d, 2H), 7.73 (s, 1H), 7.81 (m, 4H) | DMSO-$d_6$ |
| 55 | 4-{5-[4-(5-ethyl-2-isopropyl-1,3-thiazol-4-yl)phenoxy]pentyloxy}-benzamidine | 1.32 (d, 6H), 1.59 (m, 2H), 1.79 (m, 4H), 2.47 (s, 3H), 3.21 (m, 1H), 4.02 (t, 2H), 4.09 (t, 2H), 6.98 (d, 2H), 7.09 (d, 2H), 7.55 (d, 2H), 7.74 (d, 2H) | DMSO-$d_6$ |
| 56 | 4-{5-[4-(5-ethyl-2-phenyl-1,3-thiazol-4-yl)phenoxy]pentyloxy}-benzamidine | 1.29 (t, 3H), 1.59 (m, 2H), 1.81 (brm, 4H), 2.95 (q, 2H), 4.04 (t, 2H), 4.11 (t, 2H0, 7.03 (d, 2H), 7.15 (d, 2H), 7.47 (m, 3H), 7.59 (d, 2H), 7.84 (d, 2H), 7.91 (m, 2H) | DMSO-$d_6$ |
| 57 | N-hydroxy-4-{5-[4-(2-amino-1,3-thiazol-4-yl)phenoxy]pentyloxy}-benzamidine | 1.56 (m, 2H), 1.77 (m, 4H), 3.98 (m, 4H), 5.72 (s, 2H), 6.80-6.99 (m, 7H), 7.58 (d, 2H), 7.69 (d, 2H), 9.46 (s, 1H) | DMSO-$d_6$ |
| 58 | N-hydroxy-4-{5-[4-(2-amino-5-methyl-1,3-thiazol-4-yl)phenoxy]pentyloxy}-benzamidine | 1.57 (m, 2H), 1.77 (m, 4H), 2.27 (s, 3H), 3.99 (m, 4H), 5.72 (s, 2H), 6.70 (s, 2H), 6.91 (m, 4H), 7.45 (d, 2H), 7.57 (d, 2H), 9.44 (s, 1H) | DMSO-$d_6$ |
| 59 | N-hydroxy-4-{5-[4-(2-guanidino-5-methyl-1,3-thiazol-4-yl)phenoxy]pentyloxy}-benzamidine | 1.56 (m, 2H), 1.78 (m, 4H), 2.30 (s, 3H), 4.00 (t, 4H), 5.71 (s, 2H), 6.91 (d, 2H), 6.94 (d, 2H), 7.47 (d, 2H), 7.57 (d, 2H), 9.44 (s, 1H) | DMSO-$d_6$ |
| 60 | N-hydroxy-4-{5-[4-(2-amino-5-ethyl-1,3-thiazol-4-yl)phenoxy]pentyloxy}-benzamidine | 1.15 (t, 3H), 1.57 (m, 2H), 1.76 (m, 4H), 2.68 (q, 2H), 3.99 (m, 4H), 5.69 (s, 2H), 6.72 (s, 2H), 6.91 (m, 4H), 7.39 (d, 2H), 7.57 (d, 2H), 9.43 (s, 1H) | DMSO-$d_6$ |
| 61 | N-hydroxy-4-{5-[4-(2-amino-5-isopropyl-1,3- | 1.17 (d, 6H), 1.56 (m, 2H), 1.78 (m, 3H), 3.20 (m, 1H), 4.00 (m, 4H), 5.70 (brm, | DMSO-$d_6$ |

TABLE 1-continued

| No. | Chemical name | NMR data | Sol. |
|---|---|---|---|
|  | thiazol-4-yl)phenoxy]pentyloxy}-benzamidine | 1H), 6.91 (m, 4H), 7.35 (m, 2H), 7.57 (m, 2H), 9.43 (s, 1H) |  |
| 62 | N-hydroxy-4-{5-[4-(2-guanidino-5-isopropyl-1,3-thiazol-4-yl)phenoxy]pentyloxy}-benzamidine | 1.17 (d, 6H), 1.56 (brm, 2H), 1.77 (brm, 4H), 3.22 (m, 1H), 4.00 (m, 4H), 5.71 (s, 2H), 6.93 (m, 5H), 7.38 (d, 2H), 7.57 (d, 2H), 9.44 (s, 1H) | DMSO-$d_6$ |
| 63 | N-hydroxy-4-{5-[4-(2-amino-5-butyl-1,3-thiazol-4-yl)phenoxy]pentyloxy}-benzamidine | 0.83 (t, 3H), 1.30 (m, 2H), 1.48 (m, 2H), 1.56 (m, 2H), 1.77 (brm, 4H), 2.65 (t, 2H), 3.99 (m, 4H), 5.73 (brs, 2H), 6.72 (s, 2H), 6.91 (m, 4H), 7.38 (d, 2H), 7.57 (d, 2H), 9.45 (s, 1H) | DMSO-$d_6$ |
| 64 | N-hydroxy-4-{5-[4-(5-butyl-2-guanidino-1,3-thiazol-4-yl)phenoxy]pentyloxy}-benzamidine | 0.83 (t, 3H), 1.28 (m, 2H), 1.53 (m, 4H), 1.78 (m, 4H), 2.69 (m, 2H), 4.00 (m, 4H), 5.73 (brs, 2H), 6.91 (d, 2H), 6.95 (d, 2H), 7.42 (d, 2H), 7.57 (d, 2H), 9.45 (s, 1H) | DMSO-$d_6$ |
| 65 | N-hydroxy-4-{5-[4-(2-amino-5-benzyl-1,3-thiazol-4-yl)phenoxy]pentyloxy}-benzamidine | 1.55 (brm,, 2H), 1.77 (brm, 4H), 3.98 (m, 4H), 4.02 (s, 1H), 5.79 (s, 2H), 6.79 (s, 2H), 6.91 (m, 4H), 7.19 (m, 3H), 7.29 (m, 2H), 7.43 (d, 2H), 7.57 (d, 2H), 9.47 (s, 1H) | DMSO-$d_6$ |
| 66 | N-hydroxy-4-{5-[4-(5-benzyl-2-guanidino-1,3-thiazol-4-yl)phenoxy]pentyloxy}-benzamidine | 1.55 (m, 2H), 1.77 (brm, 4H), 4.99 (m, 4H), 4.05 (s, 2H), 5.71 (s, 2H), 4.92 (m, 4H), 7.19 (m, 3H), 7.29 (m, 2H), 7.45 (d, 2H), 7.57 (d, 2H), 9.44 (s, 1H) | DMSO-$d_6$ |
| 67 | N-hydroxy-4-{5-[4-(2-amino-5-cyclopentylmethyl-1,3-thiazol-4-yl)phenoxy]pentyloxy}-benzamidine | 1.09 (brm, 2H), 1.48 (brm, 4H), 1.56 (m, 2H), 1.69 (m, 2H), 1.77 (brm, 4H), 1.97 (m, 1H), 2.65 (d, 2H), 3.98 (m, 4H), 5.70 (s, 2H), 6.72 (s, 2H), 6.90 (m, 4H), 7.38 (d, 2H), 7.57 (d, 2H), 9.44 (s, 1H) | DMSO-$d_6$ |
| 68 | N-hydroxy-4-{5-[4-(5-cyclopentylmethyl-2-(1-propyl-piperidin-4-yl)-1,3-thiazol-4-yl)phenoxy]pentyloxy}-benzamidine | 0.84 (t, 3H), 1.11 (m, 2H), 1.43-1.78 (brm, 17H), 2.04 (m, 4H), 2.24 (m, 2H), 2.85 (m, 5H), 4.01 (m, 4H), 5.70 (s, 2H), 6.90 (d, 2H), 6.98 (d, 2H), 7.47 (d, 2H), 7.57 (d, 2H), 9.44 (s, 1H) | DMSO-$D_6$ |
| 69 | N-hydroxy-4-{5-[4-(2-(isobutyryl)amino-5-methyl-1,3-thiazol-4-yl)phenoxy]pentyloxy}-benzamidine | 1.11 (d, 6H), 1.59 (m, 2H), 1.79 (m, 4H), 2.42 (s, 3H), 2.72 (m, 1H), 4.02 (m, 4H), 5.72 (s, 2H), 6.93 (d, 2H), 7.00 (d, 2H), 7.56 (m, 4H), 9.45 (s, 1H), 12.00 (s, 1H) | DMSO-$d_6$ |
| 70 | N-hydroxy-4-{5-[4-(5-isopropyl-2-morpholinomethyl-1,3-thiazol-4-yl)phenoxy]pentyloxy}-benzamidine | 1.25 (d, 6H), 1.58 (m, 2H), 1.80 (m, 4H), 2.50 (m, 4H), 3.33 (m, 1H), 3.60 (m, 4H), 3.76 (s, 2H), 4.01 (m, 4H), 5.70 (s, 2H), 7.00 (m, 4H), 7.45 (d, 2H), 7.60 (d, 2H), 9.44 (s, 1H) | DMSO-$d_6$ |
| 71 | N-hydroxy-4-{5-[4-(2-aminomethyl-5-benzyl-1,3-thiazol-4-yl)phenoxy]pentyloxy}-benzamidine | 1.56 (m, 2H), 1.78 (brm, 4H), 3.92 (s, 2H), 4.00 (m, 4H), 4.21 (s, 2H), 5.70 (s, 2H), 6.90 (d, 2H), 6.97 (d, 2H), 7.21 (m, 3H), 7.30 (m, 2H), 7.52 (d, 2H), 7.57 (d, 2H), 9.44 (s, 1H) | DMSO-$d_6$ |
| 72 | N-hydroxy-4-{5-[4-(5-methyl-2-(1-propyl-piperidin-4-yl)-1,3-thiazol-4-yl)phenoxy]pentyloxy}-benzamidine | 0.84 (t, 3H), 1.42 (m, 2H), 1.56 (m, 2H), 1.67 (m, 2H), 1.78 (brm, 4H), 2.00 (m, 4H), 2.24 (m, 2H), 2.46 (s, 3H), 2.89 (m, 3H), 4.00 (m, 4H), 5.71 (m, 2H), 6.90 (d, 2H), 6.98 (d, 2H), 7.56 (m, 4H), 9.44 (s, 1H) | DMSO-$d_6$ |
| 73 | N-hydroxy-4-{5-[4-(5-isopropyl-2-aminomethyl-1,3-thiazol-4-yl)phenoxy]pentyloxy}-benzamidine | 1.25 (d, 6H), 1.57 (m, 2H), 1.79 (m, 4H), 3.35 (m, 1H), 3.96-4.04 (m, 6H), 5.74 (s, 2H), 6.91 (d, 2H), 6.98 (d, 2H), 7.43 (d, 2H), 7.58 (d, 2H) | DMSO-$d_6$ |
| 74 | N-hydroxy-4-{5-[4-(5-vinyl-2-methyl-1,3-thiazol-4-yl)phenoxy]pentyloxy}-benzamidine | 1.61 (m, 2H), 1.81 (m, 4H), 2.66 (s, 3H), 3.95 (m, 4H), 5.16 (S, 1H), 5.17 (d, 1H), 5.42 (d, 1H), 6.84 (m, 3H), 6.92 (d, 2H), 7.51 (d-d, 4H) | $CDCl_3$ |
| 75 | N-hydroxy-4-{5-[4-(5-hydroxymethyl-2-methyl-1,3-thiazol-4-yl)phenoxy]pentyloxy}-benzamidine | 1.58 (m, 2H), 1.79 (m, 4H), 2.63 (s, 3H), 4.01 (m, 4H), 4.12 (t, 1H), 4.67 (m, 2H), 5.70 (brs, 2H), 6.98 (m, 2H), 7.50 (m, 2H), 7.58 (m, 2H), 8.23 (s, 1H) | DMSO-$d_6$ |

TABLE 1-continued

| No. | Chemical name | NMR data | Sol. |
|---|---|---|---|
| 76 | N-hydroxy-4-{5-[4-(5-methoxymethyl-2-methyl-1,3-thiazol-4-yl)phenoxy]pentyloxy}-benzamidine | 1.57 (m, 2H), 1.80 (m, 4H), 2.65 (s, 3H), 3.32 (s, 3H), 4.01 (m, 4H), 4.58 (s, 2H), 6.93 (m, 2H), 7.01 (m, 2H), 7.56 (m, 4H), 9.45 (brs, 1H) | DMSO-$d_6$ |
| 77 | N-hydroxy-4-{5-[4-(5-(2-chloroethyl)-2-amino-1,3-thiazol-4-yl)phenoxy]pentyloxy}-benzamidine | 1.57 (m, 2H), 1.79 (m, 4H), 3.36 (m, 2H), 3.77 (m, 2H), 4.00 (m, 4H), 5.73 (s, 2H), 6.91 (m, 4H), 7.42 (d, 2H), 7.58 (d, 2H), 9.47 (s, 1H) | DMSO-$d_6$ |
| 78 | N-hydroxy-4-{5-[4-(5-vinyl-2-amino-1,3-thiazol-4-yl)phenoxy]pentyloxy}-benzamidine | 1.58 (m, 2H), 1.79 (m, 4H), 4.01 (m, 4H), 6.82-7.75 (m, 11H) | DMSO-$d_6$ |
| 79 | N-hydroxy-4-{5-[4-(5-vinyl-2-(pyridin-3-yl)-1,3-thiazol-4-yl)phenoxy]pentyloxy}-benzamidine | 1.59 (m, 2H), 1.81 (m, 4H), 4.05 (m, 4H), 5.44 (d, 1H), 5.71 (d, 1H), 5.85 (brs, 2H), 6.94 (m, 3H), 7.07 (m, 2H), 7.61 (m, 4H), 8.33 (m, 1H), 8.68 (m, 1H), 9.16 (brs, 1H), 9.52 (brs, 1H) | DMSO-$d_6$ |
| 80 | N-hydroxy-4-{5-[4-(5-(2-chloroethyl)-2-(pyridin-3-yl)-1,3-thiazol-4-yl)phenoxy]pentyloxy}-benzamidine | 1.60 (m, 2H), 1.81 (m, 4H), 3.44 (m, 2H), 3.94 (m, 2H), 4.02-4.06 (m, 4H), 5.75 (brs, 2H), 6.91 (m, 2H), 7.06 (m, 2H), 7.61 (m, 4H), 8.30 (m, 1H), 8.68 (m, 1H), 9.13 (m, 1H), 9.46 (m, 1H) | DMSO-$d_6$ |
| 81 | N-hydroxy-4-{5-[4-(2-amino-5-cyclopentyl-1,3-thiazol-4-yl)phenoxy]pentyloxy}-benzamidine | 1.40 (m, 2H), 1.55-1.59 (m, 4H), 1.77-1.81 (m, 6H), 2.01 (m, 2H), 3.22-3.31 (m, 1H), 4.00-4.02 (m, 4H), 5.72 (s, 2H), 6.92 (m, 4H), 7.57 (d, 2H), 7.83 (d, 2H) | DMSO-$d_6$ |
| 82 | N-hydroxy-4-{5-[4-(5-ethyl-2-aminomethyl-1,3-thiazol-4-yl)phenoxy]pentyloxy}-benzamidine | 1.21 (t, 3H), 1.58 (m, 2H), 1.78 (m, 4H), 2.85 (q, 2H), 3.93 (s, 2H), 4.00 (m, 4H), 5.70 (s, 2H), 6.90 (d, 2H), 6.97 (d, 2H), 7.48 (d, 2H), 7.58 (d, 2H), 9.43 (s, 1H) | |
| 83 | N-hydroxy-4-{5-[4-(5-isopropyl-2-(piperidin-3-yl)-1,3-thiazol-4-yl)phenoxy]pentyloxy}-benzamidine | 1.25 (d, 6H), 1.57 (m, 2H), 1.80 (m, 4H), 1.91 (m, 2H), 2.17 (m, 2H), 3.05 (m, 2H), 3.37 (m, 4H), 4.02-4.09 (m, 4H), 7.00 (d, 2H), 7.13 (d, 2H), 7.44 (d, 2H), 7.67 (d, 2H) | DMSO-$d_6$ |
| 84 | N-hydroxy-4-{5-[4-(2-ethylamino-1,3-thiazol-4-yl)phenoxy]pentyloxy}-benzamidine | 1.17 (t, 3H), 1.55 (brm, 2H), 1.77 (brm, 2H), 3.25 (m, 2H), 3.99 (m, 4H), 5.73 (s, 2H), 6.84 (s, 1H), 6.90 (m, 4H), 7.57 (d, 2H), 7.71 (d, 2H) | DMSO-$d_6$ |
| 85 | N-hydroxy-4-{5-[4-(2-ethanesulphonylamino-1,3-thiazol-4-yl)phenoxy]pentyloxy}-benzamidine | 1.20 (t, 3H), 1.55 (brm, 2H), 1.77 (brm, 4H), 3.02 (q, 2H), 4.00 (m, 4H), 5.77 (brm, 2H), 6.91 (d, 2H), 6.98 (d, 2H), 7.00 (s, 1H), 7.57 (d, 2H), 7.65 (d, 2H), 9.47 (brs, 1H), 12.86 (s, 1H) | DMSO-$d_6$ |
| 86 | N-hydroxy-4-{5-[4-(5-methyl-2-methylamino-1,3-thiazol-4-yl)phenoxy]pentyloxy}-benzamidine | 1.56 (m, 2H), 1.77 (m, 4H), 2.29 (s, 3H), 2.77 (d, 3H), 3.99 (m, 4H), 5.72 (s, 2H), 6.91 (m, 4H), 7.22 (m, 1H), 7.48 (d, 2H), 7.50 (d, 2H), 9.44 (s, 1H) | DMSO-$d_6$ |
| 87 | N-hydroxy-4-{5-[4-(2-ethylamino-5-methyl-1,3-thiazol-4-yl)phenoxy]pentyloxy}-benzamidine | 1.12 (t, 3H), 1.56 (m, 2H), 1.78 (m, 4H), 2.28 (s, 3H), 3.18 (p, 2H), 3.99 (t, 4H), 5.72 (s, 2H), 6.94 (m, 4H), 7.27 (t, 1H), 7.47 (d, 2H), 7.57 (d, 2H), 9.44 (s, 1H) | DMSO-$d_6$ |
| 88 | N-hydroxy-4-{5-[4-(5-methyl-2-propylamino-1,3-thiazol-4-yl)phenoxy]pentyloxy}-benzamidine | 0.89 (t, 3H), 1.54 (m, 4H), 1.78 (m, 4H), 2.28 (s, 3H), 3.12 (m, 2H), 3.99 (m, 4H), 5.72 (s, 1H), 6.92 (m, 4H), 7.32 (t, 1H) 7.47 (d, 2H), 7.57 (d, 2H), 9.44 (s, 1H) | |
| 89 | N-hydroxy-4-{5-[4-(5-cyclopentylmethyl-2-(3-pyridylcarbonyl)amino-1,3-thiazol-4-yl)phenoxy]pentyloxy}-benzamidine | 1.15 (m, 2H), 1.57 (brm, 6H), 1.77 (brm, 6H), 2.10 (m, 1H), 2.85 (d, 2H), 4.00 (m, 4H), 5.72 (brs, 2H), 6.91 (d, 2H), 7.00 (d, 2H), 7.51 (d, 2H), 7.58 (d, 2H), 7.38 (m, 1H), 8.40 (d, 1H), 8.77 (d, 1H), 9.19 (s, 1H), 9.44 (s, 1H), 12.83 (s, 1H) | DMSO-$d_6$ |
| 90 | N-hydroxy-4-{5-[4-(2-hydroxyacetylamino-5-methyl-1,3-thiazol-4-yl)phenoxy]pentyloxy}-benzamidine | 1.56 (brm, 2H), 1.78 (brm, 4H), 2.42 (s, 3H), 4.01 (m, 4H), 4.10 (d, 2H), 5.47 (t, 1H), 5.73 (brs, 2H), 6.92 (d, 2H), 6.98 (d, 2H), 7.55 (m, 4H), 9.45 (s, 1H), 11.67 (s, 1H) | DMSO-$d_6$ |

TABLE 1-continued

| No. | Chemical name | NMR data | Sol. |
|---|---|---|---|
| 91 | N-hydroxy-4-{5-[4-(5-methyl-2-(4-pyridylcarbonyl)amino-1,3-thiazol-4-yl)phenoxy]pentyloxy}-benzamidine | 1.57 (brm, 4H), 1.79 (brm, 4H), 2.48 (s, 3H), 4.02 (m, 4H), 5.73 (brm, 2H), 6.91 (d, 2H), 7.01 (d, 2H), 7.58 (m, 4H), 7.98 (dd, 2H), 8.78 (dd, 2H), 9.45 (s, 1H) | DMSO-$d_6$ |
| 92 | N-hydroxy-4-{5-[4-(5-methyl-2-(3-pyridylcarbonyl)amino-1,3-thiazol-4-yl)phenoxy]pentyloxy}-benzamidine | 1.58 (m, 2H), 1.79 (m, 4H), 2.46 (s, 3H), 4.01 (m, 4H), 5.74 (s, 2H), 6.91 (d, 2H), 7.00 (d, 2H), 7.57 (m, 4H), 8.41 (d, 1H), 8.77 (d, 1H), 9.20 (d, 1H), 9.46 (brs, 1H), 12.80 (brs, 1H) | DMSO-$d_6$ |
| 93 | N-hydroxy-4-{5-[4-(2-ethanesulphonylamino-5-methyl-1,3-thiazol-4-yl)phenoxy]pentyloxy}-benzamidine | 0.94 (t, 3H), 1.56 (m, 2H), 1.78 (brm, 4H), 2.18 (s, 3H), 2.98 (q, 2H), 4.01 (m, 4H), 5.73 (s, 2H), 6.90 (d, 2H), 7.01 (d, 2H), 7.38 (d, 2H), 7.57 (d, 2H), 9.44 (s, 1H), 12.52 (s, 1H) | DMSO-$d_6$ |
| 94 | N-hydroxy-4-{5-[4-(2-(2-methoxyethyl)amino-5-methyl-1,3-thiazol-4-yl)phenoxy]pentyloxy}-benzamidine | 1.58 (m, 2H), 1.80 (m, 4H), 2.30 (s, 3H), 3.26 (s, 3H), 3.39 (m, 2H), 3.37 (m, 2H), 4.01 (m, 4H), 5.71 (s, 2H), 6.90 (d, 2H), 6.96 (d, 2H), 7.48 (d, 2H), 7.58 (d, 2H), 9.44 (s, 1H) | DMSO-$d_6$ |
| 95 | N-hydroxy-4-{5-[4-(2-ethanesulphonylamino-5-ethyl-1,3-thiazol-4-yl)phenoxy]pentyloxy}-benzamidine | 1.13 (t, 3H), 1.21 (t, 3H), 1.57 (m, 2H), 1.78 (brm, 4H), 2.59 (q, 2H), 2.99 (q, 2H), 4.01 (m, 4H), 5.70 (s, 2H), 6.90 (s, 2H), 7.01 (d, 2H), 7.35 (d, 2H), 7.57 (d, 2H), 9.43 (s, 1H), 12.50 (brs, 1H) | DMSO-$d_6$ |
| 96 | N-hydroxy-4-{5-[4-(5-ethyl-2-methylamino-1,3-thiazol-4-yl)phenoxy]pentyloxy}-benzamidine | 1.15 (t, 3H), 1.57 (m, 2H), 1.78 (m, 4H), 2.70 (q, 2H), 2.78 (d, 3H), 3.99 (m, 4H), 5.80 (brs, 2H), 6.92 (m, 4H), 7.25 (q, 1H), 7.42 (d, 2H), 7.58 (d, 2H), 9.48 (s, 1H) | DMSO-$d_6$ |
| 97 | N-hydroxy-4-{5-[4-(5-ethyl-2-ethylamino-1,3-thiazol-4-yl)phenoxy]pentyloxy}-benzamidine | 1.41 (m, 6H), 1.57 (m, 2H), 1.78 (t, 4H), 2.69 (q, 2H), 3.19 (q, 2H), 3.99 (t, 4H), 5.69 (s, 2H), 6.92 (m, 4H), 7.30 (t, 1H), 7.41 (d, 2H), 7.57 (d, 2H), 9.43 (s, 1H) | DMSO-$d_6$ |
| 98 | N-hydroxy-4-{5-[4-(5-ethyl-2-propylamino-1,3-thiazol-4-yl)phenoxy]pentyloxy}-benzamidine | 0.89 (t, 3H), 1.15 (t, 3H), 1.55 (brm, 4H), 1.77 (brm, 4H), 2.68 (q, 2H), 3.12 (m, 2H), 3.98 (m, 4H), 5.72 (s, 2H), 6.92 (m, 4H), 7.35 (t, 1H), 7.40 (d, 2H), 7.57 (d, 2H), 9.44 (s, 1H) | DMSO-$d_6$ |
| 99 | N-hydroxy-4-{5-[4-(5-ethyl-2-methoxyacetylamino-1,3-thiazol-4-yl)phenoxy]pentyloxy}-benzamidine | 1.23 (t, 3H), 1.57 (m, 2H), 1.78 (brm, 4H), 2.84 (q, 2H), 3.33 (s, 3H), 4.00 (m, 4H), 4.11 (s, 2H), 5.70 (s, 2H), 6.90 (d, 2H), 6.98 (d, 2H), 7.47 (d, 2H), 7.82 (d, 2H), 9.43 (s, 1H), 11.96 (s, 1H) | DMSO-$d_6$ |
| 100 | N-hydroxy-4-{5-[4-(5-ethyl-2-(4-pyridylcarbonyl)amino-1,3-thiazol-4-yl)phenoxy]pentyloxy}-benzamidine | 1.26 (t, 3H), 1.57 (m, 2H), 1.79 (brm, 4H), 2.88 (q, 2H), 4.00 (m, 4H), 5.74 (s, 2H), 6.91 (d, 2H), 7.01 (d, 2H), 7.52 (d, 2H), 7.55 (d, 2H), 7.98 (d, 2H), 8.79 (d, 2H), 9.45 (s, 1H), 12.92 (s, 1H) | DMSO-$d_6$ |
| 101 | N-hydroxy-4-{5-[4-(5-ethyl-2-(3-pyridylcarbonyl)amino-1,3-thiazol-4-yl)phenoxy]pentyloxy}-benzamidine | 1.26 (t, 3H), 1.57 (brm, 2H), 1.79 (brm, 4H), 2.88 (q, 2H), 4.00 (m, 4H), 5.71 (brs, 2H), 6.91 (d, 2H), 7.01 (d, 2H), 7.56 (m, 5H), 8.40 (m, 1H), 8.77 (dd, 1H), 9.20 (d, 1H), 9.43 (s, 1H), 12.82 (s, 1H) | DMSO-$d_6$ |
| 102 | N-hydroxy-4-{5-[4-(5-ethyl-2-(2-methoxyethyl)amino-1,3-thiazol-4-yl)phenoxy]pentyloxy}-benzamidine | 1.14 (t, 3H), 1.60 (m, 2H), 1.78 (m, 4H), 2.69 (m, 2H), 3.26 (s, 3H), 3.40 (m, 2H), 3.38 (m, 2H), 4.02 (m, 4H), 5.67 (s, 2H), 5.75 (s, 1H), 6.90~7.00 (m, 4H), 7.40 (d, 2H), 7.58 (d, 2H), 9.45 (s, 1H) | DMSO-$d_6$ |
| 103 | N-hydroxy-4-{5-[4-(5-isopropyl-2-methylamino-1,3-thiazol-4-yl)phenoxy]pentyloxy}-benzamidine | 1.17 (d, 6H), 1.56 (brm, 2H), 1.77 (brm, 2H), 2.77 (d, 3H), 3.21 (m, 1H), 5.72 (s, 2H), 6.91 (d, 2H), 6.94 (d, 2H), 7.25 (m, 1H), 7.38 (d, 2H), 7.57 (d, 2H), 9.44 (s, 1H) | DMSO-$d_6$ |
| 104 | N-hydroxy-4-{5-[4-(2-ethylamino-5-isopropyl-1,3-thiazol-4-yl)phenoxy]pentyloxy}-benzamidine | 0.85 (m, 3H), 1.17 (d, 6H), 1.58 (m, 2H), 1.82 (m, 4H), 3.20 (m, 3H), 4.04 (m, 4H), 6.95 (m, 4H), 7.39 (m, 2H), 7.82 (m, 2H) | DMSO-$d_6$ |

TABLE 1-continued

| No. | Chemical name | NMR data | Sol. |
|---|---|---|---|
| 105 | N-hydroxy-4-{5-[4-(5-butyl-2-methylamino-1,3-thiazol-4-yl)phenoxy]pentyloxy}-benzamidine | 0.83 (t, 3H), 1.30 (m, 2H), 1.48 (m, 2H), 1.56 (m, 2H), 1.77 (m, 4H), 2.67 (t, 2H), 2.78 (d, 3H), 4.01 (m, 4H), 5.72 (brs, 2H), 6.92 (m, 4H), 7.26 (m, 1H), 7.41 (d, 2H), 7.58 (d, 2H), 9.44 (s, 1H) | DMSO-$d_6$ |
| 106 | N-hydroxy-4-{5-[4-(5-butyl-2-ethylamino-1,3-thiazol-4-yl)phenoxy]pentyloxy}-benzamidine | 0.83 (t, 3H), 1.13 (t, 3H), 1.28 (m, 2H), 1.53 (m, 4H), 1.78 (m, 4H), 2.64 (t, 2H), 3.18 (m, 2H), 3.99 (m, 4H), 5.75 (brs, 2H), 6.92 (m, 4H), 7.31 (t, 1H), 7.40 (d, 2H), 7.57 (d, 2H), 9.46 (s, 1H) | DMSO-$d_6$ |
| 107 | N-hydroxy-4-{5-[4-(5-benzyl-2-methylamino-1,3-thiazol-4-yl)phenoxy]pentyloxy}-benzamidine | 1.55 (m, 2H), 1.76 (brm, 4H), 2.77 (d, 3H), 3.98 (m, 4H), 4.03 (s, 2H), 5.72 (brs, 2H), 6.91 (m, 4H), 7.20 (m, 3H), 7.29 (m, 3H), 7.46 (d, 2H), 7.57 (d, 2H), 9.44 (s, 1H) | DMSO-$d_6$ |
| 108 | N-hydroxy-4-{5-[4-(5-benzyl-2-ethylamino-1,3-thiazol-4-yl)phenoxy]pentyloxy}-benzamidine | 1.14 (t, 3H), 1.55 (m, 2H), 1.77 (brm, 4H), 3.18 (m, 2H), 4.00 (m, 4H), 4.03 (s, 2H), 6.94 (m, 4H), 7.17 (m, 3H), 7.29 (m, 2H), 7.39 (t, 1H), 7.45 (d, 2H), 7.58 (d, 2H), 9.64 (s, 1H) | DMSO-$d_6$ |
| 109 | N-hydroxy-4-{5-[4-(5-cyclopentylmethyl-2-methylamino-1,3-thiazol-4-yl)phenoxy]pentyloxy}-benzamidine | 1.10 (brm, 2H), 1.49 (brm, 4H), 1.56 (m, 2H), 1.69 (m, 2H), 1.78 (m, 4H), 1.97 (m, 1H), 2.66 (d, 2H), 2.78 (d, 3H), 3.99 (m, 4H), 5.71 (s, 2H), 6.92 (m, 4H), 7.25 (m, 1H), 7.40 (d, 2H), 7.57 (d, 2H), 9.44 (s, 1H) | DMSO-$d_6$ |
| 110 | N-hydroxy-4-{5-[4-(5-cyclopentylmethyl-2-ethylamino-1,3-thiazol-4-yl)phenoxy]pentyloxy}-benzamidine | 1.13 (m, 5H), 1.49 (m, 6H), 1.69 (m, 2H), 1.77 (m, 4H), 1.97 (m, 1H), 2.66 (d, 2H), 3.19 (m, 2H), 3.99 (m, 4H), 5.70 (s, 2H), 6.91 (m, 4H), 7.29 (t, 1H), 7.40 (d, 2H), 7.57 (d, 2H), 9.44 (s, 1H) | DMSO-$d_6$ |
| 111 | N-hydroxy-4-{5-[4-(5-cyclopentylmethyl-2-propylamino-1,3-thiazol-4-yl)phenoxy]pentyloxy}-benzamidine | 0.88 (t, 3H), 1.10 (brm, 2H), 1.55 (brm, 8H), 1.77 (brm, 6H), 1.97 (m, 1H), 2.65 (d, 2H), 3.11 (m, 2H), 3.99 (m, 4H), 5.70 (s, 2H), 6.90 (d, 2H), 6.92 (d, 2H), 7.33 (t, 1H), 7.39 (d, 2H), 7.57 (d, 2H), 9.44 (s, 1H) | DMSO-$d_6$ |
| 112 | N-hydroxy-4-{5-[4-(5-cyclopentylmethyl-2-(4-pyridylcarbonyl)amino-1,3-thiazol-4-yl)phenoxy]pentyloxy}-benzamidine | 1.55 (m, 2H), 1.49 (brm, 6H), 1.77 (brm, 6H), 2.10 (m, 1H), 2.86 (d, 2H), 4.00 (m, 4H), 5.74 (s, 2H), 6.91 (d, 2H), 7.01 (d, 2H), 7.51 (d, 2H), 7.58 (d, 2H), 7.97 (d, 2H), 8.79 (d, 2H), 9.46 (s, 1H), 12.91 (s, 1H) | DMSO-$d_6$ |
| 113 | N-hydroxy-4-{5-[4-(5-cyclopentyl-2-propylamino-1,3-thiazol-4-yl)phenoxy]pentyloxy}-benzamidine | 0.89 (t, 3H), 1.55-1.62 (m, 8H), 1.77-1.80 (m, 8H), 3.31-3.37 (m, 3H), 4.00-4.02 (m, 4H), 6.90-7.05 (m, 4H), 7.39-7.80 (m, 4H) | DMSO-$d_6$ |
| 114 | N-hydroxy-4-{5-[4-(5-isopropyl-2-[(pyridin-3-ylmethyl)amino]-1,3-thiazol-4-yl)phenoxy]pentyloxy}-benzamidine | 0.82 (d, 6H), 1.17-1.25 (m, 2H), 1.78-1.80 (m, 4H), 3.25 (m, 1H), 3.37 (s, 2H), 4.01 (m, 4H), 6.94-7.83 (m, 12H) | DMSO-$d_6$ |
| 115 | N-hydroxy-4-{5-[4-(5-(2-chloroethyl)-2-methylamino-1,3-thiazol-4-yl)phenoxy]pentyloxy}-benzamidine | 1.58 (m, 2H), 1.80 (m, 4H), 2.81 (s, 3H), 3.13 (m, 2H), 3.78 (m, 2H), 4.01 (m, 4H), 5.73 (m, 2H), 6.93 (m, 4H), 7.44 (m, 2H), 7.59 (m, 2H), 9.46 (s, 1H) | DMSO-$d_6$ |
| 116 | N-hydroxy-4-{5-[4-(2-methylamino-1,3-thiazol-4-yl)phenoxy]pentyloxy}-benzamidine | 1.57 (m, 2H), 1.77-1.81 (m, 4H), 2.86 (d, 3H), 3.99-4.01 (m, 4H), 5.72 (s, 2H), 6.88-6.93 (m, 5H), 7.59 (d, 2H), 7.74 (d, 2H), 9.46 (s, 1H) | DMSO-$d_6$ |
| 117 | N-hydroxy-4-{5-[4-(5-ethyl-2-(pyridin-3-ylmethyl)amino-1,3-thiazol-4-yl)phenoxy]pentyloxy}-benzamidine | 1.24 (t, 3H), 1.57 (m, 2H), 1.79 (m, 4H), 2.87 (q, 2H), 3.79 (s, 2H), 3.91 (s, 2H), 4.02 (m, 4H), 5.74 (s, 1H), 6.94 (d-d, 4H), 7.35 (m, 1H), 7.48 (d, 2H), 7.77 (d, 1H), 7.82 (d, 2H), 8.45 (d, 1H), 8.54 (s, 1H) | DMSO-$d_6$ |
| 118 | N-hydroxy-4-{5-[4-(2-(ethanesulphonyl-methyl-amino)-1,3- | 1.20 (t, 3H), 1.57 (m, 2H), 1.79 (m, 4H), 3.50 (m, 5H), 4.01 (m, 4H), 5.71 (s, 2H), 6.96 (m, 4H), 7.55 (m, 2H), 7.81 (m, 3H), | DMSO-$d_6$ |

TABLE 1-continued

| No. | Chemical name | NMR data | Sol. |
|---|---|---|---|
| | thiazol-4-yl)phenoxy]pentyloxy}-benzamidine | 9.44 (s, 1H) | |
| 119 | N-hydroxy-4-[5-(4-{2-[methyl-(2-morpholinoethyl)amino]-1,3-thiazol-4-yl}phenoxy)pentyloxy]-benzamidine | 1.56 (brm, 2H), 1.78 (brm, 4H), 2.43 (m, 4H), 2.55 (m, 2H), 3.05 (s, 3H), 3.52 (m, 4H), 3.60 (m, 2H), 3.99 (brm, 4H), 5.70 (s, 2H), 6.91 (m, 4H), 6.95 (s, 1H), 7.57 (d, 2H), 7.73 (d, 2H), 9.44 (s, 1H) | DMSO-$d_6$ |
| 120 | N-hydroxy-4-[5-(4-{2-[(2-hydroxyethyl)-methyl-amino]-5-methyl-1,3-thiazol-4-yl}phenoxy)pentyloxy]-benzamidine | 1.56 (m, 2H), 1.78 (brm, 4H), 2.31 (s, 3H), 3.02 (s, 3H), 3.44 (t, 2H), 3.59 (q, 2H), 4.00 (t, 4H), 4.79 (t, 1H), 5.71 (s, 2H), 6.90 (d, 2H), 6.94 (d, 2H), 7.48 (d, 2H), 7.57 (d, 2H), 9.43 (s, 1H) | DMSO-$d_6$ |
| 121 | N-hydroxy-4-[5-(4-{2-[ethyl-(2-hydroxyethyl)-amino]-5-methyl-1,3-thiazol-4-yl}phenoxy)pentyloxy]-benzamidine | 1.14 (t, 3H), 1.56 (m, 2H), 1.78 (brm, 4H), 2.31 (s, 3H), 3.41 (m, 4H), 3.58 (m, 2H), 4.00 (m, 4H), 4.82 (t, 1H), 5.73 (s, 2H), 6.91 (d, 2H), 6.94 (d, 2H), 7.48 (d, 2H), 7.57 (d, 2H), 9.45 (s, 1H) | DMSO-$d_6$ |
| 122 | N-hydroxy-4-[5-(4-{2-[bis-(2-methoxyethyl)-amino]-5-methyl-1,3-thiazol-4-yl}phenoxy)pentyloxy]-benzamidine | 1.59 (m, 2H), 1.79 (m, 4H), 2.32 (s, 3H), 3.26 (s, 6H), 3.55 (s, 8H), 4.03 (m, 4H), 5.70 (s, 2H), 6.91 (d, 2H), 6.95 (d, 2H), 7.49 (d, 2H), 7.82 (d, 2H), 9.44 (s, 1H) | DMSO-$d_6$ |
| 123 | N-hydroxy-4-[5-(4-{5-methyl-2-[methyl-(2-morpholinoethyl)-amino]-1,3-thiazol-4-yl}phenoxy)pentyloxy]-benzamidine | 1.56 (m, 2H), 1.77 (brm, 4H), 2.32 (s, 3H), 2.41 (brm, 4H), 2.51 (m, 2H), 2.99 (s, 3H), 3.51 (brm, 4H), 3.99 (t, 4H), 5.70 (s, 2H), 6.90 (d, 2H), 6.94 (d, 2H), 7.48 (d, 2H), 7.57 (d, 2H), 9.44 (s, 1H) | DMSO-$d_6$ |
| 124 | N-hydroxy-4-[5-(4-{2-[ethyl-1-(2-morpholinoethyl)-amino]-5-methyl-1,3-thiazol-4-yl}phenoxy)pentyloxy]-benzamidine | 1.15 (t, 3H), 1.56 (m, 2H), 1.77 (brm, 4H), 2.31 (s, 3H), 2.42 (brm, 4H), 2.52 (m, 2H), 3.40 (m, 2H), 3.49 (m, 2H), 3.54 (brm, 4H), 3.99 (m, 4H), 5.71 (brs, 2H), 6.90 (d, 2H), 6.94 (d, 2H), 7.48 (d, 2H), 7.57 (d, 2H), 9.44 (s, 1H) | DMSO-$d_6$ |
| 125 | N-hydroxy-4-{5-[2-(benzyl-methyl-amino)-5-methyl-1,3-thiazol-4-yl]phenoxy)pentyloxy}-benzamidine | 1.57 (m, 2H), 1.77 (brm, 4H), 2.29 (s, 3H), 2.98 (s, 3H), 3.99 (m, 4H), 4.64 (s, 2H), 5.70 (s, 2H), 6.90 (d, 2H), 6.94 (d, 2H), 7.30 (m, 5H), 7.51 (d, 2H), 7.57 (d, 2H), 9.44 (s, 1H) | DMSO-$d_6$ |
| 126 | N-hydroxy-4-[5-{4-[5-methyl-2-(methyl-pyridin-3-yl-methyl-amino)-1,3-thiazol-4-yl]phenoxy}pentyloxy]-benzamidine | 1.56 (brm, 2H), 1.77 (brm, 4H), 2.33 (s, 3H), 3.00 (s, 3H), 4.00 (m, 4H), 4.68 (s, 2H), 5.71 (s, 2H), 6.90 (d, 2H), 6.95 (d, 2H), 7.36 (m, 1H), 7.51 (d, 2H), 7.57 (d, 2H), 7.72 (d, 1H), 8.48 (d, 1H), 8.55 (s, 1H), 9.44 (s, 1H) | DMSO-$d_6$ |
| 127 | N-hydroxy-4-{5-{4-[2-(benzyl-ethyl-amino)-5-methyl-1,3-thiazol-4-yl]phenoxy}pentyloxy]-benzamidine | 1.12 (t, 3H), 1.56 (brm, 2H), 1.77 (brm, 4H), 2.31 (s, 3H), 3.40 (q, 2H), 3.99 (m, 4H), 4.62 (s, 2H), 5.71 (s, 2H), 6.90 (d, 2H), 6.94 (d, 2H), 7.26 (m, 1H), 7.31 (m, 4H) 7.50 (d, 2H), 7.57 (d, 2H), 9.44 (s, 1H) | DMSO-$d_6$ |
| 128 | N-hydroxy-4-[5-(4-{2-[bis-(2-hydroxyethyl)-amino]-5-methyl-1,3-thiazol-4-yl}phenoxy)pentyloxy]-benzamidine | 1.57 (m, 2H), 1.80 (m, 4H), 2.24 (s, 3H), 3.0~4.5 (brs, 2H), 3.67 (s, 8H), 4.05 (m, 4H), 5.72 (s, 2H), 7.03 (d, 2H), 7.12 (d, 2H), 7.44 (d, 2H), 7.82 (d, 2H), 9.45 (s, 1H) | DMSO-$d_6$ |
| 129 | N-hydroxy-4-[5-(4-{5-ethyl-2-[(2-hydroxyethyl)-methyl-amino]-1,3-thiazol-4-yl}phenoxy)pentyloxy]-benzamidine | 1.17 (t, 3H), 1.57 (m, 2H), 1.78 (brm, 4H), 2.72 (q, 2H), 3.03 (s, 3H), 3.45 (m, 2H), 3.59 (m, 2H), 4.01 (m, 4H), 4.79 (t, 1H), 5.70 (s, 2H), 6.90 (d, 2H), 6.96 (d, 2H), 7.42 (d, 2H), 7.57 (d, 2H), 9.43 (s, 1H) | DMSO-$d_6$ |
| 130 | N-hydroxy-4-[5-(4-{5-ethyl-2-[ethyl-(2-hydroxyethyl)-amino]-1,3-thiazol-4-yl}phenoxy)pentyloxy]-benzamidine | 1.15 (m, 6H), 1.56 (brm, 2H), 1.76 (brm, 4H), 2.71 (q, 2H), 3.43 (m, 4H), 4.00 (t, 4H), 4.81 (t, 1H), 5.70 (s, 2H), 6.90 (d, 2H), 6.94 (d, 2H), 7.42 (d, 2H), 7.81 (d, 2H), 9.43 (s, 1H) | DMSO-$d_6$ |
| 131 | N-hydroxy-4-[5-(4-{5-ethyl-2-[methyl-(2-morpholinoethyl)- | 1.17 (t, 3H), 1.56 (m, 2H), 1.77 (m, 4H), 2.41 (brm, 4H), 2.51 (m, 2H), 2.72 (q, 2H), 3.00 (s, 3H), 3.53 (brm, 6H), | DMSO-$d_6$ |

TABLE 1-continued

| No. | Chemical name | NMR data | Sol. |
|---|---|---|---|
| | amino]-1,3-thiazol-4-yl}phenoxy)pentyloxy]-benzamidine | 3.99 (t, 4H), 5.70 (s, 2H), 6.90 (d, 2H), 6.94 (d, 2H), 7.42 (d, 2H), 7.57 (d, 2H), 9.43 (s, 1H) | |
| 132 | N-hydroxy-4-[5-(4-{5-ethyl-2-[ethyl-(2-morpholinoethyl)-amino]-1,3-thiazol-4-yl}phenoxy)pentyloxy]-benzamidine | 1.15 (m, 6H), 1.56 (m, 2H), 1.78 (brm, 4H), 2.42 (brm, 4H), 2.51 (m, 2H), 2.70 (q, 2H), 3.40 (m, 2H), 3.48 (m, 2H), 3.53 (brm, 4H), 4.00 (m, 4H), 5.70 (s, 2H), 6.90 (d, 2H), 6.94 (d, 2H), 7.42 (d, 2H), 7.57 (d, 2H), 9.43 (s, 1H) | DMSO-$d_6$ |
| 133 | N-hydroxy-4-[5-{4-[2-(benzyl-methyl-amino)-5-ethyl-1,3-thiazol-4-yl]phenoxy}pentyloxy]-benzamidine | 1.17 (t, 3H), 1.57 (brm, 2H), 1.77 (brm, 4H), 2.74 (q, 2H), 2.98 (s, 3H), 3.99 (m, 4H), 4.64 (s, 2H), 5.71 (s, 2H), 6.90 (d, 2H), 6.94 (d, 2H), 7.30 (m, 5H), 7.45 (d, 2H), 7.57 (d, 2H), 9.44 (s, 1H) | DMSO-$d_6$ |
| 134 | N-hydroxy-4-[5-(4-{5-ethyl-2-[methyl-(pyridin-3-ylmethyl)amino]-1,3-thiazol-4-yl}phenoxy)pentyloxy]-benzamidine | 1.18 (t, 3H), 1.56 (m, 2H), 1.77 (brm, 4H), 2.74 (q, 2H), 3.01 (s, 3H), 3.99 (t, 4H), 4.69 (s, 2H), 5.70 (s, 2H), 5.90 (d, 2H), 6.95 (d, 2H), 7.37 (m, 1H), 7.45 (d, 2H), 7.57 (d, 2H), 7.72 (d, 1H), 8.47 (d, 1H), 8.55 (s, 1H), 9.43 (s, 1H) | DMSO-$d_6$ |
| 135 | N-hydroxy-4-(5-{4-[2-(benzyl-ethyl-amino)-5-ethyl-1,3-thiazol-4-yl]phenoxy}pentyloxy)-benzamidine | 1.15 (m, 6H), 1.56 (m, 2H), 1.76 (brm, 4H), 2.73 (q, 2H), 3.41 (q, 2H), 3.99 (t, 4H), 4.63 (s, 2H), 5.70 (s, 2H), 6.90 (d, 2H), 6.94 (d, 2H), 7.25 (m, 1H), 7.32 (m, 4H) 7.44 (d, 2H), 7.57 (d, 2H), 9.43 (s, 1H) | DMSO-$d_6$ |
| 136 | N-hydroxy-4-{5-(4-[5-ethyl-2-(ethyl-[pyridin-3-ylmethyl]amino)-1,3-thiazol-4-yl]phenoxy)pentyloxy}-benzamidine | 1.15 (m, 6H), 1.56 (m, 2H), 1.76 (m, 4H), 2.73 (q, 2H), 3.44 (q, 2H), 3.99 (t, 4H), 4.66 (s, 2H), 5.70 (s, 2H), 5.74 (s, 1H), 6.90 (d, 2H), 6.94 (d, 2H), 7.36 (m, 1H), 7.43 (d, 2H), 7.57 (d, 2H), 7.73 (d, 2H), 8.46 (d, 1H), 8.56 (d, 1H), 9.44 (s, 1H) | DMSO-$d_6$ |
| 137 | N-hydroxy-4-[5-(4-{2-[bis-(pyridin-3-ylmethyl)amino]-5-ethyl-1,3-thiazol-4-yl}phenoxy)pentyloxy]-benzamidine | 1.15 (t, 3H), 1.56 (brm, 2H), 1.79 (brm, 4H), 2.73 (q, 2H), 3.99 (t, 2H), 4.09 (t, 2H), 4.91 (s, 4H), 6.95 (d, 2H), 7.14 (d, 2H), 7.41 (d, 2H), 7.67 (d, 2H), 7.82 (m, 2H), 8.26 (m, 2H), 8.73 (m, 2H), 8.79 (s, 2H). | DMSO-$d_6$ |
| 138 | N-hydroxy-4-{5-[4-(2-dipropylamino-5-ethyl-1,3-thiazol-4-yl)phenoxy]pentyloxy}-benzamidine | 0.86 (t, 6H), 1.17 (t, 3H), 1.59 (brm, 6H), 1.77 (brm, 4H), 2.71 (q, 2H), 3.30 (m, 4H), 3.99 (m, 4H), 5.71 (brs, 2H), 6.91 (d, 2H), 6.94 (d, 2H), 7.42 (d, 2H), 7.57 (d, 2H), 9.44 (s, 1H) | DMSO-$d_6$ |
| 139 | N-hydroxy-4-[5-(4-{2-[bis-(2-hydroxyethyl)amino]-5-ethyl-1,3-thiazol-4-yl}phenoxy)pentyloxy]-benzamidine | 1.17 (t, 3H), 1.57 (brm, 2H), 1.77 (brm, 4H), 2.71 (q, 2H), 3.48 (m, 4H), 3.63 (m, 4H), 3.99 (m, 4H), 4.87 (t, 2H), 5.69 (s, 2H), 6.90 (d, 2H), 6.94 (d, 2H), 7.41 (d, 2H), 7.57 (d, 2H), 9.43 (s, 1H) | DMSO-$d_6$ |
| 140 | N-hydroxy-4-[5-(4-{2-[(2-hydroxyethyl)-methyl-amino]-5-isopropyl-1,3-thiazol-4-yl}phenoxy)pentyloxy]-benzamidine | 1.26 (d, 6H), 1.57 (m, 2H), 1.79 (m, 4H), 3.33 (m, 5H), 3.47 (m, 1H), 3.61 (m, 2H), 4.00 (m, 4H), 5.72 (s, 2H), 6.90~7.00 (b, 4H), 7.45 (d, 2H), 7.57 (d, 2H), 9.45 (s, 1H) | DMSO-$d_6$ |
| 141 | N-hydroxy-4-[5-(4-{5-isopropyl-2-[methyl-(pyridin-3-ylmethyl)amino]-1,3-thiazol-4-yl}phenoxy)pentyloxy]-benzamidine | 1.20 (d, 6H), 1.56 (m, 2H), 1.79 (m, 4H), 3.01 (s, 3H), 3.24 (m, 1H), 3.32 (s, 2H), 4.00 (m, 4H), 5.70 (s, 2H), 6.90 (b, 4H), 7.40 (b, 3H), 7.57 (d, 2H), 7.92 (m, 1H), 8.47~8.56 (b, 2H), 9.43 (s, 1H) | DMSO-$d_6$ |
| 142 | N-hydroxy-4-(5-{4-[2-(ethanesulphonyl-methyl-amino)-5-isopropyl-1,3-thiazol-4-yl]phenoxy}pentyloxy)-benzamidine | 1.24 (m, 9H), 1.56 (brm, 2H), 1.79 (brm, 4H), 3.41 (s, 3H), 3.46 (q, 2H), 4.00 (m, 4H), 5.74 (s, 2H), 6.91 (d, 2H), 6.95 (d, 2H), 7.45 (d, 2H), 7.57 (d, 2H), 9.45 (s, 1H) | DMSO-$d_6$ |
| 143 | N-hydroxy-4-[5-(4-{5-butyl-2-[(2-hydroxyethyl)-methyl-amino]-1,3-thiazol-4-yl}phenoxy)pentyloxy]-benzamidine | 0.84 (t, 3H), 1.32 (m, 2H), 1.54 (m, 4H), 1.78 (m, 4H), 2.70 (t, 2H), 3.303 (s, 3H), 3.46 (t, 2H), 3.54 (m, 2H), 4.01 (m, 4H), 5.71 (s, 2H), 6.91 (d, 2H), 6.94 (d, 2H), 7.42 (d, 2H), 7.58 (d, 2H), 9.46 (s, 1H) | DMSO-$d_6$ |

TABLE 1-continued

| No. | Chemical name | NMR data | Sol. |
|---|---|---|---|
| 144 | N-hydroxy-4-[5-(4-{5-butyl-2-[methyl-(2-morpholinoethyl)amino]-1,3-thiazol-4-yl}phenoxy)pentyloxy]-benzamidine | 0.83 (t, 3H), 1.30 (m, 2H), 1.53 (m, 4H), 1.77 (brm, 4H), 2.42 (brm, 4H), 2.52 (m, 2H), 2.69 (m, 2H), 2.99 (s, 3H), 3.52 (brm, 6H), 4.00 (m, 4H), 5.72 (s, 2H), 6.92 (m, 4H), 7.41 (d, 2H), 7.57 (d, 2H), 9.44 (s, 1H) | DMSO-d$_6$ |
| 145 | N-hydroxy-4-[5-(4-{5-butyl-2-[methyl-(pyridin-3-ylmethyl)amino]-1,3-thiazol-4-yl}phenoxy)pentyloxy]-benzamidine | 0.82 (t, 3H), 1.29 (m, 2H), 1.52 (brm, 4H), 1.76 (brm, 4H), 2.70 (m, 2H), 3.00 (s, 3H), 3.98 (m, 4H), 4.68 (s, 2H), 5.76 (s, 2H), 6.90 (d, 2H), 6.94 (d, 2H), 7.37 (m, 1H), 7.44 (d, 2H), 7.58 (d, 2H), 7.72 (d, 1H), 8.47 (d, 1H), 8.55 (s, 1H), 9.48 (s, 1H) | DMSO-d$_6$ |
| 146 | N-hydroxy-4-{5-[4-(5-butyl-2-dipropylamino-1,3-thiazol-4-yl)phenoxy]pentyloxy}-benzamidine | 0.84 (m, 9H), 1.30 (m, 2H), 1.57 (m, 8H), 1.77 (brm, 4H), 2.68 (m, 2H), 3.33 (m, 4H), 4.00 (m, 4H), 5.70 (s, 2H), 6.90 (d, 2H), 6.94 (d, 2H), 7.41 (d, 2H), 7.57 (d, 2H), 9.43 (s, 1H) | DMSO-d$_6$ |
| 147 | N-hydroxy-4-[5-(4-{5-cyclopentylmethyl-2-[methyl-(pyridin-3-ylmethyl)amino]-1,3-thiazol-4-yl}phenoxy)pentyloxy]-benzamidine | 1.10 (m, 2H), 1.51 (m, 6H), 1.76 (brm, 6H), 1.99 (m, 1H), 2.71 (d, 2H), 3.00 (s, 3H), 3.99 (t, 4H), 4.68 (s, 2H), 5.72 (s, 2H), 6.90 (d, 2H), 6.95 (d, 2H), 7.36 (m, 1H), 7.43 (d, 2H), 7.57 (d, 2H), 7.72 (d, 1H), 8.48 (d, 1H), 8.55 (s, 1H), 9.45 (s, 1H) | DMSO-d$_6$ |
| 148 | N-hydroxy-4-[5-(4-{5-cyclopentylmethyl-2-[methyl-(2-morpholinoethyl)amino]-1,3-thiazol-4-yl}phenoxy)pentyloxy]-benzamidine | 1.11 (brm, 2H), 1.52-1.56 (brm, 6H), 1.77 (brm, 6H), 2.0 (m, 1H), 2.69 (m, 2H), 3.00 (s, 3H), 3.33 (m, 4H), 3.55 (m, 6H), 4.00 (m, 4H), 5.81 (s, 2H), 6.93 (m, 4H), 7.40 (d, 2H), 7.57 (d, 2H), 9.50 (s, 1H) | DMSO-d$_6$ |
| 149 | N-hydroxy-4-{5-[4-(5-cyclopentylmethyl-2-dipropylamino-1,3-thiazol-4-yl)phenoxy]pentyloxy}-benzamidine | 0.85 (m, 6H), 1.08 (m, 2H), 1.46-1.77 (brm, 16H), 1.99 (m, 1H), 2.67 (d, 2H), 3.30 (m, 4H), 3.99 (m, 4H), 6.04 (s, 2H), 6.90 (d, 2H), 6.93 (d, 2H), 7.41 (d, 2H), 7.59 (d, 2H), 9.60 (s, 1H) | DMSO-d$_6$ |
| 150 | N-hydroxy-4-{5-[4-(5-butyl-2-diethylamino-1,3-thiazol-4-yl)phenoxy]pentyloxy}-benzamidine | 0.84 (m, 3H), 1.14 (t, 6H), 1.30 (m, 2H), 1.55 (m, 4H), 1.77 (m, 4H), 2.69 (m, 2H), 3.40 (m, 4H), 3.98 (m, 4H), 5.73 (s, 2H), 6.92 (d-d, 4H), 7.43 (d, 2H), 7.60 (d, 2H), 9.49 (s, 1H) | DMSO-d$_6$ |
| 151 | N-hydroxy-4-{5-[4-(5-butyl-2-ethylmethylamino-1,3-thiazol-4-yl)phenoxy]pentyloxy}-benzamidine | 0.85 (t, 3H), 1.12 (t, 3H), 1.30 (m, 2H), 1.53 (m, 4H), 1.78 (m, 4H), 2.70 (m, 2H), 2.96 (s, 3H), 3.42 (m, 2H), 5.74 (s, 2H), 6.93 (m, 4H), 7.43d, 2H), 7.59 (d, 2H), 9.47 (s, 1H) | DMSO-d$_6$ |
| 152 | N-hydroxy-4-{5-[4-(5-butyl-2-dimethylamino-1,3-thiazol-4-yl)phenoxy]pentyloxy}-benzamidine | 0.81 (t, 3H), 1.25 (m, 2H), 1.52 (m, 4H), 1.76 (m, 4H), 2.67 (m, 2H), 2.97 (s, 6H), 3.97 (m, 4H), 5.70 (s, 2H), 6.91 (d-d, 4H), 7.41 (d, 2H), 7.57 (d, 2H), 9.50 (s, 1H) | DMSO-d$_6$ |
| 153 | N-hydroxy-4-[5-(4-{5-cyclopentyl-2-[methyl-(2-morpholinoethyl)amino]-1,3-thiazol-4-yl}phenoxy)pentyloxy]-benzamidine | 1.56-1.59 (m, 6H), 1.73-1.81 (m, 6H), 2.00-2.10 (m, 2H), 2.38-2.49 (m, 4H), 2.50-2.51 (m, 2H), 3.01 (s, 3H), 3.25 (m, 1H), 3.52--3.55 (m, 6H), 4.00-4.03 (m, 4H), 5.74 (s, 2H), 6.91-6.97 (m, 4H), 7.41 (d, 2H), 7.59 (d, 2H), 9.47 (s, 1H) | DMSO-d$_6$ |
| 154 | N-hydroxy-4-[5-(4-{5-isobutyl-2-[methyl-(2-morpholinoethyl)amino]-1,3-thiazol-4-yl}phenoxy)pentyloxy]-benzamidine | 0.88 (d, 6H), 1.78 (m, 2H), 1.80-1.82 (m, 5H), 2.43 (s, 3H), 2.50 (m, 2H), 2.53 (m, 2H), 3.01 (m, 2H), 3.18 (m, 2H), 3.54 (m, 6H), 4.02 (m, 4H), 5.76 (s, 2H), 6.94-6.97 (m, 4H), 7.41 (d, 2H), 7.60 (d, 2H), 9.46 (s, 1H) | DMSO-d$_6$ |
| 155 | N-hydroxy-4-(5-{4-[5-(2-chloroehtyl)-2-dimethylamino-1,3-thiazol-4-yl]phenoxy}pentyloxy)-benzamidine | 1.58-1.66 (m, 2H), 1.78-1.81 (m, 4H), 3.14 (s, 6H), 3.15 (t, 2H), 3.81 (t, 2H), 4.02 (m, 4H), 5.72 (s, 2H), 6.91-6.98 (m, 4H), 7.46 (d, 2H), 7.59 (d, 2H), 9.45 (s, 1H) | DMSO-d$_6$ |
| 156 | N-hydroxy-4-{5-[4-(5-cyclopentyl-2-diethylamino-1,3- | 0.86-0.88 (m, 6H), 1.58-1.61 (m, 10H), 1.78 (m, 8H), 3.32-3.39 (m, 5H), 4.02-4.05 (m, 4H), 6.95-7.18 (m, 4H), 7.40 (d, | DMSO-d$_6$ |

TABLE 1-continued

| No. | Chemical name | NMR data | Sol. |
|---|---|---|---|
|  | thiazol-4-yl)phenoxy]pentyloxy}-benzamidine | 2H), 7.83 (d, 2H) |  |
| 157 | N-hydroxy-4-{5-[4-(5-isopropyl-2-dipropylamino-1,3-thiazol-4-yl)phenoxy]pentyloxy}-benzamidine | 0.84-0.88 (m, 6H), 1.24 (d, 6H), 1.57-1.63 (m, 6H), 1.77-1.79 (m, 4H), 3.28-3.38 (m, 5H), 3.97-4.01 (m, 4H), 5.71 (s, 2H), 6.89-6.95 (m, 4H), 7.41-4.59 (m, 4H), 9.45 (s, 1H) | DMSO-$d_6$ |
| 158 | N-hydroxy-4-{5-[4-(5-ethyl-2-diethylamino-1,3-thiazol-4-yl)phenoxy]pentyloxy}-benzamidine | 1.15 (t, 3H), 1.23 (t, 6H), 1.58 (m, 2H), 1.79-1.83 (m, 4H), 2.51 (m, 2H), 3.60-3.64 (m, 4H), 4.08-4.12 (m, 4H), 7.13-7.16 (m, 4H), 7.43 (d, 2H), 7.69 (d, 2H) | DMSO-$d_6$ |
| 159 | N-hydroxy-4-[5-(4-{5-isopropyl-2-[methyl-(2-morpholinoethyl)amino]-1,3-thiazol-4-yl}phenoxy)pentyloxy]-benzamidine | 1.22 (d, 6H), 1.56 (m, 2H), 1.78 (m, 4H), 2.43 (m, 4H), 2.55 (t, 2H), 3.05 (s, 3H), 3.34 (m, 1H), 3.51 (m, 4H), 3.61 (t, 2H), 3.99 (m, 4H), 5.70 (brs, 2H), 6.90 (m, 4H), 7.57 (m, 2H), 7.73 (m, 2H), 9.44 (brs, 1H) | DMSO-$d_6$ |
| 160 | N-hydroxy-4-{5-[4-(5-cyclopentylmethyl-2-diethylamino-1,3-thiazol-4-yl)phenoxy]pentyloxy}-benzamidine | 1.12-1.16 (m, 8H), 1.56 (m, 6H), 1.78 (m, 6H), 1.98-2.00 (m, 1H), 2.68 (d, 2H), 3.38-3.40 (m, 4H), 4.00 (m, 4H), 5.89 (s, 2H), 6.91-6.95 (d-d, 4H), 7.42 (d, 2H), 7.59 (d, 2H), 9.53 (s, 1H) | DMSO-$d_6$ |
| 161 | N-hydroxy-4-{5-[4-(5-isopropyl-2-dimethylamino-1,3-thiazol-4-yl)phenoxy]pentyloxy}-benzamidine | 1.20 (d, 6H), 1.56 (m, 2H), 1.78 (m, 4H), 2.98 (s, 6H), 3.34 (m, 1H), 3.98-4.01 (m, 4H), 5.77 (s, 2H), 6.90-6.96 (m, 4H), 7.39 (d, 2H), 7.58 (d, 2H), 9.47 (s, 1H) | DMSO-$d_6$ |
| 162 | N-hydroxy-4-{5-[4-(5-isopropyl-2-diethylamino-1,3-thiazol-4-yl)phenoxy]pentyloxy}-benzamidine | 1.14 (m, 6H), 1.20 (d, 6H), 1.56 (m, 2H), 1.78 (m, 4H), 3.30 (m, 1H), 3.40 (m, 4H), 5.84 (s, 2H), 6.91-7.59 (m, 8H), 9.51 (s, 1H) | DMSO-$d_6$ |
| 163 | N-hydroxy-4-{5-[4-(5-cyclopentylmethyl-2-dimethylamino-1,3-thiazol-4-yl)phenoxy]pentyloxy}-benzamidine | 1.10-1.18 (m, 2H), 1.44-1.57 (m, 6H), 1.70-1.79 (m, 6H), 1.98-2.01 (m, 1H), 2.69 (d, 2H), 2.98 (s, 6H), 3.97-4.02 (m, 4H), 5.77 (s, 2H), 6.90-6.94 (d-d, 4H), 7.42 (d, 2H), 7.59 (d, 2H), 9.48 (s, 1H) | DMSO-$d_6$ |
| 164 | N-hydroxy-4-{5-[4-(5-methyl-2-piperidino-1,3-thiazol-4-yl)phenoxy]pentyloxy}-benzamidine | 1.56 (m, 2H), 1.63 (brm, 6H), 1.78 (brm, 4H), 3.60 (brm, 4H), 4.02 (t, 2H), 4.06 (t, 2H), 7.04 (d, 2H), 7.09 (d, 2H), 7.40 (d, 2H), 7.66 (d, 2H) | DMSD-$d_6$ + TFA-$d_1$ |
| 165 | N-hydroxy-4-{5-[4-(5-methyl-2-morpholino-1,3-thiazol-4-yl)phenoxy]pentyloxy}-benzamidine | 1.56 (m, 2H), 1.78 (brm, 4H), 2.21 (s, 3H), 3.60 (brm, 4H), 3.74 (brm, 4H), 4.02 (t, 2H), 4.05 (t, 2H), 7.03 (d, 2H), 7.09 (d, 2H), 7.40 (d, 2H), 7.65 (d, 2H) | DMSD-$d_6$ + TFA-$d_1$ |
| 166 | N-hydroxy-4-{5-[4-(5-ethyl-2-piperidino-1,3-thiazol-4-yl)phenoxy]pentyloxy}-benzamidine | 1.09 (t, 3H), 1.55 (m, 2H), 1.61 (brm, 6H), 1.77 (brm, 4H), 2.56 (q, 2H), 3.59 (brm, 4H), 4.00 (t, 2H), 4.03 (t, 2H), 7.01 (d, 2H), 7.06 (d, 2H), 7.34 (d, 2H), 7.64 (d, 2H) | DMSD-$d_6$ + TFA-$d_1$ |
| 167 | N-hydroxy-4-{5-[4-(5-cyclopentylmethyl-2-piperidino-1,3-thiazol-4-yl)phenoxy]pentyloxy}-benzamidine | 1.01 (brm, 2H), 1.43 (brm, 4H), 1.56 (brm, 2H), 1.63 (brm, 8H), 1.78 (brm, 4H), 1.94 (m, 1H), 2.56 (d, 2H), 3.61 (brm, 4H), 4.05 (m, 4H), 7.04 (d, 2H), 7.10 (d, 2H), 7.36 (d, 2H), 7.66 (d, 2H) | DMSD-$d_6$ + TFA-$d_1$ |
| 168 | N-hydroxy-4-{5-[4-(5-cyclopentylmethyl-2-morpholino-1,3-thiazol-4-yl)phenoxy]pentyloxy}-benzamidine | 1.02 (brm, 2H), 1.43 (brm, 4H), 1.56 (brm, 2H), 1.66 (brm, 2H), 1.78 (brm, 4H), 1.94 (m, 1H), 2.58 (d, 2H), 3.61 (brm, 4H), 3.74 (brm, 4H), 4.05 (m, 4H), 7.04 (d, 2H), 7.09 (d, 2H), 7.36 (d, 2H), 7.65 (d, 2H) | DMSD-$d_6$ + TFA-$d_1$ |
| 169 | N-hydroxy-4-{5-[4-(5-isopropyl-2-morpholino-1,3-thiazol-4-yl)phenoxy]pentyloxy}-benzamidine | 1.22 (d, 6H), 1.58 (m, 2H), 1.78 (m, 4H), 3.26 (m, 1H), 3.35 (m, 4H), 3.70 (m, 4H), 4.02 (m, 4H), 5.71 (brs, 2H), 6.95 (m, 4H), 7.40 (d, 2H), 7.58 (d, 2H), 9.44 (s, 1H) | DMSO-$d_6$ |

TABLE 1-continued

| No. | Chemical name | NMR data | Sol. |
|---|---|---|---|
| 170 | N-hydroxy-4-{5-(4-[5-cyclopentylmethyl-2-(4-methylpiperazino)-1,3-thiazol-4-yl]phenoxy)pentyloxy}-benzamidine | 1.11 (brm, 2H), 1.52-1.56 (brm, 6H), 1.77 (brm, 6H), 2.00 (m, 1H), 2.50 (m, 2H), 2.69 (m, 2H), 3.00 (s, 3H), 3.33 (m, 4H), 3.55 (m, 6H), 4.00 (m, 4H), 5.81 (brs, 2H), 6.93 (m, 4H), 7.40 (d, 2H), 7.57 (d, 2H), 9.50 (brs, 1H) | DMSO-d$_6$ |
| 171 | N-hydroxy-4-{5-[4-(5-vinyl-2-morpholin-4-yl-1,3-thiazol-4-yl)phenoxy]pentyloxy}-benzamidine | 1.55 (m, 2H), 1.79 (m, 4H), 3.17 (d, 1H), 3.35 (m, 4H), 3.42 (m, 2H), 3.72 (m, 4H), 4.01 (m, 4H), 5.74 (s, 2H), 6.92 (m, 4H), 7.60 (d, 2H), 7.77 (d, 2H), 9.45 (s, 1H) | DMSO-d$_6$ |
| 172 | N-hydroxy-4-{5-[4-(5-cyclopentyl-2-morpholin-4-yl-1,3-thiazol-4-yl)phenoxy]pentyloxy}-benzamidine | 1.58-1.60 (m, 7H), 1.74-1.81 (m, 7H), 2.51 (m, 4H), 3.34-3.36 (m, 1H), 3.69-3.71 (m, 4H), 4.00-4.02 (m, 4H), 5.77 (s, 2H), 6.92-6.98 (m, 4H), 7.42 (d, 2H), 7.59 (d, 2H), 9.48 (s, 1H) | DMSO-d$_6$ |
| 173 | N-hydroxy-4-{5-[4-(5-isobutyl-2-morpholin-4-yl-1,3-thiazol-4-yl)phenoxy]pentyloxy}-benzamidine | 0.88 (d, 6H), 1.59 (m, 2H), 1.80 (m, 4H), 2.60 (m, 1H), 3.35 (m, 8H), 3.70 (m, 2H), 4.01 (m, 4H), 5.77 (brs, 2H), 6.94 (m, 4H), 7.44 (m, 2H), 7.59 (m, 2H), 9.48 (brs, 1H) | DMSO-d$_6$ |
| 174 | N-hydroxy-4-{5-(4-[5-ethyl-2-(4-methylpiperazino)-1,3-thiazol-4-yl]phenoxy)pentyloxy}-benzamidine | 1.19 (t, 3H), 1.50-1.59 (m, 2H), 1.80 (m, 4H), 2.21 (s, 3H), 2.41 (m, 4H), 3.36 (m, 6H), 4.01 (m, 4H), 5.71 (brs, 2H), 6.93-6.96 (m, 4H), 7.44 (m, 2H), 7.58 (m, 2H), 9.46 (brs, 1H) | DMSO-d$_6$ |
| 175 | N-hydroxy-4-{5-[4-(2-morpholin-4-yl-1,3-thiazol-4-yl)phenoxy]pentyloxy}-benzamidine | 1.56 (m, 2H), 1.77 (m, 4H), 3.42 (m, 8H), 3.98 (m, 4H), 5.73 (brs, 2H), 6.81 (m, 2H), 6.92 (m, 2H), 7.11 (s, 1H), 7.27 (m, 2H), 7.77 (m, 2H), 8.35 (brs, 1H) | DMSO-d$_6$ |
| 176 | N-hydroxy-4-{5-(4-[5-isopropyl-2-(4-methylpiperazino)-1,3-thiazol-4-yl]phenoxy)pentyloxy}-benzamidine | 1.23 (d, 6H), 1.58 (m, 2H), 1.77 (m, 4H), 2.21 (s, 3H), 2.40 (m, 4H), 2.21 (s, 3H), 2.40 (m, 4H), 3.33 (m, 1H), 3.35 (m, 4H), 4.00 (m, 4H), 5.71 (s, 2H), 6.93-6.97 (m, 4H), 7.40 (d, 2H), 7.58 (d, 2H), 9.45 (s, 1H) | DMSO-d$_6$ |
| 177 | N-hydroxy-4-{5-[4-(5-isopropyl-2-methyl-1,3-thiazol-4-yl)-phenoxy]-pentylamino}-benzamidine | 1.23 (d, 6H), 1.52 (m, 2H), 1.60 (m, 2H), 1.75 (m, 2H), 2.60 (s, 3H), 3.03 (m, 2H), 3.32 (m, 1H), 4.00 (t, 2H), 5.52 (s, 2H), 5.79 (m, 1H), 6.51 (d, 2H), 6.99 (d, 2H), 7.37 (d, 2H), 7.42 (d, 2H), 9.19 (s, 1H) | DMSO-d$_6$ |
| 178 | N-hydroxy-4-(2-{2-[4-(5-isopropyl-2-methyl-1,3-thiazol-4-yl)-phenoxy]-ethoxy}-ethoxy)-benzamidine | 1.25 (d, 6H), 2.64 (s, 3H), 3.33 (m, 1H), 3.90 (m, 4H), 4.14 (m, 4H), 6.90 (m, 4H), 7.40 (m, 4H) | CDCl$_3$ |
| 179 | N-hydroxy-4-{3-hydroxy-5-[4-(5-isopropyl-2-methyl-1,3-thiazol-4-yl)-phenoxy]-3-methyl-pentyloxy}-benzamidine | 1.26 (d, 6H), 1.32 (s, 3H), 2.06 (m, 4H), 2.65 (s, 3H), 3.33 (m, 1H), 4.20 (m, 4H), 5.01 (brs, 1H), 6.86 (d, 2H), 6.92 (d, 2H), 7.43 (d, 2H), 7.50 (d, 2H) | CDCl$_3$ |
| 180 | N-hydroxy-4-(2-{2-[4-(5-isopropyl-2-methyl-1,3-thiazol-4-yl)-phenoxy]-1-methyl-ethylamino}-ethoxy)-benzamidine | 1.10 (d, 3H), 1.23 (d, 6H), 2.59 (s, 3H), 2.96 (m, 2H), 3.05 (m, 1H), 3.32 (m, 2H), 3.90 (m, 2H), 4.04 (m, 2H), 5.71 (s, 2H), 6.92 (d, 2H), 6.99 (d, 2H), 7.43 (d, 2H), 7.58 (d, 2H), 9.45 (s, 1H) | DMSO-d$_6$ |
| 181 | N-hydroxy-4-[3-(4-{3-[4-(5-isopropyl-2-methyl-1,3-thiazol-4-yl)-phenoxy]-propyl}-piperazine-1-yl)-propoxy]-benzamidine | 1.23 (d, 6H), 1.85 (m, 4H), 2.40 (brm, 12H), 2.45 (s, 3H), 3.30 (m, 1H), 4.00 (m, 4H), 5.70 (s, 2H), 6.89 (d, 2H), 6.94 (d, 2H), 7.41 (d, 2H), 7.57 (d, 2H), 9.51 (s, 1H) | DMSO-d$_6$ |
| 182 | N-hydroxy-4-5-[4-(5-isopropyl-2-methyl-1,3-thiazol-4-yl)-phenoxy]-pentanoyl-amino-benzamidine | 1.23 (d, 6H), 1.77 (brs, 4H), 2.40 (m, 2H), 2.60 (s, 3H), 3.33 (m, 1H), 4.02 (brs, 2H), 5.72 (s, 2H), 6.99 (d, 2H), 7.43 (d, 2H), 7.58-7.80 (m, 4H), 9.51 (s, 1H), 10.00 (s, 1H) | DMSO-d$_6$ |
| 183 | N-hydroxy-4-({5-[4-(5-isopropyl-2-methyl-1,3-thiazol-4-yl)-phenoxy]-pentyl}-methyl-amino)-benzamidine | 1.22 (d, 6H), 1.43 (m, 2H), 1.55 (m, 2H), 1.76 (m, 2H), 2.59 (s, 3H), 2.89 (s, 3H), 3.33 (m, 1H), 3.98 (m, 2H), 5.55 (s, 2H), 6.64 (d, 2H), 6.97 (d, 2H), 7.45 (m, 4H), 9.23 (s, 1H) | DMSO-d$_6$ |
| 184 | N-hydroxy-4-{4-[4-(5-isopropyl-2-methyl-1,3- | 1.23 (d, 6H), 2.60 (s, 3H), 3.31 (m, 1H), 4.63 (brs, 4H), 5.73 (s, 2H), 6.08 (brs, | DMSO-d$_6$ |

TABLE 1-continued

| No. | Chemical name | NMR data | Sol. |
|---|---|---|---|
| | thiazol-4-yl)-phenoxy]-but-2-enyloxy}-benzamidine | 2H), 6.94 (d, 2H), 7.01 (d, 2H), 7.44 (d, 2H), 7.58 (d, 2H), 9.46 (s, 1H) | |
| 185 | N-hydroxy-4-{4-[4-(5-isopropyl-2-methyl-1,3-thiazol-4-yl)-phenoxymethyl]-benzyloxy}-benzamidine | 1.23 (d, 6H), 2.64 (s, 3H), 3.32 (m, 1H), 5.15 (s, 2H), 5.23 (s, 2H), 5.72 (s, 2H), 7.07 (d, 2H), 7.19 (d, 2H), 7.46 (m, 6H), 7.73 (d, 2H), 9.46 (s, 1H) | DMSO-$d_6$ |
| 186 | N-hydroxy-4-(2-{2-[4-(5-isopropyl-2-methyl-1,3-thiazol-4-yl)phenoxy]-ethylamino}-ethoxy)-benzamidine | 1.23 (d, 6H), 2.59 (s, 3H), 3.01 (brs, 4H), 3.33 (m, 1H), 4.09 (m, 4H), 5.71 (s, 2H), 6.92 (d, 2H), 7.00 (d, 2H), 7.43 (d, 2H), 7.58 (d, 2H), 9.45 (s, 1H) | DMSO-$d_6$ |
| 187 | N-hydroxy-2-fluoro-4-{5-[4-(5-isopropyl-2-methyl-1,3-thiazol-4-yl)-phenoxy]-pentyloxy}-benzamidine | 1.23 (d, 6H), 1.57 (m, 2H), 1.79 (m, 4H), 2.49 (s, 3H), 3.33 (m, 1H), 4.02 (m, 4H), 5.70 (s, 2H), 6.83 (m, 2H), 6.98 (d, 2H), 7.43 (m, 3H), 9.51 (s, 1H) | DMSO-$d_6$ |
| 188 | 2,N-dihydroxy-4-{5-[4-(5-isopropyl-2-methyl-1,3-thiazol-4-yl)-phenoxy]-pentyloxy}-benzamidine | 1.23 (d, 6H), 1.56 (m, 2H), 1.77 (m, 4H), 2.60 (s, 3H), 3.32 (m, 1H), 4.00 (m, 4H), 6.25 (s, 2H), 6.36 (m, 2H), 7.00 (d, 2H), 7.42 (d, 2H), 7.52 (d, 1H), 9.81 (s, 1H), 12.40 (s, 1H) | DMSO-$d_6$ |
| 189 | N-hydroxy-4-{5-[4-(5-isopropyl-2-methyl-1,3-thiazol-4-yl)-phenoxy]-pentyloxy}-3-methoxy-benzamidine | 1.24 (d, 6H), 1.58 (m, 2H), 1.80 (m, 4H), 2.61 (s, 3H), 3.35 (m, 1H), 3.77 (s, 3H) 4.02 (m, 4H), 5.77 (s, 2H), 6.98 (m, 3H), 7.26 (m, 2H), 7.46 (d, 2H), 9.48 (s, 1H) | DMSO-$d_6$ |
| 190 | N-hydroxy-2-cyclohexylamino-4-{5-[4-(5-isopropyl-2-methyl-1,3-thiazol-4-yl)-phenoxy]-pentyloxy}-benzamidine | 1.23 (m, 12H), 1.54 (m, 2H), 1.65 (m, 2H), 1.76 (m, 4H), 1.78 (m, 2H), 2.60 (s, 3H), 3.34 (m, 2H), 3.99 (m, 4H), 5.66 (s, 2H), 6.09 (m, 2H), 6.97 (d, 2H), 7.31 (d, 1H), 7.43 (d, 2H), 7.70 (d, 1H), 9.48 (s, 1H) | DMSO-$d_6$ |
| 191 | N-hydroxy-4-{5-[3-fluoro-4-(5-isopropyl-2-methyl-1,3-thiazol-4-yl)-phenoxy]-pentyloxy}-benzamidine | 1.17 (d, 6H), 1.57 (m, 2H), 1.79 (brs, 4H), 2.98 (m, 1H), 4.04 (m, 4H), 5.71 (s, 2H), 6.90 (m, 3H), 7.31 (d, 2H), 7.59 (d, 2H), 9.44 (s, 1H) | DMSO-$d_6$ |
| 192 | N-hydroxy-2-fluoro-4-{5-[3-fluoro-4-(5-isopropyl-2-methyl-1,3-thiazol-4-yl)-phenoxy]-pentyloxy}-benzamidine | 1.17 (d, 6H), 1.57 (brs, 2H), 1.79 (brs, 4H), 2.98 (m, 1H), 4.05 (m, 4H), 5.73 (s, 2H), 6.82~6.89 (m, 4H), 7.27~7.40 (m, 2H), 9.52 (s, 1H) | DMSO-$d_6$ |
| 193 | N-hydroxy-4-{3-[4-(5-isopropyl-2-methyl-1,3-thiazol-4-yl)phenoxy]propoxy}-benzamidine | 1.24 (d, 6H), 2.20 (m, 2H), 2.60 (s, 3H), 3.30 (m, 1H), 4.17 (m, 4H), 5.71 (s, 2H), 6.96 (d, 2H), 7.01 (d, 2H), 7.44 (d, 2H), 7.60 (d, 2H), 9.45 (s, 1H) | DMSO-$d_6$ |
| 194 | N-hydroxy-4-{4-[4-(5-isopropyl-2-methyl-1,3-thiazol-4-yl)phenoxy]butoxy}-benzamidine | 1.26 (d, 2H), 1.89 (m, 4H), 2.60 (s, 3H), 3.30 (m, 1H), 4.06 (m, 4H), 5.72 (s, 2H), 6.92 (d, 2H), 7.00 (d, 2H), 7.44 (d, 2H), 7.60 (d, 2H), 9.45 (s, 1H) | DMSO-$d_6$ |
| 195 | N-hydroxy-3-{5-[4-(5-isopropyl-2-methyl-thiazol-4-yl)-phenoxy]-pentylamino}-benzamidine | 1.24 (d, 6H), 1.50-1.62 (m, 3H), 1.77-1.79 (m, 2H), 2.65 (s, 3H), 3.02-3.04 (m, 1H), 3.37-3.44 (m, 3H), 3.99-4.03 (m, 2H), 6.57-6.98 (m, 4H), 7.00 (d, 2H), 7.44 (d, 2H) | DMSO-$d_6$ |
| 196 | N-hydroxy-4-{4-[2-cyclohexyl-5-ethyl-thiazol-4-yl)-phenoxy]-butoxy}-benzamidine | 1.22 (t, 3H), 1.39-1.44 (m, 3H), 1.59 (m, 1H), 1.77 (m, 2H), 1.89 (m, 4H), 2.03 (m, 2H), 2.90 (m, 3H), 4.18 (m, 4H), 7.00 (m, 4H), 7.49 (m, 2H), 7.60 (m, 2H) | DMSO-$d_6$ |
| 197 | N-hydroxy-4-[3-(4-{5-ethyl-2-[(2-hydroxyethyl)-methyl-amino]-thiazol-4-yl}phenoxy)propoxy]-benzamidine | 1.17 (m, 3H), 2.19 (m, 2H), 2.72 (m, 2H), 3.05 (s, 3H), 3.39-3.79 (m, 4H), 4.16-4.20 (m, 4H), 5.72 (s, 2H), 6.96 (m, 4H), 7.40-7.84 (m, 4H), 9.47 (s, 1H) | DMSO-$d_6$ |
| 198 | N-hydroxy-4-[4-(4-{5-ethyl-2-[(2-hydroxyethyl)-methyl-amino]-thiazol-4-yl}phenoxy)butoxy]-benzamidine | 1.15 (t, 3H), 1.90 (m, 4H), 2.64 (q, 2H), 3.25 (s, 3H), 3.40-3.80 (m, 4H), 4.10-4.15 (m, 4H), 7.09-7.15 (m, 4H), 7.42 (d, 2H), 7.73 (d, 2H) | DMSO-$d_6$ |
| 199 | N-hydroxy-4-[5-(4-{5-ethyl-2-[methyl- | 1.86 (t, 3H), 2.50 (m, 2H), 2.73 (m, 2H), 3.15 (s, 3H), 4.17-4.25 (m, 4H), 4.96 (s, | DMSO-$d_6$ |

TABLE 1-continued

| No. | Chemical name | NMR data | Sol. |
|---|---|---|---|
| | (pyridin-3-ylmethyl)amino]-thiazol-4-yl}phenoxy)propoxy]-benzamidine | 2H), 7.01 (d, 2H), 7.17 (d, 2H), 7.44 (d, 2H), 7.73 (d, 2H), 8.06 (m, 1H), 8.54 (d, 1H), 8.87 (d, 1H), 8.94 (s, 1H) | |
| 200 | N-hydroxy-4-[5-(4-{5-ethyl-2-[methyl-(pyridin-3-ylmethyl)amino]-thiazol-4-yl}phenoxy)butoxy]-benzamidine | 1.19 (t, 3H), 1.79-1.89 (m, 4H), 2.72-2.74 (m, 2H), 3.17 (s, 3H), 4.07-4.15 (m, 4H), 4.98 (s, 2H), 7.00 (d, 2H), 7.14 (d, 2H), 7.44 (d, 2H), 7.72 (d, 2H), 8.05 (m, 1H), 8.55 (d, 1H), 8.87 (d, 1H), 8.95 (s, 1H) | DMSO-$d_6$ |
| 201 | N-hydroxy-4-{4-[4-(5-cyclopentylmethyl-2-isopropyl-thiazol-4-yl)-phenoxymethyl]-benzyloxy}-benzamidine | 1.14 (m, 2H), 1.32 (d, 6H), 1.48 (m, 4H), 1.74 (m, 2H), 2.04 (m, 1H), 2.85 (d, 2H), 3.38 (m, 1H), 5.14 (s, 4H), 5.73 (s, 2H), 7.01 (d, 2H), 7.08 (d, 2H), 7.48 (s, 4H), 7.50 (d, 2H), 7.58 (d, 2H), 9.48 (s, 1H) | DMSO-$d_6$ |
| 202 | N-hydroxy-4-{4-[4-(5-butyl-2-isopropyl-thiazol-4-yl)-phenoxymethyl]-benzyloxy}-benzamidine | 0.85 (t, 3H), 1.32 (d, 6H), 1.35 (m, 2H), 1.60 (m, 2H), 1.85 (m, 2H), 3.25 (m, 1H), 5.15 (s, 4H), 5.74 (s, 2H), 7.01 (d, 2H), 7.08 (d, 2H), 7.48 (s, 4H), 7.50 (d, 2H), 7.60 (d, 2H), 9.49 (s, 1H) | DMSO-$d_6$ |
| 203 | N-hydroxy-4-{4-[4-(5-cyclopentylmethyl-2-amino-thiazol-4-yl)-phenoxymethyl]-benzyloxy}-benzamidine | 1.07-1.09 (m, 2H), 1.47-1.50 (m, 4H), 1.70 (m, 2H), 1.99 (m, 1H), 2.34 (s, 6H), 2.62 (d, 2H), 5.18 (s, 2H), 5.25 (s, 2H), 7.17-7.24 (m, 4H), 7.41 (d, 2H), 7.50 (m, 4H), 7.68 (d, 2H) | DMSO-$d_6$ |
| 204 | N-hydroxy-4-{4-[4-(5-cyclopentylmethyl-2-amino-thiazol-4-yl)-phenoxymethyl]-benzyloxy}-2-fluoro-benzamidine | 1.05 (m, 2H), 1.49 (m, 4H), 1.71 (m, 2H), 2.00 (m, 1H), 2.34 (s, 6H), 2.63 (d, 2H), 5.15-5.26 (d, 4H), 7.05-7.24 (m, 3H), 7.41-7.62 (m, 8H) | DMSO-$d_6$ |
| 205 | N-hydroxy-4-{4-[4-(2-methylamino-thiazol-4-yl)-phenoxymethyl]-benzyloxy}-benzamidine | 2.86 (s, 3H), 5.16 (m, 4H), 6.00 (brs, 2H), 7.02 (m, 4H), 7.48 (m, 4H), 7.60 (s, 1H), 7.76 (m, 4H), 9.57 (brs, 1H) | DMSO-$d_6$ |
| 206 | N-hydroxy-4-{6-[4-(5-isopropyl-2-methyl-thiazol-4-yl)-phenoxymethyl]-pyridine-2-yl-methoxy}-benzamidine | 1.26 (d, 6H), 2.61 (s, 3H), 3.35 (m, 1H), 5.25 (m, 4H), 5.75 (brs, 2H), 7.11 (m, 1H), 7.13 (m, 2H), 7.47 (m, 4H), 7.49 (m, 2H), 7.80-7.90 (m, 2H), 9.49 (brs, 1H) | DMSO-$d_6$ |
| 207 | N-hydroxy-2-fluoro-4-{4-[4-(5-isopropyl-2-methyl-thiazol-4-yl)-phenoxy]-butoxy}-benzamidine | 1.25 (d, 6H), 1.89 (m, 4H), 2.61 (s, 3H), 3.34 (m, 1H), 4.10 (m, 4H), 6.80-6.90 (m, 2H), 7.02 (m, 2H), 7.46 (m, 3H) | DMSO-$d_6$ |
| 208 | N-hydroxy-4-{2-[4-(5-isopropyl-2-methyl-thiazol-4-yl)-phenoxymethyl]-benzyloxy}-benzamidine | 1.23 (d, 6H), 2.60 (s, 3H), 3.33 (m, 1H), 5.28 (s, 4H), 5.80 (s, 2H), 7.04-7.12 (m, 4H), 7.37 (m, 2H), 7.47 (d, 2H), 7.55 (m, 2H), 7.64 (d, 2H), 9.57 (s, 1H) | DMSO-$d_6$ |
| 209 | N-hydroxy-4-{3-[4-(5-isopropyl-2-methyl-thiazol-4-yl)-phenoxymethyl]-benzyloxy}-benzamidine | 1.23 (d, 6H), 2.60 (s, 3H), 3.31 (m, 1H), 5.14 (s, 2H), 5.15 (s, 2H), 5.72 (s, 2H), 7.00 (d, 2H), 7.08 (d, 2H), 7.42-7.46 (m, 5H), 7.55-7.61 (m, 3H), 9.46 (s, 1H) | DMSO-$d_6$ |
| 210 | N-hydroxy-4-{4-[4-(5-cyclopentylmethyl-2-cyclohexyl-thiazol-4-yl)-phenoxymethyl]-benzyloxy}-benzamidine | 1.10 (m, 2H), 1.23 (m, 1H), 1.46 (br, 9H), 1.77 (br, 4H), 2.02 (m, 3H), 2.83 (d, 2H), 2.90 (m, 1H), 5.16 (m, 4H), 5.81 (brs, 2H), 7.02 (m, 4H), 7.48 (m, 4H), 7.76 (m, 4H), 9.57 (brs, 1H) | DMSO-$d_6$ |
| 211 | N-hydroxy-4-{6-[4-(5-isopropyl-2-methyl-thiazol-4-yl)phenoxy]-hexyloxy}-benzamidine | 1.24 (d, 6H), 1.49 (m, 4H), 1.76 (m, 4H), 2.61 (s, 3H), 3.32-3.37 (m, 1H), 3.99-4.02 (m, 4H), 5.81 (s, 2H), 6.91 (d, 2H), 6.99 (d, 2H), 7.44 (d, 2H), 7.59 (d, 2H), 9.49 (s, 1H) | DMSO-$d_6$ |
| 212 | N-hydroxy-4-{5-[2-ethyl-5-hydroxy-4-(2-methyl-thiazol-4-yl)phenoxy]-pentyloxy}-benzamidine | 1.13 (t, 3H), 1.61 (m, 2H), 1.81 (m, 4H), 2.51 (m, 2H), 2.79 (s, 3H), 3.97-4.10 (m, 4H), 6.60 (s, 1H), 7.12 (d, 2H), 7.69-7.86 (m, 4H), 8.81 (s, 1H), 9.26 (s, 1H) | DMSO-$d_6$ |
| 213 | N-hydroxy-4-{5-[2-ethyl-4-(2-methyl-thiazol-4-yl)-5-propoxy-phenoxy]-pentyloxy}-benzamidine | 1.03 (t, 3H), 1.13 (t, 3H), 1.62 (m, 2H), 1.79-1.85 (m, 6H), 2.55 (m, 2H), 2.69 (s, 3H), 4.01-4.08 (m, 6H), 5.73 (s, 2H), 6.67 (s, 1H), 6.92 (d, 2H), 7.59-7.93 (m, 4H), 9.47 (s, 1H) | DMSO-$d_6$ |

TABLE 1-continued

| No. | Chemical name | NMR data | Sol. |
|---|---|---|---|
| 214 | N-hydroxy-4-(5-{4-[5-(2-isobutylamino-ethyl)-2-methyl-thiazol-4-yl]-phenoxy}-pentyloxy)-benzamidine | 0.86 (d, 6H), 1.59 (m, 2H), 1.80 (m, 5H), 2.60 (s, 3H), 2.73 (m, 2H), 2.94 (m, 2H), 3.34 (m, 2H), 4.02 (m, 4H), 5.72 (s, 2H), 6.93 (m, 4H), 7.49-7.60 (m, 4H), 9.45 (s, 2H) | DMSO-$d_6$ |
| 215 | 4-(5-{4-[5-(2-isobutylaminoethyl)-2-methyl-thiazol-4-yl]-phenoxy}-pentyloxy)-benzamidine | 0.85 (d, 6H), 1.58 (m, 2H), 1.79 (m, 5H), 2.59 (s, 3H), 2.71 (m, 2H), 2.92 (m, 2H), 3.32 (m, 2H), 4.01 (m, 4H), 6.93 (m, 4H), 7.57 (m, 4H), 9.09 (brs, 3H) | DMSO-$d_6$ |
| 216 | N-hydroxy-4-(5-{4-[2-methyl-5-(2-piperidin-1-yl-ethyl)-thiazol-4-yl]-phenoxy}-pentyloxy)-benzamidine | 1.52 (m, 2H), 1.58 (m, 6H), 1.79 (m, 4H), 2.50 (d, 2H), 2.60 (s, 3H), 2.98 (d, 2H), 3.38 (m, 4H), 4.02 (m, 4H), 5.73 (s, 2H), 6.93-7.00 (m, 4H), 7.48-7.60 (m, 4H), 9.46 (s, 1H) | DMSO-$d_6$ |
| 217 | N-hydroxy-4-[5-(4-{2-methyl-5-[2-(2-morpholin-4-yl-ethylamino)-ethyl]-thiazol-4-yl}-phenoxy)-pentyloxy]-benzamidine | 1.58-1.60 (m, 2H), 1.79-1.81 (m, 4H), 2.31-2.33 (m, 6H), 2.51-2.58 (m, 2H), 2.61 (s, 3H), 2.76 (m, 2H), 2.95 (m, 2H), 3.53 (m, 4H), 4.01-4.04 (m, 4H), 5.73 (s, 2H), 6.94-7.00 (m, 4H), 7.51 (d, 2H), 7.60 (d, 2H) | DMSO-$d_6$ |
| 218 | N-hydroxy-4-[5-(4-{5-[2-(3-imidazol-1-yl-propylamino)-ethyl]-2-methyl-thiazol-4-yl]-phenoxy)-pentyloxy]-benzamidine | 1.23 (m, 2H), 1.60 (m, 2H), 1.81 (m, 6H), 1.91 (m, 2H), 2.61 (s, 3H), 2.82 (m, 2H), 3.02 (m, 2H), 4.02 (m, 4H), 6.91-7.00 (m, 5H), 7.15 (s, 1H), 7.51 (d, 2H), 7.59 (d, 2H), 7.85 (d, 1H) | DMSO-$d_6$ |
| 219 | N-hydroxy-4-(5-{4-[5-(2-isopropylamino-ethyl)-2-methyl-thiazol-4-yl]-phenoxy}-pentyloxy)-benzamidine | 1.05 (d, 6H), 1.63 (m, 2H), 1.81-1.85 (m, 4H), 2.65 (s, 3H), 2.85-2.89 (m, 3H), 3.06-3.08 (m, 2H), 3.94-3.97 (m, 4H), 4.84 (brs, 2H), 6.34 (brs, 1H), 6.85-6.89 (m, 4H), 7.46-7.51 (m, 4H) | CDCl$_3$ |
| 220 | N-hydroxy-4-[5-(4-{5-[2-(3-isopropoxy-propylamino)-ethyl]-2-methyl-thiazole-4-yl}-phenoxy)-pentyloxy]-benzamidine | 1.05 (d, 6H), 1.65 (m, 2H), 1.79-1.84 (m, 6H), 2.64 (s, 3H), 2.77 (t, 2H), 2.91 (t, 2H), 3.15 (t, 2H), 3.40 (t, 2H), 3.50 (m, 1H), 3.94-3.97 (m, 4H), 4.93 (brs, 2H), 6.54 (brs, 1H), 6.84-6.88 (m, 4H), 7.45 (m, 4H) | CDCl$_3$ |
| 221 | N-hydroxy-4-(5-{4-[5-(2-butylamino-ethyl)-2-methyl-thiazol-4-yl]-phenoxy}-pentyloxy)-benzamidine | 0.85 (t, 3H), 1.29-1.35 (m, 6H), 1.58 (m, 2H), 1.78 (m, 4H), 2.60 (s, 3H), 2.72 (m, 2H), 2.93 (m, 2H), 4.02 (m, 4H), 5.72 (s, 2H), 6.91-6.97 (m, 4H), 7.49-7.58 (m, 4H) | DMSO-$d_6$ |
| 222 | N-hydroxy-4-(5-{4-[5-(2-imidazol-1-yl-ethyl)-2-methyl-thiazol-4-yl]-phenoxy}-pentyloxy)-benzamidine | 1.64 (m, 2H), 1.86 (m, 4H), 2.66 (m, 3H), 3.30 (t, 2H), 4.01-4.14 (m, 6H), 6.89-7.77 (m, 11H) | CDCl$_3$ |
| 223 | N-hydroxy-4-(5-{4-[5-(2-cyclohexylamino-ethyl)-2-methyl-thiazol-4-yl]-phenoxy}-pentyloxy)-benzamidine | 0.98-1.01 (m, 2H), 1.13-1.63 (m, 3H), 1.58-1.70 (m, 5H), 1.78-1.80 (m, 6H), 2.40 (m, 1H), 2.60 (s, 3H), 2.79 (m, 2H), 2.95 (m, 2H), 4.01-4.04 (m, 4H), 5.72 (s, 2H), 6.93-7.00 (m, 4H), 7.50 (d, 2H), 7.60 (d, 2H), 9.46 (s, 1H) | DMSO-$d_6$ |
| 224 | N-hydroxy-4-(5-{4-[5-(2-diethylamino-ethyl)-2-methyl-thiazol-4-yl]-phenoxy}-pentyloxy)-benzamidine | 0.93 (t, 6H), 1.59 (m, 2H), 1.79 (m, 4H), 2.49 (m, 6H), 2.59 (s, 3H), 2.92 (m, 2H), 4.02-4.04 (m, 4H), 5.72 (s, 2H), 6.93-6.70 (m, 4H), 7.48-7.82 (m, 4H), 9.46 (s, 1H) | DMSO-$d_6$ |
| 225 | N-hydroxy-4-{5-[4-(5-{2-[bis-(2-hydroxy-ethyl)-amino]-ethyl}-2-methyl-thiazol-4-yl)-phenoxy]-pentyloxy}-benzamidine | 1.59 (m, 2H), 1.79 (m, 4H), 2.55-2.59 (m, 4H), 2.60 (s, 3H), 2.75 (m, 2H), 2.95 (m, 2H), 3.41-3.43 (m, 4H), 4.01-.04 (m, 4H), 5.72 (s, 2H), 6.93-7.00 (m, 4H), 7.50 (d, 2H), 7.59 (d, 2H), 9.46 (s, 1H) | DMSO-$d_6$ |
| 226 | N-hydroxy-4-(5-{4-[5-(2-diisopropylamino-ethyl)-2-methyl-thiazol-4-yl]-phenoxy}-pentyloxy)-benzamidine | 1.29-1.42 (m, 12H), 1.65 (m, 2H), 1.84-1.89 (m, 4H), 2.71 (s, 3H), 2.93 (m, 2H), 3.52 (m, 2H), 3.64 (m, 2H), 4.00-4.04 (m, 4H), 6.92 (m, 4H), 7.46 (d, 2H), 7.78 (d, 2H) | CDCl$_3$ |
| 227 | N-hydroxy-4-[5-(4-{5-[2-(2,6-dimethyl-morpholin-4-yl)-ethyl]-2-methyl-thiazol-4-yl}-phenoxy)-pentyloxy]-benzamidine | 1.03 (d, 6H), 1.60-1.63 (m, 4H), 1.78-1.80 (m, 4H), 2.47-2.50 (m, 2H), 2.60 (s, 3H), 2.74 (m, 2H), 2.98 (m, 2H), 3.52-3.56 (m, 2H), 4.02-4.04 (m, 4H), 5.72 (s, 2H), 6.93-7.00 (m, 4H), 7.48 (d, 2H), 7.58 (d, 2H), 9.46 (s, 1H) | DMSO-$d_6$ |

TABLE 1-continued

| No. | Chemical name | NMR data | Sol. |
|---|---|---|---|
| 228 | N-hydroxy-4-(5-{4-[2-methyl-5-(2-thiomorpholin-4-yl-ethyl)-thiazol-4-yl]-phenoxy}-pentyloxy)-benzamidine | 1.58 (m, 2H), 1.78-1.81 (m, 4H), 2.50-2.55 (m, 2H), 2.60 (s, 3H), 2.62 (m, 4H), 2.67 (m, 4H), 2.98 (m, 2H), 4.02-4.04 (m, 4H), 5.72 (s, 2H), 6.93-7.00 (m, 4H), 7.49 (d, 2H), 7.58 (d, 2H), 9.46 (s, 1H) | DMSO-$d_6$ |
| 229 | N-hydroxy-4-(5-{4-[2-amino-5-(2-morpholin-4-yl-ethyl)-thiazol-4-yl]-phenoxy}-pentyloxy)-benzamidine | 1.59 (m, 2H), 1.79 (m, 4H), 2.91 (m, 2H), 3.34 (m, 6H), 3.63 (m, 4H), 4.03 (m, 4H), 5.76 (s, 2H), 6.93 (m, 4H), 7.43 (d, 2H), 7.59 (d, 2H), 9.53 (brs, 1H) | DMSO-$d_6$ |
| 230 | N-hydroxy-4-[5-(4-{5-[2-(2-dimethylamino-ethylamino)-ethyl]-2-methyl-thiazol-4-yl}-phenoxy)-pentyloxy]-benzamidine | 1.57 (m, 2H), 1.78 (m, 4H), 2.09 (s, 6H), 2.60 (s, 3H), 3.22-3.34 (m, 8H), 4.02 (m, 4H), 6.98 (d, 2H), 7.11 (d, 2H), 7.50 (d, 2H), 7.76 (d, 2H) | DMSO-$d_6$ |
| 231 | N-hydroxy-4-(5-{4-[2-methyl-5-(2-morpholin-4-yl-ethyl)-thiazol-4-yl]-phenoxy}-pentyloxy)-benzamidine | 1.63 (m, 2H), 1.83 (m, 4H), 2.49 (m, 4H), 2.59 (m, 2H), 2.65 (s, 3H), 3.03 (m, 2H), 3.71 (m, 4H), 3.98 (m, 4H), 4.95 (brs, 1H), 6.85-6.91 (d-d, 4H), 7.44-7.47 (d-d, 4H) | CDCl$_3$ |
| 232 | N-hydroxy-4-[5-(4-{2-methyl-5-[2-(4-methyl-piperazin-1-yl)-ethyl]-thiazol-4-yl}-phenoxy)-pentyloxy]-benzamidine | 1.64 (m, 2H), 1.83 (m, 4H), 2.29 (s, 3H), 2.58-2.63 (m, 10H), 2.64 (s, 3H), 2.99 (m, 2H), 3.96 (m, 4H), 4.85 (brs, 1H), 6.85-6.89 (d-d, 4H), 7.43-7.71 (d-d, 4H) | CDCl$_3$ |
| 233 | N-hydroxy-4-{5-[4-(5-{2-[bis-(2-methoxy-ethyl)-amino]-ethyl}-2-methyl-thiazol-4-yl)-phenoxy]-pentyloxy}-benzamidine | 1.59 (m, 2H), 1.80 (m, 4H), 2.60 (s, 3H), 2.66 (m, 4H), 2.73 (m, 2H), 2.94 (m, 2H), 3.19 (s, 6H), 3.35 (m, 4H), 4.03 (m, 4H), 5.73 (s, 2H), 6.92 (d, 2H), 6.99 (d, 2H), 7.49 (d, 2H), 7.60 (d, 2H), 9.45 (s, 1H) | DMSO-$d_6$ |
| 234 | N-hydroxy-4-(5-{4-[5-(2-tert-butylamino-ethyl)-2-methyl-thiazol-4-yl]-phenoxy}-pentyloxy)-benzamidine | 1.06 (s, 9H), 1.58 (m, 2H), 1.80 (m, 4H), 2.61 (s, 3H), 2.80 (m, 2H), 2.98 (m, 2H), 4.03 (m, 4H), 6.91-7.01 (m, 4H), 7.50-7.82 (m, 4H) | DMSO-$d_6$ |
| 235 | N-hydroxy-4-(5-{4-[5-(2-isobutylamino-ethyl)-2-methyl-thiazol-4-yl]-phenoxy}-pentyloxy)-benzamidine | 0.86 (d, 6H), 1.59 (m, 2H), 1.80 (m, 5H), 2.60 (s, 3H), 2.73 (m, 2H), 2.94 (m, 2H), 3.34 (m, 2H), 4.02 (m, 4H), 5.72 (s, 2H), 6.93 (m, 4H), 7.49-7.60 (m, 4H), 9.45 (s, 2H) | DMSO-$d_6$ |
| 236 | N-hydroxy-4-(5-{4-[5-(2-morpholin-4-yl-ethyl)-2-pyridine-3-yl-thiazol-4-yl]-phenoxy}-pentyloxy)-benzamidine | 1.65 (m, 2H), 1.88 (m, 4H), 2.10 (m, 2H), 2.92 (m, 4H), 3.43 (m, 2H), 4.04 (m, 8H), 6.90-7.00 (m, 4H), 7.37 (m, 1H), 7.57-7.60 (m, 4H), 8.24 (d, 1H), 8.63 (d, 1H), 9.14 (s, 1H) | CDCl$_3$ |
| 237 | N-hydroxy-4-[5-(4-{5-[2-(4-methyl-piperazin-1-yl)-ethyl]-2-pyridin-3-yl-thiazol-4-yl}-phenoxy)-pentyloxy]-benzamidine | 1.70 (m, 2H), 1.89 (m, 4H), 2.81 (s, 3H), 2.86 (m, 2H), 3.01-3.22 (m, 8H), 3.46 (m, 2H), 4.05 (m, 4H), 6.95-6.97 (m, 4H), 7.53-7.59 (m, 4H), 7.76 (m, 1H), 8.35 (d, 1H), 8.64 (d, 1H), 9.16 (s, 1H) | CDCl$_3$ |
| 238 | N-hydroxy-4-(5-{4-[2-pyridin-3-yl-5-(2-thiomorpholin-4-yl-ethyl)-thiazol-4-yl]-phenoxy}-pentyloxy)-benzamidine | 1.60 (m, 2H), 1.82 (m, 4H), 2.51-2.93 (m, 4H), 3.35-3.41 (m, 8H), 4.08 (m, 4H), 6.97-7.08 (m, 4H), 7.55 (m, 1H), 7.66-7.85 (m, 4H), 8.31 (d, 1H), 8.68 (d, 1H), 9.13 (s, 1H) | DMSO-$d_6$ |
| 239 | N-hydroxy-4-(5-{4-[5-(2-imidazol-1-yl-ethyl)-2-pyridin-3-yl-thiazol-4-yl]-phenoxy}-pentyloxy)-benzamidine | 1.60 (m, 2H), 1.82 (m, 4H), 3.54 (m, 2H), 4.07 (m, 4H), 4.53 (t, 2H), 6.99-7.17 (m, 5H), 7.53-7.75 (m, 6H), 7.85 (m, 1H), 8.30 (d, 1H), 8.71 (m, 1H), 9.07 (s, 1H) | DMSO-$d_6$ |
| 240 | N-hydroxy-4-(5-{4-[2-isopropyl-5-(2-morpholin-4-yl-ethyl)-thiazol-4-yl]-phenoxy}-pentyloxy)-benzamidine | 1.32 (d, 6H), 1.58 (m, 2H), 1.78 (m, 4H), 2.39 (m, 4H), 2.52 (m, 2H), 2.98 (m, 2H), 3.25 (m, 1H), 3.57 (m, 4H), 4.04 (m, 4H), 5.72 (s, 2H), 6.96 (m, 4H), 7.50 (d, 2H), 7.59 (d, 2H), 9.46 (s, 1H) | DMSO-$d_6$ |
| 241 | N-hydroxy-4-[5-(4-{2-isopropyl-5-[2-(4-methyl-piperazin-1-yl)-ethyl]-thiazol-4-yl}-phenoxy)-pentyloxy]-benzamidine | 1.32 (d, 6H), 1.56 (m, 2H), 1.80 (m, 4H), 2.22 (s, 3H), 2.49 (m, 10H), 2.97 (m, 2H), 3.22 (m, 1H), 4.04 (m, 4H), 5.72 (s, 2H), 6.96 (m, 4H), 7.50 (d, 2H), 7.59 (d, 2H), 9.46 (s, 1H) | DMSO-$d_6$ |

TABLE 1-continued

| No. | Chemical name | NMR data | Sol. |
|---|---|---|---|
| 242 | N-hydroxy-4-(5-{4-[5-(2-imidazol-1-yl-ethyl)-2-isopropyl-thiazol-4-yl]-phenoxy}-pentyloxy)-benzamidine | 1.31 (d, 6H), 1.59 (m, 2H), 1.79 (m, 4H), 3.27 (m, 5H), 4.04 (m, 4H), 5.71 (s, 2H), 6.88 (s, 1H), 6.98 (m, 4H), 7.14 (s, 1H), 7.40 (d, 2H), 7.58 (d, 2H), 7.81 (d, 1H), 9.45 (s, 1H) | DMSO-$d_6$ |
| 243 | N-hydroxy-4-[5-(4-{2-isopropyl-5-[2-(2-morpholin-4-yl-ethylamino)-ethyl]-thiazol-4-yl}-phenoxy)-pentyloxy]-benzamidine | 1.32 (d, 6H), 1.58 (m, 2H), 1.79 (m, 4H), 2.32 (m, 6H), 2.60 (m, 2H), 2.81 (m, 2H), 2.99 (m, 2H), 3.23 (m, 1H), 3.52 (m, 4H), 4.03 (m, 4H), 5.71 (s, 2H), 6.98 (m, 4H), 7.53 (m, 4H) | DMSO-$d_6$ |
| 244 | N-hydroxy-4-[5-(4-{5-[2-(3-imidazol-1-yl-propylamino)-ethyl]-2-isopropyl-thiazol-4-yl}-phenoxy)-pentyloxy]-benzamidine | 1.32 (d, 6H), 1.57 (m, 2H), 1.81 (m, 6H), 2.43 (m, 2H), 2.74 (m, 2H), 2.94 (m, 2H), 3.22 (m, 1H), 4.01 (m, 6H), 5.71 (s, 2H), 6.87 (s, 1H), 6.99 (m, 4H), 7.12 (s, 1H), 7.57 (m, 4H), 7.82 (d, 1H) | DMSO-$d_6$ |
| 245 | N-hydroxy-4-(5-{4-[2-isopropyl-5-(2-thiomorpholin-4-yl-ethyl)-thiazol-4-yl]-phenoxy}-pentyloxy)-benzamidine | 1.32 (d, 6H), 1.58 (m, 2H), 1.80 (m, 4H), 2.60 (m, 10H), 2.97 (m, 2H), 3.22 (m, 1H), 4.01 (m, 4H), 5.70 (s, 2H), 6.92 (d, 2H), 6.98 (d, 2H), 7.47 (d, 2H), 7.59 (d, 2H), 9.44 (s, 1H) | DMSO-$d_6$ |
| 246 | N-hydroxy-4-(5-{4-[2-cyclohexyl-5-(2-morpholin-4-yl-ethyl)-thiazol-4-yl]-phenoxy}-pentyloxy)-benzamidine | 1.21 (m, 2H), 1.42 (m, 4H), 1.59 (m, 2H), 1.62 (m, 1H), 1.79 (m, 6H), 2.02 (m, 2H), 2.50 (m, 4H), 2.90 (m, 1H), 2.98 (m, 2H), 3.56 (m, 4H), 4.02 (m, 4H), 5.73 (s, 2H), 6.93 (d, 2H), 6.99 (d, 2H), 7.49 (d, 2H), 7.57 (d, 2H), 9.46 (s, 1H) | DMSO-$d_6$ |
| 247 | N-hydroxy-4-[5-(4-{2-cyclohexyl-5-[2-(4-methyl-piperazin-1-yl)-ethyl]-thiazol-4-yl}-phenoxy)-pentyloxy]-benzamidine | 1.22 (m, 1H), 1.42 (m, 4H), 1.58 (m, 2H), 1.68 (m, 1H), 1.79 (m, 6H), 2.04 (m, 2H), 2.14 (m, 4H), 2.50 (m, 7H), 2.90 (m, 1H), 2.97 (m, 2H), 3.45 (m, 2H), 4.01 (m, 4H), 5.72 (s, 2H), 6.92 (d, 2H), 6.98 (d, 2H), 7.48 (d, 2H), 7.57 (d, 2H), 9.46 (s, 1H) | DMSO-$d_6$ |
| 248 | N-hydroxy-4-[5-(4-{2-cyclohexyl-5-[2-(2-morpholin-4-yl-ethylamino)-ethyl]-thiazol-4-yl}-phenoxy)-pentyloxy]-benzamidine | 1.23 (m, 1H), 1.42 (m, 4H), 1.57 (m, 2H), 1.68 (m, 1H), 1.79 (m, 6H), 2.02 (m, 2H), 2.33 (m, 6H), 2.60 (m, 2H), 2.80 (m, 2H), 2.91 (m, 1H), 2.98 (m, 2H), 3.52 (m, 4H), 4.02 (m, 4H), 5.72 (s, 2H), 6.90 (d, 2H), 6.98 (d, 2H), 7.50 (d, 2H), 7.58 (d, 2H), 9.47 (s, 1H) | DMSO-$d_6$ |
| 249 | N-hydroxy-4-(5-{4-[2-cyclohexyl-5-(2-thiomorpholin-4-yl-ethyl)-thiazol-4-yl]-phenoxy}-pentyloxy)-benzamidine | 1.25 (m, 1H), 1.42 (m, 4H), 1.58 (m, 2H), 1.67 (m, 1H), 1.79 (m, 6H), 2.01 (m, 2H), 2.56 (m, 2H), 2.60 (m, 4H), 2.67 (m, 4H), 2.90 (m, 1H), 2.96 (m, 2H), 4.01 (m, 4H), 5.72 (s, 2H), 6.91 (d, 2H), 6.99 (d, 2H), 7.47 (d, 2H), 7.58 (d, 2H), 9.46 (s, 1H) | DMSO-$d_6$ |
| 250 | N-hydroxy-4-(5-{4-[2-cyclohexyl-5-(2-dimethylamino-ethyl)-thiazol-4-yl]-phenoxy}-pentyloxy)-benzamidine | 1.21 (m, 2H), 1.42 (m, 4H), 1.57 (m, 2H), 1.67 (m, 1H), 1.78 (m, 6H), 2.02 (m, 2H), 2.15 (s, 6H), 2.45 (t, 2H), 2.90 (m, 1H), 2.93 (t, 2H), 4.01 (m, 4H), 5.73 (s, 2H), 6.93 (d, 2H), 6.98 (d, 2H), 7.49 (d, 2H), 7.58 (d, 2H), 9.47 (s, 1H) | DMSO-$d_6$ |
| 251 | N-hydroxy-4-(5-{4-[2-cyclohexyl-5-(2-dipropylamino-ethyl)-thiazol-4-yl]-phenoxy}-pentyloxy)-benzamidine | 0.79 (m, 6H), 1.22 (m, 1H), 1.32 (m, 4H), 1.35 (m, 4H0, 1.58 (m, 2H), 1.66 (m, 1H), 1.76 (m, 7H), 2.00 (m, 2H), 2.33 (m, 3H), 2.60 (m, 2H), 2.92 (m, 3H), 4.01 (m, 4H), 5.72 (s, 2H), 6.90 (d, 2H), 6.97 (d, 2H), 7.47 (d, 2H), 7.57 (d, 2H), 9.46 (s, 1H) | DMSO-$d_6$ |
| 252 | N-hydroxy-4-(5-{4-[2-cyclohexyl-5-(2-cyclopropylamino-ethyl)-thiazol-4-yl]-phenoxy}-pentyloxy)-benzamidine | 0.20 (m, 2H), 0.33 (m, 2H), 1.22 (m, 2H), 1.42 (m, 4H), 1.58 (m, 2H), 1.65 (m, 1H), 1.79 (m, 6H), 2.04 (m, 3H), 2.80 (s, 2H), 2.96 (m, 2H), 4.02 (m, 4H), 5.72 (s, 2H), 6.90 (d, 2H), 6.98 (d, 2H), 7.49 (d, 2H), 7.58 (d, 2H), 9.46 (s, 1H) | DMSO-$d_6$ |
| 253 | N-hydroxy-4-[5-(4-{2-amino-5-[2-(2-morpholin-4-yl-ethylamino)-ethyl]-thiazol-4-yl}-phenoxy)-pentyloxy]-benzamidine | 1.58 (m, 1H), 1.79 (m, 4H), 2.35 (m, 6H), 2.69 (m, 2H), 2.78 (m, 4H), 3.54 (m, 4H), 4.01 (m, 4H), 5.71 (s, 2H), 6.93 (m, 4H), 7.44 (d, 2H), 7.59 (d, 2H) | DMSO-$d_6$ |
| 254 | N-hydroxy-4-(5-{4-[5-(2-morpholin-4-yl-ethyl)-2-phenyl-thiazol-4-yl]-phenoxy}-pentyloxy)-benzamidine | 1.57 (m, 2H), 1.79 (m, 4H), 2.41 (m, 4H), 2.55 (m, 2H), 3.06 (m, 2H), 3.59 (m, 4H), 4.02 (m, 4H), 7.01 (m, 4H), 7.57 (m, 7H), 7.92 (m, 2H) | DMSO-$d_6$ |

TABLE 1-continued

| No. | Chemical name | NMR data | Sol. |
|---|---|---|---|
| 255 | N-hydroxy-4-(5-{4-[2-ethyl-5-(2-morpholin-4-yl-ethyl)-thiazol-4-yl]-phenoxy}-pentyloxy)-benzamidine | 1.28 (t, 3H), 1.59 (m, 2H), 1.79 (m, 4H), 2.39 (m, 4H), 2.49 (m, 2H), 2.92 (q, 2H), 2.98 (t, 2H), 3.56 (t, 4H), 4.01 (q, 4H), 5.70 (s, 2H), 6.92 (d, 2H), 6.98 (d, 2H0, 7.49 (d, 2H), 7.57 (d, 2H), 9.43 (s, 1H) | DMSO-$d_6$ |
| 256 | N-hydroxy-4-(5-{4-[2-ethyl-5-(2-thiomorpholin-4-yl-ethyl)-thiazol-4-yl]-phenoxy}-pentyloxy)-benzamidine | 1.28 (m, 3H), 1.57 (m, 2H), 1.79 (m, 5H), 2.50 (m, 2H), 2.54 (d, 1H), 2.60 (m, 3H), 2.66 (m, 2H), 2.91 (m, 4H), 3.16 (d, 2H), 4.00 (m, 4H), 5.70 (s, 2H), 6.91 (d, 2H), 6.98 (d, 2H0, 7.47 (d, 2H), 7.58 (d, 2H), 9.43 (s, 1H) | DMSO-$d_6$ |
| 257 | N-hydroxy-4-(4-{4-[2-methyl-5-(2-morpholin-4-yl-ethyl)-thiazol-4-yl]-phenoxy}-butoxy)-benzamidine | 1.89 (m, 4H), 2.39 (m, 4H), 2.50 (m, 2H), 2.60 (s, 3H), 2.98 (t, 2H), 3.57 (t, 4H), 4.06 (m, 4H), 5.71 (s, 2H), 6.94 (d, 2H), 6.99 (d, 2H), 7.49 (d, 2H0, 7.58 (d, 2H), 9.45 (s, 1H) | DMSO-$d_6$ |
| 258 | 4-(5-{4-[2-cyclohexyl-5-(2-morpholin-4-yl-ethyl)-thiazol-4-yl]-phenoxy}-pentyloxy)-benzamidine | 1.20 (m, 2H), 1.41 (m, 4H), 1.59 (m, 2H), 1.62 (m, 1H), 1.78 (m, 6H), 2.01 (m, 2H), 2.49 (m, 2H), 2.90 (m, 1H), 2.98 (m, 2H), 3.56 (m, 4H), 4.02 (m, 4H), 6.93 (d, 2H), 6.99 (d, 2H), 7.49 (d, 2H), 7.57 (d, 2H), 9.10 (brs, 3H) | DMSO-$d_6$ |
| 259 | 4-(5-{4-[2-methyl-5-(2-morpholin-4-yl-ethyl)-thiazol-4-yl]-phenoxy}-pentyloxy)-benzamidine | 1.59 (m, 2H), 1.81 (m, 4H), 2.40 (m, 4H), 2.60 (s, 3H), 2.96 (m, 2H), 3.31 (m, 2H), 3.57 (m, 4H), 4.10 (m, 4H), 6.98 (d, 2H), 7.16 (d, 2H), 7.49 (d, 2H), 7.80 (d, 2H), 9.09 (brs, 3H) | DMSO-$d_6$ |
| 260 | N-hydroxy-4-(5-{4-[2-methylamino-5-(2-morpholin-4-yl-ethyl)-thiazol-4-yl]-phenoxy}-pentyloxy)-benzamidine | 1.57 (m, 2H), 1.79 (m, 4H), 2.39 (m, 4H), 2.50 (m, 2H), 2.81 (s, 3H), 2.84 (m, 2H), 3.58 (m, 4H), 4.00 (m, 4H), 5.74 (brs, 2H), 6.92 (m, 4H), 7.27 (m, 1H), 7.44 (m, 2H), 7.59 (m, 2H), 9.47 (brs, 1H) | DMSO-$d_6$ |
| 261 | N-hydroxy-4-[5-(4-{2-methylamino-5-[2-(4-methyl-piperazin-1-yl)-ethyl]-thiazol-4-yl}-phenoxy)-pentyloxy]-benzamidine | 1.58 (m, 2H), 1.80 (m, 4H), 2.50 (s, 3H), 2.79 (m, 6H), 2.85 (s, 3H), 3.38 (m, 6H), 4.01 (m, 4H), 5.75 (brs, 2H), 6.92 (m, 4H), 7.43 (m, 2H), 7.60 (m, 2H), 9.46 (brs, 1H) | DMSO-$d_6$ |
| 262 | N-hydroxy-4-(5-{4-[2-methylamino-5-(2-thiomorpholin-4-yl-ethyl)-thiazol-4-yl]-phenoxy}-pentyloxy)-benzamidine | 1.58 (m, 2H), 1.79 (m, 4H), 2.60 (m, 4H), 2.65 (m, 4H), 2.78 (m, 4H), 3.33 (s, 3H), 5.71 (s, 2H), 6.93 (m, 4H), 7.43 (d, 2H), 7.58 (d, 2H), 9.44 (s, 1H) | DMSO-$d_6$ |
| 263 | N-hydroxy-4-[5-(4-{2-methylamino-5-[2-(2-morpholin-4-yl-ethylamino)-ethyl]-thiazol-4-yl}-phenoxy)-pentyloxy]-benzamidine | 1.58 (m, 2H), 1.79 (m, 4H), 2.30 (m, 4H), 2.55 (m, 4H), 2.71 (m, 2H), 2.79 (m, 4H), 3.34 (s, 3H), 3.52 (m, 4H), 4.00 (m, 4H), 5.71 (s, 2H), 6.94 (m, 4H), 7.46 (d, 2H0, 7.59 (d, 2H), 9.46 (s, 1H) | DMSO-$d_6$ |
| 264 | N-hydroxy-4-[5-(4-{5-[2-(3-imidazol-1-yl-propylamino)-ethyl]-2-methylamino-thiazol-4-yl}-phenoxy)-pentyloxy]-benzamidine | 1.58 (m, 2H), 1.78 (m, 6H), 2.42 (m, 2H), 2.66 (m, 2H), 2.78 (m, 4H), 3.34 (s, 3H), 4.01 (m, 4H), 5.71 (s, 2H), 6.86 (s, 1H), 6.94 (m, 4H), 7.13 (s, 1H), 7.25 (d, 1H), 7.44 (d.2H), 7.58 (d, 2H), 9.46 (s, 1H) | DMSO-$d_6$ |
| 265 | 4-(5-{4-[2-methylamino-5-(2-morpholin-4-yl-ethyl)-thiazol-4-yl]-phenoxy}-pentyloxy)-benzamidine | 1.58 (m, 2H), 1.78 (m, 4H), 2.40 (m, 4H), 2.49 (m, 2H), 2.80 (s, 3H), 2.84 (m, 2H), 3.58 (m, 4H), 4.01 (m, 4H), 6.92 (m, 4H), 7.27 (m, 1H), 7.44 (m, 2H), 7.59 (m, 2H), 9.09 (brs, 3H) | DMSO-$d_6$ |
| 266 | N-hydroxy-4-(5-{4-[2-dimethylamino-5-(2-morpholin-4-yl-ethyl)-thiazol-4-yl]-phenoxy}-pentyloxy)-benzamidine | 1.58 (m, 2H), 1.79 (m, 4H), 2.38 (m, 4H), 2.48 (m, 2H), 2.86 (t, 2H), 3.00 (s, 6H), 3.57 (m, 4H), 4.01 (m, 4H), 5.71 (s, 2H), 6.94 (m, 4H), 7.45 (d, 2H), 7.58 (d, 2H), 9.45 (s, 1H) | DMSO-$d_6$ |
| 267 | N-hydroxy-4-(5-{4-[2-dimethylamino-5-(2-thiomorpholin-4-yl-ethyl)-thiazol-4-yl]-phenoxy}-pentyloxy)-benzamidine | 1.58 (m, 2H), 1.79 (m, 4H), 2.51 (m, 2H), 2.61 (m, 4H), 2.66 (m, 4H), 2.89 (m, 2H), 3.00 (s, 6H), 4.01 (m, 4H), 5.71 (s, 2H), 6.95 (m, 4H), 7.44 (d, 2H), 7.59 (d, 2H), 9.44 (s, 1H) | DMSO-$d_6$ |
| 268 | N-hydroxy-4-(5-{4-[2-(isobutyryl-methyl-amino)-5-(2-morpholin-4-yl-ethyl)-thiazol-4-yl]-phenoxy}-pentyloxy)-benzamidine | 1.15 (d, 6H), 1.58 (m, 2H), 1.79 (m, 4H), 2.40 (m, 4H), 2.78 (m, 1H), 2.97 (m, 2H), 3.33 (s, 3H), 3.57 (m, 4H), 3.69 (m, 2H), 4.01 (m, 4H), 5.71 (s, 2H), 6.93 (d, 2H), 6.99 (d, 2H), 7.51 (d, 2H), 7.60 (d, 2H), 9.44 (s, 1H) | DMSO-$d_6$ |

TABLE 1-continued

| No. | Chemical name | NMR data | Sol. |
|---|---|---|---|
| 269 | N-hydroxy-4-(5-{4-[2-[benzyl-(2-morpholin-4-yl-ethyl)-amino]-5-(2-morpholine-4-yl-ethyl)-thiazol-4-yl]-phenoxy}-pentyloxy)-benzamidine | 1.57 (m, 2H), 1.78 (m, 4H), 2.37 (m, 8H), 2.49 (m, 2H), 2.83 (m, 2H), 3.16 (m, 2H), 3.53 (m, 10H), 3.98 (m, 4H), 4.66 (s, 2H), 5.72 (s, 2H), 6.95 (m, 4H), 7.27 (m, 1H), 7.33 (m, 4H), 7.43 (m, 2H), 7.56 (m, 2H), 9.46 (s, 1H) | DMSO-d$_6$ |
| 270 | N-hydroxy-4-(5-{4-[2-diethylamino-5-(2-morpholin-4-yl-ethyl)-thiazol-4-yl]-phenoxy}-pentyloxy)-benzamidine | 1.15 (m, 6H), 1.57 (m, 2H), 1.79 (m, 4H), 2.38 (m, 4H), 2.48 (m, 2H), 2.83 (m, 2H), 3.40 (m, 4H), 3.57 (m, 4H), 4.02 (m, 4H), 5.71 (s, 2H), 6.94 (m, 4H), 7.45 (d, 2H), 7.58 (d, 2H), 9.45 (s, 1H) | DMSO-d$_6$ |
| 271 | N-hydroxy-4-(5-{4-[2-[bis-(2-methoxy-ethyl)-amino]-5-(2-morpholin-4-yl-ethyl)-thiazol-4-yl]-phenoxy}-pentyloxy)-benzamidine | 1.57 (m, 2H), 1.79 (m, 4H), 2.39 (m, 4H), 2.49 (m, 2H), 2.84 (m, 2H), 3.27 (s, 6H), 3.56 (m, 12H), 4.01 (m, 4H), 5.71 (s, 2H), 6.93 (m, 4H), 7.43 (d, 2H), 7.59 (d, 2H), 9.44 (s, 1H) | DMSO-d$_6$ |
| 272 | N-hydroxy-4-(5-{4-[2-morpholin-4-yl-5-(2-morpholin-4-yl-ethyl)-thiazol-4-yl]-phenoxy}-pentyloxy)-benzamidine | 1.58 (m, 2H), 1.80 (m, 4H), 2.43 (m, 4H), 3.32 (m, 8H), 3.58 (m, 8H), 4.05 (m, 4H), 5.71 (brs, 2H), 6.92 (m, 4H), 7.43 (m, 2H), 7.59 (m, 2H), 945 (brs, 1H) | DMSO-d$_6$ |
| 273 | N-hydroxy-4-(5-{4-[2-morpholin-4-yl-5-(2-thiomorpholin-4-yl-ethyl)-thiazol-4-yl]-phenoxy}-pentyloxy)-benzamidine | 1.58 (m, 2H), 1.80 (m, 4H), 2.68 (m, 8H), 2.85 (m, 2H), 3.33 (m, 6H), 3.70 (m, 4H), 4.02 (m, 4H), 5.71 (s, 2H), 6.95 (m, 4H), 7.44 (d, 2H), 7.59 (d, 2H), 9.44 (s, 1H) | DMSO-d$_6$ |
| 274 | N-hydroxy-4-[5-(4-{5-[2-(4-methyl-piperazin-1-yl)-ethyl]-2-morpholin-4-yl-thiazol-4-yl}-phenoxy)-pentyloxy]-benzamidine | 1.58 (m, 2H), 1.78 (m, 4H), 2.41 (s, 3H), 2.51 (m, 5H), 2.75 (m, 3H), 2.88 (m, 2H), 3.08 (m, 6H), 3.70 (m, 4H), 4.01 (m, 4H), 6.96 (m, 4H), 7.45 (d, 2H), 7.69 (d, 2H) | DMSO-d$_6$ |
| 275 | N-hydroxy-4-[5-(4-{2-morpholin-4-yl-5-[2-(2-morpholin-4-yl-ethylamino)-ethyl]-thiazol-4-yl}-phenoxy)-pentyloxy]-benzamidine | 1.59 (m, 2H), 1.79 (m, 4H), 2.30 (m, 4H), 2.50 (m, 4H), 2.97 (m, 2H), 3.37 (m, 4H), 3.50 (m, 6H), 3.71 (t, 4H), 4.01 (t, 4H), 5.70 (d, 2H), 6.94 (m, 4H), 7.42 (d, 2H), 7.51 (d, 2H), 7.58 (d, 2H), 9.44 (s, 1H) | DMSO-d$_6$ |
| 276 | N-hydroxy-4-(5-{4-[5-(2-morpholin-4-yl-ethyl)-2-piperidin-1-yl-methyl-thiazol-4-yl]-phenoxy}-pentyloxy)-benzamidine | 1.38 (m, 2H), 1.49-1.56 (m, 6H0, 1.76 (m, 4H), 2.37-2.49 (m, 8H), 2.98 (m, 2H), 3.54 (m, 4H), 3.67 (m, 2H), 3.99 (m, 6H), 6.90-6.97 (m, 4H), 7.47-7.56 (m, 4H) | DMSO-d$_6$ |
| 277 | 4-(5-{4-[2-morpholin-4-yl-5-(2-morpholin-4-yl-ethyl)-thiazol-4-yl]-phenoxy}-pentyloxy)-benzamidine | 1.59 (m, 2H), 1.80 (m, 4H), 2.43 (m, 4H), 3.32 (m, 8H), 3.598 (m, 8H), 4.05 (m, 4H), 6.92 (m, 4H), 7.42 (m, 2H), 7.59 (m, 2H), 9.10 (brs, 3H) | DMSO-d$_6$ |
| 278 | N-hydroxy-4-(5-{4-[5-(2-isobutyrylamino-ethyl)-2-methyl-thiazol-4-yl]-phenoxy}-pentyloxy)-benzamidine | 0.97 (d, 6H), 1.59 (m, 2H), 1.80 (m, 4H), 2.30 (m, 1H), 2.62 (s, 3H), 2.97 (m, 2H), 3.26 (m, 2H), 4.03 (m, 4H), 5.71 (s, 2H), 6.97 (m, 4H), 7.50 (d, 2H), 7.59 (d, 2H), 7.96 (m, 1H), 9.45 (s, 1H) | DMSO-d$_6$ |
| 279 | N-hydroxy-4-{5-[4-(5-{2-[isobutyl-(pyridin-3-carbonyl)-amino]-ethyl}-2-methyl-thiazol-4-yl)-phenoxy]-pentyloxy}-benzamidine | 0.62 (d, 3H), 0.86 (d, 3H), 1.22 (s, 3H), 1.57 (m, 2H), 1.79 (m, 5H), 2.56 (s, 2H), 2.66 (s, 1H), 2.98 (m, 2H), 3.15 (m, 1H), 3.21 (m, 1H), 3.42 (m, 1H), 3.63 (m, 1H), 4.02 (t, 2H), 4.09 (m, 2H), 5.72 (s, 2H), 6.91 (d, 2H), 6.98 (d, 2H), 7.09 (d, 4H), 7.23 (d, 2H), 8.59 (d, 2H), 9.45 (s, 1H) | DMSO-d$_6$ |
| 280 | N-hydroxy-4-{5-[4-(5-{2-[cyclopropyl-(pyridin-4-carbonyl)-amino]-ethyl}-2-isopropyl-thiazol-4-yl)-phenoxy]-pentyloxy}-benzamidine | 0.37 (m, 2H), 0.44 (m, 2H), 1.33 (d, 6H), 1.58 (m, 2H), 1.79 (m, 4H), 2.70 (m, 1H), 3.24 (m, 2H), 3.35 (m, 2H), 3.68 (m, 1H), 4.00 (m, 4H), 5.72 (s, 2H), 6.90 (d, 2H), 7.00 (m, 2H), 7.35 (m, 2H), 7.59 (m, 4H), 8.63 (m, 2H), 9.45 (s, 1H) | DMSO-d$_6$ |
| 281 | N-hydroxy-4-{5-[4-(2-cyclohexyl-5-{2-[cyclopropyl-(pyridin-3-carbonyl)-amino]-ethyl}-thiazol-4-yl)-phenoxy]-pentyloxy}-benzamidine | 0.36 (m, 2H), 0.47 (m, 2H), 1.22 (m, 1H), 1.43 (m, 4H), 1.57 (m, 2H), 1.66 (m, 1H), 1.78 (m, 6H), 2.02 (m, 2H), 2.77 (m, 1H), 2.95 (m, 1H), 3.27 (m, 2H), 3.70 (m, 2H), 4.02 (m, 4H), 5.72 (s, 2H), 6.90 (d, 2H), 6.97 (m, 2H), 7.43 (m, 1H), 7.59 (m, 3H), 7.82 (m, 2H), 8.60 (m, 2H), 9.46 (s, 1H) | DMSO-d$_6$ |

TABLE 1-continued

| No. | Chemical name | NMR data | Sol. |
|-----|---------------|----------|------|
| 282 | N-hydroxy-4-{5-[4-(5-methylcarbamoyl-2-methyl-thiazol-4-yl)-phenoxy]-pentyloxy}-benzamidine | 1.57 (m, 2H), 1.80 (m, 4H), 2.69 (s, 6H), 4.03 (m, 4H), 5.73 (brs, 2H), 6.97 (m, 4H), 7.61 (m, 4H), 9.46 (brs, 1H) | DMSO-$d_6$ |
| 283 | N-hydroxy-4-{5-[4-(5-isopropylcarbamoyl-2-methyl-thiazol-4-yl)-phenoxy]-pentyloxy}-benzamidine | 1.04 (d, 6H), 1.58 (m, 2H), 1.80 (m, 4H), 2.70 (s, 3H), 4.02 (m, 4H), 4.16 (m, 1H), 5.73 (brs, 2H), 6.98 (m, 4H), 7.60 (m, 4H), 9.46 (brs, 1H) | DMSO-$d_6$ |
| 284 | N-hydroxy-4-{5-[4-(5-{3-imidazol-1-yl-propylcarbamoyl}-2-methyl-thiazol-4-yl)-phenoxy]-pentyloxy}-benzamidine | 1.57 (m, 2H), 1.77 (m, 6H), 2.11 (brs, 3H), 3.36 (m, 2H), 3.91 (m, 2H), 4.00 (m, 4H), 5.71 (m, 2H), 6.80 (m, 2H), 6.94 (m, 4H), 7.25 (m, 2H), 7.56 (m, 1H), 7.75 (m, 1H), 7.84 (m, 1H), 8.30 (brs, 1H) | DMSO-$d_6$ |
| 285 | N-hydroxy-4-{5-[4-(2-amino-5-methylcarbamoyl-thiazol-4-yl)-phenoxy]-pentyloxy}-benzamidine | 1.57 (m, 2H), 1.78 (m, 4H), 2.60 (s, 3H), 4.01 (m, 4H), 5.75 (brs, 2H), 6.914 (m, 4H), 7.46 (m, 2H), 7.58 (m, 2H), 9.48 (brs, 1H) | DMSO-$d_6$ |
| 286 | N-hydroxy-4-{5-[4-(2-methyl-5-morpholin-4-yl-thiazol-4-yl)-phenoxy]-pentyloxy}-benzamidine | 1.58 (m, 2H), 1.79 (m, 4H), 2.59 (s, 3H), 2.78 (m, 4H), 3.73 (m, 4H), 4.01 (m, 4H), 5.71 (s, 2H), 6.93-6.98 (m, 4H), 7.58 (d, 2H), 8.05 (d, 2H), 9.45 (s, 1H) | DMSO-$d_6$ |
| 287 | N-hydroxy-4-(5-{4-[2-methyl-5-(4-methyl-piperazin-1-yl)-thiazol-4-yl]-phenoxy}-pentyloxy)-benzamidine | 1.58 (m, 2H), 1.80 (m, 4H), 2.23 (s, 3H), 2.48 (m, 4H), 2.58 (s, 3H), 2.80 (m, 4H), 4.02 (m, 4H), 5.71 (s, 2H), 6.96 (m, 4H), 7.59 (d, 1H), 7.83 (d, 1H), 8.04 (d, 2H), 9.44 (s, 1H) | DMSO-$d_6$ |
| 288 | N-hydroxy-4-{5-[4-(2-amino-5-morpholin-4-yl-thiazol-4-yl)-phenoxy]-pentyloxy}-benzamidine | 1.58 (m, 2H), 1.81 (m, 4H), 2.72 (m, 4H), 3.17 (s, 2H), 3.71 (m, 4H), 4.03 (m, 4H), 6.80 (d, 1H), 6.91 (d, 1H), 6.99 (d, 2H), 7.62 (d, 2H), 7.83 (d, 1H), 8.01 (d, 1H) | DMSO-$d_6$ |
| 289 | N-hydroxy-4-(5-{4-[5-(4-methyl-piperazin-1-yl)-2-morpholin-4-yl-thiazol-4-yl]-phenoxy}-pentyloxy)-benzamidine | 1.58 (m, 2H), 1.79 (m, 4H), 2.23 (s, 3H), 2.49 (m, 4H), 2.77 (m, 4H), 3.36 (m, 4H), 3.70 (m, 4H), 4.02 (m, 4H), 5.72 (s, 2H), 6.94 (m, 4H), 7.59 (d, 2H), 8.05 (d, 2H), 9.45 (s, 1H) | DMSO-$d_6$ |
| 290 | N-hydroxy-4-{5-[4-(2,5-di-morpholin-4-yl-thiazol-4-yl)-phenoxy]-pentyloxy}-benzamidine | 1.60 (m, 2H), 1.79 (m, 4H), 2.75 (m, 4H), 3.39 (m, 4H), 3.72 (m, 8H), 4.01 (m, 4H), 5.72 (s, 2H), 6.93 (m, 4H), 7.59 (d, 2H), 8.06 (d, 2H), 9.45 (s, 1H) | DMSO-$d_6$ |
| 291 | N-hydroxy-4-{5-[4-(2-morpholin-4-yl-5-thiomorpholin-4-yl-thiazol-4-yl)-phenoxy]-pentyloxy}-benzamidine | 1.60 (m, 2H), 1.79 (m, 4H), 2.51 (m, 6H), 2.77 (m, 2H), 2.98 (m, 2H), 3.34 (m, 4H), 3.70 (m, 6H), 4.02 (m, 4H), 5.72 (s, 2H), 6.92 (m, 4H), 7.59 (d, 2H), 7.77 (d, 1H), 8.03 (d, 1H), 9.45 (s, 1H) | DMSO-$d_6$ |
| 292 | N-hydroxy-4-{5-[4-(2-morpholin-4-yl-5-pyrolidin-1-yl-thiazol-4-yl)-phenoxy]-pentyloxy}-benzamidine | 1.59 (m, 2H), 1.80 (m, 4H), 1.89 (m, 4H), 2.91 (m, 4H), 3.36 (m, 4H), 3.70 (m, 4H), 4.02 (m, 4H), 5.72 (s, 2H), 6.93 (m, 4H), 7.48 (d, 2H), 7.94 (d, 2H), 9.45 (s, 1H) | DMSO-$d_6$ |
| 293 | N-hydroxy-4-{5-[4-(2-methyl-5-morpholin-4-ylmethyl-thiazol-4-yl)-phenoxy]-pentyloxy}-benzamidine | 1.59 (m, 2H), 1.80 (m, 4H), 2.51 (m, 4H), 3.34 (s, 3H), 3.61 (m, 4H), 3.77 (s, 2H), 4.03 (m, 4H), 5.71 (s, 2H), 6.92 (d, 2H), 7.01 (d, 2H), 7.58 (m, 4H), 9.44 (s, 1H) | DMSO-$d_6$ |
| 294 | N-hydroxy-4-(5-{4-[2-methyl-5-(4-methyl-piperazin-1-ylmethyl)-thiazol-4-yl]-phenoxy}-pentyloxy)-benzamidine | 1.61 (m, 2H), 1.81 (m, 4H), 2.17 (s, 3H), 2.35 (m, 4H), 2.51 (m, 4H), 3.33 (s, 3H), 3.75 (s, 1H), 3.80 (s, 1H), 4.03 (m, 4H), 5.71 (s, 2H), 6.92 (d, 2H), 7.01 (d, 2H), 7.58 (m, 4H), 9.44 (s, 1H) | DMSO-$d_6$ |
| 295 | N-hydroxy-4-{5-[4-(2-methyl-5-thiomorpholin-4-ylmethyl-thiazol-4-yl)-phenoxy]-pentyloxy}-benzamidine | 1.59 (m, 2H), 1.80 (m, 4H), 2.65 (m, 4H), 2.78 (m, 4H), 3.33 (s, 3H), 3.79 (s, 2H), 4.03 (m, 4H), 5.71 (s, 2H), 6.93 (d, 2H), 7.00 (d, 2H), 7.58 (m, 4H), 9.44 (s, 1H) | DMSO-$d_6$ |
| 296 | N-hydroxy-4-{5-[4-(2-methyl-5-piperidin-1-ylmethyl-thiazol-4-yl)-phenoxy]-pentyloxy}-benzamidine | 1.41 (m, 2H), 1.53 (m, 4H), 1.59 (m, 2H), 1.80 (m, 4H), 2.49 (m, 4H), 3.33 (s, 3H), 3.70 (s, 1H), 3.75 (s, 1H), 4.03 (m, 4H), 5.71 (s, 2H), 6.92 (d, 2H), 7.01 (d, 2H), 7.58 (m, 4H), 9.44 (s, 1H) | DMSO-$d_6$ |
| 297 | N-hydroxy-4-{5-[4-(5-dimethylaminomethyl-2- | 1.59 (m, 2H), 1.80 (m, 4H), 2.28 (d, 6H), 3.33 (s, 3H), 3.69 (s, 1H), 3.74 (s, 1H), | DMSO-$d_6$ |

TABLE 1-continued

| No. | Chemical name | NMR data | Sol. |
|---|---|---|---|
|  | methyl-thiazol-4-yl)-phenoxy]-pentyloxy}-benzamidine | 4.03 (m, 4H), 5.71 (s, 2H), 6.92 (d, 2H), 7.01 (d, 2H), 7.58 (m, 4H), 9.44 (s, 1H) |  |
| 298 | N-hydroxy-4-{5-[4-(5-butylaminomethyl-2-methyl-thiazol-4-yl)-phenoxy]-pentyloxy}-benzamidine | 0.88 (t, 3H), 1.32-1.42 (m, 4H), 1.58 (m, 2H), 1.80 (m, 4H), 2.48 (s, 3H), 2.51 (m, 2H), 3.92 (s, 2H), 4.02 (m, 4H), 5.72 (s, 2H), 6.91-6.98 (m, 4H), 7.55-7.61 (m, 4H), 9.46 (s, 1H) | DMSO-d$_6$ |
| 299 | N-hydroxy-4-(5-{4-[5-(isobutylamino-methyl)-2-methyl-thiazol-4-yl]-phenoxy}-pentyloxy)-benzamidine | 0.89 (d, 6H), 1.58 (m, 2H), 1.68 (m, 1H), 1.80 (m, 4H), 2.40 (d, 2H), 2.48 (s, 3H), 3.91 (s, 2H), 4.00 (m, 4H), 5.72 (s, 2H), 6.92 (d, 2H), 7.00 (d, 2H), 7.55-7.60 (m, 4H), 9.45 (s, 1H) | DMSO-d$_6$ |
| 300 | N-hydroxy-4-(5-{4-[5-(tert-butylamino-methyl)-2-methyl-thiazol-4-yl]-phenoxy}-pentyloxy)-benzamidine | 1.08 (s, 9H), 1.58 (m, 2H), 1.81 (m, 4H), 2.47 (s, 3H), 3.88 (s, 2H), 4.02 (m, 4H), 5.72 (s, 2H), 6.93 (d, 2H), 6.98 (d, 2H), 7.55-7.58 (m, 4H), 9.46 (s, 1H) | DMSO-d$_6$ |
| 301 | N-hydroxy-4-{5-[4-(2-methyl-5-propylaminomethyl-thiazol-4-yl)-phenoxy]-pentyloxy}-benzamidine | 0.86 (t, 3H), 1.44-1.46 (m, 2H), 1.58 (m, 2H), 1.80 (m, 4H), 2.48 (s, 3H), 2.51 (m, 2H), 3.91 (s, 2H), 4.02 (m, 4H), 5.72 (s, 2H), 6.92 (d, 2H), 6.97 (d, 2H), 7.55-7.60 (m, 4H), 9.46 (s, 1H) | DMSO-d$_6$ |
| 302 | N-hydroxy-4-[5-(4-{2-methyl-5-[(2-morpholin-4-yl-ethylamino)-methyl]-thiazol-4-yl}-phenoxy)-pentyloxy]-benzamidine | 1.58 (m, 2H), 1.80 (m, 4H), 2.35 (m, 2H), 2.40 (m, 4H), 2.48 (s, 3H), 2.70 (m, 2H), 3.56 (m, 4H), 3.95 (s, 2H), 4.01 (m, 4H), 5.72 (s, 2H), 6.93 (d, 2H), 6.99 (d, 2H), 7.55-7.60 (m, 4H), 9.46 (s, 1H) | DMSO-d$_6$ |
| 303 | N-hydroxy-4-[5-(4-{5-[(3-imidazol-1-yl-propylamino)-methyl]-2-methyl-thiazol-4-yl}-phenoxy)-pentyloxy]-benzamidine | 1.59 (m, 2H), 1.78 (m, 4H), 1.85 (m, 2H), 2.48 (s, 3H), 2.51 (m, 4H), 3.91 (s, 2H), 4.02 (m, 4H), 5.72 (s, 2H), 6.87 (s, 1H), 6.93 (d, 2H), 6.98 (m, 3H), 7.16 (s, 1H), 7.55-7.61 (m, 4H), 9.46 (s, 1H) | DMSO-d$_6$ |
| 304 | N-hydroxy-4-{5-[4-(2-methyl-5-pyrolidin-1-ylmethyl-thiazol-4-yl)-phenoxy]-pentyloxy}-benzamidine | 1.59 (m, 2H), 1.69 (m, 4H), 1.80 (m, 4H), 2.49 (m, 4H), 2.62 (s, 1.603H), 3.79 (s, 2H), 4.03 (m, 4H), 5.73 (s, 2H), 6.93-7.00 (m, 4H), 7.54-7.58 (m, 4H), 9.46 (s, 1H) | DMSO-d$_6$ |
| 305 | N-hydroxy-4-{5-[4-(5-imidazol-1-ylmethyl-2-methyl-thiazol-4-yl)-phenoxy]-pentyloxy}-benzamidine | 1.58 (m, 2H), 1.79 (m, 4H), 2.48 (s.3H), 4.03 (m, 4H), 5.54 (s, 2H), 5.72 (s, 2H), 6.94 (m, 3H), 7.02 (d, 2H), 7.29 (s, 1H), 7.56-7.61 (m, 4H), 7.81 (s, 1H), 9.46 (s, 1H) | DMSO-d$_6$ |
| 306 | N-hydroxy-4-(5-{4-[5-(benzylamino-methyl)-2-methyl-thiazol-4-yl]-phenoxy}-pentyloxy)-benzamidine | 1.58 (m, 2H), 1.79 (m, 4H), 2.49 (s.3H), 3.78 (s, 2H), 3.91 (s, 2H), 4.01 (m, 4H), 5.72 (s, 2H) 6.92 (d, 2H), 7.00 (d, 2H), 7.25 (m, 1H), 7.36 (m, 4H) 7.55-7.61 (m, 4H), 9.46 (s, 1H) | DMSO-d$_6$ |
| 307 | N-hydroxy-4-{5-[4-(5-cyclopropylaminomethyl-2-methyl-thiazol-4-yl)-phenoxy]-pentyloxy}-benzamidine | 0.30 (m, 2H), 0.39 (m, 2H), 1.59 (m, 2H), 1.80 (m, 4H), 2.20 (m, 1H), 2.48 (s, 3H), 3.96 (s, 2H), 4.02 (m, 4H), 5.72 (s, 2H), 6.92 (d, 2H), 7.00 (d, 2H), 7.58 (m, 4H), 9.45 (s, 1H) | DMSO-d$_6$ |
| 308 | N-hydroxy-4-{5-[4-(2-methylamino-5-morpholin-4-yl-thiazol-4-yl)-phenoxy]-pentyloxy}-benzamidine | 1.58 (m, 2H), 1.80 (m, 4H), 2.72 (m, 4H), 3.34 (s, 3H), 3.71 (m, 4H), 4.01 (m, 4H), 5.77 (s, 2H), 6.92 (m, 4H), 7.59 (d, 2H), 8.05 (d, 2H), 9.47 (s, 1H) | DMSO-d$_6$ |
| 309 | N-hydroxy-4-(5-{4-[2-(methyl-pyridin-4-ylmethyl-amino)-5-morpholin-4-ylmethyl-thiazol-4-yl]-phenoxy}-pentyloxy)-benzamidine | 1.59 (m, 2H), 1.78 (m, 4H), 2.40 (m, 4H), 3.07 (s, 3H), 3.34 (m, 2H), 3.56 (m, 4H), 4.01 (m, 4H), 4.73-4.80 (m, 2H), 5.72 (brs, 2H), 6.91 (m, 4H), 7.28 (m, 2H), 7.49 (m, 2H), 7.57 (m, 2H), 8.53 (m, 2H), 9.45 (brs, 1H) | DMSO-d$_6$ |
| 310 | N-hydroxy-4-[5-(4-{2-[(2-hydroxy-ethyl)-methyl-amino]-5-morpholin-4-ylmethyl-thiazol-4-yl}-phenoxy)-pentyloxy]-benzamidine | 1.58 (m, 2H), 1.78 (m, 4H), 2.40 (m, 4H), 3.04 (s, 3H), 3.37 (m, 4H), 3.46 (m, 2H), 3.60 (m, 4H), 3.98 (m, 4H), 4.82 (t, 1H), 5.72 (brs, 2H), 6.88 (m, 4H), 7.42 (d, 2H), 7.58 (d, 2H), 9.45 (brs, 1H) | DMSO-d$_6$ |
| 311 | N-hydroxy-4-(5-{4-[2-(ethyl-methyl-amino)-5-morpholin-4-ylmethyl-thiazol-4-yl]-phenoxy}-pentyloxy)-benzamidine | 1.12 (t, 3H), 1.58 (m, 2H), 1.79 (m, 4H), 2.50 (m, 4H), 2.97 (s, 3H), 3.01 (m, 2H), 3.35 (m, 2H), 3.44 (m, 4H), 3.98 (m, 4H), 5.72 (brs, 2H), 6.89 (m, 4H), 7.42 (d, 2H), 7.58 (d, 2H), 9.46 (brs, 1H) | DMSO-d$_6$ |

TABLE 1-continued

| No. | Chemical name | NMR data | Sol. |
|---|---|---|---|
| 312 | N-hydroxy-4-(5-{4-[2-(benzyl-methyl-amino)-5-morpholin-4-ylmethyl-thiazol-4-yl]-phenoxy}-pentyloxy)-benzamidine | 1.57-1.60 (m, 2H), 1.77-1.81 (m, 4H), 2.40 (s, 4H), 3.00 (s, 3H), 3.55 (s, 6H), 4.01-4.03 (m, 4H), 4.68 (s, 2H), 5.71 (s, 2H), 6.92 (d, 2H), 6.98 (d, 2H), 7.28-7.37 (m, 5H), 7.52 (d, 2H), 7.59 (d, 2H), 9.45 (s, 1H) | DMSO-$d_6$ |
| 313 | N-hydroxy-4-[5-(4-{2-[methyl-(2-morpholin-4-yl-ethyl)-amino]-5-morpholin-4-ylmethyl-thiazol-4-yl}-phenoxy)-pentyloxy]-benzamidine | 1.58 (m, 2H), 1.79 (m, 4H), 2.40 (m, 8H), 2.51 (m, 4H), 3.01 (s, 3H), 3.55 (m, 12H), 3.99 (m, 4H), 5.74 (m, 2H), 6.91 (d, 2H), 6.93 (d, 2H), 7.49 (d, 2H), 7.60 (d, 2H), 9.48 (s, 1H) | DMSO-$d_6$ |
| 314 | N-hydroxy-4-[5-(4-{2-[methyl-(2-morpholin-4-yl-ethyl)-amino]-5-thiomorpholin-4-ylmethyl-thiazol-4-yl}-phenoxy)-pentyloxy]-benzamidine | 1.59 (m, 2H), 1.77 (m, 4H), 2.41 (m, 4H), 2.51 (m, 2H), 2.63 (m, 8H), 3.01 (s, 3H), 3.54 (m, 8H), 4.00 (m, 4H), 5.74 (m, 2H), 6.93 (m, 4H), 7.47 (d, 2H), 7.61 (d, 2H), 9.49 (s, 1H) | DMSO-$d_6$ |
| 315 | N-hydroxy-4-[5-(4-{5-{[bis-(2-methoxy-ethyl)-amino]-methyl}-2-[methyl-(2-morpholin-4-yl-ethyl)-amino]-thiazol-4-yl}-phenoxy)-pentyloxy]-benzamidine | 1.58 (m, 2H), 1.80 (m, 4H), 2.43 (m, 4H), 2.50 (m, 2H), 2.63 (m, 2H), 3.01 (s, 3H), 3.18 (m, 4H), 3.36 (m, 8H), 3.55 (m, 6H), 3.74 (m, 2H), 4.01 (m, 4H), 5.72 (s, 2H), 6.92 (m, 4H) 7.42 (d, 2H), 7.59 (d, 2H), 9.46 (s, 1H) | DMSO-$d_6$ |
| 316 | N-hydroxy-4-(5-{4-[2-[methyl-(2-morpholin-4-yl-ethyl)-amino]-5-(4-methyl-piperazin-1-ylmethyl)-thiazol-4-yl]-phenoxy}-pentyloxy)-benzamidine | 1.58 (m, 2H), 1.80 (m, 4H), 2.16 (s, 3H), 2.42 (m, 6H), 3.01 (s, 3H), 3.17 (m, 8H), 3.55 (m, 8H), 4.01 (m, 4H), 5.71 (m, 2H), 6.94 (m, 4H), 7.48 (d, 2H), 7.59 (d, 2H), 9.46 (s, 1H) | DMSO-$d_6$ |
| 317 | N-hydroxy-4-[5-(4-{5-(isopropylamino-methyl)-2-[methyl-(2-morpholin-4-yl-ethyl)-amino]-thiazol-4-yl}-phenoxy)-pentyloxy]-benzamidine | 0.98 (d, 6H), 1.58 (m, 2H), 1.80 (m, 4H), 2.42 (m, 4H), 2.51 (m, 1H), 3.02 (s, 3H), 3.31 (m, 2H), 3.54 (m, 6H), 3.79 (m, 2H), 4.00 (m, 4H), 5.72 (s, 2H), 6.93-6.96 (m, 4H), 7.49 (d, 2H), 7.58 (d, 2H), 8.32 (s, 1H), 9.45 (s, 1H) | DMSO-$d_6$ |
| 318 | N-hydroxy-4-[5-(4-{5-[(2-methoxy-ethylamino)-methyl]-2-[methyl-(2-morpholin-4-yl-ethyl)-amino]-thiazol-4-yl}-phenoxy)-pentyloxy]-benzamidine | 1.57 (m, 2H), 1.78 (m, 4H), 2.42 (m, 4H), 2.50 (m, 6H), 3.02 (s, 3H), 3.36 (m, 5H), 3.53 (m, 6H), 4.00 (m, 4H), 5.71 (brs, 2H), 6.91 (m, 4H), 7.44 (m, 2H), 7.59 (m, 2H), 9.46 (brs, 1H) | DMSO-$d_6$ |
| 319 | N-hydroxy-4-[5-(4-{2-[(2-methoxy-ethyl)-methyl-amino]-5-morpholin-4-ylmethyl-thiazol-4-yl}-phenoxy)-pentyloxy]-benzamidine | 1.58 (m, 2H), 1.80 (m, 4H), 2.37 (m, 4H), 3.03 (s, 3H), 3.26 (s, 3H), 3.55 (m, 10H), 4.00 (m, 4H), 5.72 (s, 2H), 6.93-6.97 (m, 4H), 7.49 (d, 2H), 7.59 (d, 2H), 9.46 (s, 1H) | DMSO-$d_6$ |
| 320 | N-hydroxy-4-(5-{4-[2-(methyl-propyl-amino)-5-morpholin-4-ylmethyl-thiazol-4-yl]-phenoxy}-pentyloxy)-benzamidine | 0.88 (t, 3H), 1.59 (m, 4H), 1.79 (m, 4H), 2.39 (m, 4H), 3.00 (s, 3H), 3.35 (m, 2H), 3.55 (m, 6H), 4.00 (m, 4H), 5.72 (s, 2H), 6.95 (m, 4H), 7.49 (d, 2H), 7.60 (d, 2H), 9.45 (s, 1H) | DMSO-$d_6$ |
| 321 | N-hydroxy-4-(5-{4-[2-(methyl-pyridin-3-ylmethyl-amino)-5-morpholin-4-ylmethyl-thiazol-4-yl]-phenoxy}-pentyloxy)-benzamidine | 1.58 (m, 2H), 1.78 (m, 4H), 2.38 (m, 4H), 3.03 (s, 3H), 3.56 (m, 6H), 4.01 (m, 4H), 4.72 (s, 2H), 5.72 (s, 2H), 6.92 (d, 2H), 6.98 (d, 2H), 7.39 (m, 1H), 7.52 (d, 2H), 7.59 (d, 2H), 7.74 (m, 1H), 8.49 (m, 1H), 8.57 (m, 1H), 9.46 (s, 1H) | DMSO-$d_6$ |
| 322 | N-hydroxy-4-{5-[4-(2-methyl-5-methylamino-thiazol-4-yl)-phenoxy]-pentyloxy}-benzamidine | 1.58 (m, 2H), 1.79 (m, 4H), 2.50 (s, 3H), 2.61 (s, 3H), 4.04 (m, 4H), 5.70 (s, 2H), 6.92 (m, 4H), 7.58 (d, 2H), 7.89 (d, 1H), 7.97 (d, 1H), 9.43 (s, 1H) | DMSO-$d_6$ |
| 323 | N-hydroxy-4-[5-(4-{2-methyl-5-[(pyridin-4-carbonyl)-amino]-thiazol-4-yl}-phenoxy)-pentyloxy]-benzamidine | 1.20 (m, 2H), 1.84 (m, 4H), 2.65 (s, 3H), 4.01 (m, 4H), 5.73 (s, 2H), 6.92 (d, 2H), 7.01 (d, 2H), 7.58 (d, 2H), 7.74 (d, 2H), 7.85 (d, 2H), 8.80 (d, 2H), 9.45 (s, 1H) | DMSO-$d_6$ |
| 324 | N-hydroxy-4-[5-(4-{2-methyl-5-[(pyridin-3-carbonyl)-amino]-thiazol-4-yl}-phenoxy)-pentyloxy]-benzamidine | 1.58 (m, 2H), 1.78 (m, 4H), 2.64 (s, 3H), 4.01 (m, 4H), 5.70 (s, 2H), 6.91 (d, 2H), 7.02 (d, 2H), 7.58 (m, 3H), 7.78 (d, 2H), 8.29 (d, 1H), 8.77 (d, 1H), 9.10 (s, 1H), 9.43 (s, 1H) | DMSO-$d_6$ |

TABLE 1-continued

| No. | Chemical name | NMR data | Sol. |
|-----|---------------|----------|------|
| 325 | N-hydroxy-4-[5-(4-{2-phenyl-5-[(pyridin-3-carbonyl)-amino]-thiazol-4-yl}-phenoxy)-pentyloxy]-benzamidine | 1.58 (m, 2H), 1.79 (m, 4H), 4.07 (m, 4H), 7.06 (d, 1H), 7.09 (m, 3H), 7.51 (m, 5H), 7.87 (m, 3H), 7.97 (d, 2H), 8.32 (d, 1H), 8.79 (d, 1H), 9.13 (s, 1H) | DMSO-$d_6$ |
| 326 | N-hydroxy-4-{5-[4-(5-dimethylamino-2-methyl-thiazol-4-yl)-phenoxy]-pentyloxy}-benzamidine | 1.58 (m, 2H), 1.79 (m, 4H), 2.57 (s, 3H), 2.61 (s, 6H), 4.00 (m, 4H), 5.70 (s, 2H), 6.91 (d, 2H), 6.96 (d, 2H), 7.59 (d, 2H), 7.98 (d, 2H), 9.44 (s, 1H) | DMSO-$d_6$ |
| 327 | N-hydroxy-4-{5-[4-(5-dimethylamino-2-phenyl-thiazol-4-yl)-phenoxy]-pentyloxy}-benzamidine | 1.58 (m, 2H), 1.79 (m, 4H), 2.70 (s, 6H), 4.02 (m, 4H), 5.71 (s, 2H), 6.92 (d, 2H), 7.01 (d, 2H), 7.47 (m, 3H), 7.60 (d, 2H), 7.89 (d, 2H), 8.04 (d, 2H), 9.46 (s, 1H) | DMSO-$d_6$ |
| 328 | N-hydroxy-4-{5-[4-(2-cyclohexyl-5-dimethylamino-thiazol-4-yl)-phenoxy]-pentyloxy}-benzamidine | 1.23 (m, 1H), 1.41 (m, 4H), 1.59 (m, 2H), 1.65 (m, 1H), 1.79 (m, 6H), 2.03 (m, 2H), 2.61 (s, 6H), 2.85 (m, 1H), 4.01 (m, 4H), 5.72 (s, 2H), 6.94 (m, 4H), 7.60 (d, 2H), 7.99 (d, 2H), 9.46 (s, 1H). | DMSO-$d_6$ |
| 329 | N-hydroxy-4-{5-[4-(2-methyl-5-[1,2,4]triazol-1-yl-thiazol-4-yl)-phenoxy]-pentyloxy}-benzamidine | 1.55 (m, 2H), 1.76 (m, 4H), 2.74 (s, 3H), 3.99 (m, 4H), 5.71 (s, 2H), 6.90 (m, 4H), 7.17 (d, 2H), 7.58 (d, 2H), 8.36 (s, 1H), 8.84 (s, 1H), 9.45 (s, 1H) | DMSO-$d_6$ |
| 330 | N-hydroxy-4-{5-[4-(5-amino-2-phenyl-thiazol-4-yl)-phenoxy]-pentyloxy}-benzamidine | 1.59 (m, 2H), 1.80 (m, 4H), 4.02 (m, 4H), 5.73 (s, 2H), 5.88 (s, 2H), 6.94 (d, 2H), 6.98 (d, 2H), 7.40 (t, 1H), 7.42 (d, 2H), 7.59 (d, 2H), 7.74 (d, 2H), 7.76 (d, 2H), 9.45 (s, 1H) | DMSO-$d_6$ |
| 331 | N-hydroxy-4-{5-[4-(5-amino-2-methyl-thiazol-4-yl)-phenoxy]-pentyloxy}-benzamidine | 1.58 (m, 2H), 1.77 (m, 4H), 2.44 (s, 3H), 3.99 (m, 4H), 5.34 (s, 2H), 5.71 (s, 2H), 6.92 (m, 4H), 7.59 (d, 2H), 7.67 (d, 2H), 9.44 (s, 1H) | DMSO-$d_6$ |
| 332 | N-hydroxy-4-{5-[4-(5-amino-2-pyridin-3-yl-thiazol-4-yl)-phenoxy]-pentyloxy}-benzamidine | 1.60 (m, 2H), 1.81 (m, 4H), 4.03 (m, 4H), 5.72 (s, 2H), 6.05 (s, 2H), 6.92 (d, 2H), 7.00 (d, 2H), 7.45 (d, 1H), 7.59 (d, 2H), 7.75 (d, 2H), 8.10 (d, 1H), 8.52 (t, 1H), 8.95 (s, 1H), 9.45 (s, 1H) | DMSO-$d_6$ |
| 333 | N-hydroxy-4-{5-[4-(5-amino-2-ethyl-thiazol-4-yl)-phenoxy]-pentyloxy}-benzamidine | 1.23 (t, 3H), 1.58 (m, 2H), 1.78 (m, 4H), 2.78 (q, 2H), 4.01 (m, 4H), 5.38 (s, 2H), 5.72 (s, 2H), 6.93 (d, 4H), 7.59 (d, 2H), 7.67 (d, 2H), 9.46 (s, 1H). | DMSO-$d_6$ |
| 334 | N-hydroxy-4-{5-[4-(5-amino-2-cyclohexyl-thiazol-4-yl)-phenoxy]-pentyloxy}-benzamidine | 1.23 (m, 1H), 1.36 (m, 4H), 1.57 (m, 2H), 1.64 (m, 1H), 1.81 (m, 6H), 1.98 (m, 2H), 2.74 (m, 1H), 4.00 (m, 4H), 5.36 (s, 2H), 5.71 (s, 2H), 6.92 (d, 4H), 7.59 (d, 2H), 7.66 (d, 2H), 9.45 (s, 1H). | DMSO-$d_6$ |
| 335 | N-hydroxy-4-{5-[4-(2-methylamino-5-morpholin-4-ylmethyl-thiazol-4-yl)-phenoxy]-pentyloxy}-benzamidine | 1.58 (m, 2H), 1.78 (m, 4H), 2.41 (m, 4H), 2.80 (s, 3H), 3.34 (m, 2H), 3.56 (m, 4H), 4.01 (m, 4H), 5.73 (brs, 2H), 6.92 (m, 4H), 7.36 (m, 1H), 7.49 (d, 2H), 7.59 (d, 2H), 9.46 (brs, 1H) | DMSO-$d_6$ |
| 336 | N-hydroxy-4-{5-[4-(2-morpholin-4-yl-5-morpholin-4-ylmethyl-thiazol-4-yl)-phenoxy]-pentyloxy}-benzamidine | 1.60 (m, 2H), 1.80 (m, 4H), 2.38 (m, 4H), 3.35 (m, 4H), 3.57 (m, 6H), 3.70 (m, 4H), 4.03 (m, 4H), 5.72 (s, 2H), 7.49 (d, 2H), 7.59 (d, 2H), 9.45 (s, 1H) | DMSO-$d_6$ |
| 337 | N-hydroxy-4-{5-[4-(5-morpholin-4-yl-2-piperidin-1-yl-thiazol-4-yl)-phenoxy]-pentyloxy}-benzamidine | 1.59 (m, 8H), 1.79 (m, 4H), 2.75 (m, 4H), 3.41 (m, 4H), 3.73 (m, 4H), 4.00 (m, 4H), 5.72 (s, 2H), 6.92 (m, 4H), 7.59 (d, 2H), 8.06 (d, 2H), 9.45 (s, 1H) | DMSO-$d_6$ |

EXAMPLE 1

Effect of Individual or Combination Treatment of Etidronic Acid (2 μM) and Compounds 187, 138, 119 and 169 on Osteoclast Differentiation The differentiation of osteoclast from mouse bone marrow cells was induced by using co-culture system, and inhibitory effect of the drug on osteoclast differentiation was evaluated by treatment of single or combination formulation. Co-culture was performed using mouse-derived bone marrow cells and osteoblasts.

1. Preparation of Bone Marrow Cells and Osteoblasts

Co-culture was performed using mouse-derived bone marrow cells and osteoblasts.

Femora and tibia were aseptically ectomized from 6~8 week-old male ddY mice to harvest bone marrow cells by a general method using a syringe. The red blood cells were removed from the bone marrow cells, followed by centrifugation. The bone marrow cells were suspended in α-MEM medium supplemented with 10% fetal bovine serum, and the numbers of the eukaryotic cells in the harvested bone marrow cells were counted and then immediately used for a co-culture system.

The calvaria were aseptically ectomized from 1~2 day-old neonatal ICR mice, and osteoblasts were isolated by sequential treatment with an enzyme solution of 0.2% collagenase. The cell suspended supernatant was centrifuged, and the recovered osteoblasts were propagated in α-MEM medium supplemented with 10% fetal bovine serum for a predetermined period of time. Then, these cells were diluted to a desired cell number, and used for the experiment.

2. Measurement of Osteoclast Differentiation Via Co-culture System

The bone marrow cells ($1 \times 10^5$ cells/well) and osteoblasts (3,000 cells/well) prepared in the above were plated in a 96-well plate using a-MEM medium supplemented with 10% fetal bovine serum. At this time, differentiation factors, 1α,25-dihydroxyvitamin $D_3$ ($10^{-8}$ M, hereinbelow, referred to as vitamin $D_3$) and dexamethasone ($10^{-8}$ M), were co-added to the medium to induce osteoclast differentiation. The medium was replaced with fresh media containing the differentiation factors every 2 to 3 days.

After 7 days, when multinucleated osteoclasts were observed, the medium was removed from the wells, and then the cells were fixed with PBS containing 10% Formalin. Tartrate-Resistant Acid Phosphatase (hereinbelow, referred to as TRAP) was used as a marker to measure the mature osteoclast in consideration of its characteristics showing a positive reaction to a TRAP staining solution. The TRAP staining solution was prepared in such the manner that a substrate, naphtol AS-MS phosphate and a coloring agent (Fast Red Violet LB salt) were dissolved in N,N-dimethylformamide. A 0.1 N $NaHCO_3$ buffer solution containing 50 mM tartaric acid was added thereto, and the mixture was stored at a refrigerator prior to use as a staining solution. The osteoclasts with 6-7 or more nuclei showing a TRAP-positive reaction were counted under a microscope.

3. Effect of Test Substance on Osteoclast Differentiation

Individual treatment of etidronic acid, Compound 187, Compound 138, Compound 119, or Compound 169 and combination treatment of etidronic acid with Compound 187, Compound 138, Compound 119 or Compound 169 were performed to evaluate their effects on osteoclast differentiation by the above experiment. All experiments were performed using α-MEM medium supplemented with 10% fetal bovine serum, containing the differentiation factors, vitamin $D_3$ and dexamethasone.

Compound 187, Compound 138, Compound 119 and Compound 169 were dissolved in DMSO at a concentration of 0.1 mM, and then diluted 1,000 fold with the differentiation media to a final concentration of 0.1 μM. Etidronic acid was dissolved in purified water at a concentration of 2 mM, and then diluted 1,000 fold with the media to a final concentration of 2 μM. In this connection, a control group was maintained in 0.1% DMSO.

As the above described, the sample substances and cells, which were diluted to the desired concentrations, were plated in 96-well plate, and co-cultured. On days 3 and 5 of culture, the media were replaced with fresh differentiation media containing the sample substances. On day 7 of culture, TRAP staining was performed to count the mature multinucleated osteoclast that was formed by differentiation. The mature osteoclasts with 6 or more nuclei were counted under a microscope. The results were expressed as a percentage (%) of the number of mature osteoclast observed in each experimental group, when the number of mature osteoclast in the control group (solvent only) was regarded as 100%. The experiment was performed with 4 wells per experimental group (n=4), and the results were expressed as mean value±standard deviation. In addition, the experiment was repeated at least three times, and Student t-test was applied for significant difference between experimental groups. The results are shown in the following Table 2.

TABLE 2

Effect of individual or combination treatment of etidronic acid with Compound 187, Compound 138, Compound 119, or Compound 169 on osteoclast differentiation

| | % number of osteoclast (vs. solvent control group) | | | | | |
|---|---|---|---|---|---|---|
| | con(—) | Etidronic acid | Compound 187 | Compound 138 | Compound 119 | Compound 169 |
| A. Solvent control group | 100 ± 8.1 | | | | | |
| B. Individual treatment of Compound (0.1 μM) | | | 67 ± 7.4* | 71 ± 6.5* | 66 ± 8.3* | 78 ± 8.6* |
| C. Individual treatment of etidronic acid (2 μM) | | 86 ± 6.9* | | | | |
| D. Combination treatment of compound + etidronic acid | | | 41 ± 7.5*#@ | 40 ± 8.4*#@ | 38 ± 8.2*#@ | 49 ± 9.7*#@ |

[Note]
A. Control group (con(—)): 0.1% DMSO solvent
B. Individual treatment of Compounds 187, 138, 119, or 169 (0.1 μM)
C. Individual treatment of etidronic acid (2 μM)
D. Combination treatment of etidronic acid (2 μM) with compound 187, 138, 119, or 169 (0.1 μM)
*p < 0.0001 vs. solvent control group,
p < 0.0001 vs. individual treatment group of each compound
@p < 0.0001 vs. individual treatment group of etidronic acid As shown in Table 2, when the number of multinucleated osteoclast showing a TRAP-positive reaction in the solvent control group was regarded as 100%, the numbers of multinucleated osteoclast, which were obtained in the individual treatment groups of Compound 187, Compound 138, Compound 119 and Compound 169, were expressed as percentage. When each substance was singly added to the co-cultured cells at the same concentration of 0.1 μM, the substances showed inhibitory effect on osteoclast differentiation, in which their relative numbers of multinucleated osteoclasts to that of the control group was found to be 67%, 71%, 66% and 78%, respectively.

In addition, in the experimental group that was singly treated with 2 μM etidronic acid, its relative number of multinucleated osteoclast to that of the solvent control group was measured as 86%. Such significant reduction indicates that etidronic acid is an osteoclast differentiation inhibitor.

When the combination treatment of etidronic acid with Compound 187, Compound 138, Compound 119 or Compound 169 was simultaneously performed, the relative number of multinucleated osteoclast to that of the solvent control group was found to be 41% in the combination treatment group of etidronic acid with Compound 187. This result indicates that the value is much lower than the sum of each individual treatment, showing the strong inhibitory effect on osteoclast differentiation. This notable result was also observed in the combination treatment of etidronic acid with Compound 138 (40%), Compound 119 (38%) or Compound 169 (49%). Taken together, the results demonstrate that the combination treatment of two substances exhibited much stronger efficacy than expected from the sum of each individual treatment.

EXAMPLE 2

Effect of Individual or Combination Treatment of Clodronic Acid (1 μM) and Compounds 187, 138, 119 and 169 on Osteoclast Differentiation The experiment was performed in the same manner as in Example 1 to evaluate the effect of individual or combination treatment of clodronic acid and Compound 187, Compound 138, Compound 119 and Compound 169 on osteoclast differentiation, except using 1 μM clodronic acid instead of 2 μM etidronic acid.

Clodronic acid was dissolved in purified water at a concentration of 1 mM, and then diluted 1,000 fold with the media to a final concentration of 1 μM.

The results are shown in the following Table 3.

As mentioned in Example 1, in the experimental group that was singly treated with Compound 187, Compound 138, Compound or Compound 169, its relative number of multinucleated osteoclast to that of the solvent control group was found to be significantly low. In the experimental group that was singly treated with 1 μM clodronic acid, its relative number of multinucleated osteoclast to that of the solvent control group was measured as 88%, resulting in significant reduction (Table 3). The combination treatment of the substances was performed in the same manner. Consequently, a statistically significant increase in the inhibitory effect on osteoclast differentiation was observed in the combination treatment group of clodronic acid with Compound (54%), Compound 119 (47%) or Compound 169 (59%), except for the combination treatment group of clodronic acid with Compound 187.

EXAMPLE 3

Effect of Individual or Combination Treatment of Pamidronic Acid (0.1 μM) and Compounds 187, 138, 119 and 169 on Osteoclast Differentiation The experiment was performed in the same manner as in Example 1 to evaluate the effect of individual or combination treatment of pamidronic acid and compounds 187, 138, 119 and 169 on osteoclast differentiation, except using μM pamidronic acid instead of 2 μM etidronic acid.

Pamidronic acid was dissolved in purified water at a concentration of 0.1 mM, and then diluted 1,000 fold with the media to a final concentration of 0.1 μM.

TABLE 3

Effect of individual or combination treatment of clodronic acid with Compound 187, Compound 138, Compound 119, or Compound 169 on osteoclast differentiation

| | | | % number of osteoclast (vs. solvent control group) | | | |
|---|---|---|---|---|---|---|
| | con(—) | Clodronic acid | Compound 187 | Compound 138 | Compound 119 | Compound 169 |
| A. Solvent control group | 100 ± 8.1 | | | | | |
| B. Individual treatment of Compound (0.1 μM) | | | 67 ± 7.4* | 71 ± 6.5* | 66 ± 8.3* | 78 ± 8.6* |
| C. Individual treatment of clodronic acid (1 μM) | | 88 ± 9.7* | | | | |
| D. Combination treatment of compound + clodronic acid | | | 60 ± 15.2*#@ | 54 ± 11.9*#@ | 47 ± 13.0*#@ | 59 ± 14.0*#@ |

[Note]
A. Control group (con(—)): 0.1% DMSO solvent
B. Individual treatment of Compounds 187, 138, 119, or 169 (0.1 μM)
C. Individual treatment of clodronic acid (1 μM)
D. Combination treatment of clodronic acid (1 μM) with Compounds 187, 138, 119, or 169 (0.1 μM)
*p < 0.0001 vs. solvent control group,
p < 0.0001 vs. individual treatment group of each compound
@p < 0.0001 vs. individual treatment group of clodronic acid The results are shown in the following Table 4.

TABLE 4

Effect of individual or combination treatment of
pamidronic acid with Compound 187, Compound 138, Compound
119 or Compound 169 on osteoclast differentiation

| | % number of osteoclast (vs. solvent control group) | | | | | |
|---|---|---|---|---|---|---|
| | con(—) | Pamidronic acid | Compound 187 | Compound 138 | Compound 119 | Compound 169 |
| A. Solvent control group | 100 ± 8.1 | | | | | |
| B. Individual treatment of Compound (0.1 μM) | | | 67 ± 7.4* | 71 ± 6.5* | 66 ± 8.3* | 78 ± 8.6* |
| C. Individual treatment of pamidronic acid (0.1 μM) | | 82 ± 6.7* | | | | |
| D. Combination treatment of compound + pamidronic acid | | | 47 ± 10.5*#@ | 42 ± 6.2*#@ | 37 ± 5.0*#@ | 50 ± 8.7*#@ |

[Note]
A. Control group (con(—)): 0.1% DMSO solvent
B. Individual treatment of Compounds 187, 138, 119, or 169 (0.1 μM)
C. Individual treatment of pamidronic acid (0.1 μM)
D. Combination treatment of pamidronic acid (0.1 μM) with Compounds 187, 138, 119, or 169 (0.1 μM)
*p < 0.0001 vs. solvent control group,
p < 0.0001 vs. individual treatment group of each compound
@p < 0.0001 vs. individual treatment group of pamidronic acid As shown in Table 4, in the experimental group that was singly treated with pamidronic acid (0.1 μM), its relative number of multinucleated osteoclast to that of the control group was measured as 82%, resulting in significant reduction. As the above mentioned, the combination treatment of pamidronic acid with Compound 187, Compound 138, Compound 119 or Compound 169 was performed in the same manner. The results are as follows: 47% in the combination treatment of pamidronic acid with Compound 187, 42% in the combination treatment of pamidronic acid with Compound 138, 37% in the combination treatment of pamidronic acid with Compound 119, and 50% in the combination treatment of pamidronic acid with Compound 169. In particular, the combination treatment of pamidronic acid with Compound 138, Compound 119 or Compound 169 showed much stronger inhibitory effect, in which the value was about 10% or more than the sum of each individual treatment.

EXAMPLE 4

Effect of Individual or Combination Treatment of Alendronic Acid (0.2 μM) and Compounds 187, 138, 119 and on Osteoclast Differentiation The experiment was performed in the same manner as in Example 1 to evaluate the effect of individual or combination treatment of alendronic acid and compounds 187, 138, 119 and 169 on osteoclast differentiation, except using μM alendronic acid instead of 2 μM etidronic acid.

Alendronic acid was dissolved in purified water at a concentration of 0.2 mM, and then diluted 1,000 fold with the media to a final concentration of 0.2 μM.

The results are shown in the following Table 5.

TABLE 5

Effect of individual or combination treatment of
alendronic acid with Compound 187, Compound 138, Compound
119, or Compound 169 on osteoclast differentiation

| | % number of osteoclast (vs. solvent control group) | | | | | |
|---|---|---|---|---|---|---|
| | con(—) | Alendronic acid | Compound 187 | Compound 138 | Compound 119 | Compound 169 |
| A. Solvent control group | 100 ± 8.1 | | | | | |
| B. Individual treatment of Compound (0.1 μM) | | | 67 ± 7.4* | 71 ± 6.5* | 66 ± 8.3* | 78 ± 8.6* |
| C. Individual treatment of alendronic acid (0.2 μM) | | 80 ± 5.7* | | | | |

TABLE 5-continued

Effect of individual or combination treatment of alendronic acid with Compound 187, Compound 138, Compound 119, or Compound 169 on osteoclast differentiation

| | | % number of osteoclast (vs. solvent control group) | | | | |
|---|---|---|---|---|---|---|
| | con(—) | Alendronic acid | Compound 187 | Compound 138 | Compound 119 | Compound 169 |
| D. Combination treatment of compound + alendronic acid | | | 32 ± 8.1*#@ | 32 ± 8.9*#@ | 29 ± 5.3*#@ | 44 ± 7.4*#@ |

[Note]
A. Control group (con(—)): 0.1% DMSO solvent
B. Individual treatment of Compounds 187, 138, 119, or 169 (0.1 μM)
C. Individual treatment of alendronic acid (0.2 μM)
D. Combination treatment of alendronic acid (0.2 μM) with Compounds 187, 138, 119, or 169 (0.1 μM)
*$p < 0.0001$ vs. solvent control group,
$p < 0.0001$ vs. individual treatment group of each compound
@$p < 0.0001$ vs. individual treatment group of alendronic acid The alendronic acid (0.2 μM) showing a relative value of 80% in its individual treatment was treated in combination with Compound 187, Compound 138, Compound 119 or Compound which has the inhibitory effect on osteoclast differentiation. The results are shown in Table 5. When the combination treatment of alendronic acid with Compound 187 that showed a relative value of 67% in its individual treatment was simultaneously performed at the same concentration, the number of osteoclast was notably reduced as low as 32%. This notable result was also observed in the combination treatment of alendronic acid with Compound 138 (32%), Compound 119 (29%) or Compound 169 (44%), indicating that the combination treatment of the substances exhibited much stronger efficacy than expected from the sum of each individual treatment.

EXAMPLE 5

Effect of Individual or Combination Treatment of Risedronic Acid (0.1 μM) and Compounds 187, 138, 119 and 169 on Osteoclast Differentiation The experiment was performed in the same manner as in Example 1 to evaluate the effect of individual or combination treatment of risedronic acid and Compound 187, Compound 138, Compound 119, or Compound 169 on osteoclast differentiation, except using 0.1 μM risedronic acid instead of 2 μM etidronic acid.

Risedronic acid was dissolved in purified water at a concentration of 0.1 mM, and then diluted 1,000 fold with the media to a final concentration of 0.1 μM.

The results are shown in the following Table 6.

TABLE 6

Effect of individual or combination treatment of risedronic acid with Compound 187, Compound 138, Compound 119, or Compound 169 on osteoclast differentiation

| | | % number of osteoclast (vs. solvent control group) | | | | |
|---|---|---|---|---|---|---|
| | con(—) | Risedronic acid | Compound 187 | Compound 138 | Compound 119 | Compound 169 |
| A. Solvent control group | 100 ± 8.1 | | | | | |
| B. Individual treatment of Compound (0.1 μM) | | | 67 ± 7.4* | 71 ± 6.5* | 66 ± 8.3* | 78 ± 8.6* |
| C. Individual treatment of risedronic acid (0.1 μM) | | 82 ± 5.2* | | | | |
| D. Combination treatment of compound + risedronic acid | | | 40 ± 6.6*#@ | 35 ± 8.2*#@ | 38 ± 6.8*#@ | 42 ± 7.6*#@ |

[Note]
A. Control group (con(—)): 0.1% DMSO solvent
B. Individual treatment of Compounds 187, 138, 119, or 169 (0.1 μM)
C. Individual treatment of risedronic acid (0.1 μM)
D. Combination treatment of risedronic acid (0.1 μM) with Compounds 187, 138, 119, or 169 (0.1 μM)
*$p < 0.0001$ vs. solvent control group,
$p < 0.0001$ vs. individual treatment group of each compound
@$p < 0.0001$ vs. individual treatment group of risedronic acid The combination treatment of risedronic acid with four substances was also performed to evaluate the inhibitory effect on osteoclast differentiation (Table 6). In the individual treatment of 0.1 μM risedronic acid, the relative number of multinucleated osteoclast was found to be about 82%, resulting in significant reduction compared to the solvent control group. When risedronic acid was added to the co-cultured cells in combination with Compound 187, Compound 138, Compound 119, or Compound 169, the relative numbers of multinucleated osteoclasts were found to be as low as 40%, 35%, 38 and 42%, respectively. This result has a significant difference from those of the control group and individual treatment groups.

EXAMPLE 6

Effect of Individual or Combination Treatment of Ibandronic Acid (0.1 μM) and Compounds 187, 138, 119 and 169 on Osteoclast Differentiation The experiment was performed in the same manner as in Example 1 to evaluate the effect of individual or combination treatment of ibandronic acid and Compound 187, Compound 138, Compound 119 and Compound 169 on osteoclast differentiation, except using 0.1 μM ibandronic acid instead of 2 μM etidronic acid.

Ibandronic acid was dissolved in purified water at a concentration of 0.1 mM, and then diluted 1,000 fold with the media to a final concentration of 0.1 μM.

The results are shown in the following Table 7.

In the individual treatment of ibandronic acid (0.1 μM), a significant reduction (77%) was observed in the number of multinucleated osteoclast showing a TRAP-positive reaction. In the combination treatment of ibandronic acid with Compound 187, the relative number of multinucleated osteoclast was found to be 42%, resulting in a significant reduction compared to that of each individual treatment. As shown in Table 7, the combination treatment of ibandronic acid with other compounds also exhibited a significant reduction in the number of multinucleated osteoclast.

EXAMPLE 7

Effect of Individual or Combination Treatment of Zoledronic Acid (0.01 μM) and Compounds 187, 138, 119 and 169 on Osteoclast Differentiation The experiment was performed in the same manner as in Example 1 to evaluate the effect of individual or combination treatment of zoledronic acid and Compound 187, Compound 138, Compound 119 and Compound 169 on osteoclast differentiation, except using 0.01 μM zoledronic acid instead of 2 μM etidronic acid.

Zoledronic acid was dissolved in purified water at a concentration of 0.01 mM, and then diluted 1,000 fold with the media to a final concentration of 0.01 μM.

TABLE 7

Effect of individual or combination treatment of ibandronic acid with Compound 187, Compound 138, Compound 119, or Compound 169 on osteoclast differentiation

| | | % number of osteoclast (vs. solvent control group) | | | | |
|---|---|---|---|---|---|---|
| | con(—) | Ibandronic acid | Compound 187 | Compound 138 | Compound 119 | Compound 169 |
| A. Solvent control group | 100 ± 8.1 | | | | | |
| B. Individual treatment of Compound (0.1 μM) | | | 67 ± 7.4* | 71 ± 6.5* | 66 ± 8.3* | 78 ± 8.6* |
| C. Individual treatment of ibandronic acid (0.1 μM) | | 77 ± 8.2* | | | | |
| D. Combination treatment of compound + ibandronic acid | | | 42 ± 8.1*#@ | 45 ± 7.6*#@ | 36 ± 9.8*#@ | 54 ± 8.7*#@ |

[Note]
A. Control group (con(—)): 0.1% DMSO solvent
B. Individual treatment of Compounds 187, 138, 119, or 169 (0.1 μM)
C. Individual treatment of ibandronic acid (0.1 μM)
D. Combination treatment of ibandronic acid (0.1 μM) with Compounds 187, 138, 119, or 169 (0.1 μM)
*$p < 0.0001$ vs. solvent control group,
$p < 0.0001$ vs. individual treatment group of each compound
@$p < 0.0001$ vs. individual treatment group of ibandronic acid The results are shown in the following Table 8.

TABLE 8

Effect of individual or combination treatment of zoledronic acid with Compound 187, Compound 138, Compound 119, or Compound 169 on osteoclast differentiation

| | | % number of osteoclast (vs. solvent control group) | | | | |
|---|---|---|---|---|---|---|
| | con(—) | Zoledronic acid | Compound 187 | Compound 138 | Compound 119 | Compound 169 |
| A. Solvent control group | 100 ± 8.1 | | | | | |
| B. Individual treatment of Compound (0.1 μM) | | | 67 ± 7.4* | 71 ± 6.5* | 66 ± 8.3* | 78 ± 8.6* |
| C. Individual treatment of zoledronic acid (0.01 μM) | | 84 ± 4.1* | | | | |
| D. Combination treatment of compound + zoledronic acid | | | 43 ± 4.5*#@ | 48 ± 8.9*#@ | 42 ± 8.1*#@ | 59 ± 8.2*#@ |

[Note]
A. Control group (con(—)): 0.1% DMSO solvent
B. Individual treatment of Compounds 187, 138, 119, or 169 (0.1 μM)
C. Individual treatment of zoledronic acid (0.1 μM)
D. Combination treatment of zoledronic acid (0.01 μM) with Compounds 187, 138, 119, or 169 (0.1 μM)
*p < 0.0001 vs. solvent control group,
p < 0.0001 vs. individual treatment group of each compound
@p < 0.0001 vs. individual treatment group of zoledronic acid The combination treatment of zoledronic acid (0.01 μM) with each of four substances that significantly reduced the number of osteoclast was also performed. In the individual treatment of zoledronic acid, a significant reduction (84%) in the number of multinucleated osteoclast was observed. In the combination treatment of zoledronic acid with Compound 187, the relative number of multinucleated osteoclast was found to be 43%, which is much lower than expected from the sum of each individual treatment. This result also demonstrates that the combination treatment exhibited synergistic effect. The combination treatment of zoledronic acid with other compounds was also found to exhibit the same effect (Table 8).

EXAMPLE 8

Effect of Individual or Combination Treatment of Alendronic Acid (0.1 μM) and Benzamidine Derivatives of Formula 1 on Osteoclast Differentiation The differentiation of osteoclast from mouse bone marrow cells was induced by using co-culture system, and inhibitory effect of the drug on osteoclast differentiation was evaluated by treatment of single or combination formulation. Co-culture was performed using mouse bone marrow cells and ST cells of bone marrow-derived stromal cell.

1. Preparation of Bone Marrow Cells and Osteoblasts

Femora and tibia were aseptically ectomized from 6~8 week-old male ddY mice to harvest bone marrow cells by a general method using a syringe. The red blood cells were removed from the bone marrow cells, followed by centrifugation. The bone marrow cells were suspended in α-MEM medium supplemented with 10% fetal bovine serum, and the numbers of the eukaryotic cells in the harvested bone marrow cells were counted and then immediately used for a co-culture system.

ST2 cells (RIKEN Cell Bank, Tsukuba, Japan) were cultured in α-MEM medium supplemented with 10% fetal bovine serum until confluent. Then, these cells were diluted to a desired cell number, and used for the experiment.

2. Measurement of Osteoclast Differentiation Via Co-culture System

The bone marrow cells ($1 \times 10^5$ cells/well) and ST2 cells (3,000 cells/well) prepared in the above were plated in a 96-well plate using α-MEM medium supplemented with 10% fetal bovine serum. At this time, differentiation factors, 1α,25-dihydroxyvitamin $D_3$ ($10^{-8}$ M, hereinbelow, referred to as vitamin $D_3$) and dexamethasone ($10^{-8}$ M), were co-added to the medium to induce osteoclast differentiation. The medium was replaced with fresh media containing the differentiation factors every 2 to 3 days.

After 7 days, when multinucleated osteoclasts were observed, the medium was removed from the wells, and then the cells were fixed with PBS containing 10% Formalin. Tartrate-Resistant Acid Phosphatase (hereinbelow, referred to as TRAP) was used as a marker to measure the mature osteoclast in consideration of its characteristics showing a positive reaction to a TRAP staining solution. The TRAP staining solution was prepared in such the manner that a substrate, naphtol AS-MS phosphate and a coloring agent (Fast Red Violet LB salt) were dissolved in N,N-dimethylformamide. A 0.1 N $NaHCO_3$ buffer solution containing 50 mM tartaric acid was added thereto, and the mixture was stored at a refrigerator prior to use as a staining solution. The osteoclasts with 6-7 or more nuclei showing a TRAP-positive reaction were counted under a microscope.

3. Effect of Test Substance on Osteoclast Differentiation

Alendronic acid was dissolved in distilled water at a concentration of 0.1 mM, and benzamidine derivatives were dissolved in DMSO at a concentration of 0.1 mM. All of them were diluted 1,000 fold with the differentiation media to a final concentration of 0.1 μM, respectively. In this connection, a control group was maintained in 0.1% DMSO.

As the above described, the sample substances and cells, which were diluted to the desired concentrations, were plated in 96-well plate, and co-cultured. On days 3 and 5 of culture, the media were replaced with fresh differentiation media containing the sample substances. On day 7 of culture, TRAP staining was performed to count the mature multinucleated osteoclast that was formed by differentiation. The mature osteoclasts with 6 or more nuclei were counted under a microscope. The results were expressed as a percentage (%) of the number of mature osteoclast observed in each experimental group, when the number of mature osteoclast in the control group (solvent only) was regarded as 100%. The experiment was performed with 4 wells per experimental group (n=4), and the results were expressed as mean value±standard deviation. In addition, the experiment was repeated at least two times, and Student t-test was applied for significant difference between experimental groups.

EXAMPLE 9

Effect of Individual or Combination Treatment of Risedronic Acid (0.1 µM) and Benzamidine Derivatives of Formula 1 on Osteoclast Differentiation The experiment was performed in the same manner as in Example 8 to evaluate the effect of individual or combination treatment of risedronic acid and benzamidine derivatives of Formula 1 on osteoclast differentiation, except using 0.1 µM risedronic acid instead of 0.1 µM alendronic acid.

Risedronic acid was dissolved in distilled water at a concentration of 0.1 mM, and then diluted 1,000 fold with the media to a final concentration of 0.1 µM.

The Results of Experiments 8 and 9

Individual treatment of Compounds: When the number of multinucleated osteoclast showing a TRAP-positive reaction in the solvent control group was regarded as 100%, the numbers of multinucleated osteoclast, obtained in the individual treatment groups of benzamidine derivatives of Formula 1 were expressed as percentage. When each substance was singly added to the co-cultured cells at the same concentration of 0.1 µM, the substances showed various inhibitory effects on osteoclast differentiation.

Individual treatment of alendronic acid or risedronic acid: In the experimental group that was singly treated with 0.1 µM alendronic acid or risedronic acid, its relative numbers of multinucleated osteoclast to that of the solvent control group were measured as 76% (alendronic acid) and 69% (risedronic acid). Such significant reduction indicates that alendronic acid and risedronic acid are inhibitor of osteoclast differentiation.

Combination treatment: Effects of combination treatment on osteoclast differentiation were evaluated by comparing with those of individual treatment of Compounds and those of individual treatment of alendronic acid or risedronic acid.

TABLE 9

Effect of individual or combination treatment of alendronic acid or risedronic acid with benzamidine derivatives of Formula 1 on osteoclast differentiation
% number of osteoclast (vs. solvent control group)

| Compounds | Individual treatment (compounds) | Combination treatment (alendronic acid + compounds) | Combination treatment (risedronic acid + compounds) |
|---|---|---|---|
| Control (DMSO) | 100 ± 9.1 | 76 ± 6.2* | 69 ± 6.7* |
| 3 | 52 ± 8.9 | 40 ± 4.6$^b$ | 33 ± 6.8$^c$ |
| 7 | 52 ± 4.8 | 35 ± 7.1$^b$ | 34 ± 10.1$^c$ |
| 8 | 65 ± 10.4 | 22 ± 3.4$^{ab}$ | 27 ± 3.8$^{ac}$ |
| 9 | 64 ± 3.4 | 52 ± 15.8 | 43 ± 2.6$^{ac}$ |
| 15 | 69 ± 5.5 | 43 ± 11.4 | 45 ± 9.2$^{ac}$ |
| 21 | 52 ± 10.4 | 22 ± 7.1$^{ab}$ | 47 ± 10.1 |
| 37 | 68 ± 18.9 | 30 ± 9.9$^b$ | 36 ± 14.4$^c$ |
| 40 | 66 ± 7.1 | 28 ± 4.1$^{ab}$ | 20 ± 3.4$^{ac}$ |
| 41 | 31 ± 9.4 | 29 ± 5.0$^b$ | 31 ± 2.6$^c$ |
| 42 | 69 ± 11.4 | 33 ± 1.9$^{ab}$ | 32 ± 8.0$^{ac}$ |
| 43 | 74 ± 14.6 | 32 ± 6.6$^{ab}$ | 40 ± 7.8$^c$ |
| 45 | 72 ± 4.6 | 49 ± 8.1$^{ab}$ | 38 ± 11.9$^{ac}$ |
| 46 | 71 ± 9.4 | 36 ± 5.1$^{ab}$ | 31 ± 8.5$^{ac}$ |
| 47 | 57 ± 7.9 | 42 ± 4.6$^b$ | 32 ± 3.0$^{ac}$ |
| 54 | 41 ± 8.3 | 20 ± 4.1$^{ab}$ | 19 ± 4.9$^{ac}$ |
| 59 | 55 ± 6.5 | 34 ± 2.2$^{ab}$ | 33 ± 5.1$^{ac}$ |
| 67 | 74 ± 11.7 | 53 ± 6.4$^b$ | 36 ± 1.7$^{ac}$ |
| 68 | 42 ± 6.9 | 14 ± 1.4$^{ab}$ | 8 ± 1.9$^{ac}$ |
| 69 | 80 ± 11.6 | 49 ± 7.8$^b$ | 44 ± 1.4$^{ac}$ |
| 72 | 63 ± 1.1 | 30 ± 4.0$^{ab}$ | 12 ± 3.2$^{ac}$ |
| 74 | 60 ± 0.7 | 36 ± 4.3$^{ab}$ | 28 ± 5.4$^{ac}$ |
| 76 | 53 ± 6.5 | 31 ± 6.8$^{ab}$ | 22 ± 3.8$^a$ |
| 78 | 67 ± 2.1 | 36 ± 4.2$^{ab}$ | 20 ± 1.7$^a$ |
| 79 | 44 ± 7.5 | 22 ± 6.7$^{ab}$ | 16 ± 4.0$^{ac}$ |
| 80 | 65 ± 1.4 | 42 ± 9.9$^b$ | 38 ± 3.7$^{ac}$ |
| 84 | 44 ± 4.3 | 30 ± 5.1$^{ab}$ | 6 ± 4.4$^{ac}$ |
| 88 | 63 ± 7.6 | 61 ± 11.7 | 29 ± 4.7$^{ac}$ |
| 89 | 58 ± 5.1 | 38 ± 1.9$^{ab}$ | 39 ± 2.7$^{ac}$ |
| 90 | 87 ± 10.0 | 54 ± 8.6$^{ab}$ | 39 ± 8.4$^{ac}$ |
| 91 | 60 ± 8.8 | 35 ± 2.7$^{ab}$ | 32 ± 7.0$^{ac}$ |
| 94 | 45 ± 3.0 | 20 ± 4.8$^{ab}$ | 16 ± 3.3$^{ac}$ |
| 95 | 90 ± 5.4 | 37 ± 10.3$^{ab}$ | 33 ± 6.8$^{ac}$ |
| 96 | 74 ± 8.1 | 55 ± 10.0 | 34 ± 7.1$^{ac}$ |
| 97 | 57 ± 5.2 | 30 ± 5.7$^{ab}$ | 13 ± 4.3$^{ac}$ |
| 98 | 47 ± 3.2 | 29 ± 1.6$^{ab}$ | 11 ± 3.2$^{ac}$ |
| 100 | 46 ± 8.4 | 14 ± 6.9$^{ab}$ | 12 ± 3.0$^{ac}$ |
| 101 | 50 ± 5.9 | 24 ± 3.2$^{ab}$ | 18 ± 2.8$^{ac}$ |
| 102 | 47 ± 4.0 | 37 ± 3.6$^b$ | 21 ± 2.6$^{ac}$ |
| 105 | 87 ± 11.0 | 42 ± 3.0$^b$ | 41 ± 8.8$^{ac}$ |
| 109 | 60 ± 9.6 | 49 ± 9.8$^b$ | 30 ± 6.5$^{ac}$ |
| 111 | 76 ± 12.2 | 51 ± 6.0 | 32 ± 5.2$^{ac}$ |
| 112 | 77 ± 9.8 | 35 ± 7.6$^{ab}$ | 31 ± 8.0$^{ac}$ |
| 115 | 77 ± 12.4 | 51 ± 8.9 | 45 ± 8.3$^{ac}$ |
| 119 | 78 ± 9.0 | 29 ± 4.9$^{ab}$ | 29 ± 8.7$^{ac}$ |
| 120 | 80 ± 6.5 | 54 ± 2.4$^{ab}$ | 55 ± 9.1$^{ac}$ |
| 121 | 95 ± 3.9 | 55 ± 11.1$^{ab}$ | 39 ± 5.7$^{ac}$ |
| 122 | 71 ± 4.4 | 37 ± 8.1$^{ab}$ | 49 ± 7.3$^{ac}$ |
| 124 | 49 ± 3.0 | 21 ± 4.3$^{ab}$ | 17 ± 5.2$^{ac}$ |
| 125 | 66 ± 4.4 | 43 ± 3.3$^{ab}$ | 21 ± 9.0$^{ac}$ |
| 126 | 50 ± 2.5 | 23 ± 5.8$^{ab}$ | 22 ± 2.1$^{ac}$ |
| 127 | 75 ± 14.3 | 37 ± 6.8$^{ab}$ | 33 ± 7.3$^{ac}$ |
| 132 | 62 ± 7.7 | 37 ± 8.3$^{ab}$ | 30 ± 3.4$^{ac}$ |
| 133 | 54 ± 8.3 | 42 ± 8.3$^b$ | 25 ± 5.7$^{ac}$ |
| 134 | 57 ± 4.3 | 39 ± 3.4$^{ab}$ | 24 ± 4.0$^{ac}$ |
| 137 | 19 ± 2.9 | 11 ± 4.3$^b$ | 7 ± 2.2$^{ac}$ |
| 138 | 57 ± 7.2 | 18 ± 6.8$^{ab}$ | 31 ± 3.2$^{ac}$ |
| 139 | 64 ± 4.6 | 49 ± 7.8 | 38 ± 6.9$^{ac}$ |
| 141 | 84 ± 8.8 | 65 ± 2.8 | 60 ± 7.5$^{ac}$ |
| 144 | 82 ± 6.7 | 44 ± 10.5$^{ab}$ | 37 ± 4.3$^{ac}$ |
| 146 | 81 ± 8.9 | 79 ± 7.8 | 60 ± 13.6$^c$ |
| 147 | 46 ± 4.1 | 31 ± 3.2$^{ab}$ | 14 ± 3.0$^{ac}$ |
| 148 | 65 ± 4.3 | 33 ± 8.3$^{ab}$ | 19 ± 2.4$^a$ |
| 149 | 63 ± 9.9 | 40 ± 8.8 | 31 ± 2.5$^{ac}$ |
| 151 | 58 ± 2.5 | 36 ± 2.9$^{ab}$ | 31 ± 3.7 a |
| 152 | 65 ± 2.2 | 46 ± 8.8$^b$ | 48 ± 4.9$^{ac}$ |
| 153 | 55 ± 3.1 | 27 ± 3.5$^{ab}$ | 22 ± 4.5$^{ac}$ |
| 157 | 78 ± 13.5 | 39 ± 8.3$^{ab}$ | 36 ± 15.1$^{ac}$ |
| 161 | 79 ± 5.1 | 56 ± 4.3$^{ab}$ | 47 ± 14.0$^a$ |
| 162 | 98 ± 8.2 | 78 ± 1.8 | 61 ± 7.5$^{ac}$ |
| 163 | 65 ± 8.8 | 55 ± 7.6 | 41 ± 7.3$^{ac}$ |
| 165 | 75 ± 3.8 | 29 ± 7.5$^{ab}$ | 30 ± 3.1$^{ac}$ |
| 166 | 73 ± 4.4 | 43 ± 9.4$^{ab}$ | 35 ± 3.9$^{ac}$ |
| 167 | 72 ± 9.8 | 25 ± 1.9$^b$ | 31 ± 7.6$^{ac}$ |
| 168 | 70 ± 9.1 | 39 ± 5.2$^{ab}$ | 29 ± 9.7$^{ac}$ |

TABLE 9-continued

Effect of individual or combination treatment of alendronic acid or risedronic acid with benzamidine derivatives of Formula 1 on osteoclast differentiation % number of osteoclast (vs. solvent control group)

| Compounds | Individual treatment (compounds) | Combination treatment (alendronic acid + compounds) | Combination treatment (risedronic acid + compounds) |
|---|---|---|---|
| 172 | 57 ± 5.1 | 33 ± 5.3$^{ab}$ | 26 ± 5.1$^a$ |
| 174 | 70 ± 2.5 | 46 ± 2.6$^{ab}$ | 35 ± 5.1$^{ac}$ |
| 177 | 74 ± 10.1 | 34 ± 10.2$^{ab}$ | 34 ± 5.7$^{ac}$ |
| 182 | 82 ± 12.0 | 45 ± 6.7 | 41 ± 5.1$^c$ |
| 183 | 66 ± 7.4 | 26 ± 6.1$^{ab}$ | 37 ± 5.3$^{ac}$ |
| 184 | 62 ± 4.6 | 38 ± 3.7$^{ab}$ | 38 ± 6.9$^{ac}$ |
| 185 | 81 ± 7.0 | 57 ± 13.9 | 45 ± 1.4$^{ac}$ |
| 188 | 56 ± 5.4 | 35 ± 3.2$^{ab}$ | 23 ± 5.1$^{ac}$ |
| 193 | 48 ± 4.4 | 34 ± 5.0$^{ab}$ | 27 ± 4.8$^{ac}$ |
| 194 | 74 ± 10.1 | 33 ± 7.1$^{ab}$ | 30 ± 7.0$^{ac}$ |
| 196 | 68 ± 7.1 | 37 ± 4.6$^{ab}$ | 42 ± 8.8$^{ac}$ |
| 208 | 92 ± 5.8 | 75 ± 6.3 | 67 ± 6.5$^{ac}$ |
| 209 | 74 ± 7.4 | 41 ± 12.0$^{ab}$ | 50 ± 6.1$^{ac}$ |
| 216 | 70 ± 5.0 | 72 ± 13.0 | 48 ± 7.8$^{ac}$ |
| 218 | 56 ± 1.9 | 39 ± 10.4$^b$ | 25 ± 7.5$^{ac}$ |
| 219 | 61 ± 10.5 | 51 ± 5.4$^b$ | 40 ± 3.8$^c$ |
| 220 | 69 ± 3.2 | 53 ± 4.7$^{ab}$ | 40 ± 5.1$^{ac}$ |
| 222 | 74 ± 7.1 | 49 ± 6.8$^{ab}$ | 36 ± 6.6$^{ac}$ |
| 223 | 81 ± 3.8 | 73 ± 8.2 | 60 ± 12.6 |
| 224 | 77 ± 8.4 | 53 ± 2.9$^{ab}$ | 58 ± 10.8 |
| 225 | 70 ± 7.1 | 50 ± 4.8$^{ab}$ | 48 ± 4.9$^{ac}$ |
| 227 | 42 ± 4.6 | 24 ± 5.0$^{ab}$ | 17 ± 4.4$^{ac}$ |
| 228 | 49 ± 3.5 | 31 ± 4.8$^{ab}$ | 20 ± 5.8$^{ac}$ |
| 231 | 82 ± 14.6 | 50 ± 9.8$^b$ | 40 ± 3.1$^{ac}$ |
| 232 | 47 ± 9.4 | 39 ± 5.2$^b$ | 37 ± 4.9$^c$ |
| 234 | 44 ± 7.5 | 30 ± 6.1$^b$ | 22 ± 4.0$^{ac}$ |
| 235 | 38 ± 7.6 | 33 ± 1.8 | 25 ± 4.4$^c$ |
| 241 | 61 ± 6.8 | 24 ± 4.6$^{ab}$ | 12 ± 1.4$^{ac}$ |
| 242 | 58 ± 3.4 | 18 ± 3.5$^{ab}$ | 13 ± 2.8$^{ac}$ |
| 243 | 36 ± 4.9 | 24 ± 7.7$^b$ | 12 ± 2.3$^{ac}$ |
| 244 | 46 ± 2.9 | 19 ± 3.3$^{ab}$ | 11 ± 1.7$^{ac}$ |
| 245 | 35 ± 5.7 | 23 ± 4.9$^b$ | 16 ± 4.1$^{ac}$ |
| 247 | 63 ± 4.2 | 39 ± 3.7$^{ab}$ | 17 ± 4.5$^{ac}$ |
| 248 | 49 ± 8.7 | 33 ± 5.6$^b$ | 27 ± 4.9$^{ac}$ |
| 249 | 36 ± 4.0 | 24 ± 4.0$^{ab}$ | 13 ± 4.8$^{ac}$ |
| 250 | 52 ± 7.2 | 45 ± 5.2$^b$ | 12 ± 1.4$^{ac}$ |
| 251 | 45 ± 9.6 | 20 ± 6.4$^{ab}$ | 18 ± 4.4$^{ac}$ |
| 252 | 44 ± 2.7 | 33 ± 6.6$^b$ | 19 ± 4.0$^{ac}$ |
| 254 | 40 ± 8.3 | 29 ± 6.3$^b$ | 11 ± 2.5$^{ac}$ |
| 255 | 50 ± 3.9 | 18 ± 1.7$^{ab}$ | 12 ± 3.1$^{ac}$ |
| 256 | 49 ± 0.9 | 26 ± 3.0$^{ab}$ | 12 ± 2.4$^{ac}$ |
| 262 | 47 ± 4.2 | 24 ± 2.6$^{ab}$ | 7 ± 4.9$^{ac}$ |
| 266 | 64 ± 4.0 | 36 ± 9.6$^{ab}$ | 26 ± 4.3$^{ac}$ |
| 267 | 68 ± 8.6 | 33 ± 5.3$^{ab}$ | 13 ± 2.4$^{ac}$ |
| 268 | 52 ± 9.1 | 28 ± 1.7$^b$ | 17 ± 3.4$^{ac}$ |
| 269 | 38 ± 3.7 | 23 ± 5.2$^{ab}$ | 17 ± 4.4$^{ac}$ |
| 270 | 45 ± 6.9 | 28 ± 4.5$^b$ | 14 ± 2.1$^{ac}$ |
| 271 | 30 ± 5.3 | 13 ± 3.7$^{ab}$ | 16 ± 2.9$^{ac}$ |
| 273 | 53 ± 3.4 | 25 ± 4.5$^{ab}$ | 11 ± 2.9$^{ac}$ |
| 274 | 65 ± 8.9 | 31 ± 2.9$^{ab}$ | 13 ± 1.3$^{ac}$ |
| 276 | 41 ± 12.1 | 21 ± 2.9$^b$ | 11 ± 3.1$^c$ |
| 280 | 40 ± 5.0 | 25 ± 6.4$^b$ | 8 ± 1.4$^{ac}$ |
| 281 | 30 ± 7.6 | 22 ± 5.9$^b$ | 6 ± 2.5$^{ac}$ |
| 282 | 73 ± 7.1 | 49 ± 9.9$^{ab}$ | 45 ± 5.2$^{ac}$ |
| 284 | 73 ± 7.7 | 36 ± 5.0$^{ab}$ | 19 ± 5.8$^{ac}$ |
| 285 | 70 ± 8.0 | 53 ± 0.9 | 40 ± 3.9$^{ac}$ |
| 286 | 43 ± 6.1 | 29 ± 4.1$^b$ | 26 ± 1.5$^{ac}$ |
| 289 | 36 ± 9.1 | 21 ± 7.4$^b$ | 10 ± 3.1$^{ac}$ |
| 290 | 52 ± 6.2 | 23 ± 4.7$^{ab}$ | 12 ± 2.0$^{ac}$ |
| 291 | 44 ± 4.9 | 20 ± 3.8$^{ab}$ | 12 ± 3.5$^{ac}$ |
| 293 | 36 ± 10.0 | 15 ± 2.6$^b$ | 11 ± 2.6$^c$ |
| 294 | 27 ± 4.5 | 13 ± 2.4$^{ab}$ | 9 ± 2.7$^{ac}$ |
| 296 | 46 ± 3.6 | 13 ± 2.6$^{ab}$ | 8 ± 1.7$^{ac}$ |
| 298 | 55 ± 6.1 | 16 ± 3.3$^{ab}$ | 8 ± 2.9$^{ac}$ |
| 299 | 40 ± 6.9 | 14 ± 2.9$^{ab}$ | 11 ± 6.0$^{ac}$ |
| 300 | 48 ± 3.0 | 12 ± 1.7$^{ab}$ | 8 ± 5.2$^{ac}$ |
| 301 | 49 ± 5.1 | 10 ± 2.3$^{ab}$ | 6 ± 2.3$^{ac}$ |
| 302 | 59 ± 10.6 | 16 ± 4.5$^{ab}$ | 9 ± 2.8$^{ac}$ |
| 303 | 53 ± 10.7 | 12 ± 2.5$^{ab}$ | 8 ± 2.2$^{ac}$ |
| 304 | 54 ± 6.4 | 27 ± 6.4$^{ab}$ | 16 ± 4.5$^{ac}$ |
| 305 | 58 ± 6.1 | 15 ± 4.8$^{ab}$ | 11 ± 4.1$^{ac}$ |
| 306 | 48 ± 6.4 | 18 ± 4.3$^{ab}$ | 16 ± 3.3$^{ac}$ |
| 307 | 43 ± 8.9 | 30 ± 3.0$^b$ | 16 ± 4.8$^{ac}$ |
| 309 | 50 ± 6.1 | 13 ± 5.1$^{ab}$ | 8 ± 3.0$^{ac}$ |
| 310 | 49 ± 3.3 | 33 ± 5.1$^{ab}$ | 18 ± 4.5$^{ac}$ |
| 311 | 46 ± 10.7 | 21 ± 4.2$^b$ | 12 ± 5.8$^{ac}$ |
| 313 | 53 ± 6.0 | 23 ± 5.9$^{ab}$ | 13 ± 3.3$^{ac}$ |
| 314 | 43 ± 7.0 | 15 ± 1.7$^{ab}$ | 9 ± 3.2$^{ac}$ |
| 317 | 45 ± 3.2 | 18 ± 4.6$^{ab}$ | 16 ± 3.2$^{ac}$ |
| 318 | 43 ± 3.7 | 27 ± 3.0$^{ab}$ | 12 ± 1.8$^{ac}$ |
| 319 | 54 ± 5.9 | 25 ± 2.6$^{ab}$ | 11 ± 3.3$^{ac}$ |
| 321 | 48 ± 7.0 | 19 ± 4.1$^{ab}$ | 18 ± 3.0$^{ac}$ |
| 326 | 46 ± 11.0 | 34 ± 2.7$^b$ | 15 ± 6.0$^{ac}$ |
| 330 | 46 ± 4.7 | 23 ± 3.9$^{ab}$ | 12 ± 2.4$^{ac}$ |
| 331 | 43 ± 2.7 | 18 ± 4.6$^{ab}$ | 7 ± 1.2$^{ac}$ |
| 335 | 54 ± 0.9 | 41 ± 2.0$^{ab}$ | 23 ± 5.0$^{ac}$ |
| 336 | 52 ± 4.0 | 22 ± 3.2$^{ab}$ | 16 ± 3.0$^{ac}$ |
| 337 | 53 ± 3.7 | 20 ± 3.0$^{ab}$ | 16 ± 3.6$^{ac}$ |

$^a$p < 0.01 vs. individual treatment group of each compound
$^b$p < 0.01 vs. individual treatment group of alendronic acid
$^c$p < 0.01 vs. individual treatment group of risedronic acid

INDUSTRIAL APPLICABILITY

A pharmaceutical composition according to the present invention which comprises benzmidine derivatives or salt thereof, is useful for the prevention and treatment of osteoporosis.

What is claimed is:

1. A method of treating osteoporosis comprising administering to a patient in need thereof an effective amount of pharmaceutical composition comprising the following compounds (a) and (b) for the purpose of using simultaneously, separately, or sequentially as active ingredients:
    (a) a benzamidine derivative represented by the following Formula 1 or salt thereof, and
    (b) bisphosphonate represented by the following Formula 2,

[Formula 1]

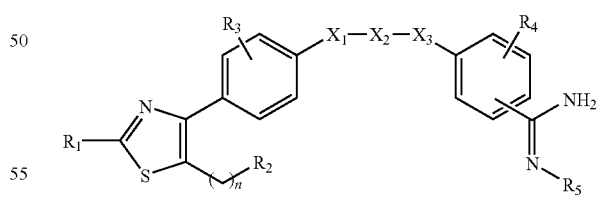

wherein $R_1$ is $C_1$~$C_6$ alkyl which is unsubstituted or substituted with pyridinyl;
straight or branched $C_1$~$C_6$ alkyl which is substituted with

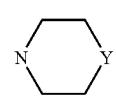

unsubstituted or substituted with hydroxy; $C_3$~$C_6$ cycloalkyl; phenyl; benzyl; pyridinyl which is unsubstituted or substituted with $C_1$~$C_6$ alkyl; guanidino; $NR_6R_7$; $CH_2NR_6R_7$;

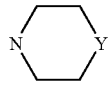

group which is substituted with straight or branched $C_1$~$C_6$ alkyl; or

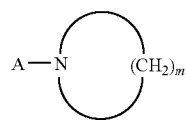

(wherein A is $C_1$~$C_6$ alkyl, and m is an integer of 2 to 6);

$R_2$ is hydrogen; straight or branched $C_1$~$C_6$ alkyl which is unsubstituted or substituted with $NR_8R_9$; $C_3$~$C_6$ cycloalkyl; phenyl; benzyl; $C_2$~$C_6$ alkenyl; carbonyl which is substituted with $NR_8R_9$; amino; dimethylamino; morpholinyl; thiomorpholinyl; 4-methylpiperazinyl; or straight or branched $C_1$~$C_6$ alkyl which is substituted with hydroxy, $C_1$~$C_6$ alkoxy, halogen, $C_3$~$C_6$ cycloalkyl,

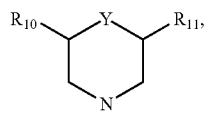

imidazolyl, or pyrrolidinyl;

$R_3$ and $R_4$ are each independently hydrogen; halogen; hydroxy; $C_1$~$C_6$ alkyl which is unsubstituted or substituted with halogen; $C_3$~$C_6$ cycloalkylamino; $C_1$~$C_6$ alkoxy; $C_1$~$C_6$ alkanoyloxy; $C_2$~$C_6$ alkenyloxy; phenyl-$C_1$~$C_6$ alkoxy; phenoxy; $C_2$~$C_6$ alkenoyloxy or phenyl-$C_1$~$C_6$ alkanoyloxy; $C_3$~$C_6$ cycloalkyloxy which is substituted with one group selected from carboxy, esterified carboxy and amidated carboxy; or an aminooxy group;

$R_5$ is hydrogen or hydroxy group;

$R_6$ and $R_7$ are each independently hydrogen; $C_1$~$C_6$ alkyl which is unsubstituted or substituted with one group selected from hydroxy, $C_1$~$C_6$ alkoxy, pyridine and

phenyl; benzyl; pyridinyl; carbonyl which is substituted with one group selected from $C_1$~$C_6$ alkyl, hydroxy, $C_1$~$C_6$ alkyl substituted with hydroxy, $C_1$~$C_6$ alkoxy, phenyl, benzyl, pyridine and

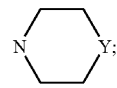

or $C_1$~$C_6$ alkanesulfonyl;

$R_8$ and $R_9$ are each independently hydrogen; $C_1$~$C_6$ alkyl which is unsubstituted or substituted with one group selected from hydroxy, $C_1$~$C_6$ alkoxy, morpholine, imidazole and $NR_6R_7$; $C_1$~$C_6$ alkoxy; $C_3$~$C_6$ cycloalkyl; phenyl; benzyl; pyridinyl; morpholine; carbonyl which is substituted with one group selected from $C_1$~$C_6$ alkyl, $C_1$~$C_6$ alkoxy, phenyl, benzyl, pyridine and

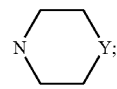

carbonyl which is substituted with $C_1$~$C_6$ alkyl substituted with one group selected from halogen, $C_1$~$C_6$ alkoxy and imidazole; or $C_1$~$C_6$ alkanesulfonyl;

$R_{10}$ and $R_{11}$ are each independently hydrogen, $C_1$~$C_2$ alkyl, $C_1$~$C_3$ alkoxy or halide;

$X_1$-$X_2$-$X_3$ is

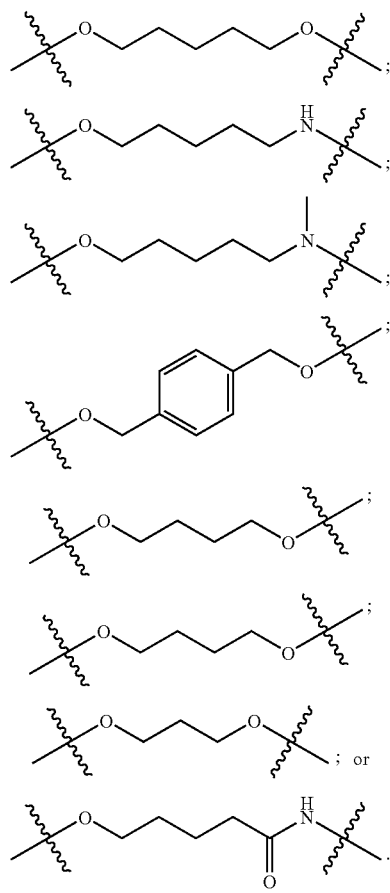

Y is O, S, NR$_6$ or CH$_2$ group; and n is an integer of 0, 1 and 2,

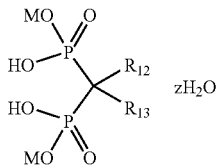

[Formula 2]

wherein R$_{12}$ is methyl, chloro, 2-aminoethyl, 3-aminopropyl, 4-aminobutyl, 5-aminopentyl, 4-chlorophenylthio, 3-pyridylmethyl, (imidazo[1,2-a]pyridine-3-yl)methyl, 2-(N-methyl-N-n-pentyl)aminoethyl, cycloheptylamino, (1-imidazolyl)methyl or 1-pyrrolidinylethyl, R$_{13}$ is hydrogen, chloro or hydroxy group, M is hydrogen or sodium, and Z is any number, preferably an integer of 0 to 7.

2. The method of claim 1, wherein the R$_1$ is C$_1$~C$_5$ alkyl; C$_1$~C$_5$ alkyl substituted with piperidinyl; C$_3$~C$_6$ cycloalkyl; phenyl; pyridinyl; guanidino; NR$_6$R$_7$; piperidinyl or piperazinyl substituted with straight C$_1$~C$_3$ alkyl; morpholinyl; or piperidinyl;

the R$_2$ is hydrogen; straight or branched C$_1$~C$_4$ alkyl which is unsubstituted or substituted with NR$_8$R$_9$; C$_3$~C$_6$ cycloalkyl; benzyl; C$_2$~C$_6$ alkenyl; carbonyl which is substituted with NR$_8$R$_9$; amino; dimethylamino; morpholinyl; thiomorpholinyl; 4-methylpiperazinyl; or straight or branched C$_1$~C$_3$ alkyl which is substituted with C$_1$~C$_3$ alkoxy, halogen, C$_3$~C$_6$ cycloalkyl, morpholinyl, dimethylmorpholinyl, thiomorpholinyl, 4-methylpiperazinyl, piperidinyl, imidazolyl, or pyrrolidinyl, the R$_3$ is hydrogen, the R$_4$ is hydrogen, hydroxy or fluoro, the R$_5$ is hydrogen or hydroxy;

the R$_6$ and R$_7$ are each independently hydrogen; C$_1$~C$_3$ alkyl which is unsubstituted or substituted with one group selected from hydroxy, C$_1$~C$_3$ alkoxy, pyridinyl, morpholinyl and piperidinyl; benzyl; carbonyl which is substituted with one group selected from C$_1$~C$_3$ alkyl, C$_1$~C$_3$ alkyl substituted with hydroxy and pyridinyl; or C$_1$~C$_3$ alkanesulfonyl; and the R$_8$ and R$_9$ are each independently hydrogen; C$_1$~C$_4$ alkyl which is unsubstituted or substituted with one group selected from hydroxy, C$_1$~C$_3$ alkoxy, morpholinyl and imidazolyl; C$_3$~C$_6$ cycloalkyl; benzyl; or pyridinoyl.

3. The method of claim 2, wherein the R$_1$ is methyl; ethyl; isopropyl; tert-butyl; pentyl; piperidin-1-ylmethyl; cyclohexyl; phenyl; pyridin-3-yl; guanidino;

NR$_6$R$_7$; 1-propyl-piperidin-4-yl; 4-methyl-piperazin-1-yl; morpholin-4-yl; or piperidin-4-yl;

the R$_2$ is hydrogen; methyl, ethyl, propyl, isopropyl or butyl which is unsubstituted or substituted with NR$_8$R$_9$; cyclopentyl; benzyl; ehthenyl; carbonyl which is substituted with NR$_8$R$_9$; amino; dimethylamino; morpholin-4-yl; thiomorpholin-4-yl; 4-methylpiperazin-1-yl; or straight or branched C$_1$~C$_3$ alkyl which is substituted with methoxy, chloro, cyclopentyl, morpholin-4-yl, 2,6-dimethylmorpholin-4-yl, thiomorpholin-4-yl, 4-methylpiperazin-1-yl, piperidin-1-yl, imidazol-1-yl, or pyrrolidin-1-yl;

the R$_6$ and R$_7$ are each independently hydrogen; methyl; ethyl; propyl; C$_1$~C$_3$ alkyl which is substituted with one group selected from hydroxy, methoxy, pyridin-3-yl, pyridin-4-yl, morpholin-4-yl and piperidin-1-yl; benzyl; carbonyl which is substituted with one group selected from isopropyl, hydroxymethyl, pyridin-3-yl and pyridin-4-yl; or ethanesulfonyl; and the R$_8$ and R$_9$ are each independently hydrogen; methyl; ethyl; propyl; isopropyl;

butyl; isobutyl; tert-butyl; C$_1$~C$_3$ alkyl which is substituted with one group selected from hydroxy, methoxy, isopropoxy, morpholin-4-yl and imidazol-1-yl; cyclopropyl; cyclohexyl; benzyl; 3-pyridinoyl or 4-pyridinoyl.

4. The method of claim 2, wherein the only one between the R$_6$ and the R$_7$ is hydrogen.

5. The method of claim 2, wherein the R$_6$ and R$_7$ are both hydrogen; or C$_1$~C$_6$ alkyl which is unsubstituted or substituted with one group selected from hydroxy, C$_1$~C$_6$ alkoxy and pyridinyl.

6. The method of claim 5, wherein the R$_6$ and R$_7$ are both hydrogen; methyl; methyl substituted with pyridinyl; ethyl; ethyl substituted with hydroxy or methoxy; or propyl.

7. The method of claim 2, wherein the R$_6$ is methyl; and the R$_7$ is C$_1$~C$_6$ alkyl which is unsubstituted or substituted with one group selected from hydroxy, C$_1$~C$_6$alkoxy, pyridinyl and morpholinyl; benzyl; or carbonyl which is substituted with C$_1$~C$_6$ alkyl.

8. The method of claim 7, wherein the R$_7$ is methyl which is substituted with pyridin-3-yl or pyridin-4-yl; ethyl which is unsubstituted or substituted with one group selected from hydroxy, methoxy and morpholin-4-yl; benzyl; carbonyl which is substituted with isopropyl.

9. The method of claim 2, wherein the R$_6$ is ethyl; and the R$_7$ is C$_1$~C$_6$ alkyl which is unsubstituted or substituted with hydroxy or morpholinyl; or benzyl.

10. The method of claim 9, wherein the R$_7$ is ethyl which is substituted with hydroxy or morpholinyl; or benzyl.

11. The method of claim 2, wherein only one group between the R$_8$ and the R$_9$ is hydrogen.

12. The method of claim 2, wherein the R$_8$ and R$_9$ are both C$_1$~C$_6$ alkyl which is unsubstituted or substituted with hydroxy.

13. The method of claim 12, wherein the R$_8$ and R$_9$ are both ethyl, hydroxyethyl or propyl.

14. The method of claim 2, wherein the R$_8$ is C$_3$~C$_6$ cycloalkyl; and the R$_9$ is carbonyl substituted with pyridinyl.

15. The method of claim 14, wherein the R$_9$ is 3-pyridinoyl or 4-pyridinoyl.

16. The method of claim 1, wherein the R$_1$ is C$_1$~C$_6$ alkyl which is unsubstituted or substituted with pyridinyl; and the R$_2$ is hydrogen; straight or branched C$_1$~C$_6$ alkyl which is unsubstituted or substituted with NR$_8$R$_9$; C$_3$~C$_6$ cycloalkyl; C$_2$~C$_6$ alkenyl; carbonyl which is substituted with NR$_8$R$_9$; amino; dimethylamino; morpholinyl; or straight or branched C$_1$~C$_6$ alkyl which is substituted with hydroxy, C$_1$~C$_6$alkoxy, halogen, C$_3$~C$_6$ cycloalkyl,

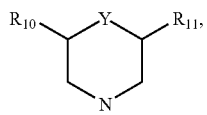

imidazolyl, or pyrrolidinyl.

17. The method of claim 1, wherein
the $R_1$ is straight or branched $C_1$~$C_6$ alkyl which is substituted with

unsubstituted or substituted with hydroxyl; and
the $R_2$ is straight or branched $C_1$~$C_6$ alkyl which is substituted with hydroxy, $C_1$~$C_6$alkoxy, halogen, $C_3$~$C_6$ cycloalkyl,

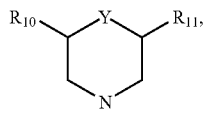

imidazolyl, or pyrrolidinyl.

18. The method of claim 1, wherein
the $R_1$ is $C_3$~$C_6$ cycloalkyl; and
the $R_2$ is hydrogen; straight or branched $C_1$~$C_6$ alkyl which is unsubstituted or substituted with $NR_8R_9$; or straight or branched $C_1$~$C_6$ alkyl which is substituted with hydroxy, $C_1$~$C_6$ alkoxy, halogen, $C_3$~$C_6$ cycloalkyl,

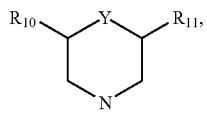

imidazolyl, or pyrrolidinyl.

19. The method of claim 1, wherein
the $R_1$ is phenyl or benzyl; and
the $R_2$ is phenyl; benzyl; amino; or straight or branched $C_1$~$C_6$ alkyl which is substituted with hydroxy, $C_1$~$C_6$ alkoxy, halogen, $C_3$~$C_6$ cycloalkyl,

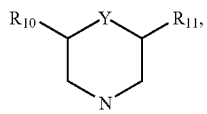

midazolyl, or pyrrolidinyl.

20. The method of claim 1, wherein
the $R_1$ is pyridinyl which is unsubstituted or substituted with $C_1$~$C_6$ alkyl; and
the $R_2$ is hydrogen; straight or branched $C_1$~$C_6$ alkyl which is unsubstituted or substituted with $NR_8R_9$; phenyl; benzyl; $C_2$~$C_6$ alkenyl; or straight or branched $C_1$~$C_6$ alkyl which is substituted with hydroxy, $C_1$~$C_6$ alkoxy, halogen, $C_3$~$C_6$ cycloalkyl,

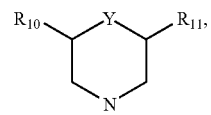

imidazolyl, or pyrrolidinyl.

21. The method of claim 1, wherein
the $R_1$ is guanidino; and
the $R_2$ is straight or branched $C_1$~$C_6$ alkyl which is unsubstituted or substituted with $NR_8R_9$.

22. The method of claim 1, wherein
the $R_1$ is $NR_6R_7$ or $CH_2NR_6R_7$; and
the $R_2$ is hydrogen; straight or branched $C_1$~$C_6$ alkyl which is unsubstituted or substituted with $NR_8R_9$; $C_3$~$C_6$ cycloalkyl; $C_2$~$C_6$ alkenyl; carbonyl which is substituted with $NR_8R_9$; or straight or branched $C_1$~$C_6$ alkyl which is substituted with hydroxy, $C_1$~$C_6$alkoxy, halogen, $C_3$~$C_6$ cycloalkyl,

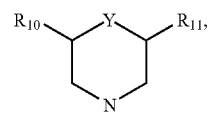

imidazolyl, or pyrrolidinyl.

23. The method of claim 1, wherein
the $R_1$ is

group which is substituted with straight or branched $C_1$~$C_6$ alkyl; and
the $R_2$ is straight or branched $C_1$~$C_6$ alkyl which is unsubstituted or substituted with $NR_8R_9$; $C_3$~$C_6$ cycloalkyl; morpholinyl; thiomorpholinyl; 4-methylpiperazinyl; or straight or branched $C_1$~$C_6$ alkyl which is substituted with hydroxy, $C_1$~$C_6$alkoxy, halogen, $C_3$~$C_6$ cycloalkyl,

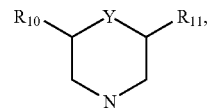

imidazolyl, or pyrrolidinyl.

24. The method of claim 1, wherein the compound of Formula 1 is selected from the group consisting of:
1) N-hydroxy-4-{5-[4-(2-isopropyl-5-methyl-1,3-thiazol-4-yl)phenoxy]pentyloxy}-benzamidine,
2) 4-{5-[4-(2-isopropyl-5-methyl-1,3-thiazol -4-yl)phenoxy]pentyloxy}-benzamidine,
3) N-hydroxy-4-{5-[4-(2-methyl-1,3-thiazol-4-yl)phenoxy]pentyloxy}-benzamidine,
4) N-hydroxy-4-{5-[4-(2-ethyl-1,3-thiazol-4-yl)phenoxy]pentyloxy}-benzamidine,
5) N-hydroxy-4-{5-[4-(2-isopropyl-1,3-thiazol-4-yl)phenoxy]pentyloxy}-benzamidine,
6) N-hydroxy-4-{5-[4-(2-phenyl-1,3-thiazol-4-yl)phenoxy]pentyloxy}-benzamidine, 7) N-hydroxy-4-{5-[4-(2-pyridine-3-yl-1,3-thiazol-4-yl)phenoxy]pentyloxy}-benzamidine,
8) N-hydroxy-4-{5-[4-(2-cyclohexyl-1,3-thiazol-4-yl)phenoxy]pentyloxy}-benzamidine,
9) N-hydroxy-4-{5-[4-(2-pentyl-1,3-thiazol-4-yl)phenoxy]pentyloxy}-benzamidine,
10) N-hydroxy-4-{5-[4-(2,5-dimethyl-1,3-thiazol-4-yl)phenoxy]pentyloxy}-benzamidine,
11) N-hydroxy-4-{5-[4-(2-ethyl-5-methyl-1,3-thiazol-4-yl)phenoxy]pentyloxy}-benzamidine,
12) N-hydroxy-4-{5-[4-(5-methyl-2-phenyl-1,3-thiazol-4-yl)phenoxy]pentyloxy}-benzamidine,
13) N-hydroxy-4-{5-[4-(5-methyl-2-pyridin-3-yl-1,3-thiazol-4-yl) phenoxy]pentyloxy}-benzamidine,
14) N-hydroxy-4-{5-[4-(2-cyclohexyl-5-methyl-1,3-thiazol-4-yl) phenoxy]pentyloxy}-benzamidine,
15) N-hydroxy-4-{5-[4-(5-methyl-2-pentyl-1,3-thiazol-4-yl)phenoxy]pentyloxy}-benzamidine,
16) N-hydroxy-4-{5-[4-(2-t-butyl-5-methyl-1,3-thiazol-4-yl)phenoxy]pentyloxy}-benzamidine,
17) N-hydroxy-4-{5-[4-(5-ethyl-2-methyl-1,3-thiazol-4-yl)phenoxy]pentyloxy}-benzamidine,
18) N-hydroxy-4-{5-[4-(2,5-diethyl-1,3-thiazol-4-yl)phenoxy]pentyloxy}-benzamidine,
19) N-hydroxy-4-{5-[4-(5-ethyl-2-isopropyl-1,3-thiazol-4-yl)phenoxy]pentyloxy}-benzamidine,
20) N-hydroxy-4-{5-[4-(5-ethyl-2-phenyl-1,3-thiazol-4-yl)phenoxy]pentyloxy}-benzamidine,
21) N-hydroxy-4-{5-[4-(5-ethyl-2-pyridin-3-yl -1,3-thiazol-4-yl)phenoxy]pentyloxy}-benzamidine,
22) N-hydroxy-4-{5-[4-(2-cyclohexyl-5-ethyl-1,3-thiazol-4-yl)phenoxy]pentyloxy}-benzamidine,
23) N-hydroxy-4-{5-[4-(5-ethyl-2-pentyl-1,3-thiazol-4-yl)phenoxy]pentyloxy}-benzamidine,
24) N-hydroxy-4-{5-[4-(2-ethyl-5-isopropyl-1,3-thiazol-4-yl)phenoxy]pentyloxy}-benzamidine,
25) N-hydroxy-4-{5-[4-(2,5-diisopropyl-1,3-thiazol-4-yl)phenoxy]pentyloxy}-benzamidine,
26) N-hydroxy-4-{5-[4-(5-isopropyl-2-phenyl-1,3-thiazol-4-yl)phenoxy]pentyloxy}-benzamidine,
27) N-hydroxy-4-{5-[4-(5-isopropyl-2-pyridin-3-yl-1,3-thiazol-4-yl)phenoxy]pentyloxy}-benzamidine,
28) N-hydroxy-4-{5-[4-(5-isopropyl-2-pentyl-1,3-thiazol-4-yl)phenoxy]pentyloxy}-benzamidine,
29) N-hydroxy-4-{5-[4-(2-methyl-5-propyl-1,3-thiazol-4-yl)phenoxy]pentyloxy}-benzamidine,
30) N-hydroxy-4-{5-[4-(5-butyl-2-methyl-1,3-thiazol-4-yl)phenoxy]pentyloxy}-benzamidine,
31) N-hydroxy-4-{5-[4-(5-butyl-2-ethyl-1,3-thiazol-4-yl)phenoxy]pentyloxy}-benzamidine,
32) N-hydroxy-4-{5-[4-(5-butyl-2-isopropyl-1,3-thiazol-4-yl)phenoxy]pentyloxy}-benzamidine,
33) N-hydroxy-4-{5-[4-(5-butyl-2-phenyl-1,3-thiazol-4-yl)phenoxy]pentyloxy}-benzamidine,
34) N-hydroxy-4-{5-[4-(5-butyl-2-pyridin-3-yl -1,3-thiazol-4-yl)phenoxy]pentyloxy}-benzamidine,
35) N-hydroxy-4-{5-[4-(5-butyl-2-cyclohexyl-1,3-thiazol-4-yl)phenoxy]pentyloxy}-benzamidine,
36) N-hydroxy-4-{5-[4-(5-butyl-2-pentyl-1,3-thiazol-4-yl)phenoxy]pentyloxy}-benzamidine,
37) N-hydroxy-4-{5-[4-(5-butyl-2-t-butyl-1,3-thiazol-4-yl)phenoxy]pentyloxy}-benzamidine,
38) N-hydroxy-4-{5-[4-(5-benzyl-2-methyl-1,3-thiazol-4-yl)phenoxy]pentyloxy}-benzamidine,
39) N-hydroxy-4-{5-[4-(5-benzyl-2-isopropyl-1,3-thiazol-4-yl)phenoxy]pentyloxy}-benzamidine,
40) N-hydroxy-4-{5-[4-(5-benzyl-2-phenyl-1,3-thiazol-4-yl)phenoxy]pentyloxy}-benzamidine,
41) N-hydroxy-4-{5-[4-(5-benzyl-2-pyridin-3-yl-1,3-thiazol-4-yl)phenoxy]pentyloxy}-benzamidine,
42) N-hydroxy-4-{5-[4-(5-(2-chloro-ethyl)-2-methyl-1,3-thiazol-4-yl)phenoxy]pentyloxy}-benzamidine,
43) N-hydroxy-4-{5-[4-(5-cyclopentyl-2-methyl-1,3-thiazol-4-yl)phenoxy]pentyloxy}-benzamidine,
44) N-hydroxy-4-{5-[4-(5-isobutyl-2-methyl-1,3-thiazole-4-yl)phenoxy]pentyloxy}-benzamidine,
45) N-hydroxy-4-{5-[4-(5-cyclopentylmethyl-2-methyl -1,3-thiazol-4-yl)phenoxy]pentyloxy}-benzamidine,
46) N-hydroxy-4-{5-[4-(5-cyclopentylmethyl-2-ethyl -1,3-thiazol-4-yl)phenoxy]pentyloxy}-benzamidine,
47) N-hydroxy-4-{5-[4-(5-cyclopentylmethyl-2-isopropyl-1,3-thiazol-4-yl)phenoxy]pentyloxy}-benzamidine,
48) N-hydroxy-4-{5-[4-(5-cyclopentylmethyl-2-phenyl -1,3-thiazol-4-yl)phenoxy]pentyloxy}-benzamidine,
49) N-hydroxy-4-{5-[4-(5-cyclopentylmethyl-2-pyridin-3-yl-1,3-thiazol-4-yl)phenoxy]pentyloxy}-benzamidine,
50) N-hydroxy-4-{5-[4-(5-cyclopentylmethyl-2-cyclohexyl-1,3-thiazol-4-yl)phenoxy]pentyloxy}-benzamidine,
51) N-hydroxy-4-{5-[4-(5-cyclopentylmethyl-2-pentyl -1,3-thiazol-4-yl)phenoxy]pentyloxy}-benzamidine,
52) 4-{5-[4-(2-methyl-1,3-thiazol-4-yl)phenoxy]pentyloxy}-benzamidine,
53) 4-{5-[4-(2-isopropyl-1,3-thiazol-4-yl)phenoxy]pentyloxy}-benzamidine,
54) 4-{5-[4-(2,5-dimethyl-1,3-thiazol-4-yl)phenoxy]pentyloxy}-benzamidine,
55) 4-{5-[4-(5-ethyl-2-isopropyl-1,3-thiazol -4-yl)phenoxy]pentyloxy}-benzamidine,
56) 4-{5-[4-(5-ethyl-2-phenyl-1,3-thiazol-4-yl)phenoxy]pentyloxy}-benzamidine,
57) N-hydroxy-4-{5-[4-(2-amino-1,3-thiazol-4-yl)phenoxy]pentyloxy}-benzamidine,
58) N-hydroxy-4-{5-[4-(2-amino-5-methyl-1,3-thiazol-4-yl)phenoxy]pentyloxy}-benzamidine,
59) N-hydroxy-4-{5-[4-(2-guanidino-5-methyl-1,3-thiazol-4-yl)phenoxy]pentyloxy}-benzamidine,
60) N-hydroxy-4-{5-[4-(2-amino-5-ethyl-1,3-thiazol-4-yl)phenoxy]pentyloxy}-benzamidine,
61) N-hydroxy-4-{5-[4-(2-amino-5-isopropyl-1,3-thiazol-4-yl)phenoxy]pentylox}-benzamidine,
62) N-hydroxy-4-{5-[4-(2-guanidino-5-isopropyl-1,3-thiazol-4-yl)phenoxy]pentyloxy}-benzamidine,
63) N-hydroxy-4-{5-[4-(2-amino-5-butyl-1,3-thiazol-4-yl)phenoxy]pentyloxy}-benzamidine,
64) N-hydroxy-4-{5-[4-(5-butyl-2-guanidino-1,3-thiazol-4-yl)phenoxy]pentyloxy}-benzamidine,
65) N-hydroxy-4-{5-[4-(2-amino-5-benzyl-1,3-thiazol-4-yl)phenoxy]pentyloxy}-benzamidine,
66) N-hydroxy-4-{5-[4-(5-benzyl-2-guanidino-1,3-thiazol-4-yl)phenoxy]pentyloxy}-benzamidine,
67) N-hydroxy-4-{5-[4-(2-amino-5-cyclopentylmethyl -1,3-thiazol-4-yl)phenoxy]pentyloxy}-benzamidine,
68) N-hydroxy-4-{5-[4-(5-cyclopentylmethyl-2-(1-propyl-piperidin-4-yl)-1,3-thiazol-4-yl)phenoxy]pentyloxy}-benzamidine, 69) N-hydroxy-4-{5-[4-(2-(isobutyryl)amino-5-methyl -1,3-thiazol-4-yl)phenoxy]pentyloxy}-benzamidine,
70) N-hydroxy-4-{5-[4-(5-isopropyl-2-morpholinomethyl-1,3-thiazol-4-yl)phenoxy]pentyloxy}-benzamidine,
71) N-hydroxy-4-{5-[4-(2-aminomethyl-5-benzyl-1,3-thiazol-4-yl)phenoxy]pentyloxy}-benzamidine,
72) N-hydroxy-4-{5-[4-(5-methyl-2-(1-propyl -piperidin-4-yl)-1,3-thiazol-4-yl)phenoxy]pentyloxy}-benzamidine,
73) N-hydroxy-4-{5-[4-(5-isopropyl-2-aminomethyl-1,3-thiazol-4-yl)phenoxy]pentyloxy}-benzamidine,
74) N-hydroxy-4-{5-[4-(5-vinyl-2-methyl-1,3-thiazol-4-yl)phenoxy]pentyloxy}-benzamidine,
75) N-hydroxy-4-{5-[4-(5-hydroxymethyl-2-methyl-1,3-thiazol-4-yl)phenoxy]pentyloxy}-benzamidine,
76) N-hydroxy-4-{5-[4-(5-methoxymethyl-2-methyl-1,3-thiazol-4-yl)phenoxy]pentyloxy}-benzamidine,
77) N-hydroxy-4-{5-[4-(5-(2-chloroethyl)-2-amino-1,3-thiazol-4-yl)phenoxy]pentyloxy}-benzamidine,
78) N-hydroxy-4-{5-[4-(5-vinyl-2-amino-1,3-thiazol-4-yl)phenoxy]pentyloxy}-benzamidine,
79) N-hydroxy-4-{5-[4-(5-vinyl-2-(pyridin-3-yl)-1,3-thiazol-4-yl)phenoxy]pentyloxy}-benzamidine,
80) N-hydroxy-4-{5-[4-(5-(2-chloroethyl)-2-(pyridin-3-yl)-1,3-thiazol-4-yl)phenoxy]pentyloxy}-benzamidine,
81) N-hydroxy-4-{5-[4-(2-amino-5-cyclopentyl-1,3-thiazol-4-yl)phenoxy]pentyloxy}-benzamidine,
82) N-hydroxy-4-{5-[4-(5-ethyl-2-aminomethyl-1,3-thiazol-4-yl)phenoxy]pentyloxy}-benzamidine,
83) N-hydroxy-4-{5-[4-(5-isopropyl-2-(piperidin-3-yl)-1,3-thiazol-4-yl)phenoxy]pentyloxy}-benzamidine,
84) N-hydroxy-4-{5-[4-(2-ethylamino-1,3-thiazol-4-yl)phenoxy]pentyloxy}-benzamidine,
85) N-hydroxy-4-{5-[4-(2-ethanesulphonylamino-1,3-thiazol-4-yl)phenoxy]pentyloxy}-benzamidine,
86) N-hydroxy-4-{5-[4-(5-methyl-2-methylamino-1,3-thiazol-4-yl)phenoxy]pentyloxy}-benzamidine,
87) N-hydroxy-4-{5-[4-(2-ethylamino-5-methyl-1,3-thiazol-4-yl)phenoxy]pentyloxy}-benzamidine,
88) N-hydroxy-4-{5-[4-(5-methyl-2-propylamino-1,3-thiazol-4-yl)phenoxy]pentyloxy}-benzamidine,
89) N-hydroxy-4-{5-[4-(5-cyclopentylmethyl-2-(3-pyridylcarbonyl)amino-1,3-thiazol-4-yl)phenoxy]pentyloxy}-benzamidine,
90) N-hydroxy-4-{5-[4-(2-hydroxyacetylamino-5-methyl-1,3-thiazol-4-yl)phenoxy]pentyloxy}-benzamidine,
91) N-hydroxy-4-{5-[4-(5-methyl-2-(4-pyridylcarbonyl)amino-1,3-thiazol-4-yl)phenoxy]pentyloxy}-benzamidine,
92) N-hydroxy-4-{5-[4-(5-methyl-2-(3-pyridylcarbonyl)amino-1,3-thiazol-4-yl)phenoxy]pentyloxy}-benzamidine,
93) N-hydroxy-4-{5-[4-(2-ethanesulphonylamino-5-methyl-1,3-thiazol-4-yl)phenoxy]pentyloxy}-benzamidine,
94) N-hydroxy-4-{5-[4-(2-(2-methoxyethypamino-5-methyl-1,3-thiazol-4-yl)phenoxy]pentyloxy}-benzamidine,
95) N-hydroxy-4-{5-[4-(2-ethanesulphonylamino-5-ethyl-1,3-thiazol-4-yl)phenoxy]pentyloxy}-benzamidine,
96) N-hydroxy-4-{5-[4-(5-ethyl-2-methylamino-1,3-thiazol-4-yl)phenoxy]pentyloxy}-benzamidine,
97) N-hydroxy-4-{5-[4-(5-ethyl-2-ethylamino-1,3-thiazol-4-yl)phenoxy]pentyloxy}-benzamidine,
98) N-hydroxy-4-{5-[4-(5-ethyl-2-propylamino-1,3-thiazol-4-yl)phenoxy]pentyloxy}-benzamidine,
99) N-hydroxy-4-{5-[4-(5-ethyl-2-methoxyacetylamino -1,3-thiazol-4-yl)phenoxy]pentyloxy}-benzamidine, 100) N-hydroxy-4-{5-[4-(5-ethyl-2-(4-pyridylcarbonyl)amino-1,3-thiazol-4-yl)phenoxy]pentyloxy}-benzamidine,
101) N-hydroxy-4-{5-[4-(5-ethyl-2-(3-pyridylcarbonyl)amino-1,3-thiazol-4-yl)phenoxy]pentyloxy}-benzamidine,
102) N-hydroxy-4-{5-[4-(5-ethyl-2-(2-methoxyethypamino-1,3-thiazol-4-yl)phenoxy]pentyloxy}-benzamidine,
103) N-hydroxy-4-{5-[4-(5-isopropyl-2-methylamino-1,3-thiazol-4-yl)phenoxy]pentyloxy}-benzamidine,
104) N-hydroxy-4-{5-[4-(2-ethylamino-5-isopropyl-1,3-thiazol-4-yl)phenoxy]pentyloxy}-benzamidine,
105) N-hydroxy-4-{5-[4-(5-butyl-2-methylamino-1,3-thiazol-4-yl)phenoxy]pentyloxy}-benzamidine,
106) N-hydroxy-4-{5-[4-(5-butyl-2-ethylamino-1,3-thiazol-4-yl)phenoxy]pentyloxy}-benzamidine,
107) N-hydroxy-4-{5-[4-(5-benzyl-2-methylamino-1,3-thiazol-4-yl)phenoxy]pentyloxy}-benzamidine,
108) N-hydroxy-4-{5-[4-(5-benzyl-2-ethylamino-1,3-thiazol-4-yl)phenoxy]pentyloxy}-benzamidine,
109) N-hydroxy-4-{5-[4-(5-cyclopentylmethyl-2-methylamino-1,3-thiazol-4-yl)phenoxy]pentyloxy}-benzamidine,
110) N-hydroxy-4-{5-[4-(5-cyclopentylmethyl-2-ethylamino-1,3-thiazol-4-yl)phenoxy]pentyloxy}-benzamidine,
111) N-hydroxy-4-{5-[4-(5-cyclopentylmethyl-2-propylamino-1,3-thiazol-4-yl)phenoxy]pentyloxy}-benzamidine,
112) N-hydroxy-4-{5-[4-(5-cyclopentylmethyl-2-(4-pyridylcarbonyl)amino-1,3-thiazol-4-yl)phenoxy]pentyloxy}-benzamidine,
113) N-hydroxy-4-{5-[4-(5-cyclopentyl-2-propylamino -1,3-thiazol-4-yl)phenoxy]pentyloxy}-benzamidine,
114) N-hydroxy-4-{5-[4-(5-isopropyl-2-[(pyridin-3-ylmethypamino]-1,3-thiazol-4-yl)phenoxy]pentyloxy}-benzamidine,
115) N-hydroxy-4-{5-[4-(5-(2-chloroethyl)-2-methylamino-1,3-thiazol-4-yl)phenoxy]pentyloxy}-benzamidine,
116) N-hydroxy-4-{5-[4-(2-methylamino-1,3-thiazol-4-yl)phenoxy]pentyloxy}-benzamidine,
117) N-hydroxy-4-{5-[4-(5-ethyl-2-(pyridin-3-ylmethyl)amino-1,3-thiazol-4-yl)phenoxy]pentyloxy}-benzamidine,
118) N-hydroxy-4-{5-[4-(2-(ethanesulphonyl-methylamino) -1,3-thiazol-4-yl)phenoxy]pentyloxy}-benzamidine,
119) N-hydroxy-4-[5-(4-{2-[methyl-(2-morpholinoethypamino]-1,3-thiazol-4-yl}phenoxy)pentyloxy]-benzamidine,
120) N-hydroxy-4-[5-(4-{2-[(2-hydroxyethyl) -methylamino]-5-methyl-1,3-thiazol-4-yl}phenoxy)pentyloxy]-benzamidine,
121) N-hydroxy-4-[5-(4-{2-[ethyl-(2-hydroxyethyl) -amino]-5-methyl-1,3-thiazol-4-yl}phenoxy)pentyloxy]-benzamidine,
122) N-hydroxy-4-[5-(4-{2-[bis-(2-methoxyethyl) -amino]-5-methyl-1,3-thiazol-4-yl}phenoxy)pentyloxy]-benzamidine, 123) N-hydroxy-4-[5-(4-{5-methyl-2-[methyl-(2-morpholinoethyl)-amino]-1,3-thiazol-4-yl}phenoxy)pentyloxy]-benzamidine,
124) N-hydroxy-4-[5-(4-{2-[ethyl-1-(2-morpholinoethyl)-amino]-5-methyl-1,3-thiazol-4-yl}phenoxy)pentyloxy]-benzamidine,
125) N-hydroxy-4-{5-(4-[2-(benzyl-methyl-amino)-5-methyl-1,3-thiazol-4-yl]phenoxy)pentyloxy}-benzamidine,
126) N-hydroxy-4-[5-{4-[5-methyl-2-(methyl -pyridin-3-yl-methyl-amino)-1,3-thiazol-4-yl]phenoxy}pentyloxy]-benzamidine,
127) N-hydroxy-4-[5-{4-[2-(benzyl-ethyl-amino)-5-methyl-1,3-thiazol-4-yl]phenoxy}pentyloxy]-benzamidine,
128) N-hydroxy-4-[5-(4-{2-[bis-(2-hydroxyethyl) -amino]-5-methyl-1,3-thiazol-4-yl}phenoxy)pentyloxy]-benzamidine,
129) N-hydroxy-4-[5-(4-{5-ethyl-2-[(2-hydroxyethyl)-methyl-amino]-1,3-thiazol-4-yl}phenoxy)pentyloxy]-benzamidine,
130) N-hydroxy-4-[5-(4-{5-ethyl-2-[ethyl-(2-hydroxyethyl)-amino]-1,3-thiazol-4-yl}phenoxy)pentyloxy]-benzamidine,
131) N-hydroxy-4-[5-(4-{5-ethyl-2-[methyl-(2-morpholinoethyl)-amino]-1,3-thiazol-4-yl}phenoxy)pentyloxy]-benzamidine,
132) N-hydroxy-4-[5-(4-{5-ethyl-2-[ethyl-(2-morpholinoethyl)-amino]-1,3-thiazol-4-yl}phenoxy)pentyloxy]-benzamidine,
133) N-hydroxy-4-[5-{4-[2-(benzyl-methyl-amino)-5-ethyl-1,3-thiazol-4-yl]phenoxy}pentyloxy]-benzamidine,
134) N-hydroxy-4-[5-(4-{5-ethyl-2-[methyl-(pyridn -3-ylmethyl)amino]-1,3-thiazol-4-yl}phenoxy)pentyloxy]-benzamidine,
135) N-hydroxy-4-(5-{4-[2-(benzyl-ethyl-amino)-5-ethyl-1,3-thiazol-4-yl]phenoxy}pentyloxy)-benzamidine,
136) N-hydroxy-4-{5-(4-[5-ethyl-2-(ethyl-[pyridin -3-ylmethyl]amino)-1,3-thiazol-4-yl]phenoxy)pentyloxy}-benzamidine,
137) N-hydroxy-4-[5-(4-{2-[bis-(pyridin-3-ylmethyl) amino]-5-ethyl-1,3-thiazol-4-yl}phenoxy)pentyloxy]-benzamidine,
138) N-hydroxy-4-{5-[4-(2-dipropylamino-5-ethyl-1,3-thiazol-4-yl)phenoxy]pentyloxy}-benzamidine,
139) N-hydroxy-4-[5-(4-{2-[bis-(2-hydroxyethyl)amino]-5-ethyl-1,3-thiazol-4-yl}phenoxy)pentyloxy]-benzamidine,
140) N-hydroxy-4-[5-(4-{2-[(2-hydroxyethyl) -methyl-amino]-5-isopropyl-1,3-thiazol-4-yl}phenoxy)pentyloxy]-benzamidine,
141) N-hydroxy-4-[5-(4-{5-isopropyl-2-[methyl -(pyridin-3-ylmethyl)amino]-1,3-thiazol-4-yl}phenoxy)pentyloxy]-benzamidine,
142) N-hydroxy-4-(5-{4-[2-(ethanesulphonyl-methyl-amino) -5-isopropyl-1,3-thiazol-4-yl]phenoxy}pentyloxy)-benzamidine,
143) N-hydroxy-4-[5-(4-{5-butyl-2-[(2-hydroxyethyl)-methyl-amino]-1,3-thiazol-4-yl}phenoxy)pentyloxy]-benzamidine,
144) N-hydroxy-4-[5-(4-{5-butyl-2-[methyl-(2-morpholinoethyp)amino]-1,3-thiazol-4-yl}phenoxy)pentyloxy]-benzamidine,
145) N-hydroxy-4-[5-(4-{5-butyl-2-[methyl -(pyridin-3-ylmethyl)amino]-1,3-thiazol-4-yl}phenoxy)pentyloxy]-benzamidine,
146) N-hydroxy-4-{5-[4-(5-butyl-2-dipropylamino-1,3-thiazol-4-yl)phenoxy]pentyloxy}-benzamidine,
147) N-hydroxy-4-[5-(4-{5-cyclopentylmethyl-2-[methyl-(pyridin-3-ylmethypamino]-1,3-thiazol-4-yl}phenoxy)pentyloxy]-benzamidine,
148) N-hydroxy-4-[5-(4-{5-cyclopentylmethyl-2-[methyl-(2-morpholinoethyl)amino]-1,3-thiazol-4-yl}phenoxy)pentyloxy]-benzamidine,
149) N-hydroxy-4-{5-[4-(5-cyclopentylmethyl-2-dipropylamino-1,3-thiazol-4-yl)phenoxy]pentyloxy}-benzamidine,
150) N-hydroxy-4-{5-[4-(5-butyl-2-diethylamino-1,3-thiazol-4-yl)phenoxy]pentyloxy}-benzamidine,
151) N-hydroxy-4-{5-[4-(5-butyl-2-ethylmethylamino -1,3-thiazol-4-yl)phenoxy]pentyloxy}-benzamidine,
152) N-hydroxy-4-{5-[4-(5-butyl-2-dimethylamino-1,3-thiazol-4-yl)phenoxy]pentyloxy}-benzamidine,
153) N-hydroxy-4-[5-(4-{5-cyclopentyl-2-[methyl -(2-morpholinoethyl)amino]-1,3-thiazol-4-yl}phenoxy)pentyloxy]-benzamidine,
154) N-hydroxy-4-[5-(4-{5-isobutyl-2-[methyl-(2-morpholinoethyl)amino]-1,3-thiazol-4-yl}-phenoxy)pentyloxy]-benzamidine,
155) N-hydroxy-4-(5-{4-[5-(2-chloroehtyl)-2-dimethylamino-1,3-thiazol-4-yl]phenoxy}pentyloxy)-benzamidine,
156) N-hydroxy-4-{5-[4-(5-cyclopentyl-2-diethylamino-1,3-thiazol-4-yl)phenoxy]pentyloxy}-benzamidine,
157) N-hydroxy-4-{5-[4-(5-isopropyl-2-dipropylamino -1,3-thiazol-4-yl)phenoxy]pentyloxy}-benzamidine,
158) N-hydroxy-4-{5-[4-(5-ethyl-2-diethylamino-1,3-thiazol-4-yl)phenoxy]pentylwry}-benzamidine,
159) N-hydroxy-4-[5-(4-{5-isopropyl-2-[methyl-(2-morpholinoethyl)amino]-1,3-thiazol-4-yl}phenoxy)pentyloxy]-benzamidine,
160) N-hydroxy-4-{5-[4-(5-cyclopentylmethyl-2-diethylamino-1,3-thiazol-4-yl)phenoxy]pentyloxy}-benzamidine,
161) N-hydroxy-4-{5-[4-(5-isopropyl-2-dimethylamino -1,3-thiazol-4-yl)phenoxy]pentyloxy}-benzamidine,
162) N-hydroxy-4-{5-[4-(5-isopropyl-2-diethylamino -1,3-thiazol-4-yl)phenoxy]pentyloxy}-benzamidine,
163) N-hydroxy-4-{5-[4-(5-cyclopentylmethyl-2-dimethylamino-1,3-thiazol-4-yl)phenoxy]pentyloxy}-benzamidine,
164) N-hydroxy-4-{5-[4-(5-methyl-2-pipendino-1,3-thiazol-4-yl)phenoxy]pentyloxy}-benzamidine,
165) N-hydroxy-4-{5-[4-(5-methyl-2-morpholino-1,3-thiazol-4-yl)phenoxy]pentyloxy}-benzamidine,
166) N-hydroxy-4-{5-[4-(5-ethyl-2-pipendino-1,3-thiazol-4-yl)phenoxy]pentylog}-benzamidine,
167) N-hydroxy-4-{5-[4-(5-cyclopentylmethyl-2-pipendino-1,3-thiazol-4-yl)phenoxy]pentyloxy}-benzamidine,
168) N-hydroxy-4-{5-[4-(5-cyclopentylmethyl-2-morpholino-1,3-thiazol-4-yl)phenoxy]pentyloxy}-benzamidine,
169) N-hydroxy-4-{5-[4-(5-isopropyl-2-morpholino-1,3-thiazol-4-yl)phenoxy]pentyloxy}-benzamidine, 170) N-hydroxy-4-{5-(4-[5-cyclopentylmethyl-2-(4-methylpiperazino)-1,3-thiazol-4-yl]phenoxy)pentyloxy}-benzamidine,
171) N-hydroxy-4-{5-[4-(5-vinyl-2-morpholin-4-yl-1,3-thiazol-4-yl)phenoxy]pentyloxy}-benzamidine,
172) N-hydroxy-4-{5-[4-(5-cyclopentyl-2-morpholin-4-yl-1,3-thiazol-4-yl)phenoxy]pentyloxy}-benzamidine,
173) N-hydroxy-4-{5-[4-(5-isobutyl-2-morpholin-4-yl-1,3-thiazol-4-yl)phenoxy]pentyloxy}-benzamidine,
174) N-hydroxy-4-{5-(4-[5-ethyl-2-(4-methylpiperazino)-1,3-thiazol-4-yl]phenoxy)pentyloxy}-benzamidine,
175) N-hydroxy-4-{5-[4-(2-morpholin-4-yl-1,3-thiazol-4-yl)phenoxy]pentyloxy}-benzamidine,
176) N-hydroxy-4-{5-(4-[5-isopropyl-2-(4-methylpiperazino)-1,3-thiazol-4-yl]phenoxy)pentyloxy}-benzamidine,
177) N-hydroxy-4-{5-[4-(5-isopropyl-2-methyl-1,3-thiazol-4-yl)-phenoxy]-pentylamino}-benzamidine,
178) N-hydroxy-4-(2-{2-[4-(5-isopropyl-2-methyl-1,3-thiazol-4-yl)-phenoxy]-ethoxy}-ethoxy)-benzamidine,
179) N-hydroxy-4-{3-hydroxy-5-[4-(5-isopropyl-2-methyl-1,3-thiazol-4-yl)-phenoxy]-3-methyl-pentyloxy}-benzamidine,
180) N-hydroxy-4-(2-{2-[4-(5-isopropyl-2-methyl-1,3-thiazol-4-yl)-phenoxy]-1-methyl-ethylamino}-ethoxy)-benzamidine,
181) N-hydroxy-4-[3-(4-{3-[4-(5-isopropyl-2-methyl-1,3-thiazol-4-yl)-phenoxy]-propyl}-piperazine-1-yl)-propoxy]-benzamidine,
182) N-hydroxy-4-{5-[4-(5-isopropyl-2-methyl-1,3-thiazol-4-yl)-phenoxy]-pentanoyl-amino}-benzamidine,
183) N-hydroxy-4-({5-[4-(5-isopropyl-2-methyl-1,3-thiazol-4-yl)-phenoxy]-pentyl}-methyl-amino)-benzamidine,
184) N-hydroxy-4-{4-[4-(5-isopropyl-2-methyl-1,3-thiazol-4-yl)-phenoxy]-but-2-enyloxy}-benzamidine,
185) N-hydroxy-4-{4-[4--(5-isopropyl-2-methyl-1,3-thiazol-4-yl)-phenoxymethyl]-benzyloxy}-benzamidine,
186) N-hydroxy-4-(2-{2-[4-(5-isopropyl-2-methyl-1,3-thiazol-4-yl)phenoxy]-ethylamino}-ethoxy)-benzamidine,
187) N-hydroxy-2-fluoro-4-{5-[4-(5-isopropyl-2-methyl-1,3-thiazol-4-yl)-phenoxyl]-pentyloxy}-benzamidine,
188) 2,N-dihydroxy-4-{5-[4-(5-isopropyl-2-methyl-1,3-thiazol-4-yl)-phenoxy]-pentyloxy}-benzamidine,
189) N-hydroxy-4-{5-[4-(5-isopropyl-2-methyl-1,3-thiazol-4-yl)-phenoxy]-pentyloxy}-3-methoxy-benzamidine,
190) N-hydroxy-2-cyclohexylamino-4-{5-[4-(5-isopropyl-2-methyl-1,3-thiazol-4-yl)-phenoxy]-pentyloxy}-benzamidine,
191) N-hydroxy-4-{5-[3-fluoro-4-(5-isopropyl-2-methyl-1,3-thiazol-4-yl)-phenoxy]-pentyloxy}-benzamidine,
192) N-hydroxy-2-fluoro-4-{5-[3-fluoro-4-(5-isopropyl-2-methyl-1,3-thiazol-4-yl)-phenoxy]-pentyloxy}-benzamidine,
193) N-hydroxy-4-{3-[4-(5-isopropyl-2-methyl-1,3-thiazol-4-yl)phenoxy]propoxy}-benzamidine,
194) N-hydroxy-4-{4-[4-(5-isopropyl-2-methyl-1,3-thiazol-4-yl)phenoxy]butoxy}-benzamidine,
195) N-hydroxy-3-{5-[4-(5-isopropyl-2-methyl -thiazol-4-yl)-phenoxy]-pentylamino}-benzamidine,
196) N-hydroxy-4-{4-[4-(2-cyclohexyl-5-ethyl -thiazol-4-yl)-phenoxy]-butoxyl}-benzamidine,
197) N-hydroxy-4-[3-(4-{5-ethyl-2-[(2-hydroxyethyl)-methyl-amino]-thiazol-4-yl}phenoxy)propoxy]-benzamidine,
198) N-hydroxy-4-[4-(4-{5-ethyl-2-[(2-hydroxyethyl)-methyl-amino]-thiazol-4-yl}phenoxy)butoxy]-benzamidine,
199) N-hydroxy-4-[3-(4-{5-ethyl-2-[methyl -(pyridin-3-ylmethypamino]-thiazol-4-yl}phenoxy)propoxy]-benzamidine,
200) N-hydroxy-4-[4-(4-{5-ethyl-2-[methyl -(pyridin-3-ylmethyl)amino]-thiazol-4-yl}phenoxy)butoxy]-benzamidine,
201) N-hydroxy-4-{4-[4-(5-cyclopentylmethyl-2-isopropyl-thiazol-4-yl)-phenoxymethyl]-benzyloxy}-benzamidine,
202) N-hydroxy-4-{4-[4-(5-butyl-2-isopropyl-thiazol -4-yl)-phenoxymethyl]-benzyloxy}-benzamidine,
203) N-hydroxy-4-{4-[4-(5-cyclopentylmethyl-2-amino -thiazol-4-yl)-phenoxymethyl]-benzyloxy}-benzamidine,
204) N-hydroxy-4-{4-[4-(5-cyclopentylmethyl-2-amino -thiazol-4-yl)-phenoxymethyl]-benzyloxy}-2-fluoro-benzamidine,
205) N-hydroxy-4-{4-[4-(2-methylamino-thiazol-4-yl) -phenoxymethyl]-benzyloxy}-benzamidine,
206) N-hydroxy-4-{6-[4-(5-isopropyl-2-methyl -thiazol-4-yl)-phenoxymethyl]-pyridine-2-yl-methoxy}-benzamidine,
207) N-hydroxy-2-fluoro-4-{4-[4-(5-isopropyl-2-methyl-thiazol-4-yl)-phenoxy]-butoxy}-benzamidine,
208) N-hydroxy-4-{2-[4-(5-isopropyl-2-methyl -thiazol-4-yl)-phenoxymethyl]-benzyloxy}-benzamidine,
209) N-hydroxy-4-{3-[4-(5-isopropyl-2-methyl -thiazol-4-yl)-phenoxymethyl]-benzyloxy}-benzamidine,
210) N-hydroxy-4-{4-[4-(5-cyclopentylmethyl-2-cyclohexyl-thiazol-4-yl)-phenoxymethyl]-benzyloxy}-benzamidine,
211) N-hydroxy-4-{6-[4-(5-isopropyl-2-methyl -thiazol-4-yl)phenoxy]-hexyloxy}-benzamidine,
212) N-hydroxy-4-{5-[2-ethyl-5-hydroxy-4-(2-methyl-thiazol-4-yl)phenoxy]-pentyloxy}-benzamidine,
213) N-hydroxy-4-{5-[2-ethyl-4-(2-methyl-thiazol-4-yl)-5-propoxy-phenoxy]-pentyloxy}-benzamidine,
214) N-hydroxy-4-(5-{4-[5-(2-isobutylamino-ethyl)-2-methyl-thiazol-4-yl]-phenoxy}-pentyloxy)-benzamidine,
215) 4-(5-{4-[5-(2-isobutylaminoethyl)-2-methyl-thiazol-4-yl]-phenoxy}-pentyloxy)-benzamidine,
216) N-hydroxy-4-(5-{4-[2-methyl-5-(2-piperidin-1-yl-ethyl)-thiazole-4-yl]-phenoxy}-pentyloxy)-benzamidine,
217) N-hydroxy-4-[5-(4-{2-methyl-5-[2-(2-morpholin-4-yl-ethylamino)-ethyl]-thiazol-4-yl}-phenoxy)-pentyloxy]-benzamidine,
218) N-hydroxy-4-[5-(4-{5-[2-(3-imidazol-1-yl-propylamino)-ethyl]-2-methyl-thiazol-4-yl}-phenoxy)-pentyloxy]-benzamidine,
219) N-hydroxy-4-(5-{4-[5-(2-isopropylaminoethyl) -2-methyl-thiazol-4-yl]-phenoxy}-pentyloxy)-benzamidine,
220) N-hydroxy-4-[5-(4-{5-[2-(3-isopropoxy -propylamino)-ethyl]-2-methyl-thiazole-4-yl}-phenoxy)-pentyloxy]-benzamidine,
221) N-hydroxy-4-(5-{4-[5-(2-butylamino-ethyl)-2-methyl-thiazol-4-yl]-phenoxy}-pentyloxy)-benzamidine, 222) N-hydroxy-4-(5-{4-[5-(2-imidazol-1-yl -ethyl)-2-methyl-thiazol-4-yl]-phenoxy}-pentyloxy)-benzamidine,
223) N-hydroxy-4-(5-{4-[5-(2-cyclohexylamino-ethyl)-2-methyl-thiazol-4-yl]-phenoxy}-pentyloxy)-benzamidine,
224) N-hydroxy-4-(5-{4-[5-(2-diethylamino-ethyl)-2-methyl-thiazol-4-yl]-phenoxy}-pentyloxy)-benzamidine,
225) N-hydroxy-4-{5-[4-(5-{2-[bis-(2-hydroxy-ethyl)-amino]-ethyl}-2-methyl-thiazol-4-yl)-phenoxy]-pentyloxy}-benzamidine,
226) N-hydroxy-4-(5-{4-[5-(2-d iisopropylamino -ethyl)-2-methyl-thiazol-4-yl]-phenoxy}-pentyloxy)-benzamidine,
227) N-hydroxy-4-[5-(4-{5-[2-(2,6-dimethyl -morpholin-4-yl)-ethyl]-2-methyl-thiazol-4-yl}-phenoxy)-pentyloxy]-benzamidine,
228) N-hydroxy-4-(5-{4-[2-methyl-5-(2-thiomorpholin-4-yl-ethyl)-thiazol-4-yl]-phenoxy}-pentyloxy)-benzamidine,
229) N-hydroxy-4-(5-{4-[2-amino-5-(2-morpholin-4-yl-ethyl)-thiazol-4-yl]-phenoxy}-pentyloxy)-benzamidine,
230) N-hydroxy-4-[5-(4-{5-[2-(2-dimethylamino-ethylamino)-ethyl]-2-methyl-thiazol-4-yl}-phenoxy)-pentyloxy]-benzamidine,
231) N-hydroxy-4-(5-{4-[2-methyl-5-(2-morpholin-4-yl-ethyl)-thiazol-4-yl]-phenoxy}-pentyloxy)-benzamidine,
232) N-hydroxy-4-[5-(4-{2-methyl-5-[2-(4-methyl-piperazin-1-yl)-ethyl]-thiazol-4-yl}-phenoxy)-pentyloxy]-benzamidine,
233) N-hydroxy-4-{5-[4-(5-{2-[bis-(2-methoxy-ethyl)-amino]-ethyl}-2-methyl-thiazol-4-yl)-phenoxy]-pentyloxy}-benzamidine,
234) N-hydroxy-4-(5-{4-[5-(2-tert-butylamino-ethyl)-2-methyl-thiazol-4-yl]-phenoxy}-pentyloxy)-benzamidine,
235) N-hydroxy-4-(5-{4-[5-(2-isobutylamino-ethyl)-2-methyl-thiazol-4-yl]-phenoxy}-pentyloxy)-benzamidine,
236) N-hydroxy-4-(5-{4-[5-(2-morpholin-4-yl -ethyl)-2-pyridin-3-yl-thiazol-4-yl]-phenoxy}-pentyloxy)-benzamidine,
237) N-hydroxy-4-[5-(4-{5-[2-(4-methyl -piperazin-1-yl)-ethyl]-2-pyridin-3-yl-thiazol-4-yl}-phenoxy)-pentyloxy]-benzamidine,
238) N-hydroxy-4-(5-{4-[2-pyridin-3-yl-5-(2-thiomorpholin-4-yl-ethyl)-thiazol-4-yl]-phenoxy}-pentyloxy)-benzamidine,
239) N-hydroxy-4-(5-{4-[5-(2-imidazol-1-yl -ethyl)-2-pyridin-3-yl-thiazol-4-yl]-phenoxy}-pentyloxy)-benzamidine,
240) N-hydroxy-4-(5-{4-[2-isopropyl-5-(2-morpholin-4-yl-ethyl)-thiazol-4-yl]-phenoxy}-pentyloxy)-benzamidine,
241) N-hydroxy-4-[5-(4-{2-isopropyl-5-[2-(4-methyl-piperazin-1-yl)-ethyl]-thiazol-4-yl}-phenoxy)-pentyloxy]-benzamidine,
242) N-hydroxy-4-(5-{4-[5-(2-imidazol-1-yl -ethyl)-2-isopropyl-thiazol-4-yl]-phenoxy}-pentyloxy)-benzamidine,
243) N-hydroxy-4-[5-(4-{2-isopropyl-5-[2-(2-morpholin-4-yl-ethylamino)-ethyl]-thiazol-4-yl}-phenoxy)-pentyloxy]-benzamidine,
244) N-hydroxy-4-[5-(4-{5-[2-(3-imidazol-1-yl-propylamino)-ethyl]-2-isopropyl-thiazol-4-yl}-phenoxy)-pentyloxy]-benzamidine,
245) N-hydroxy-4-(5-{4-[2-isopropyl-5-(2-thiomorpholin-4-yl-ethyl)-thiazol-4-yl]-phenoxy}-pentyloxy)-benzamidine,
246) N-hydroxy-4-(5-{4-[2-cyclohexyl-5-(2-morpholin-4-yl-ethyl)-thiazol-4-yl]-phenoxy}-pentyloxy)-benzamidine,
247) N-hydroxy-4-[5-(4-{2-cyclohexyl-5-[2-(4-methyl-piperazin-1-yl)-ethyl]-thiazol-4-yl}-phenoxy)-pentyloxy]-benzamidine,
248) N-hydroxy-4-[5-(4-{2-cyclohexyl-5-[2-(2-morpholin-4-yl-ethylamino)-ethyl]-thiazol-4-yl}-phenoxy)-pentyloxy]-benzamidine,
249) N-hydroxy-4-(5-{4-[2-cyclohexyl-5-(2-thiomorpholin-4-yl-ethyl)-thiazol-4-yl]-phenoxy}-pentyloxy)-benzamidine,
250) N-hydroxy-4-(5-{4-[2-cyclohexyl-5-(2-dimethylamino-ethyl)-thiazol-4-yl]-phenoxy}-pentyloxy)-benzamidine,
251) N-hydroxy-4-(5-{4-[2-cyclohexyl-5-(2-dipropylamino-ethyl)-thiazol-4-yl]-phenoxy}-pentyloxy)-benzamidine,
252) N-hydroxy-4-(5-{4-[2-cyclohexyl-5-(2-cyclopropylamino-ethyl)-thiazol-4-yl]-phenoxy}-pentyloxy)-benzamidine,
253) N-hydroxy-4-[5-(4-{2-amino-5-[2-(2-morpholin-4-yl-ethylamino)-ethyl]-thiazol-4-yl}-phenoxy)-pentyloxy]-benzamidine,
254) N-hydroxy-4-(5-{4-[5-(2-morpholin-4-yl -ethyl)-2-phenyl-thiazol-4-yl]-phenoxy}-pentyloxy)-benzamidine,
255) N-hydroxy-4-(5-{4-[2-ethyl-5-(2-morpholin-4-yl-ethyl)-thiazol-4-yl]-phenoxy}-pentyloxy)-benzamidine,
256) N-hydroxy-4-(5-{4-[2-ethyl-5-(2-thiomorpholin-4-yl-ethyl)-thiazol-4-yl]-phenoxy}-pentyloxy)-benzamidine,
257) N-hydroxy-4-(4-{4-[2-methyl-5-(2-morpholin-4-yl-ethyl)-thiazol-4-yl]-phenoxy}-butoxy)-benzamidine,
258) 4-(5-{4-[2-cyclohexyl-5-(2-morpholin-4-yl-ethyl)-thiazol-4-yl]-phenoxy}-pentyloxy)-benzamidine,
259) 4-(5-{4-[2-methyl-5-(2-morpholin-4-yl-ethyl)-thiazol-4-yl]-phenoxy}-pentyloxy)-benzamidine,
260) N-hydroxy-4-(5-{4-[2-methylamino-5-(2-morpholin-4-yl-ethyl)-thiazol-4-yl]-phenoxy}-pentyloxy)-benzamidine,
261) N-hydroxy-4-[5-(4-{2-methylamino-5-[2-(4-methyl-piperazin-1-yl)-ethyl]-thiazol-4-yl}-phenoxy)-pentyloxy]-benzamidine,
262) N-hydroxy-4-(5-{4-[2-methylamino-5-(2-thiomorpholin-4-yl-ethyl)-thiazol-4-yl]-phenoxy}-pentyloxy)-benzamidine,
263) N-hydroxy-4-[5-(4-{2-methylamino-5-[2-(2-morpholin-4-yl-ethylamino)-ethyl]-thiazol-4-yl}-phenoxy)-pentyloxy]-benzamidine,
264) N-hydroxy-4-[5-(4-{5-[2-(3-imidazol-1-yl-propylamino)-ethyl]-2-methylamino-thiazol-4-yl}-phenoxy)-pentyloxy]-benzamidine,
265) 4-(5-{4-[2-methylamino-5-(2-morpholin-4-yl-ethyl)-thiazol-4-yl]-phenoxy}-pentyloxy)-benzamidine,
266) N-hydroxy-4-(5-{4-[2-dimethylamino-5-(2-morpholin-4-yl-ethyl)-thiazol-4-yl]-phenoxy}-pentyloxy)-benzamidine, 267) N-hydroxy-4-(5-{4-[2-dimethylamino-5-(2-thiomorpholin-4-yl-ethyl)-thiazol-4-yl]-phenoxy}-pentyloxy)-benzamidine,
268) N-hydroxy-4-(5-{4-[2-(isobutyryl-methyl-amino)-5-(2-morpholin-4-yl-ethyl)-thiazol-4-yl]-phenoxy}-pentyloxy)-benzamidine,
269) N-hydroxy-4-(5-{4-[2-[benzyl-(2-morpholin-4-yl-ethyl)-amino]-5-(2-morpholin-4-yl-ethyl)-thiazol-4-yl]-phenoxy}-pentyloxy)-benzamidine,
270) N-hydroxy-4-(5-{4-[2-diethylamino-5-(2-morpholin-4-yl-ethyl)-thiazol-4-yl]-phenoxy}-pentyloxy)-benzamidine,
271) N-hydroxy-4-(5-{4-[2-[bis-(2-methoxy-ethyl) -amino]-5-(2-morpholin-4-yl-ethyl)-thiazol-4-yl]-phenoxy}-pentyloxy)-benzamidine,
272) N-hydroxy-4-(5-{4-[2-morpholin-4-yl-5-(2-morpholine-4-yl-ethyl)-thiazol-4-yl]-phenoxy}-pentyloxy)-benzamidine,
273) N-hydroxy-4-(5-{4-[2-morpholin-4-yl-5-(2-thiomorpholin-4-yl-ethyl)-thiazol-4-yl]-phenoxy}-pentyloxy)-benzamidine,
274) N-hydroxy-4-[5-(4-{5-[2-(4-methyl -piperazin-1-yl)-ethyl]-2-morpholin-4-yl-thiazol-4-yl}-phenoxy)-pentyloxy]-benzamidine,
275) N-hydroxy-4-[5-(4-{2-morpholin-4-yl-5-[2-(2-morpholin-4-yl-ethylamino)-ethyl]-thiazol-4-yl}-phenoxy)-pentyloxy]-benzamidine,
276) N-hydroxy-4-(5-{4-[5-(2-morpholin-4-yl -ethyl)-2-piperidin-1-yl-methyl-thiazol-4-yl]-phenoxy}-pentyloxy)-benzamidine,
277) 4-(5-{4-[2-morpholin-4-yl-5-(2-morpholin-4-yl-ethyl)-thiazol-4-yl]-phenoxy}-pentyloxy)-benzamidine,
278) N-hydroxy-4-(5-{4-[5-(2-isobutyrylamino-ethyl)-2-methyl-thiazol-4-yl]-phenoxy}-pentyloxy)-benzamidine,
279) N-hydroxy-4-{5-[4-(5-{2-[isobutyl -(pyridin-3-carbonyl)-amino]-ethyl}-2-methyl-thiazol-4-yl)-phenoxy]-pentyloxy}-benzamidine,
280) N-hydroxy-4-{5-[4-(5-{2-[cyclopropyl -(pyridin-4-carbonyl)-amino]-ethyl}-2-isopropyl-thiazol-4-yl)-phenoxy]-pentyloxy}-benzamidine,
281) N-hydroxy-4-{5-[4-(2-cyciohexyl-5-{2-[cyclopropyl-(pyridin-3-carbonyl)-amino]-ethyl}-thiazol-4-yl)-phenoxy]-pentyloxy}-benzamidine,
282) N-hydroxy-4-{5-[4-(5-methylcarbamoyl-2-methyl -thiazol-4-yl)-phenoxy]-pentyloxy}-benzamidine,
283) N-hydroxy-4-{5-[4-(5-isopropylcarbamoyl-2-methyl-thiazol-4-yl)-phenoxy]-pentyloxy}-benzamidine,
284) N-hydroxy-4-{5-[4-(5-{3-imidazol-1-yl -propylcarbamoyl}-2-methyl-thiazol-4-yl)-phenoxy]-pentyloxy}-benzamidine,
285) N-hydroxy-4-{5-[4-(2-amino-5-methylcarbamoyl-thiazol-4-yl)-phenoxy]-pentyloxy}-benzamidine,
286) N-hydroxy-4-{5-[4-(2-methyl-5-morpholin-4-yl-thiazol-4-yl)-phenoxy]-pentyloxy}-benzamidine,
287) N-hydroxy-4-(5-{4-[2-methyl-5-(4-methyl -piperazin-1-yl)-thiazole-4-yl]-phenoxy}-pentyloxy)-benzamidine,
288) N-hydroxy-4-{5-[4-(2-amino-5-morpholin-4-yl-thiazol-4-yl)-phenoxy]-pentyloxy}-benzamidine,
289) N-hydroxy-4-(5-{4-[5-(4-methyl-piperazin-1-yl)-2-morpholin-4-yl-thiazol-4-yl]-phenoxy}-pentyloxy)-benzamidine,
290) N-hydroxy-4-{5-[4-(2,5-di-morpholin-4-yl -thiazol-4-yl)-phenoxy]-pentyloxy}-benzamidine,
291) N-hydroxy-4-{5-[4-(2-morpholin-4-yl-5-thiomorpholin-4-yl-thiazol-4-yl)-phenoxy]-pentyloxy}-benzamidine,
292) N-hydroxy-4-{5-[4-(2-morpholin-4-yl-5-pyrolidin-1-yl-thiazol-4-yl)-phenoxy]-pentyloxy}-benzamidine,
293) N-hydroxy-4-{5-[4-(2-methyl-5-morpholin-4-ylmethyl-thiazol-4-yl)-phenoxy]-pentyloxy}-benzamidine,
294) N-hydroxy-4-(5-{4-[2-methyl-5-(4-methyl -piperazin-1-ylmethyl)-thiazol-4-yl]-phenoxy}-pentyloxy)-benzamidine,
295) N-hydroxy-4-{5-[4-(2-methyl-5-thiomorpholin-4-ylmethyl-thiazol-4-yl)-phenoxy]-pentyloxy}-benzamidine,
296) N-hydroxy-4-{5-[4-(2-methyl-5-piperidin-1-ylmethyl-thiazol-4-yl)-phenoxy]-pentyloxy}-benzamidine,
297) N-hydroxy-4-{5-[4-(5-dimethylaminomethyl-2-methyl-thiazol-4-yl)-phenoxy]-pentyloxy}-benzamidine,
298) N-hydroxy-4-{5-[4-(5-butylaminomethyl-2-methyl -thiazol-4-yl)-phenoxy]-pentyloxy}-benzamidine,
299) N-hydroxy-4-(5-{4-[5-(isobutylamino-methyl)-2-methyl-thiazol-4-yl]-phenoxy}-pentyloxy)-benzamidine,
300) N-hydroxy-4-(5-{4-[5-(tert-butylamino-methyl)-2-methyl-thiazol-4-yl]-phenoxy}-pentyloxy)-benzamidine,
301) N-hydroxy-4-{5-[4-(2-methyl-5-propylaminomethyl-thiazol-4-yl)-phenoxy]-pentyloxy}-benzamidine,
302) N-hydroxy-4-[5-(4-{2-methyl-5-[(2-morpholin-4-yl-ethylamino)-methyl]-thiazol-4-yl}-phenoxy)-pentyloxy]-benzamidine,
303) N-hydroxy-4-[5-(4-{5-[(3-imidazol-1-yl -propylamino)-methyl]-2-methyl-thiazol-4-yl}-phenoxy)-pentyloxy]-benzamidine,
304) N-hydroxy-4-{5-[4-(2-methyl-5-pyrolidin-1-ylmethyl-thiazol-4-yl)-phenoxy]-pentyloxy}-benzamidine,
305) N-hydroxy-4-{5-[4-(5-imidazol-1-ylmethyl-2-methyl-thiazol-4-yl)-phenoxy]-pentyloxy}-benzamidine,
306) N-hydroxy-4-(5-{4-[5-(benzylamino-methyl)-2-methyl-thiazol-4-yl]-phenoxy}-pentyloxy)-benzamidine,
307) N-hydroxy-4-{5-[4-(5-cyclopropylaminomethyl-2-methyl-thiazol-4-yl)-phenoxy]-pentyloxy}-benzamidine,
308) N-hydroxy-4-{5-[4-(2-methylamino-5-morpholin-4-yl-thiazol-4-yl)-phenoxy]-pentyloxy}-benzamidine,
309) N-hydroxy-4-(5-{4-[2-(methyl-pyridin-4-ylmethyl-amino)-5-morpholin-4-ylmethyl-thiazol-4-yl]-phenoxy}-pentyloxy)-benzamidine,
310) N-hydroxy-4-[5-(4-{2-[(2-hydroxy-ethyl) -methyl-amino]-5-morpholin-4-ylmethyl-thiazol-4-yl}-phenoxy)-pentyloxy]-benzamidine,
311) N-hydroxy-4-(5-{4-[2-(ethyl-methyl-amino)-5-morpholin-4-ylmethyl-thiazol-4-yl]-phenoxy}-pentyloxy)-benzamidine,
312) N-hydroxy-4-(5-{4-[2-(benzyl-methyl-amino)-5-morpholin-4-ylmethyl-thiazol-4-yl]-phenoxy}-pentyloxy)-benzamidine,
313) N-hydroxy-4-[5-(4-{2-[methyl-(2-morpholin-4-yl-ethyl)-amino]-5-morpholin-4-ylmethyl-thiazol-4-yl}-phenoxy)-pentyloxy]-benzamidine,
314) N-hydroxy-4-[5-(4-{2-[methyl-(2-morpholin-4-yl-ethyl)-amino]-5-thiomorpholin-4-ylmethyl-thiazol-4-yl}-phenoxy)-pentyloxy]-benzamidine,
315) N-hydroxy-4-[5-(4-{5-{[bis-(2-methoxy -ethyl)-amino]-methyl}-2-[methyl-(2-morpholin-4-yl-ethyl)-amino]-thiazol-4-yl}-phenoxy)-pentyloxy]-benzamidine, 316) N-hydroxy-4-(5-{4-[2-[methyl-(2-morphlin-4-yl-ethyl)-amino]-5-(4-methyl-piperazin-1-ylmethyl)-thiazol-4-yl]-phenoxy}-pentyloxy)-benzamidine,
317) N-hydroxy-4-[5-(4-{5-(isopropylamino-methyl)-2-[methyl-(2-morpholin-4-yl-ethyl)-amino]-thiazol-4-yl}-phenoxy) -pentyloxy]-benzamidine,
318) N-hydroxy-4-[5-(4-{5-[(2-methoxy-ethyl-amino) -methyl]-2-[methyl-(2-morpholin-4-yl-ethyl)-amino]-thiazol-4-yl}-phenoxy)-pentyloxy]-benzamidine,
319) N-hydroxy-4-[5-(4-{2-[(2-methoxy-ethyl) -methyl-amino]-5-morpholin-4-ylmethyl-thiazol-4-yl}-phenoxy)-pentyloxy]-benzamidine,
320) N-hydroxy-4-(5-{4-[2-(methyl-propyl-amino)-5-morpholin-4-ylmethyl-thiazol-4-yl]-phenoxy}-pentyloxy)-benzamidine,
321) N-hydroxy-4-(5-{4-[2-(methyl-pyridin-3-ylmethyl-amino)-5-morpholin-4-ylmethyl-thiazol-4-yl]-phenoxy}-pentyloxy)-benzamidine,
322) N-hydroxy-4-{5-[4-(2-methyl-5-methylamino -thiazol-4-yl)-phenoxy]-pentyloxy}-benzamidine,
323) N-hydroxy-4-[5-(4-{2-methyl-5-[(pydin-4-carbonyl)-amino]-thiazol-4-yl}-phenoxy)-pentyloxy]-benzamidine,
324) N-hydroxy-4-[5-(4-{2-methyl-5-[(pyridin-3-carbonyl)-amino]-thiazol-4-yl}-phenoxy)-pentyloxy]-benzamidine,
325) N-hydroxy-4-[5-(4-{2-phenyl-5-[(pyridin-3-carbonyl)-amino]-thiazol-4-yl}-phenoxy)-pentyloxy]-benzamidine,
326) N-hydroxy-4-{5-[4-(5-dimethylamino-2-methyl -thiazol-4-yl)-phenoxy]-pentyloxy}-benzamidine,
327) N-hydroxy-4-{5-[4-(5-dimethylamino-2-phenyl -thiazol-4-yl)-phenoxy]-pentyloxy}-benzamidine,
328) N-hydroxy-4-{5-[4-(2-cyclohexyl-5-dimethylamino-thiazol-4-yl)-phenoxy]-pentyloxy}-benzamidine,
329) N-hydroxy-4-{5-[4-(2-methyl-5-[1,2,4]triazol-1-yl-thiazol-4-yl)-phenoxy]-pentyloxy}-benzamidine,
330) N-hydroxy-4-{5-[4-(5-amino-2-phenyl-thiazol-4-yl) -phenoxy]-pentyloxy}-benzamidine,
331) N-hydroxy-4-{5-[4-(5-amino-2-methyl-thiazol-4-yl)-phenoxy]-pentyloxy}-benzamidine,
332) N-hydroxy-4-{5-[4-(5-amino-2-pyridin-3-yl-thiazol-4-yl)-phenoxy]-pentyloxy}-benzamidine,
333) N-hydroxy-4-{5-[4-(5-amino-2-ethyl-thiazol-4-yl)-phenoxy]-pentyloxy}-benzamidine,
334) N-hydroxy-4-{5-[4-(5-amino-2-cyclohexyl -thiazol-4-yl)-phenoxy]-pentyloxy}-benzamidine,
335) N-hydroxy-4-{5-[4-(2-methylamino-5-morpholin-4-ylmethyl-thiazol-4-yl)-phenoxy]-pentyloxy}-benzamidine,
336) N-hydroxy-4-{5-[4-(2-morpholine-4-yl-5-morpholin-4-ylmethyl-thiazol-4-yl)-phenoxy]-pentyloxy}-benzamidine, and
337) N-hydroxy-4-{5-[4-(5-morpholin-4-yl-2-piperidin-1-yl-thiazol-4-yl)-phenoxy]-pentyloxy}-benzamidine.

25. The method of claim 1, wherein the bisphosphonate of Formula 2 is selected from the group consisting of etidronic acid, clodronic acid, pamidronic acid, tiludronic acid, risedronic acid, minodronic acid, ibandronic acid, zoledronic acid and alendronic acid.

26. The method of claim 1, wherein the pharmaceutical composition is prepared in a form of combination formulation comprising (a) the benzamidine derivative represented by the following Formula 1 or salt thereof, and (b) bisphosphonate represented by the following Formula 2.

27. The method of claim 1, wherein the pharmaceutical composition is prepared in a form of single formulation comprising (a) the benzamidine derivative represented by the following Formula 1 or salt thereof, and (b) bisphosphonate represented by the following Formula 2.

28. The method of claim 1, wherein two single formulations comprising each of (a) the benzamidine derivative represented by the following Formula 1 or salt thereof, and (b) bisphosphonate represented by the following Formula 2 are provided in one kit.

* * * * *

UNITED STATES PATENT AND TRADEMARK OFFICE
CERTIFICATE OF CORRECTION

PATENT NO.      : 8,008,329 B2                          Page 1 of 1
APPLICATION NO. : 12/533842
DATED           : August 30, 2011
INVENTOR(S)     : Jei Man Ryu et al.

It is certified that error appears in the above-identified patent and that said Letters Patent is hereby corrected as shown below:

Title Page:

In Item (54) Title: please correct the Title to read as follows:

Item (54)  METHOD OF TREATING OR PREVENTING OSTEOPOROSIS COMPRISING ADMINISTERING TO A PATIENT IN NEED THEREOF AN EFFECTIVE AMOUNT OF PHARMACEUTICAL COMPOSITION COMPRISING BENZAMIDINE DERIVATIVE OR ITS SALT, AND BISPHOSPHONATE Signed and Sealed this
Twenty-second Day of November, 2011

David J. Kappos
*Director of the United States Patent and Trademark Office*

UNITED STATES PATENT AND TRADEMARK OFFICE
CERTIFICATE OF CORRECTION

PATENT NO. : 8,008,329 B2  Page 1 of 1
APPLICATION NO. : 12/533842
DATED : August 30, 2011
INVENTOR(S) : Jei Man Ryu et al.

It is certified that error appears in the above-identified patent and that said Letters Patent is hereby corrected as shown below:

Title Page, Item (54) and at Column 1, lines 1-7, Title: please correct the Title to read as follows:

METHOD OF TREATING OR PREVENTING OSTEOPOROSIS COMPRISING ADMINISTERING TO A PATIENT IN NEED THEREOF AN EFFECTIVE AMOUNT OF PHARMACEUTICAL COMPOSITION COMPRISING BENZAMIDINE DERIVATIVE OR ITS SALT, AND BISPHOSPHONATE

This certificate supersedes the Certificate of Correction issued November 22, 2011.

Signed and Sealed this
Third Day of January, 2012

David J. Kappos
*Director of the United States Patent and Trademark Office*